United States Patent
Mookerjee et al.

(10) Patent No.: US 11,312,979 B2
(45) Date of Patent: Apr. 26, 2022

(54) METHOD AND CELL LINE FOR PRODUCTION OF PHYTOCANNABINOIDS AND PHYTOCANNABINOID ANALOGUES IN YEAST

(71) Applicant: Hyasynth Biologicals Inc., Montreal (CA)

(72) Inventors: Shoham Mookerjee, Montreal (CA); Alexander James Campbell, Montreal (CA); Zachary Douglas Wiltshire, Montreal (CA); Kevin John Chen, Montreal (CA)

(73) Assignee: Hyasynth Biologicals Inc., Montreal (CA)

( * ) Notice: Subject to any disclaimer, the term of this patent is extended or adjusted under 35 U.S.C. 154(b) by 0 days.

(21) Appl. No.: 16/486,610

(22) PCT Filed: Feb. 19, 2018

(86) PCT No.: PCT/CA2018/050189
§ 371 (c)(1),
(2) Date: Aug. 16, 2019

(87) PCT Pub. No.: WO2018/148848
PCT Pub. Date: Aug. 23, 2018

(65) Prior Publication Data
US 2020/0283807 A1    Sep. 10, 2020

Related U.S. Application Data

(60) Provisional application No. 62/460,526, filed on Feb. 17, 2017.

(51) Int. Cl.
| | |
|---|---|
| C12P 17/16 | (2006.01) |
| C12P 7/22 | (2006.01) |
| C12N 9/10 | (2006.01) |
| C07K 14/395 | (2006.01) |
| C12N 9/04 | (2006.01) |
| C12N 9/12 | (2006.01) |
| C12N 9/00 | (2006.01) |
| C12N 15/52 | (2006.01) |

(52) U.S. Cl.
CPC .............. *C12P 7/22* (2013.01); *C07K 14/395* (2013.01); *C12N 9/0006* (2013.01); *C12N 9/1029* (2013.01); *C12N 9/1085* (2013.01); *C12N 9/1288* (2013.01); *C12N 9/93* (2013.01); *C12N 15/52* (2013.01); *C12Y 205/01041* (2013.01); *C12Y 101/01001* (2013.01); *C12Y 203/01* (2013.01); *C12Y 207/08007* (2013.01); *C12Y 602/01001* (2013.01)

(58) Field of Classification Search
CPC .... C12N 9/1085; C12N 15/52; C12N 9/1029; C12N 9/93; C12Y 207/08007; C12Y 101/01001; C12Y 205/01; C12P 7/22

USPC ............ 435/135, 146, 156, 252.2, 193, 197, 435/320.1
See application file for complete search history.

(56) References Cited

U.S. PATENT DOCUMENTS

| | | |
|---|---|---|
| 7,361,482 B2 | 4/2008 | Chang et al. |
| 7,361,483 B2 | 4/2008 | Kuzuyama et al. |
| 8,124,390 B2 | 2/2012 | Kuzuyama et al. |
| 8,884,100 B2 | 11/2014 | Page et al. |
| 9,359,625 B2 | 6/2016 | Winnicki et al. |
| 9,394,510 B2 | 7/2016 | Peet et al. |
| 9,670,494 B2 | 6/2017 | Nielsen et al. |
| 9,765,308 B2 | 9/2017 | Page et al. |
| 2008/0020438 A1 | 1/2008 | Matsuda et al. |
| 2012/0122180 A1 | 5/2012 | Austin et al. |
| 2013/0197248 A1 | 8/2013 | Nielsen et al. |
| 2014/0141476 A1 | 5/2014 | Page et al. |

(Continued)

FOREIGN PATENT DOCUMENTS

| | | |
|---|---|---|
| EP | 1338608 A2 | 8/2003 |
| WO | 03072602 A2 | 3/2003 |

(Continued)

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Cannabis Sativa OLS mRNA for Olivetol Synthase—Taura et al., "Characterization of Olivetol Synthase, a Polyketide Synthase Putatively Involved in Cannabinoid Biosynthetic Pathway," FEBS Letters 583 (2009) 2061-2066, (available online on May 19, 2009).

(Continued)

*Primary Examiner* — Robert B Mondesi
*Assistant Examiner* — Mohammad Y Meah
(74) *Attorney, Agent, or Firm* — Fish & Richardson P.C.

(57) ABSTRACT

A method and cell line for producing phytocannabinoids and phytocannabinoid analogues in yeast. The method applies, and the cell line includes, a yeast cell transformed with a polyketide synthase CDS and a cytosolic prenyltransferase CDS. The polyketide synthase enzyme catalyzes synthesis of olivetol or methyl-olivetol, and may include *Cannabis sativa* olivetolic acid synthase or *Dictyostelium discoideum* polyketide synthase ("DiPKS"). The yeast cell may be modified to include a phosphopantethienyl transferase for increased activity of DiPKS. The yeast cell may be modified to mitigate mitochondrial acetaldehyde catabolism for increasing malonyl-CoA available for synthesizing olivetol or methyl-olivetol. The prenyltransferase enzyme catalyzes synthesis of cannabigerol or a cannabigerol analogue, and may include an αββα cytosolic prenyltransferase enzyme from *Streptomyces* sp CL190. The yeast cell may be modified to mitigate depletion of geranyl pyrophosphate for increasing available geranyl pyrophosphate for prenylation.

39 Claims, 12 Drawing Sheets
Specification includes a Sequence Listing.

(56) References Cited

U.S. PATENT DOCUMENTS

| | | | |
|---|---|---|---|
| 2014/0330032 | A1 | 11/2014 | Lynch et al. |
| 2016/0010126 | A1 | 1/2016 | Poulos et al. |
| 2016/0138056 | A1 | 5/2016 | Jensen et al. |

FOREIGN PATENT DOCUMENTS

| | | | |
|---|---|---|---|
| WO | 2006060839 A2 | 6/2006 | |
| WO | 2006081537 A2 | 8/2006 | |
| WO | 2011127569 A1 | 10/2011 | |
| WO | 2012017083 A1 | 2/2012 | |
| WO | 2013006953 A1 | 1/2013 | |
| WO | 2014018982 A1 | 1/2014 | |
| WO | 2014207113 A1 | 12/2014 | |
| WO | 2015032911 A1 | 3/2015 | |
| WO | 2016010827 A1 | 1/2016 | |
| WO | 2016159869 A1 | 10/2016 | |
| WO | 2017139496 A1 | 8/2017 | |
| WO | 2017161041 A1 | 9/2017 | |
| WO | 2018200888 A1 | 11/2018 | |

OTHER PUBLICATIONS

European Patent Application No. 18754525.6, Extended European Search Report dated Dec. 11, 2020.

Hanus et al., "Phytocannabinoids: A Unified Critical Inventory," Natural Product Reports, Nov. 23, 2016, vol. 33 (12), pp. 1357-1392.

Singapore Patent Application No. SG11201907504P, Search Report and Written opinion dated Dec. 1, 2020.

Stehle et al., "Biotechnological Synthesis of Tetrahydrocannabinolic Acid Heterologe Biosynthese Der Tetrahydrocannabinolsäure," Pharmakon, Mar. 2017, vol. 5(2), pp. 142-147.

Zucko et al., "Polyketide Synthase Genes and the Natural Products Potential of Dictyostellum Discoideum," Bioinformatics, 2007, vol. 23(19), pp. 2543-2549.

AB164375 Nucleic Add Sequence, NCBI [orfine database], Sequence Deposited Mar. 28, 2008 (Mar. 28, 2008), Retrieved from the internet [URL: https://www.ncbi.nlm.nih.gon/nuccore/AB164375].

Austin et al., "Biosynthesis of Dictyostefium Discoideum Differentiation-Inducing Factor by a Hybrid Type I Fatty Acid-Type III Polyketide Synthase," Nature Chemical Biology, Sep. 2006, vol. 2 (9), pp. 434-502.

Baba et al., "Yeast Coq5 C-Methyltransferase Is Required for Stability of Other Polypeptides Involved in Coenzyme Q Biosynthesis," The Journal of Biological Chemistry, Mar. 2004, vol. 279 (11), pp. 10052-10059.

Bonitz et al., "Evolutionary Relationships of Microbial Aromatic Prenyltransferases," PLos One, Nov. 2011, vol. 6 (11), pp. e27336.

Carvalho et al., "Designing Microorganisms for Heterologous Biosynthesis of Cannabinoids," FEMS Yeast Research, Jun. 2017, vol. 17 (4), pp. 1-11, ISSN 1567-1356.

Chambon et al., "Isolation and Properties of Yeast Matants Affected in Farnesyl Diphosphate Synthetase," Current Genetics. Jul. 1990, vol. 18 (1), pp. 41-46.

Cheon et al., "A Biosynthetic Pathway for Hexanoic Acid Production in Kluyveromyces Marxianus," Journal of Biotechnology, Jul. 2014, vol. 182-183, pp. 30-36.

Degenhardt et al., "Chapter 2. The Biosynthesis of Cannabinoids," Dec. 20117, pp. 13-23.

Fellermeier et al., "Biosynthesis of Cannabinoids. Incorporation Experiments With (13)C-Labeled Glucoses," European Journal of Biochemistry, Mar. 2001, vol. 268 (6), pp. 1596-1604.

Fellermeier, "Prenylation of Olivetolate by a Hemp Transferase Yields Cannabiqerolic Add, the Precursor of Tetrahycrocannabinol," FEBS Letters, May 1998, vol. 427 (2), pp. 283-285.

Fischer et al., "Metabolic Engineering of Monoterpene Synthesis in Yeast," Biotechnology and Bioengineering, Aug. 2011, vol. 108(B), pp. 1883-1892.

Flagfeldt et al., "Characterzalion of Chromosomal Integraitian Sites for Heterologous Gene Expression in *Saccharomyces cerevisiae*," Yeast, Oct. 2009, vol. 26(10) pp. 545-551.

Flemming et al., "Chemistry and Biological Activity of Tetrahydrocannabinol and its Derivatives," Topscs in Heterocyclic Chemistry, Bioactive Heterocycles IV, Aug. 2007, vol. 10, pp. 1-42.

Gagne et al., "Identification of Olivetolic Acid Cyclase From Cannabis Sativa Reveals a Unique Catalytic Route to Plant Polyketides," Proceedings of the National Academy of Sciences of the Unfed States of America, Jul. 2012, vol. 109(31), pp. 12811-12816.

Gagne, "The Polyketide Origins of Cannabinoids in Cannabis Sativa," A Thesis Submitted to the College of Graduate Studies and Research In Partial Fulfillment of the Requirements For the Degree of Doctor of Philosophy In the Department of Biology, University of Saskatcheswan, 2013, 263 pages.

Ghosh et al., "Dissecting the Functional Rote of Polyketide Synthases in Dictyostelium Discoideum: Biosynthesis of the Differentiation Regulating Factor 4-methyl-5-pentylbenzene-1,3-diol," The Journal af Biological Chemistry, Apr. 2008, vol. 283 (17), pp. 11348-11354, ISSN 0021-9258.

Gietz et al., "High-Efficiency Yeast Transformation Using tore LiAc/SS Carrier DNA/PEG Method," Nature Protocols, 2007, vol. 2 (1), pp. 31-34.

Gietz et al., "Yeast Transformation by the LiAc/SS Carrier DNA/PEG Method," Methods in Molecular Biology, 2014, vol. 1205. https://doi.org/10.1007/978-1-4939-1363-3_1.

Huang et al., "Effect of Organic Acids on the Growth and Lipid Accumulation of Oleaginous Yeast Trichosporon Fermentans," Biotechnology for Biofuels, Jan. 2012, vol. 5(1), pp. 4.

Hunkova et al., "Toxic Effects of Fatty Adds on Yeast Cells: Dependence of Inhibitory Effects on Fatty Acid Concentration," Biotechnology and Bioengineering, Nov. 1977, vol. 19 (11), pp. 1623-1641.

International Patent Application No. PCT/CA2018/050189, International Prelimnary Report on Patentability dated Jun. 11, 2019.

International Patent Application No. PCT/CA2018/050189, International Search Report and Written Opinion dated May 17, 2018.

Jensen et al., "EasyClone: Method for Iterative Chromosomal Integration of Multiple Genes in *Saccharomyces cerevisiae*," FEMS Yeast Research, Mar. 2014, vol. 14(2), pp. 238-248. https://doi.org/10.1111/1567-1364.12118.

Kaminska et al., "The Isoprenoid Biosynthetic Pathway in *Saccharomyces cerevisiae* is Affected in a maft-1 Mutant With Altered tRNA Synthesis" FEMS Yeast Research, Mar. 2002, vol. 2 (1), pp. 31-37.

Kim et al., "Characterization of NpgA a 4"-Phosphopantetheinyl Transferase of Aspergillus Niduans, and Evidence of Its Involvement in Fungal Growth and Formation of Conidia and Cleistathecia for Development," Journal of Microbiology, Jan. 2015, vol. 53 (1), pp. 21-31.

Krivoruchko et al., "Microbial Acetyl-CoA Metabolise artd Metabolic Engineering," Metabolic Engineering, Mar. 2015, vol. 28, pp. 28-42.

Kuzuyama et al., "Structual Basis for the Promiscuoues Biosynthetic Prenylation of Aromatic Natural Products," Nature, Jun. 2005, vol. 435 (7044), pp. 983-987.

Liu et al., "Overproduction of Geraniol by Enhanced Precursor Suppy in *Saccharomyces cerevisiae*," Journal of Biotechnology, Dec. 2013, vol. 158 (4), pp. 446-451.

NCBI GenBank online database under Accession No. NC 007087.3.

NCBI GenBank online database under accession No. NCBI AB187169.

Oswald et al., "Monoterpenoid Biosynthesis in *Sacchanomyces cerevisise*," FEMS Yeast Research, May 2007, vol. 7(3), pp. 413-421. https://doi.org/10.1111/j.1567-1364.2006.00172.x.

Pamplantyil., "Identification, Isolaton and Functional Characterization of Prenyltransferases in *Cannabis sativa* L.," Faculty of Biochemical and Chemical Engineering, The Technical University of Dortmund, Dissertation, 2016, 139 pages.

Razdan., "Structure-Activity Relationships in Cannabinoids," Pharmacologica Reviews, Jun. 1986, vol. 38 (2) pp. 75-149.

Ro et al., "Production of the Antimalarial Drug Precurses Artemisinic Acid si Engineered Yeast," Nature Letters, Apr. 2006, vol. 440(7086) pp. 940-943.

(56) References Cited

OTHER PUBLICATIONS

Ryan et al., "CRISPR-Cas9 Genome Engineering in *Saccharomyces cerevisiae* Cells," Cold Sping Harbor Protocols, Jun. 2016, vol. 201 6(6). https://doi.org/10.1101/pdb.prot086827.

Schreckenbach, "Enzymatische Oligomenisierung von Alkendiphosphaten," Martin Luther University Halle-Wittenberg, Dissertation, 2017, 159 pages.

Shi et al., "Improving Production of Malony Coenzyme A-Derived Metabolites by Abolishing Snf1-Dependent Regulation of Acc1" American Society far Microbiology, May 2014, vol. 5 (3), pp. e01130-14.

Shiba et al., "Engineering of the Pyruvate Dehydrogenase Bypass in *Saccharomyces cerevisiae* for High-Level Production of Isoprenoids," Metabolic Engineering, Mar. 2007, vol. 9 (2), pp. 160-168.

Skiba et al., "Domain Organization and Active Site Architecture of a Polyketide Synthase C-Methyltransferase," ACS Chemical Biology, Dec. 2016, vol. 11 (12), pp. 3319-3327.

Stout et al., "The Hexanoyl-CoA Precursor for Cannabinoid Biosynthesis is Framed by an Acyl-activating Enzyme in Cannabis Sativa Trichomes," The Plant Journal, Aug. 2012, vol. 71 (3), pp. 353-365.

Sugiyama et al., "Metabolic Engineering for the Prodtrclion of Prenylated Polyphenols in Transgenic Legume Plants Using Bacterial and Plant Prenyltransferases," Metabolic Engineering, Nov. 2011, vol. 13(6), pp. 629-637.

Taura et al., "Characterization of Olivetol Synthase, A Polyketide Synthase Putatively Involved in Cannabinoid Biosynthetic Pathway," FEBS Letters, Jun. 2009, vol. 583 (12), pp. 2061-2066, ISSN 0014-5793.

Taura et al., "First Direct Evidence for the Mechanism of. DELTA.1 -tetrahydrocannabinolic Acid Biosynthesis," Journal of the American Chemical Society, Sep. 1995, vol. 117, pp. 9766-9767.

Tello et al., "The ABBA Family of Aromatic Prenyltransferases: Broadening Natural Product Diversity," Cellular and Molecular Life Sciences, May 2003, vol. 65 (10), pp. 1459-1463.

Viegas et al., "Inhibition of Yeast Growth by Octanoic and Decanoic Acids Produced during Ethanolic Fermentation," Applied and Environmental Microbiology, Jan. 1989, vol. 55 (1), pp. 21-28.

Zirpel at al., "Engineering Yeasts as Platfom Organisms for Cannabinoid Biosynthesis," Journal of Biotechnology, Oct. 2017, vol. 259, pp. 204-212, ISSN 0168-1656.

Zirpel et al., "Production of DELTA 9-Tetrahydrocannabinolic Acid From Cannabigerolic Acid by Whole Cells of Pichia (*Komagataella*) Pastoris Expressing DELTA 9-Tetrahydrocannabinolic Acid Synthase From *Cannabis sativa* L," Biotechnology letters, Sep. 2015, vol. 37 (9), pp. 1869-1875.

\* cited by examiner

METHOD AND CELL LINE FOR PRODUCTION OF PHYTOCANNABINOIDS AND PHYTOCANNABINOID ANALOGUES IN YEAST

CROSS REFERENCE TO RELATED APPLICATIONS

This application claims the benefit of priority of U.S. Provisional Patent Application No. 62/460,526, entitled METHOD AND CELL LINE FOR PRODUCTION OF PHYTOCANNABINOIDS IN YEAST, filed Feb. 17, 2017, which is hereby incorporated by reference in its entirety.

FIELD

The present disclosure relates generally to production of phytocannabinoids and analogues of phytocannabinoids in yeast.

BACKGROUND

Phytocannabinoids are naturally produced in *Cannabis sativa*, other plants, and some fungi. Over 105 phytocannabinoids are known to be biosynthesized in *C. sativa*, or result from thermal or other decomposition from phytocannabinoids biosynthesized in *C. sativa*. While the *C. sativa* plant is also a valuable source of grain, fiber, and other material, growing *C. sativa* for phytocannabinoid production, particularly indoors, is costly in terms of energy and labour. Subsequent extraction, purification, and fractionation of phytocannabinoids from the *C. sativa* plant is also labour and energy intensive.

Phytocannabinoids are pharmacologically active molecules that contribute to the medical and psychotropic effects of *C. sativa*. Biosynthesis of phytocannabinoids in the *C. sativa* plant scales similarly to other agricultural projects. As with other agricultural projects, large scale production of phytocannabinoids by growing *C. sativa* requires a variety of inputs (e.g. nutrients, light, pest control, $CO_2$, etc.). The inputs required for cultivating *C. sativa* must be provided. In addition, cultivation of *C. sativa*, where allowed, is currently subject to heavy regulation, taxes, and rigorous quality control where products prepared from the plant are for commercial use, further increasing costs. Phytocannabinoid analogues are pharmacologically active molecules that are structurally similar to phytocannabinoids. Phytocannabinoid analogues are often synthesized chemically, which can be labour intensive and costly. As a result, it may be economical to produce the phytocannabinoids and phytocannabinoid analogues in a robust and scalable, fermentable organism. *Saccharomyces cerevisiae* is an example of a fermentable organism that has been used to produce industrial scales of similar molecules.

The time, energy, and labour involved in growing *C. sativa* for production of naturally-occurring phytocannabinoids provides a motivation to produce transgenic cell lines for production of phytocannabinoids in yeast. One example of such efforts is provided in United States Patent Application Publication no. US 2016/0010126 to Poulos and Farnia.

SUMMARY

It is an object of the present disclosure to obviate or mitigate at least one disadvantage of previous approaches to producing phytocannabinoids in yeast, and of previous approaches to producing phytocannabinoid analogues.

Many of the 105 phytocannabinoids found in *Cannabis sativa* may be synthesized in yeast, and it may be desirable to improve yeast-based production. Similarly, an approach that allows for production of phytocannabinoid analogues without the need for labour-intensive synthesis may be desirable.

The methods and cells lines provided herein may apply and include transgenic *Saccharomyces cerevisiae* that have been transformed with a gene coding for the NphB prenyltransferase enzyme from *Streptomyces coelicolor* ("CL190") ("AltPT"). AltPT is an $\alpha\beta\beta\alpha$ ("ABBA") type prenyltransferase enzyme. AltPT catalyzes synthesis of cannabigerolic acid ("CBGa") from olivetolic acid and geranyl pyrophosphate ("GPP"). AltPT also catalyzes synthesis of cannabigerol ("CBG") from olivetol and GPP. In *C. sativa*, a prenyltransferase enzyme catalyzes synthesis of CBGa from olivetolic acid and GPP. The *C. sativa* prenyltransferase is membrane-bound, complicating expression in *S. cerevisiae*. In contrast, AltPT is cytosolic and expresses at greater levels than the *C. sativa* prenyltransferase in *S. cerevisiae*. AltPT may provide advantages over membrane-bound *C. sativa* prenyltransferase when expressed in *S. cerevisiae* to catalyze synthesis of CBGa from olivetolic acid and GPP or CBG from olivetol and GPP. The *S. cerevisiae* may have one or more mutations in Erg20, Maf1 or UPC2, or other genes for enzymes or other proteins that support metabolic pathways that deplete GPP, the one or more mutations being for increasing available GPP. Alternatively, other species of yeast, including *Yarrowia lipolytica, Kluyveromyces marxianus, Kluyveromyces lactis, Rhodosporidium toruloides, Cryptococcus curvatus, Trichosporon pullulan* and *Lipomyces lipoferetc*, may be applied.

In some methods and cell lines provided herein, the transgenic *S. cerevisiae* includes a gene for *C. sativa* polyketide synthase (also called olivetolic acid synthase or "OAS"). OAS catalyzes synthesis of olivetol from malonyl-CoA and hexanoyl-CoA. The reaction has a 2:1:1 stoichiometric ratio of malonyl-CoA to hexanoyl-CoA to olivetolic acid. In *C. sativa*, the olivetol is carboxylated in the presence of olivetolic acid cyclase ("OAC") or another polyketide cyclase into olivetolic acid, which feeds into the CBGa synthesis metabolic pathway described above in relation to AltPT and other cytosolic prenyltransferase enzymes, catalyzed by in *C. sativa* by a membrane-bound prenyltransferase. The OAC enzyme from *C. sativa* may be excluded from the transgenic *S. cerevisiae* to drive synthesis of CBG rather than CBGa by AltPT.

In some methods and cell lines provided herein, the transgenic *S. cerevisiae* includes a gene for *Dictyostelium discoideum* polyketide synthase ("DiPKS"). DiPKS is a fusion protein consisting of both a type I fatty acid synthase ("FAS") and a polyketide synthase and is referred to as a hybrid "FAS-PKS" protein. DiPKS catalyzes synthesis of methyl-olivetol from malonyl-CoA. The reaction has a 6:1 stoichiometric ratio of malonyl-CoA to methyl-olivetol. AltPT catalyzes synthesis of methyl cannabigerol ("meCBG") from methyl-olivetol, similarly to synthesis of CBG from olivetol described above. Hexanoic acid is toxic to *S. cerevisiae*. When applying OAS, hexanoyl-CoA is a necessary precursor for synthesis of olivetol. When using DiPKS to produce methyl-olivetol rather than OAS to produce olivetol or olivetolic acid (if the, hexanoic acid need not be added to the growth media. The absence of hexanoic acid in growth media may result in increased growth of the *S. cerevisiae* cultures and greater yield of meCBG compared with yields of CBG when using OAS.

For some applications, meCBG and methylated downstream phytocannabinoid analogues that can be synthesized from meCBG (similarly to downstream phytocannabinoids being synthesized from CBGa in *C. sativa*) may be valuable. In other cases, phytocannabinoids structurally identical to the decarboxylated forms of naturally-occurring phytocannabinoids may be more desirable. For production of phytocannabinoids that are structurally identical to the decarboxylated forms of naturally-occurring phytocannabinoids, DiPKS may be modified relative to wild type DiPKS to reduce methylation of olivetol, resulting in synthesis of CBG rather than meCBG. The *S. cerevisiae* may include a co-factor loading enzyme to increase the activity of DiPKS.

Synthesis of olivetol and methyl-olivetol may be facilitated by increased levels of malonyl-CoA in the cytosol. The *S. cerevisiae* may have overexpression of native acetaldehyde dehydrogenase and expression of a mutant acetyl-CoA synthase or other gene, the mutations resulting in lowered mitochondrial acetaldehyde catabolism. Lowering mitochondrial acetaldehyde catabolism by diverting the acetaldehyde into acetyl-CoA production increases malonyl-CoA available for synthesizing olivetol. Acc1 is the native yeast malonyl CoA synthase. The *S. cerevisiae* may have overexpression of Acc1 or modification of Acc1 for increased activity and increased available malonyl-CoA. The *S. cerevisiae* may include modified expression of Maf1 or other regulators of tRNA biosynthesis. Overexpressing native Maf1 has been shown to reduce loss of isopentyl pyrophosphate ("IPP") to tRNA biosynthesis and thereby improve monoterpene yields in yeast. IPP is an intermediate in the mevalonate pathway. Upc2 is an activator for sterol biosynthesis in *S. cerevisiae*, and a Glu888Asp mutation of Upc2 may increase monoterpene production in yeast.

In a first aspect, herein provided is a method and cell line for producing phytocannabinoids and phytocannabinoid analogues in yeast. The method applies, and the cell line includes, a yeast cell transformed with a polyketide synthase CDS and a cytosolic prenyltransferase CDS. The polyketide synthase enzyme catalyzes synthesis of olivetol or methyl-olivetol, and may include *Cannabis sativa* olivetolic acid synthase or *Dictyostelium discoideum* polyketide synthase ("DiPKS"). The yeast cell may be modified to include a phosphopantethienyl transferase for increased activity of DiPKS. The yeast cell may be modified to mitigate mitochondrial acetaldehyde catabolism for increasing malonyl-CoA available for synthesizing olivetol or methyl-olivetol. The prenyltransferase enzyme catalyzes synthesis of cannabigerol or a cannabigerol analogue, and may include an αββα cytosolic prenyltransferase enzyme from *Streptomyces* sp CL190. The yeast cell may be modified to mitigate depletion of geranyl pyrophosphate for increasing available geranyl pyrophosphate for prenylation.

In a further aspect, herein provided is a method of producing phytocannabinoids or phytocannabinoid analogues, the method comprising: providing a yeast cell comprising a first polynucleotide coding for a polyketide synthase enzyme and a second polynucleotide coding for a cytosolic prenyltransferase enzyme, and propagating the yeast cell for providing a yeast cell culture. The polyketide synthase enzyme is for producing at least one precursor chemical from malonyl-CoA, the precursor chemical having structure I:

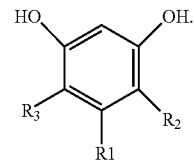

On structure I, R1 is an alkyl group with a chain length of 1, 2, 3, 4, or 5 carbons, R2 is H, carboxyl, or methyl, and R3 is H, carboxyl, or methyl. The cytosolic prenyltransferase enzyme is for prenylating the at least one precursor chemical, providing at least one species of phytocannabinoid or phytocannabinoid analogue.

In some embodiments, the yeast cell comprises a hexanoyl synthase polynucleotide coding for a hexanoyl synthase enzyme; the polyketide synthase enzyme comprises an OAS enzyme from *C. sativa*; and propagating the yeast cell comprises propagating the yeast cell in a nutrient preparation comprising hexanoic acid. In some embodiments, the yeast cell does not include a *C. sativa* polyketide cyclase enzyme and the at least one species of phytocannabinoid or phytocannabinoid analogue comprises a decarboxylated phytocannabinoid or phytocannabinoid analogue. In some embodiments, the first polynucleotide comprises a coding sequence for the OAS enzyme from *C. sativa* with a primary structure having between 80% and 100% amino acid residue sequence homology with a protein coded for by a reading frame defined by bases 3841 to 4995 of SEQ ID NO: 45. In some embodiments the first polynucleotide has between 80% and 100% base sequence homology with bases 3841 to 4995 of SEQ ID NO: 45. In some embodiments, the first polynucleotide has between 80% and 100% base sequence homology with bases 3841 to 4995 of SEQ ID NO: 45.

In some embodiments, R1 is an alkyl group with a chain length of 3 carbons, R2 is H, and R3 is H.

In some embodiments, R1 is an alkyl group with a chain length of 3 carbons, R2 is carboxyl, and R3 is H.

In some embodiments, R1 is an alkyl group with a chain length of 3 carbons, R2 is methyl, and R3 is H.

In some embodiments, R1 is an alkyl group with a chain length of 3 carbons, R2 is carboxyl, and R3 is methyl.

In some embodiments, the polyketide synthase enzyme comprises a DiPKS polyketide synthase enzyme from *D. discoideum*. In some embodiments, the first polynucleotide comprises a coding sequence for the DiPKS polyketide synthase enzyme with a primary structure having between 80% and 100% amino acid residue sequence homology with a protein coded for by a reading frame defined by bases 535 to 9978 of SEQ ID NO: 46. In some embodiments, the first polynucleotide has between 80% and 100% base sequence homology with bases 535 to 9978 of SEQ ID NO: 46. In some embodiments, the at least one precursor chemical comprises a methyl group at R2 and the at least one species of phytocannabinoid or phytocannabinoid analogue comprises a methylated phytocannabinoid analogue. In some embodiments, the DiPKS polyketide synthase enzyme comprises a mutation affecting an active site of a C-Met domain for mitigating methylation of the at least one precursor chemical, resulting in the at least one precursor chemical comprising a first precursor chemical wherein R2 is methyl and R3 is H, and a second precursor chemical wherein R2 is H and R3 is H; and the at least one species of phytocannabinoid or phytocannabinoid analogue comprises a methylated phytocannabinoid analogue and an unmethylated phytocannabinoid. In some embodiments, the DiPKS polyketide synthase comprises a DiPKSG1516D; G1518A polyketide synthase enzyme. In some embodiments, the first polynucleotide comprises a coding sequence for the DiPKSG1516D; G1518A polyketide synthase enzyme with a primary structure having between 80% and 100% amino acid residue sequence homology with a protein coded for by a reading frame defined by bases 523 to 9966 of SEQ ID NO: 37. In some embodiments, the first polynucleotide has between 80% and 100% base sequence homology with bases 523 to 9966 of SEQ ID NO: 37. In some embodiments, the DiPKS polyketide synthase comprises a DiPKSG1516R polyketide synthase enzyme. In some embodiments, the first polynucleotide comprises a coding sequence for the DiPKSG1516R polyketide synthase enzyme with a primary structure having between 80% and 100% amino acid residue sequence homology with a protein coded for by a reading frame defined by bases 523 to 9966 of SEQ ID NO: 38. In some embodiments, the first polynucleotide has between 80% and 100% base sequence homology with bases 523 to 9966 of SEQ ID NO: 38. In some embodiments, the DiPKS polyketide synthase enzyme comprises a mutation reducing activity at an active site of a C-Met domain of the DiPKS polyketide synthase enzyme, for preventing methylation of the at least one precursor chemical, resulting in the at least one precursor chemical having a hydrogen R2 group and a hydrogen R3 group; and the at least one species of phytocannabinoid or phytocannabinoid analogue comprises a decarboxylated phytocannabinoid or phytocannabinoid analogue. In some embodiments, the yeast cell comprises a phosphopantetheinyl transferase polynucleotide coding for a phosphopantetheinyl transferase enzyme for increasing the activity of DiPKS. In some embodiments, the phosphopantetheinyl transferase comprises NpgA phosphopantetheinyl transferase enzyme from *A. nidulans*. In some embodiments, the phosphopantetheinyl transferase polynucleotide comprises a coding sequence for the NpgA phosphopantetheinyl transferase enzyme from *A. nidulans* with a primary structure having between 80% and 100% amino acid residue sequence homology with a protein coded for by a reading frame defined by bases 1170 to 2201 of SEQ ID NO: 10. In some embodiments, the phosphopantetheinyl transferase polynucleotide has between 80% and 100% base sequence homology with bases 1170 to 2201 of SEQ ID NO: 10.

In some embodiments, the polyketide synthase enzyme comprises an active site for synthesizing the at least one precursor chemical from malonyl-CoA without a longer chain ketyl-CoA. In some embodiments, the at least one precursor chemical comprises a pentyl group at R1 and the at least one species of phytocannabinoid or phytocannabinoid analogue comprises a pentyl-phytocannabinoid or methylated pentyl-phytocannabinoid analogue. In some embodiments, the at least one precursor chemical comprises at least one of olivetol olivetolic acid, methyl-olivetol, or methyl-olivetolic acid, and the at least one species of phytocannabinoid or phytocannabinoid analogue comprises at least one of CBG, CBGa, meCBG, or meCBGa.

In some embodiments, the cytosolic prenyltransferase enzyme comprises an NphB prenyltransferase enzyme from *Streptomyces* sp CL190. In some embodiments, the second polynucleotide comprises a coding sequence for NphB prenyltransferase enzyme from *Streptomyces* sp CL190 with a primary structure having between 80% and 100% amino acid residue sequence homology with a protein coded for by a reading frame defined by bases 987 to 1913 of SEQ ID NO: 44. In some embodiments, the second polynucleotide has between 80% and 100% base sequence homology with bases 987 to 1913 of SEQ ID NO: 44.

In some embodiments, R1 is an alkyl group with a chain length of 5 carbons, R2 is H, and R3 is H.

In some embodiments, R1 is an alkyl group with a chain length of 5 carbons, R2 is carboxyl, and R3 is H.

In some embodiments, R1 is an alkyl group with a chain length of 5 carbons, R2 is methyl, and R3 is H.

In some embodiments, R1 is an alkyl group with a chain length of 5 carbons, R2 is carboxyl, and R3 is methyl.

In some embodiments, the yeast cell comprises a genetic modification to increase available geranylpyrophosphate. In some embodiments, the genetic modification comprises an inactivation of the Erg20 enzyme. In some embodiments, the yeast cell comprises a Erg20 polynucleotide including a coding sequence for Erg20K197E with a primary structure having between 80% and 100% amino acid residue sequence homology with a protein coded for by a reading frame defined by SEQ ID NO: 3. In some embodiments, the Erg20 polynucleotide has between 80% and 100% base sequence homology with SEQ ID NO: 3.

In some embodiments, the yeast cell comprises a genetic modification to increase available malonyl-CoA. In some embodiments, the genetic modification comprises increased expression of Maf1. In some embodiments, the yeast cell comprises a Maf1 polynucleotide including a coding sequence for Maf1 with a primary structure having between 80% and 100% amino acid residue sequence homology with a protein coded for by a reading frame defined by bases 936 to 2123 of SEQ ID NO: 8. In some embodiments, the Maf1 polynucleotide further comprises a promoter sequence, a terminator sequence and integration sequences, and has between 80% and 100% base sequence homology with SEQ ID NO: 8. In some embodiments, the genetic modification comprises a modification for increasing cytosolic expression of an aldehyde dehydrogenase and an acetyl-CoA synthase. In some embodiments, the yeast cell comprises an Acs polynucleotide including a coding sequence for AcsL641P from *S. enterica* with a primary structure having between 80% and 100% amino acid residue sequence homology with a protein coded for by a reading frame defined by bases 3938 to 5893 of SEQ ID NO: 4, and a coding sequence for Ald6 from *S. cerevisiae* with a primary structure having between 80% and 100% amino acid residue sequence homology with a protein coded for by a reading frame defined by bases 1494 to 2999 of SEQ ID NO 4. In some embodiments, the Acs polynucleotide further comprises a promoter sequence, a terminator sequence and integration sequences, and has between 80% and 100% base sequence homology with bases 51 to 7114 SEQ ID NO: 4. In some embodiments, the genetic modification comprises a modification for increasing malonyl-CoA synthase activity. In some embodiments, the yeast cell comprises an Acc1 polynucleotide including a coding sequence for Acc1S659A; S1157A from *S. cerevisiae*. In some embodiments, the Acc1 polynucleotide includes a coding sequence for the Acc1S659A; S1157A enzyme, with a portion thereof having a primary structure with between 80% and 100% amino acid residue sequence homology with a protein portion coded for by a reading frame defined by bases 9 to 1716 of SEQ ID NO: 7. Acc1S659A; S1157A. In some embodiments, the Acc1 polynucleotide further comprises a promoter sequence, a terminator sequence and integration sequences, and has between 80% and 100% base sequence homology with SEQ ID NO: 7. In some embodiments, the yeast cell comprises an Acc1 polynucleotide including the coding sequence for Acc1 from *S. cerevisiae* under regulation of a constitutive promoter. In some embodiments, the constitutive promoter comprises a PGK1 promoter from *S. cerevisiae*. In some embodiments, the PGK1 promoter has between 80% and 100% nucleotide homology with bases 7 to 750 of SEQ ID NO: 6. In some embodiments, the genetic modification comprises increased expression of an activator for sterol biosynthesis. In some embodiments, the yeast cell comprises a Upc2 polynucleotide including a coding sequence for Upc2E888D from *S. cerevisiae* with a primary structure having between 80% and 100% amino acid residue sequence homology with a protein coded for by a reading frame defined by bases 975 to 3701 of SEQ ID NO: 9. In some embodiments, the Upc2 polynucleotide further comprises a promoter sequence, a terminator sequence and integration sequences, and has between 80% and 100% base sequence homology with SEQ ID NO: 9.

In some embodiments, the second polynucleotide comprises a coding sequence for a cytosolic prenyltransferase enzyme with a primary structure having between 80% and 100% amino acid residue sequence homology with any one of SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 or SEQ ID NO: 36.

In some embodiments, the method includes extracting the at least one species of phytocannabinoid or phytocannabinoid analogue from the yeast cell culture.

In a further aspect, herein provided is yeast cell for producing phytocannabinoids or phytocannabinoid analogues, the yeast cell comprising: a first polynucleotide coding for a polyketide synthase enzyme; and a second polynucleotide coding for a cytosolic prenyltransferase enzyme.

In some embodiments, features of one or more of the yeast cell, the first polynucleotide, or the second polynucleotide described herein are included in the yeast cell.

In a further aspect, herein provided is a method of transforming a yeast cell for production of phytocannabinoids or phytocannabinoid analogues. The method comprises introducing a first polynucleotide coding for a polyketide synthase enzyme into the yeast cell line; and introducing a second polynucleotide coding for a cytosolic prenyltransferase enzyme into the yeast In some embodiments, features of one or more of the yeast cell, the first polynucleotide, or the second polynucleotide described herein are applied in transforming the yeast cell.

In a further aspect, herein provided is a phytocannabinoid analogue having the following structure II:

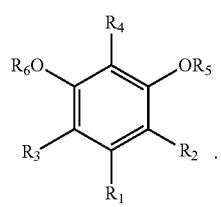

II

On structure II, R1 is an alkyl group with a chain length of 1, 2, 3, 4, or 5 carbons; R2 is a methyl group; R3 is H, a carboxyl group, or a methyl group; R4 is a geranyl group; R5 is H or the geranyl group at R4; and R6 is H or the geranyl group at R4.

In some embodiments, R1 has a chain length of 5 carbons and R3 is H. In some embodiments, the geranyl group comprises a cyclized geranyl group. In some embodiments, R5 is the cyclized geranyl group. In some embodiments, R5 and R6 are each the cyclized geranyl group. In some embodiments, R6 is the cyclized geranyl group. In some embodiments, the phytocannabinoid analogue is produced by biosynthesis in yeast.

In a further aspect, herein provided is a phytocannabinoid analogue having the following structure III:

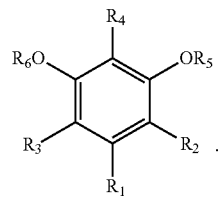

III

On structure III, R1 is a pentyl group; R2 is a methyl group; R3 is H; R4 is a geranyl group; R5 is H or the geranyl group at R4; and R6 is H or the geranyl group at R4.

In some embodiments, the geranyl group comprises a cyclized geranyl group. In some embodiments, R5 is the cyclized geranyl group. In some embodiments, R5 and R6 are each the cyclized geranyl group. In some embodiments, R6 is the cyclized geranyl group.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides methods and yeast cell lines for producing phytocannabinoids that are naturally biosynthesized in the *Cannabis sativa* plant and methylated phytocannabinoid analogues biosynthesized from methyl-olivetol. The phytocannabinoids and phytocannabinoid analogues are produced in transgenic yeast. The methods and cell lines provided herein include application of genes for enzymes absent from the *C. sativa* plant. Application of genes other than the complete set of genes in the *C. sativa* plant that code for enzymes in the biosynthetic pathway resulting in phytocannabinoids may provide one or more benefits including biosynthesis of decarboxylated phytocannabinoids, biosynthesis of methylated phytocannabinoid analogues, and biosynthesis production of phytocannabinoids without an input of hexanoic acid, which is toxic to *Saccharomyces cerevisiae* and other species of yeast.

The qualifier "decarboxylated" as used herein references a form of a phytocannabinoid or phytocannabinoid analogue lacking an acid group at, e.g. positions 2 or 4 of Δ9-tetrahydrocannabinol ("THC"), or an equivalent location in other phytocannabinoids or analogues corresponding to position 4 of olivetolic acid, which is the precursor to biosynthesis of cannabigerolic acid ("CBGa") in *C. sativa*. Acid forms of phytocannabinoids are biosynthesized from olivetolic acid in *C. sativa*. When the acid forms of phytocannabinoids are heated, the bond between the aromatic ring of the phytocannabinoid and the carboxyl group is broken. Decarboxylation results from heating carboxylated phytocannabinoids produced in *C. sativa*, which occurs rapidly during combustion or heating to temperatures generally above about 110° C. For simplicity, as used herein, "decarboxylated" refers to phytocannabinoids lacking the acid groups whether or not the phytocannabinoid included an acid group that was lost during true decarboxylation, or was biosynthesized without the carboxyl group.

Figure 1:
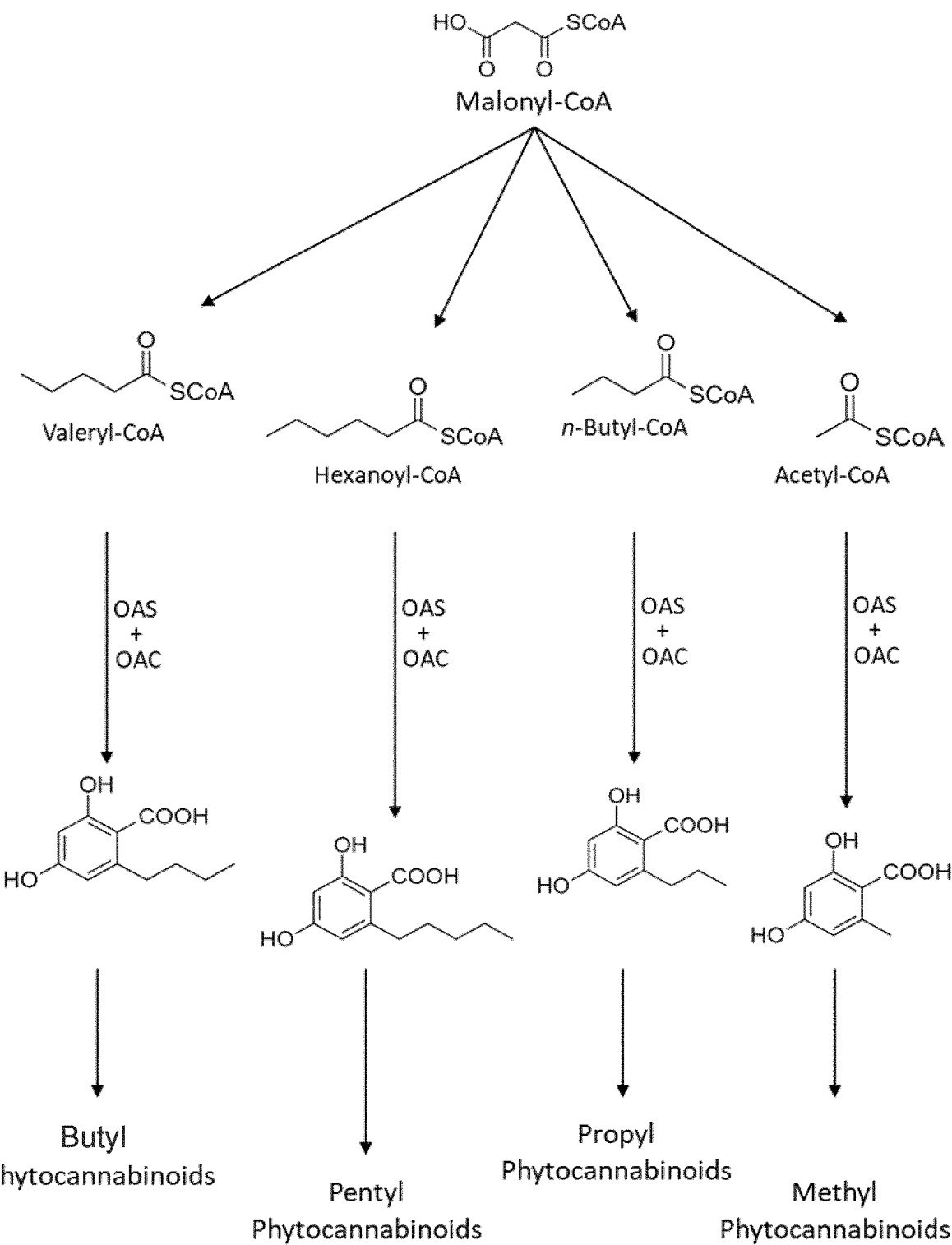
FIG. 1 is a schematic of biosynthesis of olivetolic acid and related compounds with different alkyl group chain lengths in *C. sativa*.

FIG. 1 shows biosynthesis of olivetolic acid from polyketide condensation products of malonyl-CoA and hexanoyl-CoA, as occurs in *C. sativa*. Olivetolic acid is a metabolic precursor to CBGa. CBGa is a precursor to a large number of downstream phytocannabinoids as described in further detail below. In most varieties of *C. sativa*, the majority of phytocannabinoids are pentyl-cannabinoids, which are biosynthesized from olivetolic acid, which is in turn synthesized from malonyl-CoA and hexanoyl-CoA at a 2:1 stoichiometric ratio. Some propyl-cannabinoids are observed, and are often identified with a "v" suffix in the widely-used three letter abbreviations (e.g. tetrahydrocannabivarin is commonly referred to as "THCv", cannabidivarin is commonly referred to as "CBDv", etc.). FIG. 1 also shows biosynthesis of divarinolic acid from condensation of malonyl-CoA with n-butyl-CoA, which would provide downstream propyl-phytocannabinoids.

FIG. 1 also shows biosynthesis of orsellinic acid from condensation of malonyl-CoA with acetyl-CoA, which would provide downstream methyl-phytocannabinoids. The term "methyl-phytocannabinoids" in this context means their alkyl side chain is a methyl group, where most phytocannabinoids have a pentyl group on the alkyl side chain and varinnic phytocannabinoids have a propyl group on the alkyl side chain. The context in which meCBG and other methylated phytocannabinoid analogues are called "methylated" is different from and parallel to use of "methyl" as a prefix in "methyl-phytocannabinoids" and in FIG. 1. Similarly, since olivetol has a side chain of defined length (otherwise it would be one of the other three polyketides shown in FIG. 1 and not "olivetol"), methyl-olivetol is a reference to methylation on the ring and not to a shorter side chain FIG. 1 also shows biosynthesis of 2,4-diol-6-propylbenzenoic acid from condensation of malonyl-CoA with valeryl-CoA, which would provide downstream butyl-phytocannabinoids.

Figure 2:
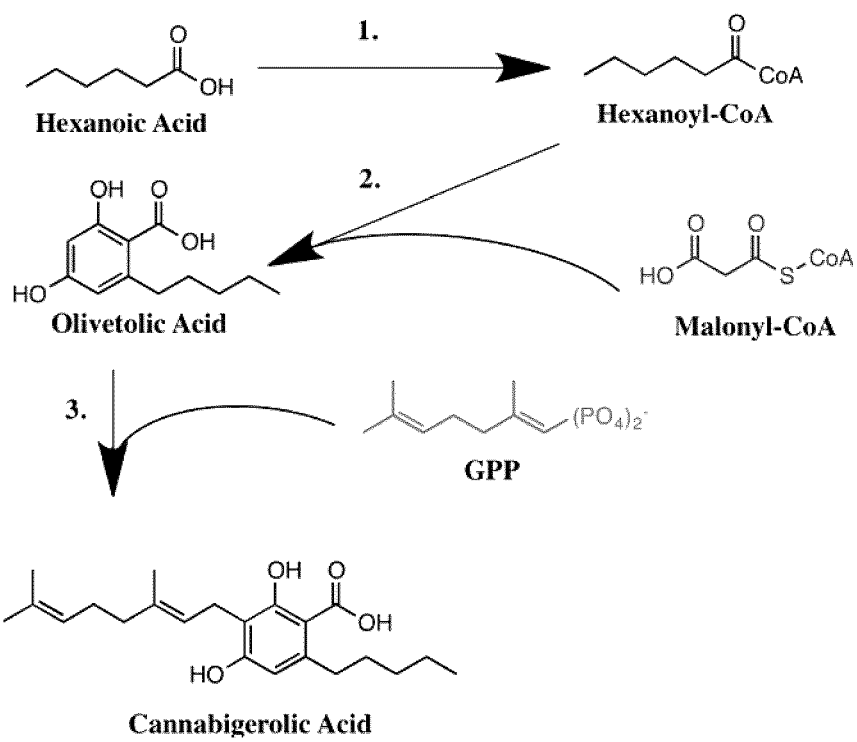
FIG. 2 is a schematic of biosynthesis of CBGa from hexanoic acid, malonyl-CoA, and geranyl pyrophosphate in *C. sativa*.

FIG. 2 shows biosynthesis of CBGa from hexanoic acid, malonyl-CoA, and geranyl pyrophosphate ("GPP") in *C. sativa*, including the olivetolic acid biosynthesis step shown in FIG. 1. Hexanoic acid is activated with coenzyme A by hexanoyl-CoA synthase ("Hex1; Reaction 1 in FIG. 2). OAS (also called olivetolic acid synthase despite synthesizing olivetol and not olivetolic acid) and OAC together catalyze production of olivetolic acid from hexanoyl CoA and malonyl-CoA (Reaction 2 in FIG. 2). Prenyltransferase combines olivetolic acid with GPP, providing CBGa Step 3 in FIG. 2).

Figure 3:
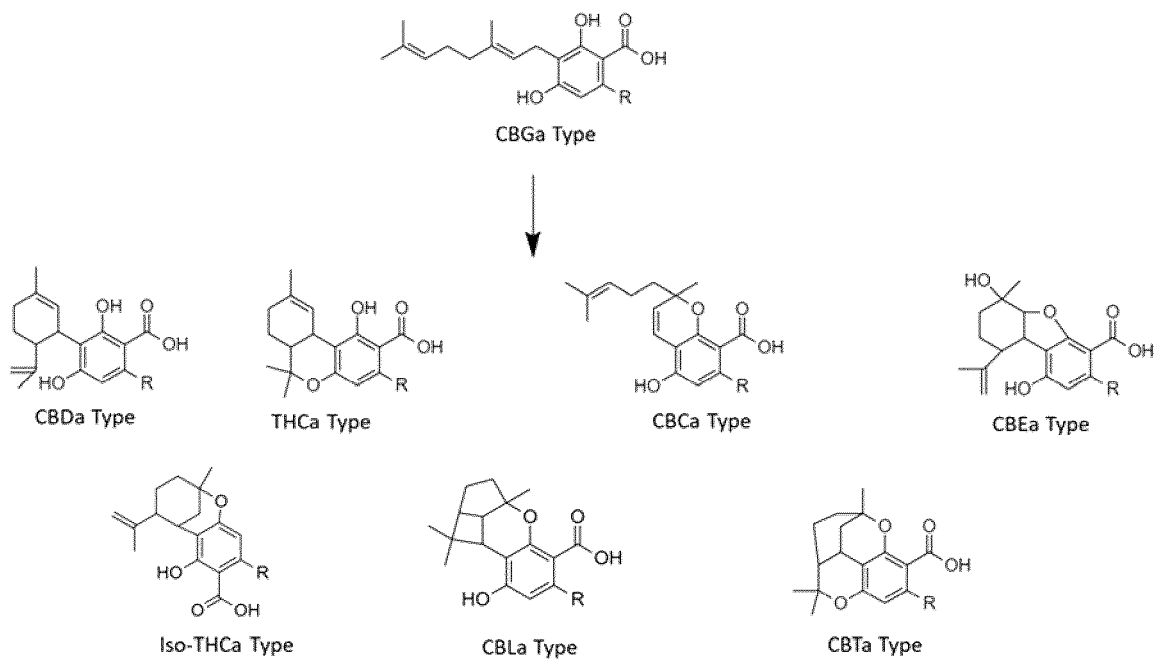
FIG. 3 is a schematic of biosynthesis of downstream phytocannabinoids in the acid form from CBGa in *C. sativa*.

FIG. 3 shows biosynthesis of downstream acid forms of phytocannabinoids in *C. sativa* from CBGa. CBGa is oxidatively cyclized into Δ9-tetrahydrocannabinolic acid ("THCa") by THCa synthase. CBGa is oxidatively cyclized into cannabidiolic acid ("CBDa") by CBDa synthase. Other phytocannabinoids are also synthesized in *C. sativa*, such as cannabichromenic acid ("CBCa"), cannabielsoinic acid ("CBEa"), iso-tetrahydrocannabinolic acid ("iso-THCa"), cannabicyclolic acid ("CBLa"), or cannabicitrannic acid ("CBTa") by other synthase enzymes, or by changing conditions in the plant cells in a way that affects the enzymatic activity in terms of the resulting phytocannabinoid structure. The acid forms of each of these general phytocannabinoid types are shown in FIG. 3 with a general "R" group to show the alkyl side chain, which would be a 5-carbon chain where olivetolic acid is synthesized from hexanoyl-CoA and malonyl-CoA. In some cases, the carboxyl group is alternatively found on a ring position opposite the R group from the position shown in FIG. 3 (e.g. positions 4 of THC rather than position 2 as shown in FIG. 3, etc.). The decarboxylated forms of the phytocannabinoids shown in FIG. 3 are, respectively, THC, cannabidiol ("CBD"), cannabichromene ("CBC"), cannabielsoin ("CBE"), iso-tetrahydrocannabinol ("iso-THC"), cannabicyclol ("CBL"), or cannabicitran ("CBT").

United States Publication No. 2016/0010126 to Poulos et al. describes expression of the five native *C. sativa* genes in *S. cerevisiae* and in *K. marxianus*. Expression of genes from the native *C. sativa* pathway in yeast for phytocannabinoid production may carry drawbacks. *C. sativa* OAS uses hexanoyl-CoA as a polyketide substrate. Hexanoic acid is toxic to *S. cerevisiae* and some other strains of yeast. In addition, synthesis of CBGa from olivetolic acid requires the membrane-bound *C. sativa* prenyltransferase enzyme, which may express poorly in fungi.

Methods and yeast cells as provided herein for production of phytocannabinoids and phytocannabinoid analogues may apply and include *S. cerevisiae* transformed with the gene for prenyltransferase NphB from *Streptomyces* sp CL 190. The *Streptomyces* sp CL 190 NphB prenyltransferase provides an alternative to the *C. sativa* prenyl transferase enzyme and is referred to below as "AltPT". AltPT is an αββα ("ABBA") type prenyltransferase enzyme. AltPT is highly promiscuous, accepting most polyketides as a substrate for prenylation. AltPT is specific for GPP as a terpenoid donor. AltPT is a cytosolic enzyme expressed in *Streptomyces* sp CL 190, a gram positive bacteria, in contrast with the membrane-bound prenyltransferase expressed in *C. sativa*, a plant. The bacterial cytosolic enzyme expresses at greater levels in yeast than the plant membrane bound enzyme. AltPT will prenylate olivetolic acid to CBGa, similarly to the reaction catalyzed by the membrane-bound prenyltransferase in *C. sativa*. AltPT will also prenylate olivetol to cannabigerol ("CBG"), or methyl-olivetol to methyl cannabigerol ("meCBG"). A synthetic sequence for AltPT that is codon optimized for yeast is included here at SEQ ID NO: 1. A complete coding DNA sequence ("CDS") for AltPT is available at the NCBI GenBank online database under accession number NCBI-AB187169.

Figure 4:
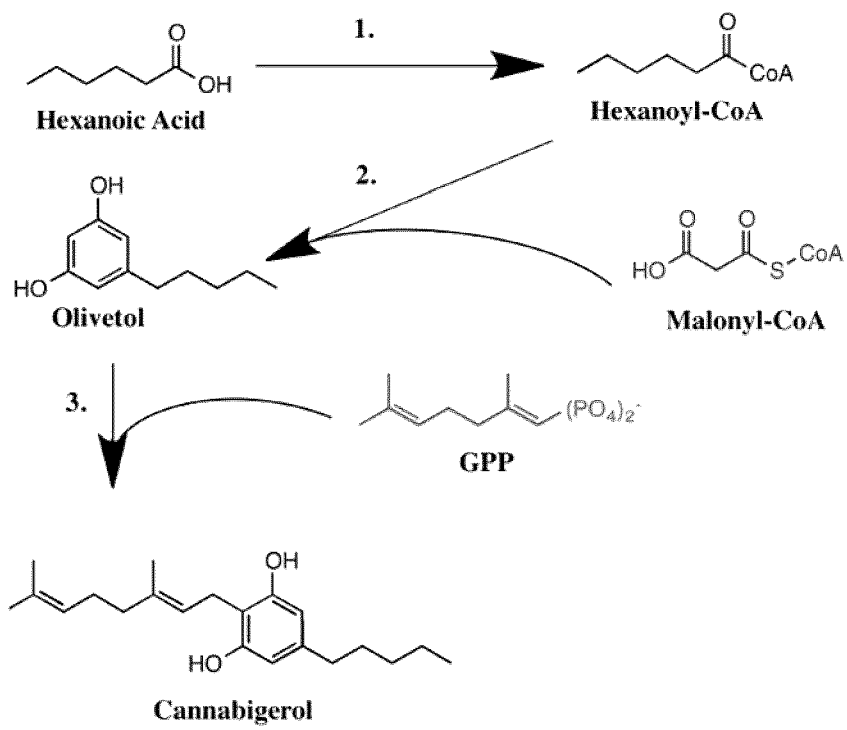
FIG. 4 is a schematic of biosynthesis of CBG in a transformed yeast cell by OAS and AltPT.

FIG. 4 shows a biosynthetic pathway in transgenic yeast for production of CBG from hexanoic acid, malonyl-CoA, and GPP. A strain of yeast as provided herein for producing CBG as shown in FIG. 4 may include genes coding for *Streptomyces* sp CL190 AltPT, *C. sativa* Hex1, and *C. sativa* OAS. Examples of such a yeast strain are provided as "HB37" and as "HB88", each of which are described in Table 7.

Figure 5:
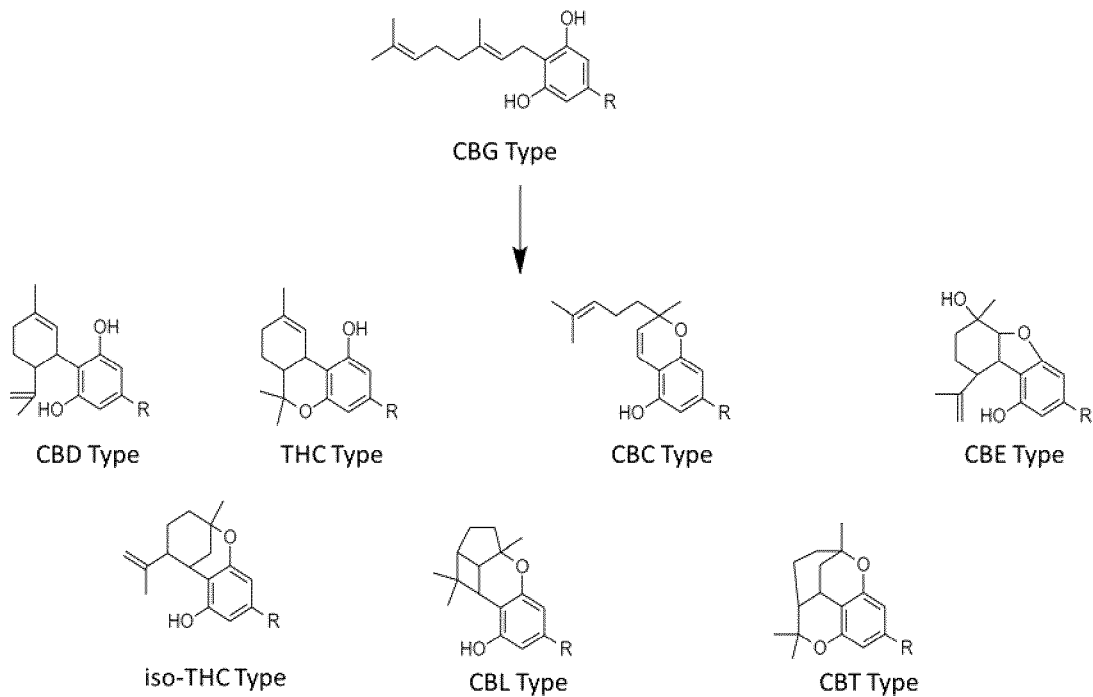
FIG. 5 is a schematic of biosynthesis of downstream phytocannabinoids in a transformed yeast cell from CBG.

FIG. 5 shows biosynthesis of downstream phytocannabinoids from CBG. CBG is oxidatively cyclized into THC, CBD, CBC, CBE, iso-THC, CBL, or CBT. The decarboxylated forms of each of these general phytocannabinoid types are shown in FIG. 5 with a general "R" group to show the alkyl side chain, which would be a 5-carbon chain in phytocannabinoids that are biosynthesized from olivetol.

FIG. 4 shows production of hexanoyl-CoA from hexanoic acid by Hex1. Hexanoic acid is activated with coenzyme A by Hex1 (Reaction 1 in FIG. 4). OAS catalyzes production of olivetol from hexanoyl CoA and malonyl-CoA (Reaction 2 in FIG. 4). AltPT condenses olivetolic acid with GPP, providing CBG (Reaction 3 in FIG. 4).

The pathway shown in FIG. 4 includes *C. sativa* HEx1 and *C. sativa* OAS. The pathway shown in FIG. 4 does not include *C. sativa* OAC. A transgenic yeast cell for carrying out the pathway of FIG. 4 would correspondingly include a gene for OAS but not a gene for *C. sativa* OAC. *C. sativa* OAC carboxylates olivetol to olivetolic acid during biosynthesis of olivetolic acid. With OAS and without OAC or another polyketide cyclase, olivetol is produced rather than olivetolic acid, which is produced in *C. sativa*. As a result, the reaction catalyzed by AltPT results in CBG rather than CBGa. Downstream reactions to produce phytocannabinoids would then correspondingly produce decarboxylated species of the phytocannabinoids, including the phytocannabinoids in FIG. 5, while acid forms, including the phytocannabinoids in FIG. 3, would be produced where OAC or another polyketide cyclase is also present, such as in *C. sativa*.

Conversion of hexanoyl-CoA to olivetol catalyzed by OAS at Reaction 2 of FIG. 4 was identified as a metabolic bottleneck in the pathway of FIG. 4. In order to increase yield at Reaction 2 of FIG. 4, multiple enzymes were functionally screened and one enzyme, a polyketide synthase from *Dictyostelium discoideum* called "DiPKS" was identified that could produce methyl-olivetol directly from malonyl-CoA. A synthetic sequence for DiPKS that is codon optimized for yeast is included here at SEQ ID NO: 2. A CDS for DiPKS is available at the NCBI GenBank online database under Accession Number NC_007087.3.

Figure 6:
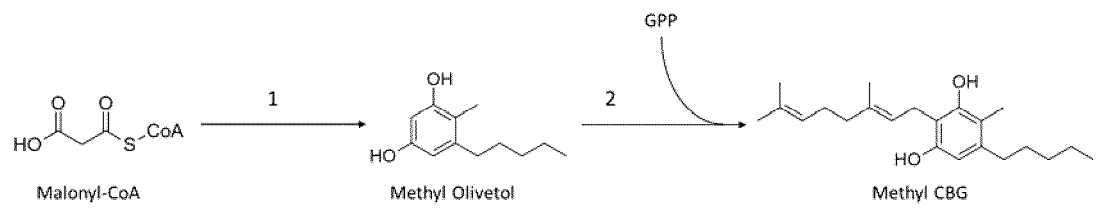
FIG. 6 is a schematic of biosynthesis of meCBG in a transformed yeast cell by DiPKS and AltPT.

FIG. 6 shows a biosynthetic pathway in transgenic yeast for production of meCBG from malonyl-CoA and GPP. A strain of yeast as provided herein for producing CBG as shown in FIG. 6 may include the gene for AltPT and a gene for DiPKS that supports production of polyketides from malonyl-CoA only, with no requirement for hexanoic acid in the media. DiPKS includes functional domains similar to domains found in a fatty acid synthase, a methyltransferase domain, and a Pks III domain (see FIG. 9). Examples of yeast strains including a codon optimized synthetic sequence coding for the wildtype DiPKS gene are provided as "HB84", "HB90", and "HB105", each of which are described in Table 7.

FIG. 6 shows production of methyl-olivetol from malonyl-CoA (Reaction 1 in FIG. 6), which is catalyzed by DiPKS. AltPT prenylates the methyl-olivetol with GPP as a prenyl group donor, providing meCBG (Reaction 2 in FIG. 6). Application of DiPKS rather than OAS facilitates production of phytocannabinoids and phytocannabinoid analogues without hexanoic acid supplementation. Since hexanoic acid is toxic to *S. cerevisiae*, eliminating a requirement for hexanoic acid in the biosynthetic pathway for CBG or meCBG may provide greater yields of CBG or meCBG than the yields of CBG in a yeast cell expressing OAS and Hex1.

Figure 7:
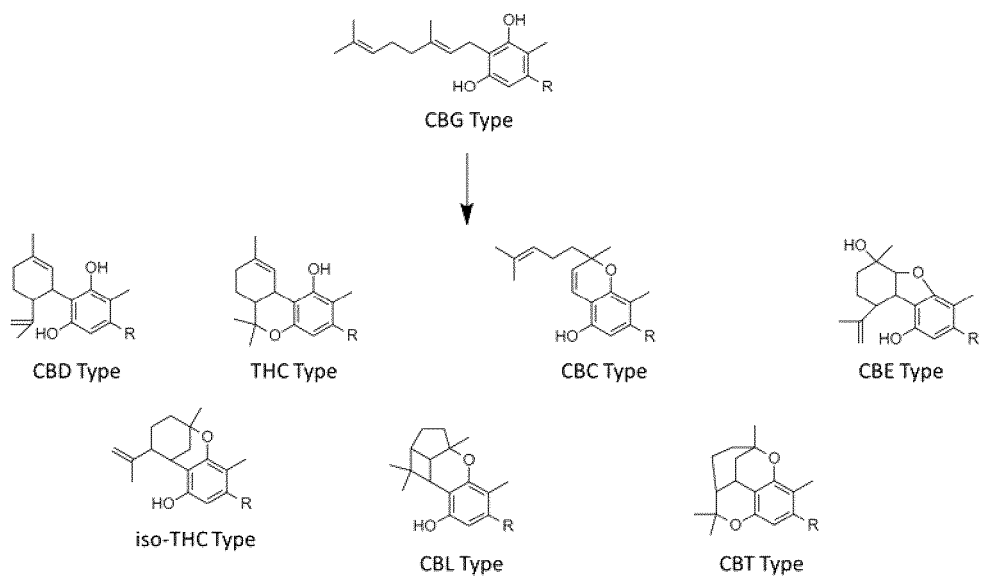
FIG. 7 is a schematic of biosynthesis of downstream methylated phytocannabinoid analogues in a transformed yeast cell from meCBG.
Figure 8:
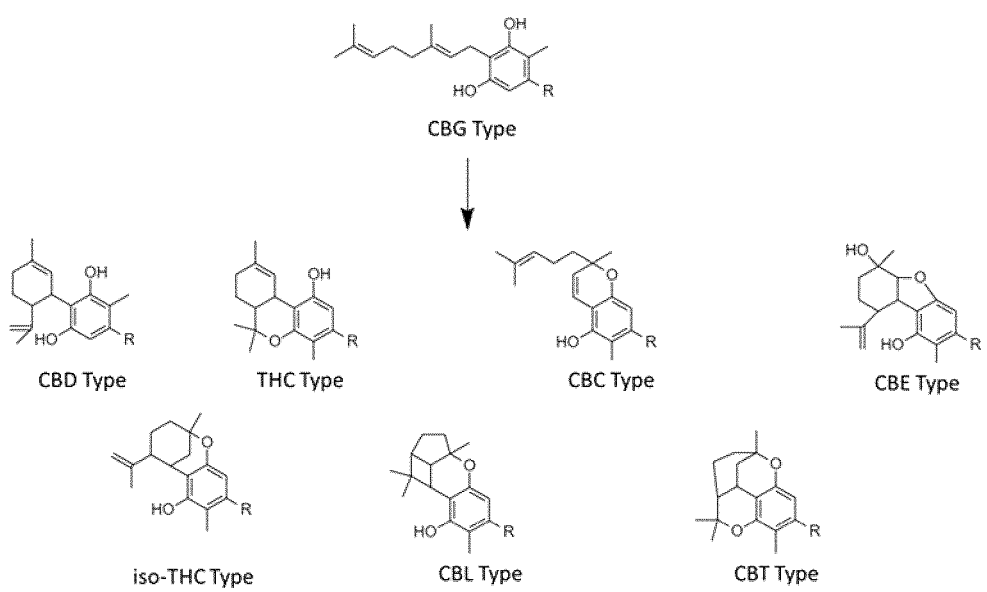
FIG. 8 is a schematic of biosynthesis of downstream methylated phytocannabinoid analogues in a transformed yeast cell from meCBG.

FIGS. 7 and 8 show downstream methylated phytocannabinoid analogues corresponding to methyl-tetrahydrocannabinol ("meTHC"), methyl-cannabidiol ("meCBD"), methyl-cannabichromene ("meCBC"), methyl-cannabielsoin ("meCBE"), iso-methyl-tetrahydrocannabinol ("iso-meTHC"), methyl-cannabicyclol ("meCBL"), or methyl-cannabicitran ("meCBT"), which are methylated analogues of THC, CBD, CBC, CBE, iso-THC, CBL, and CBT, respectively, that may be prepared when methyl-olivetol is provided as a precursor chemical rather than olivetolic acid or olivetol. The decarboxylated forms of each of these methylated phytocannabinoid analogues are shown in FIGS. 7 and 8 with a general "R" group to show the alkyl side chain, which would be a 5-carbon chain where synthesis results from hexanoyl-CoA and malonyl-CoA, or malonyl-CoA only.

Other than meCBD, a portion of the structure each of the downstream phytocannabinoid anaologues shown in FIGS. 7 and 8 includes rotationally constrained groups bonded with the aromatic ring. As a result, each of the downstream phytocannabinoid analogues shown in FIGS. 7 and 8 other than meCBD may be synthesized from meCBG in one of two rotational isomers. Depending on the rotational isomer of meCBG during synthesis, the methyl group in the resulting cyclized methylated phytocannabinoid analogues may be at the positions shown for the isomers of meTHC, meCBC, meCBE, iso-meTHC, meCBL, or meCBT in FIG. 7, or at the at the positions shown for the isomers of meTHC, meCBC, meCBE, iso-meTHC, meCBL, or meCBT in FIG. 8. References to meTHC, meCBC, meCBE, iso-meTHC, meCBL, or meCBT herein include either or both of the isomers shown in FIGS. 7 and 8.

DiPKS includes a C-methyltransferase domain that methylates olivetol at position 4 on the aromatic ring. As a result, AltPT prenylates methyl-olivetol, resulting in meCBG, a phytocannabinoid analogue, rather than CBGa, which is known to be synthesized in C. sativa. Any downstream reactions that may produce phytocannabinoids when using CBGa or CBG as an input would correspondingly produce the decarboxylated species of methylated phytocannabinoid analogues shown in FIGS. 7 and 8, whereas unmethylated acid form of phytocannabinoids would be produced in C. sativa (as in FIG. 3). If OAC or another polyketide cyclase were included, the methyl-olivetol may be converted by the OAC or the other polyketide cyclase into meCBGa, as the methylation and carboxylation carbons may be at differing positions. For example, meTHC synthesized from meCBG may be methylated at carbon 4, and could be carboxylated to methyl-tetrahydrocannabinolic acid ("meTHCa") with the carboxyl group of THCa may be at position 2. Alternatively, meTHC synthesized from meCBG may be methylated at carbon 2, in which case the carboxyl group of THCa may be at position 4. THCa is observed in C. sativa with the carboxyl group at the 2 position, or at the 4 position.

Figure 9:
FIG. 9 is a schematic of functional domains in DiPKS, with mutations to a C-methyl transferase that for lowering methylation of olivetol.

FIG. 9 is a schematic of the functional domains of DiPKS showing β-ketoacyl-synthase ("KS"), acyl transacetylase ("AT"), dehydratase ("DH"), C-methyl transferase ("C-Met"), enoyl reductase ("ER"), ketoreductase ("KR"), and acyl carrier protein ("ACP"). The "Type III" domain is a type 3 polyketide synthase. The KS, AT, DH, ER, KR, and ACP portions provide functions typically associated with a fatty acid synthase, speaking to DiPKS being a FAS-PKS protein. The C-Met domain provides the catalytic activity for methylating olivetol at carbon 4. The C-Met domain is crossed out in FIG. 9, schematically illustrating modifications to DiPKS protein that inactivate the C-Met domain and mitigate or eliminate methylation functionality. The Type III domain catalyzes iterative polyketide extension and cyclization of a hexanoic acid thioester transferred to the Type III domain from the ACP.

Figure 10:
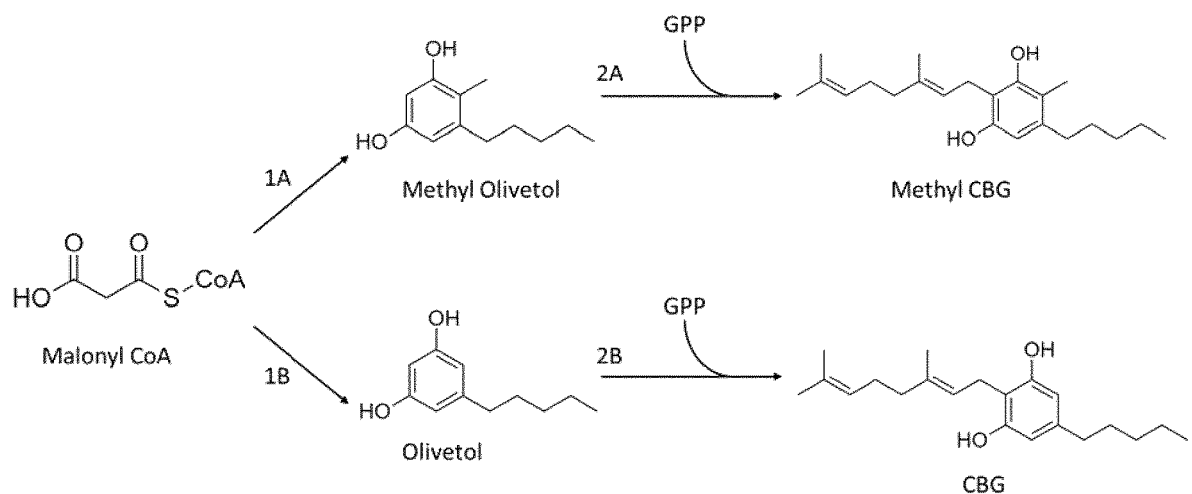
FIG. 10 is a schematic of biosynthesis of meCBG and CBG in a transformed yeast cell by DiPKS$^{G1516D;\ G1518A}$ and AltPT.

FIG. 10 shows a biosynthetic pathway in transgenic yeast for production of both meCBG and CBG from malonyl-CoA and GPP. A strain of yeast as provided herein for producing both CBG and meCBG as shown in FIG. 10 may include the gene for AltPT and a gene for a mutant DiPKS with a lowered activity at the C-Met domain, as shown schematically in FIG. 9. The C-Met domain of the DiPKS protein includes amino acid residues 1510 to 1633 of DiPKS. The C-Met domain includes three motifs. The first motif includes residues 1510 to 1518. The second motif includes residues 1596 to 1603. The third motif includes residues 1623 to 1633. Disruption of one or more of these three motifs may result in lowered activity at the C-Met domain.

An example of a yeast strain expressing a modified DiPKS with lowered activity in the C-Met domain is provided as "HB80A" in Example V below. HB80A includes a modification in a yeast-codon optimized gene coding for the wildtype DiPKS protein. HB80A includes modifications in the DiPKS gene such that the DiPKS protein is modified in the first motif of the C-Met domain. As a result of these modifications to the DiPKS gene, the DiPKS protein has substitutions of Gly1516Asp and Gly1518Ala. HB80A includes only the $DiPKS^{G1516D;\ G1518A}$ and not AltPT, and as a result catalyzes only steps 1A and 1B of FIG. 10, and neither reaction 2A nor 2B. HB80A produces methyl-olivetol and olivetol. The HB80A strain may be modified to include AltPT, such as by transforming HB80A with the pAltPT plasmid (see Table 6).

FIG. 10 shows production of both methyl-olivetol from malonyl-CoA (Reaction 1A in FIG. 10) and of olivetol from malonyl-CoA (Reaction 1B in FIG. 10). Reactions 1A and 1B are each catalyzed by $DiPKS^{G1516D;\ G1518A}$. The Gly1516Asp and Gly1518Ala substitutions are in the active site of the C-Met domain and diminish catalysis by $DiPKS^{G1516D;\ G1518A}$ of methylation on the 4 position of the olivetol ring, allowing a portion of the input malonyl-CoA to be catalyzed according to reaction 1B rather than reaction 1A. AltPT, a promiscuous ABBA prenyltransferase, catalyzes prenylation of both the methyl-olivetol with GPP and the olivetol with GPP. Production of both meCBG (Reaction 2A in FIG. 10) and CBG (Reaction 2B in FIG. 10) follows. Any downstream reactions to produce other phytocannabinoids would then correspondingly produce a mixture of methylated phytocannabinoid analogues and species with no functional group at the 4 position on the aromatic ring of CBG (or a corresponding position in downstream phytocannabinoids), whereas acid forms would be produced in C. sativa.

Figure 11:
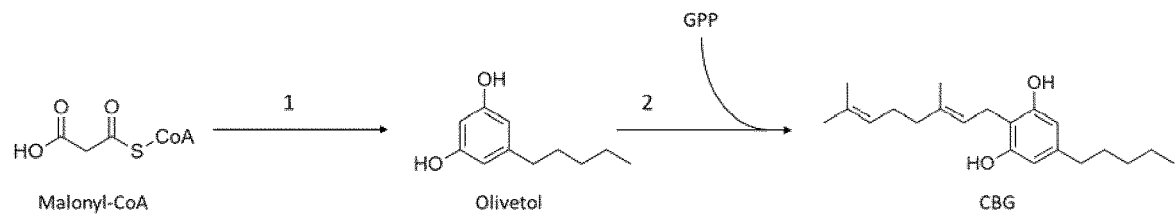
FIG. 11 is a schematic of biosynthesis of CBG in a transformed yeast cell by DiPKS$^{G1516R}$ and AltPT.

FIG. 11 shows a biosynthetic pathway in transgenic yeast for production of CBG only from malonyl-CoA and GPP. A strain of yeast as provided herein for producing CBG only as shown in FIG. 11 may include the gene for AltPT and a gene for a mutant DiPKS with a lowered activity at the C-Met domain, as shown schematically in FIG. 9.

Examples of yeast strains expressing a modified DiPKS with essentially no activity in the C-Met domain are provided as "HB135", "HB137", "HB138" and "HB139" in Examples VIII, IX and X below. Each of HB135, HB137, HB138 and HB139 includes a modification in a yeast-codon optimized gene coding for the wildtype DiPKS protein. HB135, HB137, HB138 and HB139 each include a modification of the DiPKS gene such that the DiPKS protein is modified in the first motif of the C-Met domain. As a result of this modification to the DiPKS gene, the DiPKS protein has substitutions of Gly1516Arg.

$DiPKS^{G1516R}$ catalyzes reaction 1 in FIG. 11. The Gly1516Arg substitution is in the active site of the C-Met domain and diminish catalysis by $DiPKS^{G1516R}$ of methylation on the 4 position of the olivetol ring. The input of malonyl-CoA is catalyzed according to reaction 1 of FIG. 11. HB139 also includes AltPT, and production of olivetol and CBG (reaction 2 in FIG. 11) follows. Any downstream reactions to produce other phytocannabinoids would then correspondingly produce phytocannabinoid species with no functional group at the 4 position on the aromatic ring of CBG, or a corresponding position in downstream phytocannabinoids, whereas acid forms would be produced in *C. sativa*.

Increasing Availability of Biosynthetic Precursors

The biosynthetic pathways shown in FIGS. 4, 6, 10 and 11 each require malonyl-CoA and GPP to produce CBGa, CBG, or meCBG, respectively. Yeast cells may be mutated, genes from other species may be introduced, genes may be upregulated or downregulated, or the yeast cells may be otherwise genetically modified, other than introduction of a polyketide synthase such as OAS or DiPKS, and other than introduction of a cytosolic prenyltransferase such as AltPT, to increase the availability of malonyl-CoA, GPP, or other input metabolites required to support the biosynthetic pathways of any of FIGS. 4, 6, 10 and 11.

The yeast cells may be modified for increasing available GPP. *S. cerevisiae* may have one or more other mutations in Erg20 or other genes for enzymes that support metabolic pathways that deplete GPP. Erg20 catalyzes GPP production in the yeast cell. Erg20 also adds one subunit of 3-isopentyl pyrophosphate ("IPP") to GPP, resulting in farnesyl pyrophosphate ("FPP"), a metabolite used in downstream sesquiterpene and sterol biosynthesis. Some mutations in Erg20 have been demonstrated to reduce conversion of GPP to FPP, increasing available GPP in the cell. A substitution mutation Lys197Glu in Erg20 lowers conversion of GPP to FPP by Erg20. As shown in Table 4 below, all modified base strains express the Erg20$^{K197E}$ mutant protein ("HB42", "HB82", "HB100", "HB106", and "HB110"). Similarly, each modified yeast strain based on any of HB42, HB82, HB100, HB106, or HB110 includes a integrate polynucleotide coding for the Erg20$^{K197E}$ mutant integrated into the yeast genome. SEQ ID NO: 3 is a CDS coding for the Erg20$^{K197E}$ protein and flanking sequences for homologous recombination.

The yeast strain may be modified for increasing available malonyl-CoA. Lowered mitochondrial acetaldehyde catabolism results in diversion of the acetaldehyde from ethanol catabolism into acetyl-CoA production, which in turn drives production of malonyl-CoA and downstream polyketides and terpenoids. *S. cerevisiae* may be modified to express an acetyl-CoA synthase from *Salmonella enterica* with a substitution modification of Leucine to Proline at residue 641 ("Acs$^{L641P}$"), and with aldehyde dehydrogenase 6 from *S. cerevisiae* ("Ald6"). The Leu641Pro mutation removes downstream regulation of Acs, providing greater activity with the ACS$^{L641P}$ mutant than the wild type Acs. Together, cytosolic expression of these two enzymes increases the concentration of acetyl-CoA in the cytosol. Greater acetyl-CoA concentrations in the cytosol result in lowered mitochondrial catabolism, bypassing mitochondrial pyruvate dehydrogenase ("PDH"), providing a PDH bypass. As a result, more acetyl-CoA is available for malonyl-CoA production. SEQ ID NO: 4 is plasmid based on the pGREG plasmid and including a DNA sequence coding for the genes for Ald6 and SeAcs$^{L641P}$, promoters, terminators, and integration site homology sequences for integration into the *S. cerevisiae* genome at Flagfeldt-site 19 by recombination applying clustered regularly interspaced short palindromic repeats ("CRISPR"). As shown in Table 4 below (by the term "PDH bypass"), base strains HB82, HB100, HB106, and HB110 have a portion of SEQ ID NO: 4 from bases 1494 to 2999 that code for Ald6 under the TDH$_3$ promoter, and a portion of SEQ ID NO: 4 from bases 3948 to 5893 that code for SeAcs$^{L641P}$ under the Tef1$_P$ promoter. Similarly, each modified yeast strain based on any of HB82, HB100, HB106, or HB110 includes a polynucleotide coding for Ald6 and SeAcs$^{L641P}$.

Another approach to increasing cytosolic malonyl-CoA is to upregulate Acc1, which is the native yeast malonyl-CoA synthase. The promoter sequence of the Acc1 gene was replaced by a constitutive yeast promoter for the PGK1 gene. The promoter from the PGK1 gene allows multiple copies of Acc1 to be present in the cell. The native Acc1 promoter allows only a single copy of the protein to be present in the cell at a time. The native promoter region is shown in SEQ ID NO: 5. The modified promoter region is shown in SEQ ID NO: 6.

In addition to upregulating expression of Acc1, *S. cerevisiae* may include one or more modifications of Acc1 to increase Acc1 activity and cytosolic acetyl-CoA concentrations. Two mutations in regulatory sequences were identified in literature that remove repression of Acc1, resulting in greater Acc1 expression and higher malonyl-CoA production. SEQ ID NO: 7 is a polynucleotide that may be used to modify the *S. cerevisiae* genome at the native Acc1 gene by homologous recombination. SEQ ID NO: 7 includes a portion of the coding sequence for the Acc1 gene with Ser659Ala and Ser1157Ala modifications. As a result, the *S. cerevisiae* transformed with this sequence will express Acc1$^{S659A;\ S1157A}$. A similar result may be achieved, for example, by integrating a sequence with the Tef1 promoter, the Acc1 with Ser659Ala and Ser1157Ala modifications, and the Prm9 terminator at any suitable site. The end result would be that Tef1, Acc1$^{S659A;\ S1157A}$ and Prm9 are flanked by genomic DNA sequences for promoting integration into the *S. cerevisiae* genome. This was attempted at Flagfeldt site 18 but due to the size of the construct, the approach with SEQ ID NO: 7 described above was followed instead.

*S. cerevisiae* may include modified expression of Maf1 or other regulators of tRNA biosynthesis. Overexpressing native Maf1 has been shown to reduce loss of IPP to tRNA biosynthesis and thereby improve monoterpene yields in yeast. IPP is an intermediate in the mevalonate pathway. SEQ ID NO: 8 is a polynucleotide that was integrated into the *S. cerevisiae* genome at Maf1-site 5 for genomic integration of Maf1 under the Tef1 promoter. SEQ ID NO: 8 includes the Tef1 promoter, the native Maf1 gene, and the Prm9 terminator. Together, Tef1, Maf1, and Prm9 are flanked by genomic DNA sequences for promoting integration into the *S. cerevisiae* genome. As shown in Table 4 below, base strains HB100, HB106, and HB110 express Maf1 under the Tef1 promoter. Similarly, each modified yeast strain based on any of HB100, HB106, or HB110 includes a polynucleotide including a coding sequence for Maf1 under the Tef1 promoter.

Upc2 is an activator for sterol biosynthesis in *S. cerevisiae*. A Glu888Asp mutation of Upc2 increases monoterpene production in yeast. SEQ ID NO: 9 is a polynucleotide that may be integrated into the genome to provide expression of Upc2$^{E888D}$ under the Tef1 promoter. SEQ ID NO: 9 includes the Tef1 promoter, the Upc2$^{E888D}$ gene, and the Prm9 terminator. Together, Tef1, Upc2$^{E888D}$, and Prm9 are flanked by genomic DNA sequences for promoting integration into the *S. cerevisiae* genome.

Any of the above genes, Erg20$^{K197E}$, Acs1$^{L641P}$, Ald6, Maf1, Acc1$^{S659A;\ S1157A}$ or Upc2$^{E888D}$, may be expressed from a plasmid or integrated into the genome of *S. cerevisiae*. Genome integration may be through homologous recombination, including CRISPR recombination, or any suitable approach. The promoter of Acc1 may be similarly modified through recombination. The coding and regulatory sequences in each of SEQ ID NO: 3, SEQ ID NO: 4, SEQ ID NO: 6, SEQ ID NO: 7, SEQ ID NO: 8, or SEQ ID NO: 9 may be included in a plasmid for expression (e.g. pYES, etc.) or a linear polynucleotide for integration into the S. Cerevisiae genome. Each of base strains HB42, HB82, HB100, HB106, or HB110 includes one or more integrated SEQ ID NO: 3, SEQ ID NO: 4, SEQ ID NO: 6, SEQ ID NO: 8, or SEQ ID NO: 10 (see below). Integration of SEQ ID NO: 7, or SEQ ID NO: 9 may be applied by similar approaches.

Increased DiPKS Function

As shown in FIG. 9, DiPKS includes an ACP domain. The ACP domain of DiPKS requires a phosphopantetheine group as a co-factor. NpgA is a 4'-phosphopantethienyl transferase from Aspergillus nidulans. A codon-optimized copy of NpgA for S. cerevisiae may be introduced into S. cerevisiae and transformed into the S. cerevisiae, including by homologous recombination. An NpgA gene cassette was integrated into the genome of Saccharomyces cerevisiae at Flagfeldt site 14 to create strain HB100. The sequence of the integrated DNA is shown in SEQ ID NO: 10, and includes the Tef1 Promoter, the NpgA coding sequence and the Prm9 terminator. Together the Tef1p, NpgA, and Prm9t are flanked by genomic DNA sequences promoting integration into Flagfeldt site 14 in the S. cerevisiae genome. As shown in Table 4 below, base strains HB100, HB106, and HB110 include this integrated cassette. Alternatively, bases 636 to 2782 of SEQ ID NO: 10 may be included on an expression plasmid as in strain HB98.

Expression of NpgA provides the A. nidulans phosphopantetheinyl transferase for greater catalysis of loading the phosphopantetheine group onto the ACP domain of DiPKS. As a result, the reaction catalyzed by DiPKS (reaction 1 in FIG. 6) may occur at greater rate, providing a greater amount of methyl-olivetol for prenylation to meCBG.

Other Prenyltransferase Enzymes

NphB variants were defined based on a DELTA BLAST search for ABBA prenyltransferase structures. The list was refined by looking for a binding pocket appropriate for GPP and not IPP, dimethyl allyl pyrophosphate, or other prenyl groups. SEQ ID NO: 12 to SEQ ID NO: 33 provide primary structure amino acid residue sequences for cytosolic prenyltransferase enzymes from fungi and bacteria that were located in the DELTA BLAST search. DELTA BLAST searches of the C. sativa genome were also conducted and membrane-bound prenyltransferase enzymes were located in these searches. Some C. sativa membrane-bound prenyltransferase enzymes express poorly in some species of yeast and would not be introduced into the yeast strains provided herein to prepare phytocannabinoids or phytocannabinoid analogues.

SEQ ID NO: 33 to SEQ ID NO: 36 provide primary structure amino acid residue sequences for cytosolic prenyl transferase enzymes from fungi and bacteria that were located in a manual literature search. SEQ ID NO: 33 to SEQ ID NO: 36 are primary structure amino acid residue sequences for cytosolic prenyl transferase enzymes named FNQ26, FNQ28, FUR7, and NAPT9, respectively.

Any of SEQ ID NO: 11 to SEQ ID NO: 36 may be applied to the yeast strains described herein as the cytosolic prenyltransferase. Each of these prenyltransferases are summarized in Table 1.

TABLE 1

Prenyltransferases

| SEQ ID NO: | Comments |
|---|---|
| 11 | 640387779 ATEG_00821 predicted protein [Aspergillus terreus] |
| 12 | 2515835839 B100DRAFT_06502 Aromatic prenyltransferase NphB. [Streptomyces sp. CL190] |
| 13 | 2516097927 B121DRAFT_00516 Aromatic prenyltransferase NphB. [Streptomyces sp. CL190] |
| 14 | 2516101115 B121DRAFT_03712 Aromatic prenyltransferase NphB. [Streptomyces sp. CL190] |
| 15 | 2516101748 B121DRAFT_04345 Aromatic prenyltransferase NphB. [Streptomyces sp. CL190] |
| 16 | 2516099186 B121DRAFT_01777 Aromatic prenyltransferase NphB. [Streptomyces sp. CL190] |
| 17 | 2516104298 B121DRAFT_06901 Aromatic prenyltransferase NphB. [Streptomyces sp. CL190] |
| 18 | 2585297016 EW57DRAFT_01164 Aromatic prenyltransferase NphB [Streptomyces atratus] |
| 19 | 2585373487 putative prenyltransferase [Streptomyces cinnamonensis] |
| 20 | 2585373644 aromatic prenyltransferase [Streptomyces iakyrus] |
| 21 | 2585378108 ABBA prenyltransferase Ptf_St [Streptomyces tendae] |
| 22 | 2585708813 JD81DRAFT_01144 Aromatic prenyltransferase NphB [Micromonospora sagamiensis] |
| 23 | 2516111586 B105DRAFT_07016 Aromatic prenyltransferase NphB. [Streptomyces sp. CL190] |
| 24 | 2517160389 SacsaDRAFT_00895 Aromatic prenyltransferase NphB. [Saccharomonospora saliphila] |
| 25 | 2521683528 H294DRAFT_07929 Aromatic prenyltransferase NphB [Streptomyces sp. CL190] |
| 26 | 2521683684 H294DRAFT_08085 Aromatic prenyltransferase NphB [Streptomyces sp. CL190] |
| 27 | 2524586714 H299DRAFT_04355 Aromatic prenyltransferase NphB [Streptomyces sp. CL190] |
| 28 | 2528491298 I003DRAFT_05612 Aromatic prenyltransferase NphB [Streptomyces sp. CL190] |
| 29 | 2585378750 SPLIT WT5.12c [Streptomyces sp. WT5: JN402323] |
| 30 | 2585373485 SPLIT putative prenyltransferase [Streptomyces cinnamonensis DSM 1042: AM384985] |
| 31 | 2552198934 SPLIT Aromatic prenyltransferase NphB [Nocardia concava NBRC 100430: NoneDRAFT_BAFX01000066_1.66] |
| 32 | 2521987056 SPLIT Aromatic prenyltransferase NphB [Myxococcus stipitatus DSM 14675: CP004025] |
| 33 | FNQ26 from Streptomyces cinnamonensis |
| 34 | FNQ28 from S. cinnamonensis |
| 35 | FUR7 from Streptomyces sp. (strain KO-3988) |
| 36 | NAPT9 from Streptomyces aculeolatus |

Modification of DiPKS

DiPKS may be modified to reduce or eliminate the activity of C-Met.

SEQ ID NO: 37 is a modified form of a synthetic sequence for DIPKS that is codon optimized for yeast in which DiPKS includes a Gly1516Asp substitution and a Gly1518Ala substitution that together disrupt the activity of the C-met domain. Results of DiPKS$^{G1516D, G1518A}$ expression in S. cerevisiae cultures are provided below in relation to Example IV which includes strain HB80A. Other modifications may be introduced into DiPKS to disrupt or eliminate the entire active site of C-Met or all of C-Met. Each of these modified DiPKS enzymes may be introduced into S. cerevisiae as described for wild type DiPKS.

SEQ ID NO: 38 is a modified form of a synthetic sequence for DIPKS that is codon optimized for yeast in which DiPKS includes a Gly1516Arg substitution that disrupts the activity of the C-met domain. Results of DiPKS$^{G1516R}$ expression in S. cerevisiae cultures are provided below in relation to Example VIII, which includes strain HB135 and Example IX, which includes strains HB135, HB137 and HB138.

In addition to DiPKS$^{G1516D,G1518A}$ and DiPKS$^{G1516R}$ specifically, other modifications were introduced into DiPKS to disrupt or eliminate the entire active site of C-Met or all of C-Met: (a) substitution of motif 1 with GGGSGGGSG, (b) a Gly1516Arg substitution in motif 1 and substitution of motif 2 with GGGSGGGS, (c). a Glu1634Ala, which is just outside motif 3 and disrupts tertiary structure at an active site in the C-Met domain, and (d). disruption of an active site in the C-Met domain by a His1608Gln substitution. Codon optimized sequences for each of (a) to (d) were introduced into yeast on expression plasmids, similarly to expression of DiPKS$^{G1516D,G1518A}$ and DiPKS$^{G1516R}$, into base strain HB100. In each case, no production of olivetol was These common features across the ten examples are described below, followed by results and other details relating to one or more of the ten examples.

Plasmid Construction

Plasmids assembled to apply and prepare examples of the methods and yeast cells provided herein are shown in Table 2. In Table 2, for the expression plasmids pYES, and pYES2, SEQ ID NOs 39 and 40 respectively provide the plasmids as a whole without an expression cassette. The expression cassettes of SEQ ID NOs: 10, 37, 38, and 41 to 47 can be included in to prepare the plasmids indicated in Table 2. SEQ ID NO: 4 is the pGREG plasmid including a cassette for the PDH bypass genes.

TABLE 2

Plasmids and Cassettes Used to Prepare Yeast Strains

| Plasmid | Cassette | Description |
|---|---|---|
| pYES | (none) | LEU auxotroph; ampicillin resistance; SEQ ID NO: 39 |
| pYES2 | (none) | URA auxotroph; ampicillin resistance; SEQ ID NO: 40 |
| pPDH | Bases 1 to 7214 from SEQ ID NO: 4 | High copy amplification plasmid with PDH Bypass genes for acetaldehyde dehydrogenase (Ald6) and acetyl-CoA synthase (Acs$^{L641P}$) assembled in pGREG 505/G418 flanked by integration site homology sequences as follows: C1-506-BclV-Site 19 UP region-L0 L0-TDH3$_P$-L1-Ald6-L2-Adh1$_T$-LTP1 LTP1-Tefl$_P$-L3-Acs$^{L641P}$-L4-Prm9$_T$-LTP2 LTP2-Site 19 down region-C6-506 |
| pNPGa | SEQ ID NO: 10 | High copy NpgA expression plasmid in pYES2 with: LV3-Tefl$_P$-L1-NpgA-L2-Prm9$_T$-LV5 |
| pDiPKSm1 | SEQ ID NO: 37 | High copy DiPKS$^{G1516D;G1518A}$ expression plasmid in pYES2 with: LV3-Gal1-L1-DiPKS$^{G1516D;G1518A}$-L2-Prm9$_T$-LV5 |
| pDIPKSm2 | SEQ ID NO: 38 | High copy DIPKS$^{G1516R}$ expression plasmid in pYES2 with: LV3-Gal1-L1-DiPKS$^{G1516R}$-L2-Prm9t$_T$-LV5 |
| pGFP | SEQ ID NO: 41 | High copy GFP expression plasmid in pYES2 with: LV3-Tefl$_P$-GFP-Cyc$_T$-LV5 |
| pPTGFP | SEQ ID NO: 42 | High copy C. sativa prenyltransferase fused with GFP expression plasmid in pYES2 with: LV3-Tefl$_P$-CS.PT_GFP-Cyc$_T$-LV5 |
| pAPTGFP | SEQ ID NO: 43 | High copy AltPT fused with GFP expression plasmid in pYES2 with: LV3-Tefl$_P$-APT_GFP-Cyc$_T$-LV5 |
| pAltPT | SEQ ID NO: 44 | High copy AltPT expression plasmid in pYES with: LV3-PMA1$_P$-L1-AltPT-L2-Eno2$_T$-LV5 |
| pH1OAS | SEQ ID NO: 45 | High copy Hexl and OAS expression plasmid in pYES2 with: LV3-TDH3$_P$-L1-Hex1-L2-Adh1$_T$-LTP1 TP1-Tefl$_P$-L3-OAS-L4-Prm9$_T$-LV5 |
| pDiPKS | SEQ ID NO: 46 | High copy DiPKS expression plasmid in pYES2 with: LV3-Gal1-L1-DiPKS-L2-Prm9$_T$-LV5 |
| pCRISPR | SEQ ID NO: 47 | High copy Cas9 endonuclease and targeted gRNA expression plasmid in pYES2 with: LV3-Tefl$_P$-Cas9-Adh1$_T$-LTP1 LTP1-gRNA-LV5 | observed. Substitution of either motif 1 or motif 2 with GGGSGGGS eliminated production of methyl-olivetol as well. A culture of yeast expressing the DiPKS$^{G1634A}$ mutant provided 2.67 mg methyl-olivetol per I of culture in one example batch. A culture of yeast expressing the DiPKS$^{H1608N}$ mutants provided 3.19 mg methyl-olivetol per I of culture in one example batch.

Transforming and Growing Yeast Cells

Details of specific examples of methods carried out and yeast cells produced in accordance with this description are provided below as Examples I, to X. Each of these ten specific examples applied similar approaches to plasmid construction, transformation of yeast, quantification of strain growth, and quantification of intracellular metabolites.

Plasmids for introduction into S. cerevisiae were amplified by polymerase chain reaction ("PCR") with primers from Operon Eurofins and Phusion HF polymerase (ThermoFisher F-530S) according to the manufacturer's recommended protocols using an Eppendorf Mastercycler ep Gradient 5341.

All plasmids were assembled using overlapping DNA parts and transformation assisted recombination in S. cerevisiae. The plasmids were transformed into S. cerevisiae using the lithium acetate heat shock method as described by Gietz, R. D. and Schiestl, R. H., "High-efficiency yeast transformation using the LiAc/SS carrier DNA/PEG method." Nat. Protoc. 2, 31-34 (2007). The base yeast strains used for assembling plasmids are shown in Table 3:

TABLE 3

Base Yeast Strains

| Strain | Background | Modification | Comments |
|---|---|---|---|
| HB24 | -LEU | None | Unmodified yeast with Leucine auxotrophy used to assemble plasmids |
| HB25 | -URA | None | Unmodified yeast with Uracil auxotrophy used to assemble plasmids |

The pAltPT plasmid was assembled in the HB24 leucine auxotroph. The pNPGA, pDiPKSm1, pDiPKSm2, pGFP, pPTGFP, pAPTGFP, pH1OAS, pDiPKS, pCRISPR, and pPDH plasmids were assembled in the HB25 uracil auxotroph. Transformed *S. cerevisiae* cells were selected by auxotrophic selection on agar petri dishes. Colonies recovered from the petri dishes were grown up in liquid selective media for 16 hrs at 30° C. while being shaken at 250 RPM.

After growth in liquid selective media, the transformed *S. cerevisiae* cells were collected and the plasmid DNA was extracted. The extracted plasmid DNA was transformed into *Escherichia coli*. Transformed *E. coli* were selected for by growing on agar petri dishes including ampicillin. The *E. coli* were cultured to amplify the plasmid. The plasmid grown in the *E. coli* was extracted and sequenced with Sanger dideoxy sequencing to verify accurate construction. The sequence-verified plasmid was then used for genome modification or stable transformation of the *S. cerevisiae*.

Genome Modification of *S. cerevisiae*

The *S. cerevisiae* strains described herein may be prepared by stable transformation of plasmids or genome modification. Genome modification may be accomplished through homologous recombination, including by methods leveraging CRISPR.

Methods applying CRISPR were applied to delete DNA from the *S. cerevisiae* genome and introduce heterologous DNA into the *S. cerevisiae* genome. Guide RNA ("gRNA") sequences for targeting the Cas9 endonuclease to the desired locations on the *S. cerevisiae* genome were designed with Benchling online DNA editing software. DNA splicing by overlap extension ("SOEing") and PCR were applied to assemble the gRNA sequences and amplify a DNA sequence including a functional gRNA cassette.

The functional gRNA cassette, a Cas9-expressing gene cassette, and the pYes2 (URA) plasmid were assembled into the pCRISPR plasmid and transformed into *S. cerevisiae* for facilitating targeted DNA double-stranded cleavage. The resulting DNA cleavage was repaired by the addition of a linear fragment of target DNA.

The CDS for the Erg20$^{K197E}$ protein shown in SEQ ID NO: 3 was integrated into the genome of HB13 by homologous recombination, resulting in the HB42 base strain.

Bases 51 to 7114 of SEQ ID NO: 4 were integrated into the HB42 strain by CRISPR to provide the HB82 base strain with the PDH bypass genes in *S. cerevisiae*. The pPDH plasmid was sequence verified after assembly in *S. cerevisiae*. The sequence-verified pPDH plasmid was grown in *E. coli*, purified, and digested with BciV1 restriction enzymes. As in Table 2, digestion by BciV1 provided a polynucleotide including the genes for Ald6 and SeAcs$^{L641P}$, promoters, terminators, and integration site homology sequences for integration into the *S. cerevisiae* genome at PDH-site 19 by Cas9. The resulting linear PDH bypass donor polynucleotide, shown in bases 51 to 7114 of SEQ ID NO: 4, was purified by gel separation.

With both PDH bypass genes (Ald6 and Acs$^{L641P}$) on the single PDH bypass polynucleotide, the PDH bypass donor polynucleotide was co-transformed into *S. cerevisiae* with pCRISPR. Transformation was by the lithium acetate heat shock method as described by Gietz. The pCRISPR plasmid expresses Cas9, which is targeted to a selected location of *S. cerevisiae* the genome by a gRNA molecule. At the location, the Cas9 protein creates a double stranded break in the DNA. The PDH bypass donor polynucleotide was used as a donor polynucleotide in the CRISPR reaction. The PDH bypass donor polynucleotide including Ald6, Acs$^{L641P}$, promoters, and terminators was integrated into the genome at the site of the break, Site 19, by homologous recombination, resulting in strain HB82.

The NpgA donor polynucleotide shown in SEQ ID NO: 10 was prepared and amplified. DNA SOEing was used to create a single donor DNA fragment from three polynucleotides for NpgA integration. The first polynucleotide was the 5' region of genomic homology that allows the donor to recombine into the genome at a specific locus. The second polynucleotide coded for the NpgA gene cassette. The NpgA gene cassette includes the Tef1 promoter, the NpgA coding sequence and the Prm9 terminator. The phosphopantetheinyl transferase polynucleotide included the 3' region for genomic homology to facilitate targeted integration into the *S. cerevisiae* genome.

The NpgA donor polynucleotide was co-transformed with the pCRISPR plasmid into strain HB82. The pCRISPR plasmid was expressed and endonuclease Cas9 was targeted to a location on the *S. cerevisiae* genome by a gRNA molecule. At the location, the Cas9 protein created a double stranded break in the DNA and the NpgA donor polynucleotide was integrated into the genome at the break by homologous recombination to provide the HB100 base strain.

The Maf1 donor polynucleotide shown in SEQ ID NO: 8 was prepared and amplified. DNA SOEing was used to create a single donor DNA fragment from three polynucleotides for Maf1 integration. The first polynucleotide was the 5' region of genomic homology that allows the donor to recombine into the genome at a specific locus. The second polynucleotide coded for the Maf1 gene cassette. The Maf1 gene cassette includes the Tef1 promoter, the Maf1 coding sequence and the Prm9 terminator. The Maf1 polynucleotide included the 3' region for genomic homology to facilitate targeted integration into the *S. cerevisiae* genome.

The Maf1 donor polynucleotide was co-transformed with the pCRISPR plasmid into the HB100 strain. The pCRISPR plasmid may be expressed and endonuclease Cas9 was targeted to a location on the *S. cerevisiae* genome by a gRNA molecule. At the location, the Cas9 protein may create a double stranded break in the DNA and the Maf1 donor polynucleotide may be integrated into the genome at the break by homologous recombination. Stable transformation of the Maf1 donor polynucleotide into the HB100 strain provides the HB106 base strain.

The Acc1-PGK1p donor polynucleotide shown in SEQ ID NO: 6 was prepared and amplified. DNA SOEing was used to create a single donor DNA fragment from three polynucleotides for Acc1-PGK1 integration. The first polynucleotide was the 5' region of genomic homology that allows the donor to recombine into the genome at a specific locus. The second polynucleotide coded for the PGK1 promoter region. The Acc1 polynucleotide included the 3' region for genomic homology to facilitate targeted integration into the *S. cerevisiae* genome.

The Acc1-PGK1 donor polynucleotide was co-transformed with the pCRISPR plasmid. The pCRISPR plasmid was expressed and endonuclease Cas9 was targeted to a location on the S. cerevisiae genome by a gRNA molecule. At the location, the Cas9 protein created a double stranded break in the DNA and the Acc1-PGK1 donor polynucleotide was integrated into the genome at the break by homologous recombination. Stable transformation of donor polynucleotide into the HB100 strain provides the HB110 base strain with Acc1 under regulation of the PGK1 promoter.

Table 4 provides a summary of the base strains that were prepared by genome modification of S. cerevisiae. Each base strain shown in Table 4 is a leucine and uracil auxotroph, and none of them include a plasmid.

TABLE 4

Base Transformed Strains Prepared for Confirming Protein Expression and for Phytocannabinoid Production

| Strain | Modification | Integration |
|---|---|---|
| HB42 | Erg20$^{K197E}$ | SEQ ID NOs: 3 |
| HB82 | Erg20$^{K197E}$, PDH bypass | SEQ ID NOs: 3, 4 |
| HB100 | Erg20$^{K197E}$, PDH bypass, NPGa (site 14) | SEQ ID NOs: 3, 4, 10 |
| HB106 | Erg20$^{K197E}$, PDH bypass, NPGa (site 14), Maf1 (site 5) | SEQ ID NOs: 3, 4, 10, 8 |
| HB110 | Erg20$^{K197E}$, PDH bypass, NPGa (site 14), Maf1 (site 5), Acc1 promoter replaced with PGK1$^P$ | SEQ ID NOs: 3, 4, 10, 8, 6 |

Stable Transformation for Strain Construction

Plasmids were transformed into S. cerevisiae using the lithium acetate heat shock method as described by Gietz.

Transgenic S. cerevisiae strains HB1, HB6, and HB7 were prepared from the HB25 base strain by introducing the plasmids from Table 2 into HB25 as indicated below in Table 5. Strains HB1, HB6, and HB7 were used for comparing protein expression levels in S. cerevisiae of C. sativa prenyltransferase and AltPT.

TABLE 5

Transformed Yeast Strains Including Expression Plasmids Prepared for Confirming Protein Expression and for Phytocannabinoid Production

| Strain | Base Strain | Plasmid |
|---|---|---|
| HB1 | HB25 | pGFP |
| HB6 | HB25 | pPTGFP |
| HB7 | HB25 | pAPTGFP |
| HB13 | HB25 | pEV |

Transgenic S. cerevisiae HB80, HB80A, HB98, HB102, HB135, HB137 and HB138 were prepared from the HB42, HB100, HB106 and HB110 bases strain by transformation of HB42 with expression plasmids, and HB80A was prepared by transformation of HB80, as shown below in Table 6. HB80, HB98 and HB102 each include and express DiPKS. HB80A includes and expresses DiPKS$^{G1516D;\ G1518A}$. HB135, HB137 and HB138 each include and express DiPKS$^{G1516R}$. HB98 includes and expresses DiPKS and NPGa from a plasmid.

TABLE 6

Strains including plasmids expressing polyketide synthase

| Strain | Base Strain | Plasmid |
|---|---|---|
| HB80 | HB42 | pDiPKS |
| HB80A | HB80 | pDiPKSm1 |

TABLE 6-continued

Strains including plasmids expressing polyketide synthase

| Strain | Base Strain | Plasmid |
|---|---|---|
| HB98 | HB42 | pDiPKS |
|  |  | pNPGa |
| HB102 | HB100 | pDIPKS |
| HB135 | HB100 | pDIPKSm2 |
| HB137 | HB106 | pDIPKSm2 |
| HB138 | HB110 | pDIPKSm2 |

Transgenic S. cerevisiae HB37, HB84, HB88, HB90, HB105 and HB130 were prepared from base strains indicated in Table 7 by transformation the base strains with the expression plasmids as shown below in Table 7. HB37 and HB88 each include and express AltPT and OAS. HB80, HB90 and HB105 each include and express AltPT and DiPKS. HB139 includes and expresses AltPT and DiPKS$^{G1516R}$.

TABLE 7

Strains including plasmids expressing cytosolic prenyltransferase

| Strain | Base Strain | Plasmid 1 | Plasmid 2 |
|---|---|---|---|
| HB37 | HB42 | pAltPT | pH1OAS |
| HB84 | HB42 | pAltPT | pDiPKS |
| HB88 | HB82 | pAltPT | pH1OAS |
| HB90 | HB82 | pAltPT | pDiPKS |
| HB105 | HB100 | pAltPT | pDiPKS |
| HB139 | HB106 | pAltPT | pDiPKSm2 |

Yeast Growth and Feeding Conditions

Yeast cultures were grown in overnight cultures with selective media to provide starter cultures. The resulting starter cultures were then used to inoculate triplicate 50 ml cultures to an optical density at having an absorption at 600 nm ("$A_{600}$") of 0.1. Table 6 shows details of the media used to grow each strain.

TABLE 8

Growth media used for Yeast

| Strain | Growth Media |
|---|---|
| HB13-HA | YNB + 2% glucose + 1.6 g/L 4DO* + 0.5 mM hexanoic Acid |
| HB13-No | YNB + 2% raffinose + 2% galactose + 1.6 g/L 4DO* |
| HB37-HA | YNB + 2% glucose + 1.6 g/L 4DO* + 0.5 mM hexanoic acid |
| HB84-No | YNB + 2% raffinose + 2% galactose + 1.6 g/L 4DO* |

In Table 8, "4DO*" refers to yeast synthetic dropout media supplement lacking leucine and uracil. With respect to strain HB13, "HB13-HA" refers to HB13 grown in the presence of 0.5 mM hexanoic acid and "HB13-No" refers to HB13 grown in the absence of hexanoic acid. In Table 8, "YNB" is a nutrient broth including the chemicals listed in the first two columns side of Table 9. The chemicals listed in the third and fourth columns of Table 9 are included in the 4DO* supplement.

TABLE 9

YNB Nutrient Broth and 4DO* Supplement

| Chemical | YNB Concentration | Chemical | 4DO* Concentration |
|---|---|---|---|
| Ammonium Sulphate | 5 g/L | Adenine | 18 mg/L |
| Biotin | 2 μg/L | p-Aminobenzoic acid | 8 mg/L |
| Calcium pantothenate | 400 μg/L | Alanine | 76 mg/ml |
| Folic acid | 2 μg/L | Arginine | 76 mg/ml |
| Inositol | 2 mg/L | Asparagine | 76 mg/ml |
| Nicotinic acid | 400 μg/L | Aspartic Acid | 76 mg/ml |
| p-Aminobenzoic acid | 200 μg/L | Cysteine | 76 mg/ml |
| Pyridoxine HCl | 400 μg/L | Glutamic Acid | 76 mg/ml |
| Riboflavin | 200 μg/L | Glutamine | 76 mg/ml |
| Thiamine HCL | 400 μg/L | Glycine | 76 mg/ml |
| Citric acid | 0.1 g/L | Histidine | 76 mg/ml |
| Boric acid | 500 μg/L | myo-Inositol | 76 mg/ml |
| Copper sulfate | 40 μg/L | Isoleucine | 76 mg/ml |
| Potassium iodide | 100 μg/L | Lysine | 76 mg/ml |
| Ferric chloride | 200 μg/L | Methionine | 76 mg/ml |
| Magnesium sulfate | 400 μg/L | Phenylalanine | 76 mg/ml |
| Sodium molybdate | 200 μg/L | Proline | 76 mg/ml |
| Zinc sulfate | 400 μg/L | Serine | 76 mg/ml |
| Potassium phosphate monobasic | 1.0 g/L | Threonine | 76 mg/ml |
| Magnesium sulfate | 0.5 g/L | Tryptophan | 76 mg/ml |
| Sodium chloride | 0.1 g/L | Tyrosine | 76 mg/ml |
| Calcium chloride | 0.1 g/L | Valine | 76 mg/ml |

Quantification of Metabolites

Intracellular metabolites were extracted from the *S. cerevisiae* cells using methanol extraction. One mL of liquid culture was spun down at 12,000×g for 3 minutes. 250 μL of the resulting supernatant was used for extracellular metabolite quantification. The resulting cell pellet was suspended in 200 μl of −40° C. 80% methanol. The mixture was vortexed and chilled on ice for 10 minutes. After chilling on ice for 10 minutes, the mixture was spun down at 15,000×g at 4° C. for 14 minutes. The resulting supernatant was collected. An additional 200 μl of −40° C. 80% methanol was added to the cell debris pellet and the mixture was vortexed and chilled for 10 minutes on ice. After chilling on ice for 10 minutes, the mixture was spun down at 15,000×g at 4° C. for 14 minutes. The resulting 200 μl of supernatant was added to the previously collected 200 μl of supernatant, providing a total of 400 μl of 80% methanol with intracellular metabolites.

Intracellular metabolites were quantified using high performance liquid chromatography ("HPLC") and mass spectrometry ("MS") methods. An Agilent 1260 autosampler and HPLC system connected to a ThermoFinnigan LTQ mass spectrometer was used. The HPLC system included a Zorbax Eclipse C18 2.1 μm×5.6 mm×100 mm column.

The metabolites were injected in 10 μl samples using the autosampler and separated on the HPLC using at a flow rate of 1 ml/min. The HPLC separation protocol was 20 mins total with (a) 0-2 mins of 98% Solvent A and 2% Solvent B; (b) 2-15 mins to get to 98% solvent B; (c) 15-16.5 minutes at 98% solvent B; (d) 16.5-17.5 minutes to get to 98% A; and (e) a final 2.5 minutes of equilibration at 98% Solvent A. Solvent A was acetonitrile+0.1% formic acid in MS water and solvent B was 0.1% formic acid in MS water.

After HPLC separation, samples were injected into the mass spectrometer by electrospray ionization and analyzed in positive mode. The capillary temperature was held at 380° C. The tube lens voltage was 30 V, the capillary voltage was 0 V, and the spray voltage was 5 kV. After HPLC-MS/MS, CBG was analyzed as a parent ion at 317.2 and a daughter ion at 193.1, while meCBG was analyzed as a parent ion of 331.2. Similarly, after HPLC-MS/MS, olivetol was analyzed as a parent ion at 181.2 and a daughter ion at 111, while methyl-olivetol analyzed as a parent ion at 193.2 and a daughter ion at 125.

Different concentrations of known standards were injected to create a linear standard curve. Standards for CBG and meCBG were purchased from Toronto Research Chemicals. The meCBG was custom prepared by request because Toronto Research Chemicals had not synthesized that chemical prior to being asked for the standard. Olivetol and methyl-olivetol standards were purchased from Sigma Aldrich.

Effects of Hexanoic Acid on *S. cerevisiae* Growth

The genes coding for enzymes required for hexanoic acid biosynthesis were not introduced into *S. cerevisiae*. Instead, in yeast cells including the OAS gene, such as HB37, hexanoic acid was included in the growth media.

Figure 12:
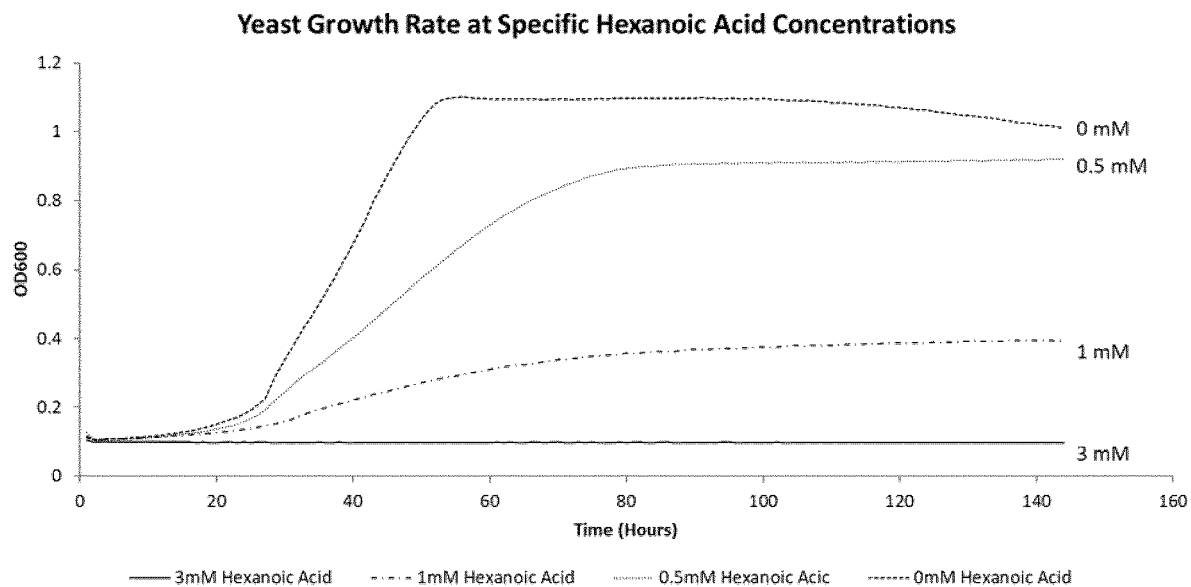
FIG. 12 shows *S. cerevisiae* growth at different concentrations of hexanoic acid.

FIG. 12 shows the effect of hexanoic acid supplementation on growth of *S. cerevisiae*. HB13 was cultured in YNB+2% glucose+1.6 g/L 4DO*+0.5 mM hexanoic acid. Hexanoic acid was added at 36 hours of culture. The hexanoic acid was added to separate culture samples at concentrations of 0, 0.5, 1.0 and 3.0 mM. Hexanoic acid is toxic to *S. cerevisiae*. Decreased growth was observed in the presence of hexanoic acid. The magnitude of the decrease in *S. cerevisiae* growth corresponds to the concentration of hexanoic acid in the growth media. The $A_{600}$ value of culture suspensions quantifies the growth rate, which is shown at hexanoic acid concentrations of 0, 0.5, 1.0 and 3.0 mM in FIG. 12.

In the presence of 0.5 mM hexanoic acid, HB13 and HB37 were grown for 96 hours with samples taken at the 24 h, 36 h, 48 h, 60, 72 h, 84 h and 96 h points. In the absence of hexanoic acid, HB13 and HB84 were grown and a single time point was taken at 72 hours. HB13 was used as a control in both experiments. The growth media are described above in relation to Tables 8 and 9.

TABLE 10

HB13 and HB37 (0.5 mM hexanoic acid) and
HB13 and HB84 (no hexanoic acid) growth

| Time Point | HB13-HA | HB13-No | HB37-HA | HB84-No |
|---|---|---|---|---|
| 24 h | 5.33 | (no data) | 3.33 | (no data) |
| 36 h | 5.80 | (no data) | 3.43 | (no data) |
| 48 h | 4.67 | (no data) | 3.33 | (no data) |
| 60 h | 6.07 | (no data) | 3.53 | (no data) |
| 72 h | 8.96 | 10.7 | 4.48 | 6.9 |
| 84 h | 7.23 | (no data) | 4.13 | (no data) |
| 96 h | 8.28 | (no data) | 4.33 | (no data) |

As shown in Table 10, HB84, outgrew HB37. In addition, HB84 does not require hexanoic acid to produce meCBG, while HB37 requires hexanoic acid to produce CBG. Similarly, HB13 showed better growth at 72 h in the absence of hexanoic acid compared with the presence of 0.5 mM hexanoic acid, consistent with the data shown in FIG. 12.

Figure 13:
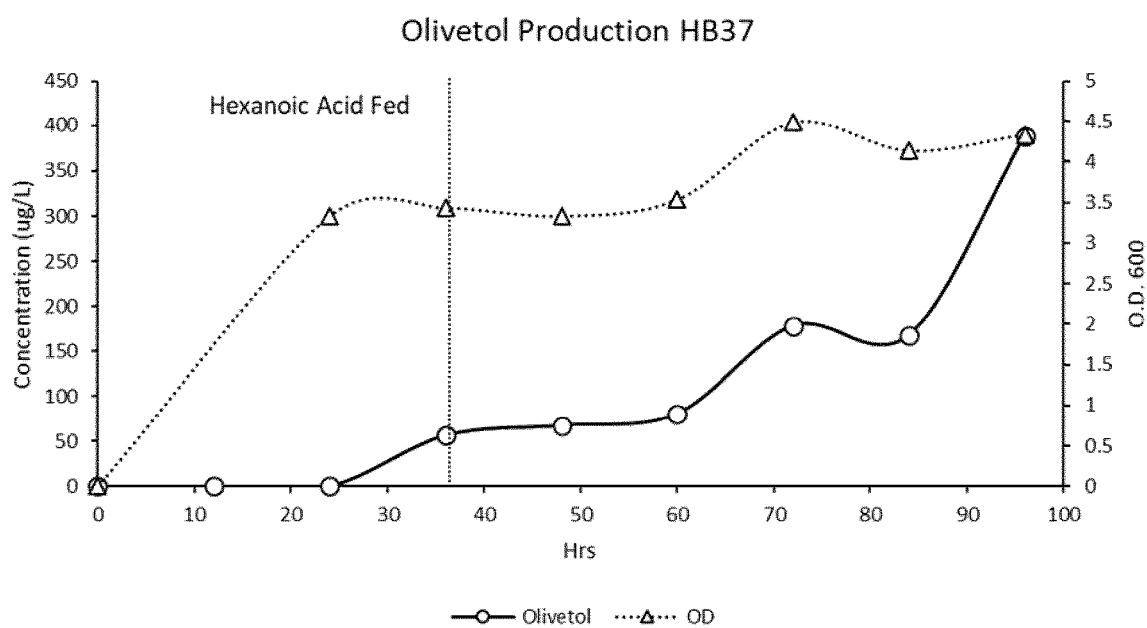
FIG. 13 shows *S. cerevisiae* growth and olivetol production before and after hexanoic acid is introduced.
Figure 14:
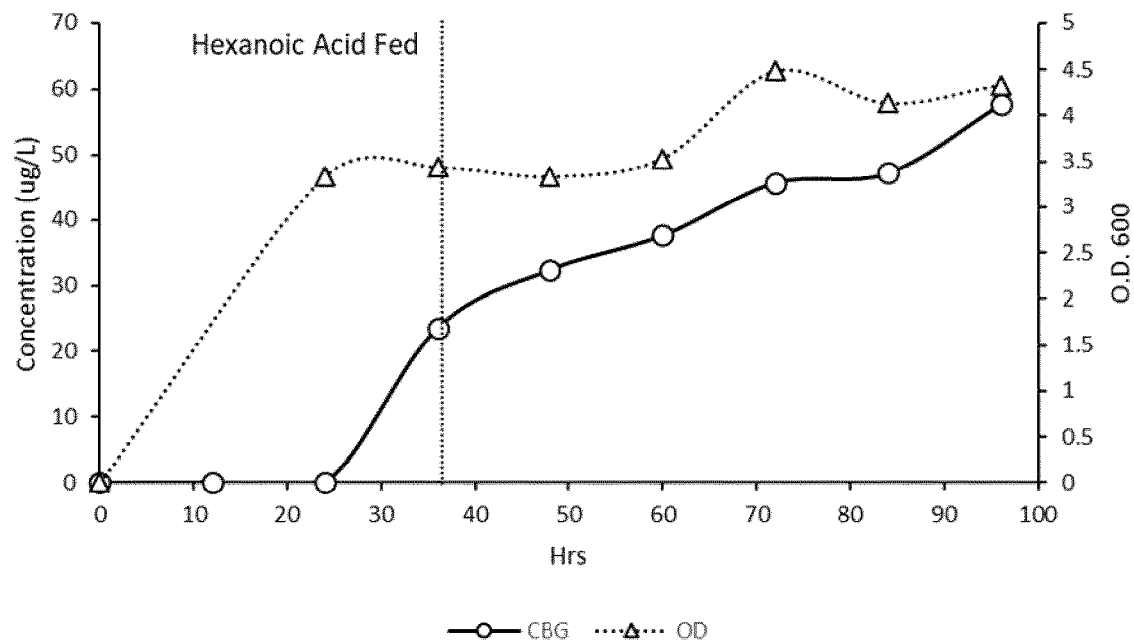
FIG. 14 shows yeast growth and CBG production before and after hexanoic acid is introduced.
Figure 15:
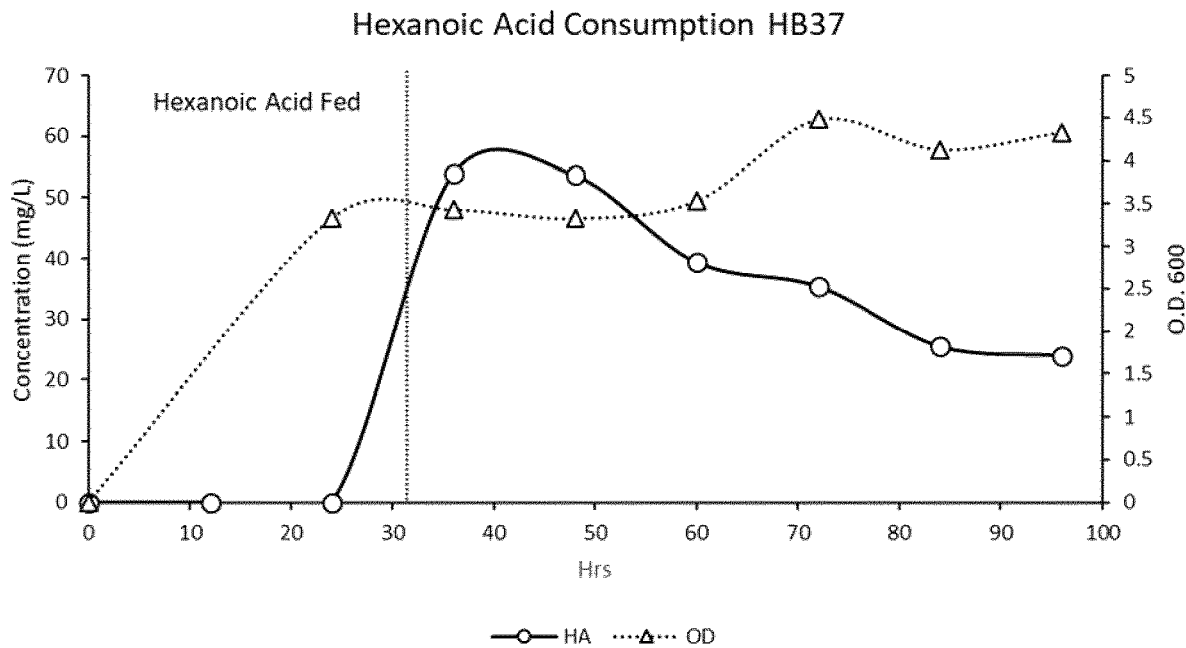
FIG. 15 shows yeast growth and hexanoic acid consumption in *S. cerevisiae* before and after hexanoic acid is introduced.

FIGS. 13 to 15 each show the $A_{600}$ values of the HB37 culture listed in Table 10 (dashed lines with triangle data points). In addition, each of FIGS. 13 to 15 shows another data series by solid lines with circle data points.

FIG. 13 shows olivetol production (μg olivetol per L of culture media) in solid lines with circle data points.

FIG. 14 shows CBG production (μg CBG per L of culture media) in solid lines with circle data points.

FIG. 15 shows hexanoic acid present in the culture (mg hexanoic acid per L of culture media) in solid lines with circle data points.

Together, FIGS. 13 to 15 are consistent with a dioxic shift occurring at between 50 and 60 hours. The dioxic shift includes a metabolic shift from glucose catabolism to acetic acid and ethanol catabolism. With the dioxic shift, many secondary metabolic pathways become more active, and the AltPT and OAS activities similarly increase.

FIGS. 12 to 15 and Table 10 show data consistent with hexanoic acid toxicity not appearing to have been mitigated to any great extent by consumption of hexanoic acid to produce phytocannabinoids until the hexanoic acid levels dropped between 50 and 60 hours, then continued to drop. As shown in FIGS. 12 and 13, olivetol and CBG were being produced beginning with the introduction of hexanoic acid. However, while CBG was produced and the hexanoic acid was converted to olivetol, the $A_{600}$ of the culture did not increase drastically as the olivetol and CBG were produced. The $A_{600}$ increased only after the hexanoic acid began to deplete as shown in FIG. 15 between 50 and 60 hours. The depletion is a result at least in part of olivetol production. However, no significant increase in culture $A_{600}$ was observed during production of olivetol and CBG following introduction of hexanoic acid at 36 hours, until hexanoic acid concentrations were depleted.

Expression of Cytosolic and Membrane-Bound Prenyltransferase

C. sativa prenyltransferase is a membrane-bound plant protein while AltPT is a cytosolic bacterial protein. Application of AltPT in S. cerevisiae rather than C. sativa prenyltransferase provides greater protein expression levels in the yeast cells. Each of HB1, HB6, HB7, and HB13 as shown in Table 5 were grown in YNB, 2% glucose, and 1.6 g/L 4DO* overnight. The resulting culture, after being grown overnight, was normalized to 1.0 $A_{600}$ and then grown for four hours in YNB, 2% glucose, and 1.6 g/L 4DO*. Fluorescence was measured from each culture suspension using a BD Acuri C6 flow cytometer.

HB1 expresses green fluorescent protein ("GFP"). Each of HB6 and HB7 express a GFP-prenyltransferase fusion protein. Neither HB6 nor HB7 include genes from the pDiPKS or pH1OAS plasmids. Correspondingly neither HB6 nor HB7 expresses a polyketide synthase gene or includes all the enzymes to complete the biosynthetic pathways in any of FIG. 4, 6, or 9.

Figure 16:
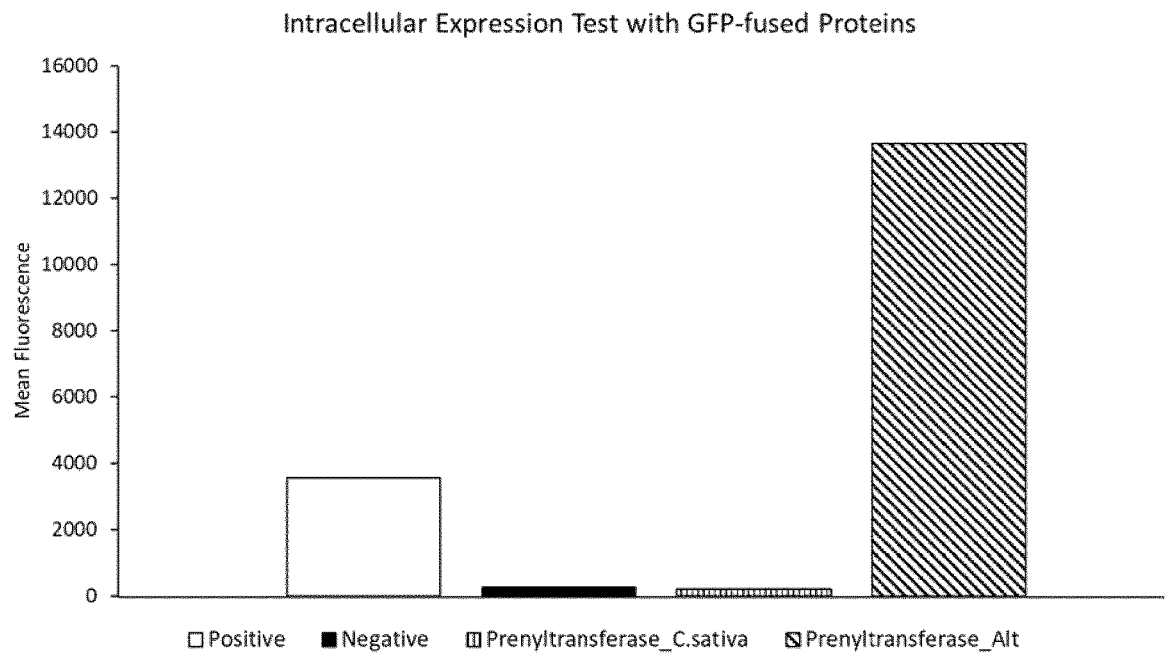
FIG. 16 shows cytosolic expression in *S. cerevisiae* of *C. sativa* membrane-bound prenyltransferase and of AltPT.

FIG. 16 shows mean fluorescence levels from cell culture samples of HB13 ("negative"), HB1 ("positive"), HB6 ("Prenyltransferase_C. sativa"), and HB7 ("Prenyltransferase_Alt"). The fluorescence levels correspond to protein expression levels, showing relative expression levels of the C. sativa prenyltransferase by HB6 and of AltPT by HB7. The ordinarily membrane-bound C. sativa prenyltransferase has low expression in the cytosol of S. cerevisiae. The cytosolic AltPT is expressed in the cytosol of S. cerevisiae at a higher level than the ordinarily membrane-bound C. sativa prenyltransferase.

Example I

The yeast strain HB37 as described above in Table 7 was cultured in the YNB+2% glucose+1.6 g/L 4DO*+0.5 mM hexanoic acid media. Production of CBG from glucose and hexanoic acid was observed, demonstrating direct production in yeast of CBG.

CBG was produced at a concentration of 10 µg/L with 0.85 mM hexanoic acid. After optimizing the hexanoic acid feeding and growth conditions, 50 µg/L of CBG was produced with 0.5 mM hexanoic acid.

Example II

The yeast strain HB84 as described above in Table 7 was cultured in the YNB+2% raffinose+2% galactose+1.6 g/L 4DO* media. Production of meCBG from raffinose and galactose was observed, demonstrating direct production in yeast of meCBG without hexanoic acid. The meCBG was produced at 42.63 mg/L. The yield of meCBG produced by HB84 represents a nearly 1,000× increase compared with the yield of CBG from HB37.

Figure 17:
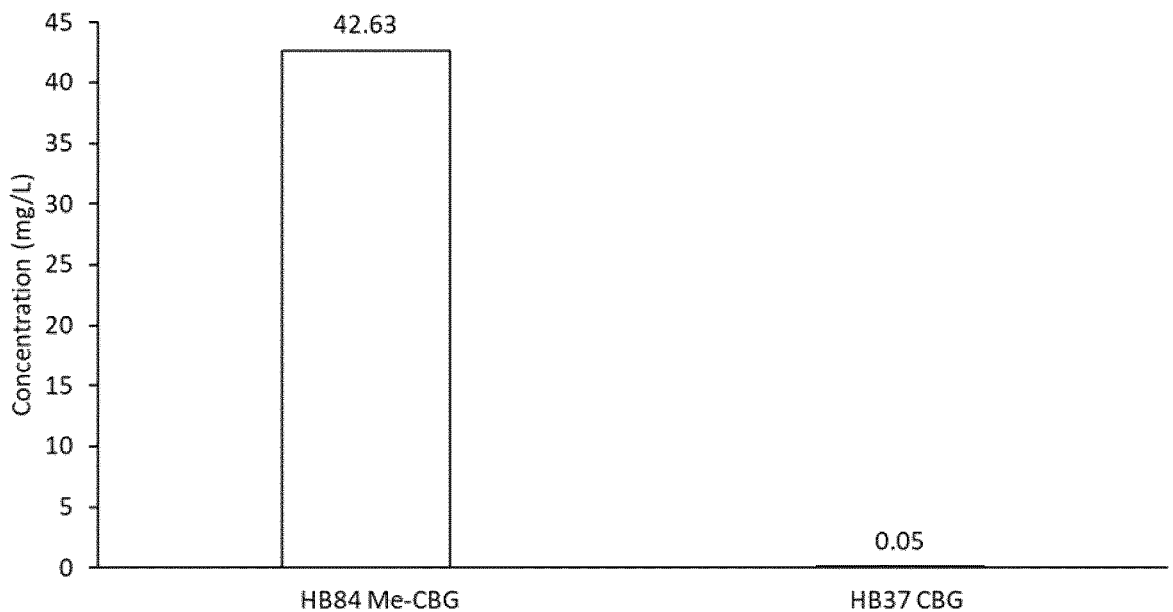
FIG. 17 shows production in *S. cerevisiae* of CBG with *C. sativa* OAS and AltPT, and of meCBG with DiPKS and AltPT.

FIG. 17 shows the yields of meCBG from HB84 ("HB_CBG_me") in Example II compared with yields of CBG from HB37 ("CBG_C_sativa") in Example I.

Example III

The yeast strain HB80 as described above in Table 6 was cultured in the YNB+2% raffinose+2% galactose+1.6 g/L 4DO* media. Production of methyl-olivetol from raffinose and galactose was observed, demonstrating direct production in yeast of methyl-olivetol without conversion to meCBG, as HB80 lacks AltPT. The methyl-olivetol was produced at concentrations of 3.259 mg/L Conversion to meCBG would be expected to follow in a strain that includes the features of HB80 and AltPT or another prenyltransferase, such as HB139.

Example IV

The yeast strain HB80A as described above in Table 6 was cultured in the YNB+2% raffinose+2% galactose+1.6 g/L 4DO* media. Production of both olivetol and methyl-olivetol from raffinose and galactose, catalyzed by DiPKS$^{G1516D;\ G1518A}$ was observed. This data demonstrates direct production in yeast of both olivetol and methyl-olivetol without inclusion of hexanoic acid. Conversion to CBG and meCBG did not follow as HB80A lacks AltPT. Conversion to CBG and meCBG would be expected to following a strain that included the features of HB80A and AltPT or another prenyltransferase, such as by transforming HB80A with pAltPT.

Figure 18:
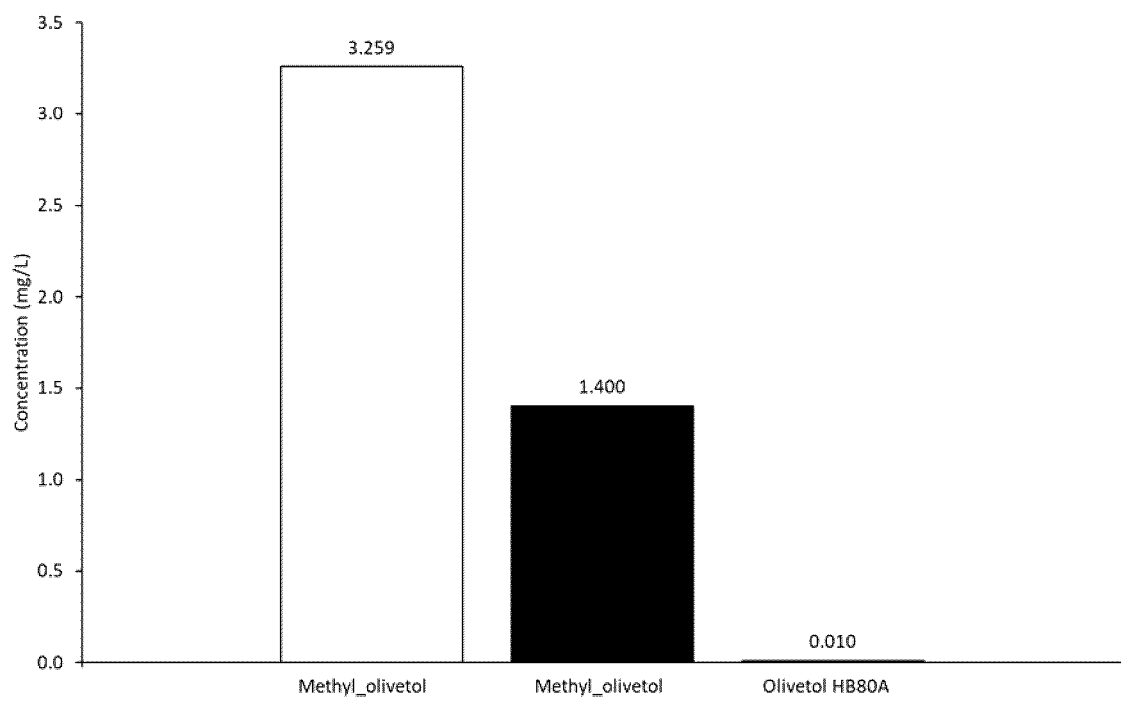
FIG. 18 shows production of methyl-olivetol by DiPKS, and of both methyl-olivetol and olivetol by DiPKS$^{G1516D;\ G1518A}$.

FIG. 18 shows concentrations of methyl-olivetol produced by HB80 ("Methyl_Olivetol HB80") from Example III, and of both olivetol and methyl-olivetol produced by HB80A ("Methyl_Olivetol HB80A" and "Olivetol HB80A", respectively). Samples of culture were taken at 72 hours. HB80A produces a majority of methyl-olivetol (1.4 mg methyl-olivetol per L of culture compared with 0.010 mg per L of culture olivetol), and produced less methyl-olivetol and olivetol combined than methyl-olivetol that is produced by HB80 (3.26 mg/L).

Example V

The yeast strain HB98 as described above in Table 6 was cultured in the YNB+2% raffinose+2% galactose+1.6 g/L 4DO* media. Production of methyl-olivetol from raffinose and galactose, catalyzed by DiPKS, was observed. This data demonstrates increased methyl-olivetol production compared with HB80 as described in Example III, and also without inclusion of hexanoic acid. Conversion to meCBG did not follow as HB80A lacks AltPT. Conversion to meCBG would be expected to following a strain that included the features of HB98 and AltPT or another prenyltransferase, such as by transforming HB98 with pAltPT or by transforming HB84 with pNPGa.

Figure 19:
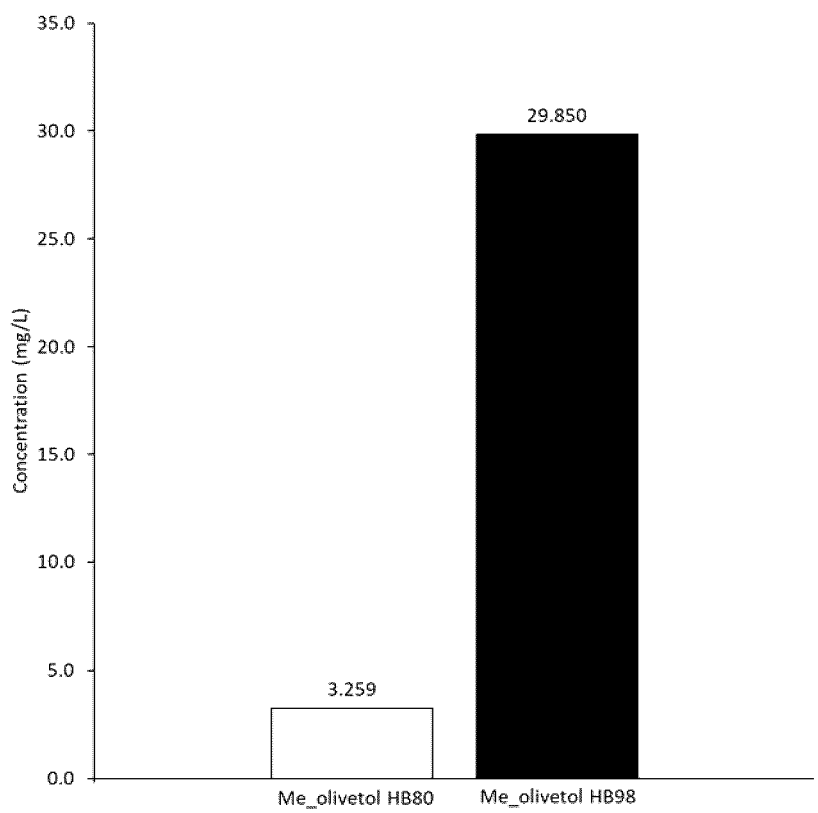
FIG. 19 shows production of methyl-olivetol by DiPKS in two separate strains of *S. cerevisiae*.

FIG. 19 shows concentrations of methyl-olivetol produced by HB80 ("Methyl_Olivetol HB80") from Example III, and of methyl-olivetol produced by HB98 ("Methyl_Olivetol HB98") from Example V. Samples of culture were taken at 72 hours. HB98 produced 29.85 mg/L methyl-olivetol while HB80 produced only 3.26 mg methyl-olivetol per L of culture. HB98 produced nearly 10× as much methyl-olivetol as HB80.

Example VI

The yeast strain HB102 as described above in Table 6 was cultured in the YNB+2% raffinose+2% galactose+1.6 g/L 4DO* media. Production of methyl-olivetol from raffinose and galactose was observed, demonstrating an increased production in yeast of methyl-olivetol at 42.44 mg/L as compared to strain HB98, which produced only 29.85 mg/L methyl-olivetol. This demonstrated that the genomically integrated version of NpgA is functional. Conversion to meCBG did not follow as HB102 lacks AltPT. Conversion to meCBG would be expected to following a strain that included the features of HB102 and AltPT or another prenyltransferase, such as HB105.

Figure 20:
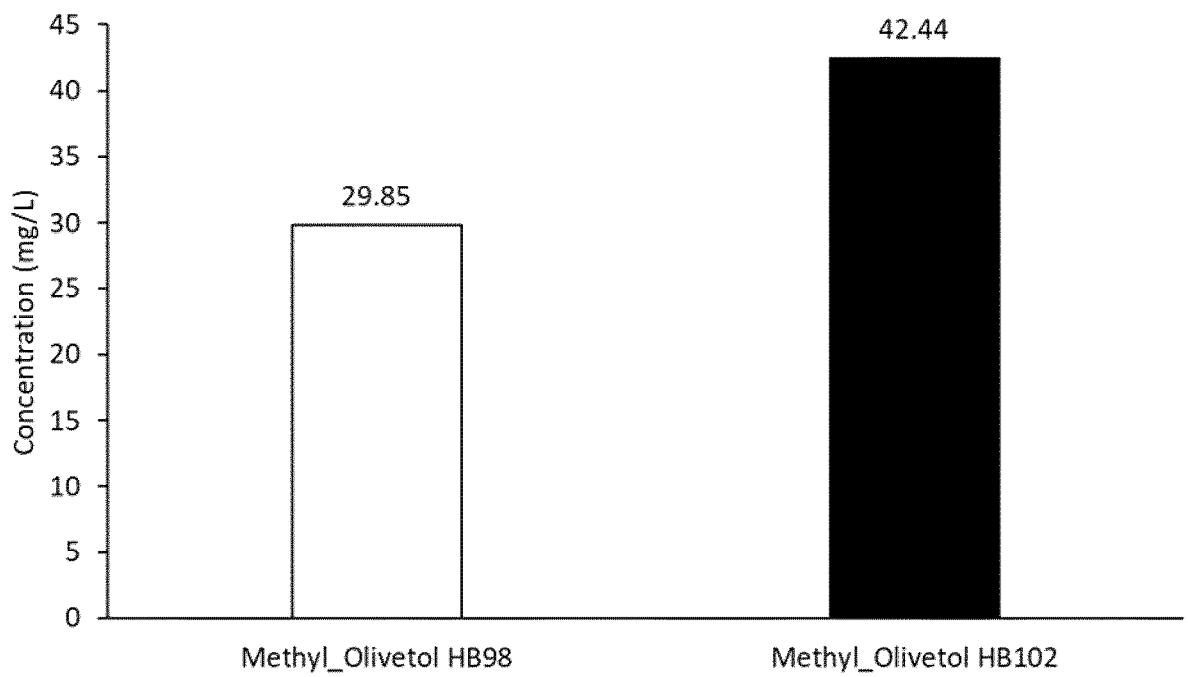
FIG. 20 shows production of methyl-olivetol by DiPKS in two separate strains of *S. cerevisiae*.

FIG. 20 shows concentrations of methyl-olivetol produced by HB102 ("Methyl_olivetol HB102") from Example VI as compared to the production of methyl-olivetol from strain HB98 in Example V ("Methyl_olivetol HB98").

Example VII

The yeast strain HB105 as described above in Table 7 was cultured in the YNB+2% raffinose+2% galactose+1.6 g/L 4DO* media. Production of meCBG from raffinose and galactose was observed at titres of 66.3 mg/L, demonstrating an increased production of meCBG compared with the yield of CBG from HB84. This demonstrates the positive effect of the PDH bypass and the integrated NpgA on meCBG titres.

Figure 21:
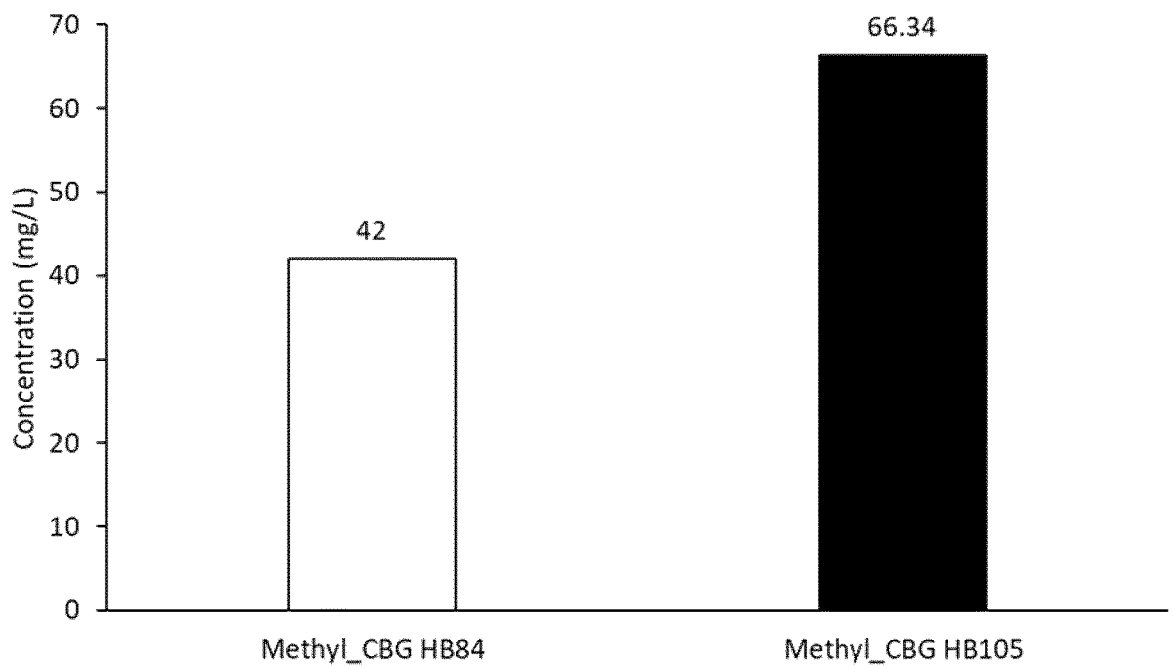
FIG. 21 shows production of meCBG by AltPT in two separate strains of *S. cerevisiae*.

FIG. 21 shows titres of meCBG produced by HB105 ("Methyl_CBG HB105") from Example VII as compared to the production of meCBG from strain HB84 in Example II ("Methyl_CBG HB84").

Example VIII

The yeast strain HB135 as described above in Table 6 was cultured in the YNB+2% raffinose+2% galactose+1.6 g/L 4DO* media. Production of olivetol from raffinose and galactose was observed, demonstrating an production in yeast of olivetol without any hexanoic acid and at high titres of 49.24 mg/L and no production of methyl-olivetol. This is comparable to the production of methyl-olivetol by strain HB102 demonstrating that the mutation of DIPKS was effective in production of Olivetol as opposed to methyl-Olivetol. Conversion to CBG and meCBG did not follow as HB135 lacks AltPT. Conversion to CBG and meCBG would be expected to following a strain that includes the features of HB135 and AltPT or another prenyltransferase.

Figure 22:
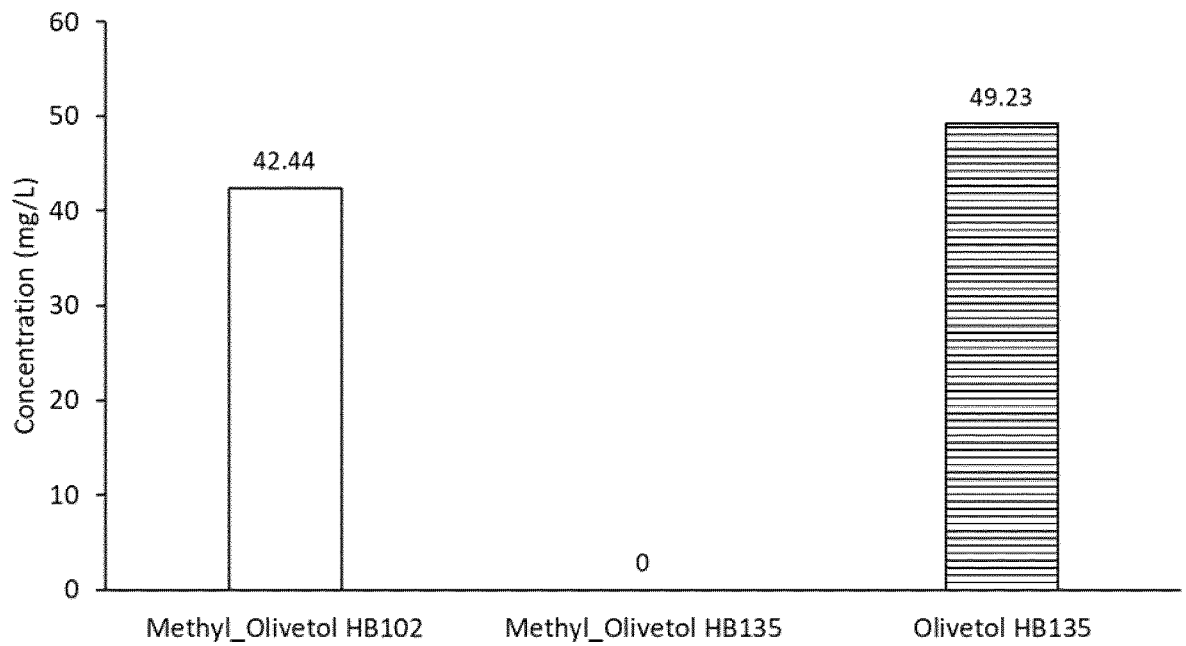
FIG. 22 shows production of methyl-olivetol by DiPKS, and of both methyl-olivetol and olivetol by DiPKS$^{G1516R}$ in two separate strains of *S. cerevisiae*.

FIG. 22 shows concentrations of olivetol and methyl-olivetol produced by HB135 ("Methyl_olivetol HB135" and "Olivetol HB135 respectively) from Example VIII as compared to the production of methyl-olivetol from strain HB102 in Example VI ("Methyl_olivetol HB102").

Example IX

The yeast strains HB137 and HB138 as described above in Table 6 were cultured in the YNB+2% raffinose+2% galactose+1.6 g/L 4DO* media. Production of olivetol from raffinose and galactose was observed in both strains. Strain HB137 produced 61.26 mg/L of olivetol and strain HB138 produced 74.26 mg/L of olivetol demonstrating the positive effect of Maf1 integration and Acc1-promoter swap on olivetol titres. Conversion to CBG did not follow as HB137 and HB138 lack AltPT. Conversion to CBG would be expected to following strains that included the features of HB137 and HB138 and AltPT or another prenyltransferase.

Figure 23:
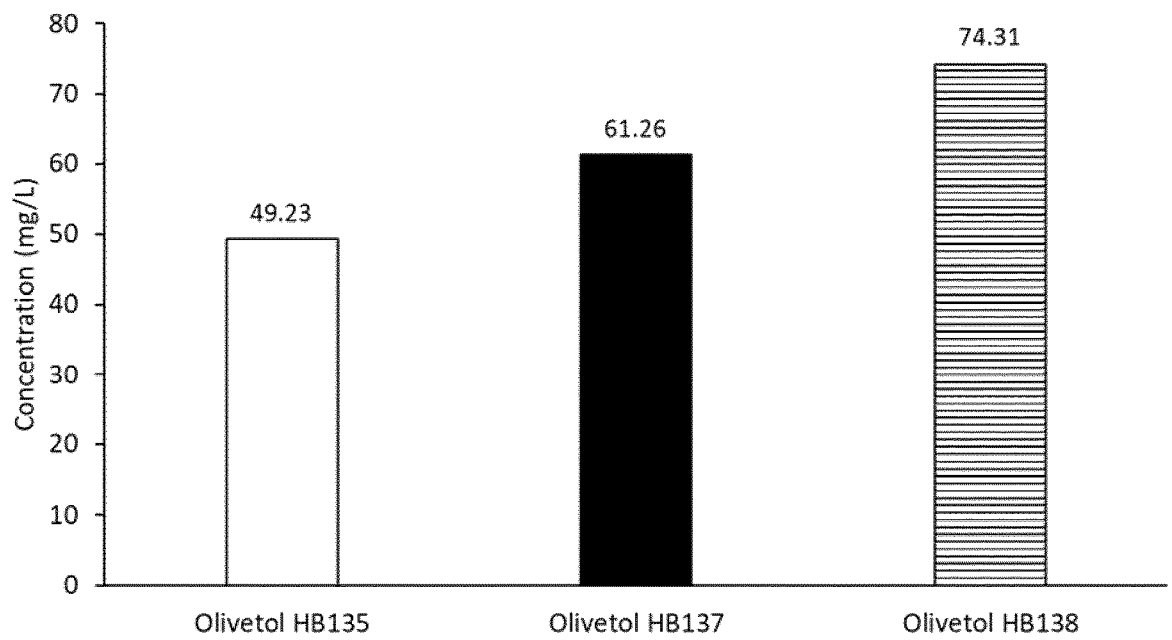
FIG. 23 shows production of olivetol by DiPKS$^{G1516R}$, in three separate strains of *S. cerevisiae*.

FIG. 23 shows the concentrations of olivetol produced by HB137 ("Olivetol HB137") and HB138 ("Olivetol HB138") from Example IX as compared to olivetol produced by HB135 ("Olivetol HB135") in Example VIII.

Example X

The yeast strain HB139 as described above in Table 7 was cultured in the YNB+2% raffinose+2% galactose+1.6 g/L 4DO* media. Production of CBG from raffinose and galactose directly was observed at titres of 0.03 mg/L. This is much lower than the titre of meCBG produced by strain HB105.

Figure 24:
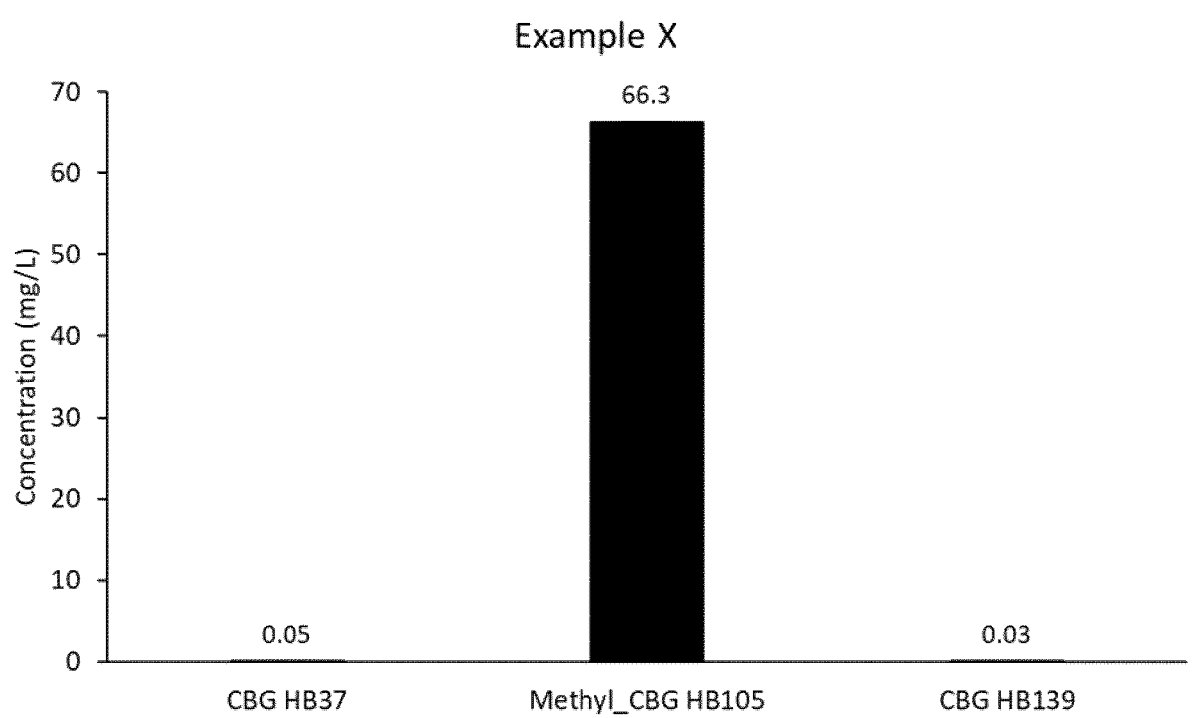
FIG. 24 shows production of CBG by *C. sativa* OAS and AltPT, meCBG by DiPKS and AltPT, and CBG by DiPKS$^{G1516R}$ and AltPT in three strains of *S. cerevisiae*.

FIG. 24 shows the concentration of CBG produced by HB139 directly from galactose and raffinose ("CBG HB139") from Example X as compared to the production of meCBG ("meCBG HB105") by HB105 from Example VII and production of CBG by HB37 ("CBG HB37") in Example I.

REFERENCES

M. B. Austin, T. Saito, M. E. Bowman, S. Haydock, A. Kato, B. S. Moore, R. R. Kay and Noel, J. P. (2006) "Biosynthesis of *Dictyostelium discoideum* differentiation-inducing factor by a hybrid type I fatty acid-type III polyketide synthase" *Nature chemical biology*, 2(9), 494.

S. W. Baba, G. I. Belogrudov, J. C. Lee, P. T. Lee, J. Strahan, J. N. Shepherd and C. F. Clarke (2003) "Yeast Coq5 C-Methyltransferase Is Required for Stability of Other Polypeptides Involved in Coenzyme Q Biosynthesis" *The Journal of Biological Chemistry*, 279(11): 10052-10059.

C. Chambon, V. Ladeveze, A. Oulmouden, M. Servouse and E Karst (1990) "Isolation and properties of yeast mutants affected in farnesyl diphosphate synthetase" *Curr Genet*, 18: 41-46.

M. J. C. Fischer, S. Meyer, P. Claudel, M. Bergdoll and F. Karst (2011) "Metabolic Engineering of Monoterpene Synthesis in Yeast" *Biotechnology and Bioengineering*, 108(8): 1883-1892.

Bai Flagfeldt, D., Siewers, V., Huang, L. and Nielsen, J. (2009) "Characterization of chromosomal integration sites for heterologous gene expression in *Saccharomyces cerevisiae*" Yeast, 26, 545-551.

S. Gagne. "The Polyketide Origins of Cannabinoids in *Cannabis Sativa*." Diss. U of Saskatchewan, 2013.

R. Ghosh, A. Chhabra, P. A. Phatale, S. K. Samrat, J. Sharma, A. Gosain, D. Mohanty, S. Saran and R. S. Gokhale (2008) "Dissecting the Functional Role of Polyketide Synthases in *Dictyostelium discoideum* biosynthesis of the differentiation regulating factor 4-methyl-5-pentylbenzene-1,3-diol" *Journal of Biological Chemistry*, 283(17), 11348-11354.

C. Huang, H. Wu, Z. Liu, J. Cai, W. Lou and M. Zong (2012) "Effect of organic acids on the growth and lipid accumulation of oleaginous yeast *Trichosporon fermentans*" *Biotechnology for Biofuels*, 5:4.

Z. Hunkova and Z. Fencl (1977) "Toxic Effects of Fatty Acids on Yeast Cells: Dependence of Inhibitory Effects on Fatty Acid Concentration" *Biotechnology and Bioengineering*, XIX: 1623-1641.

J. Kaminska, K. Grabinska, M. Kwapisz, J. Sikora, W. J. Smagowicz, G. Palamarczyk, T. Zoladek and M. Boguta, "The isoprenoid biosynthetic pathway in *Saccharomyces cerevisiae* is affected in a maf1-1 mutant with altered tRNA synthesis" (2002) *FEMS Yeast Research* 2: 31-37.

D. Ro, E. M. Paradise, M. Ouellet, K. J. Fisher, K. L. Newman, J. M. Ndungu, K. A. Ho, R. A. Eachus, T. S. Ham, J. Kirby, M. C. Y. Chang, S. T. Withers, Y. Shiba, R. Sarpong and J. D. Keasling (2006) "Production of the antimalarial drug precursor artemisinic acid in engineered yeast" *Nature Letters* 440: 930-943.

S. Shi, Y. Chen, V. Siewers and J. Nielsen, "Improving Production of Malonyl Coenzyme A-Derived Metabolites by Abolishing Snf1-Dependent Regulation of Acc1" (2014) *American Society for Microbiology* 5(3): e01130-14. doi: 10.1128/mBio.01130-14.

Y. Shiba, E. M. Paradise, J. Kirby, D. Ro and J. D. Keasling "Engineering of the pyruvate dehydrogenase bypass in *Saccharomyces cerevisiae* for high-level production of isoprenoids" (2007) *Metabolic Engineering* 9: 160-168.

M. A. Skiba, A. P. Sikkema, W. D. Fiers, W. H. Gerwick, D. H. Sherman, C. C. Aldrich and J. L. Smith "Domain Organization and Active Site Architecture of a Polyketide Synthase C-methyltransferase" *ACS Chem. Biol.*; Just Accepted Manuscript•DOI: 10.1021/acschembio.6b00759•Publication Date (Web): 10 Oct. 2016. Downloaded from http://pubs.acs.org on Oct. 11, 2016.

M. Telloa, T. Kuzuyamab, L. Heidec, J. P. Noela, and S. B. Richarda (2008) "The ABBA family of aromatic prenyltransferases: broadening natural product diversity" *Cell Mol Life Sci.*; 65(10): 1459-1463.

C. A. Viegas, M. F. Rosa, I. Sa-Correia and J. M. Novais "Inhibition of Yeast Growth by Octanoic and Decanoic Acids Produced during Ethanolic Fermentation" (1989) *Applied and Environmental Microbiology* 55(1): 21-28.

Examples Only

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art without departing from the scope, which is defined solely by the claims appended hereto.

What is claimed is:

1. A method of producing phytocannabinoids or phytocannabinoid analogues, the method comprising the steps of:
   (i) providing a yeast cell comprising a first polynucleotide comprising bases 523 to 9966 of SEQ ID NO: 38, coding for a polyketide synthase enzyme from *D. discoideum* comprising a mutation at G1516R (DiPKS$^{G1516R}$) that reduces activity at an active site of a C-Met domain as compared to wild type DiPKS from *D. discoideum*, and a second polynucleotide coding for a cytosolic prenyltransferase enzyme, wherein:
   the polyketide synthase enzyme produces at least one precursor chemical from malonyl-CoA, the precursor chemical having structure I:

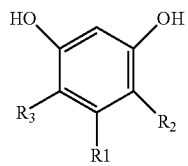

I wherein, on structure I, R1 is an alkyl group with a chain length of 1, 2, 3, 4, or 5 carbons, R2 is H, carboxyl, or methyl, and R3 is H, carboxyl, or methyl;
   the polyketide synthase enzyme is not native to *C. sativa*; and
   the cytosolic prenyltransferase enzyme prenylates the at least one precursor chemical, providing at least one species of phytocannabinoid or phytocannabinoid analogue; and (ii) propagating the yeast cell under suitable conditions to provide a yeast cell culture, thereby producing phytocannabinoids or phytocannabinoid analogues from the at least one precursor chemical.

2. The method of claim 1 wherein the at least one precursor chemical comprises a precursor chemical wherein R1 is an alkyl group with a chain length of 3 carbons, R2 is H, and R3 is H.

3. The method of claim 1 wherein the at least one precursor chemical comprises a precursor chemical wherein R1 is an alkyl group with a chain length of 3 carbons, R2 is carboxyl, and R3 is H.

4. The method of claim 1 wherein the at least one precursor chemical comprises a precursor chemical wherein R1 is an alkyl group with a chain length of 3 carbons, R2 is methyl, and R3 is H.

5. The method of claim 1 wherein the at least one precursor chemical comprises a precursor chemical wherein R1 is an alkyl group with a chain length of 3 carbons, R2 is carboxyl, and R3 is methyl.

6. The method of claim 1 wherein the at least one precursor chemical comprises a precursor chemical wherein R2 is a methyl group and the at least one species of phytocannabinoid or phytocannabinoid analogue comprises a methylated phytocannabinoid analogue.

7. The method of claim 1 wherein:
   the DiPKS polyketide synthase enzyme mutation prevents methylation of the at least one precursor chemical, resulting in the at least one precursor chemical having a hydrogen R2 group and a hydrogen R3 group; and
   the at least one species of phytocannabinoid or phytocannabinoid analogue comprises a decarboxylated phytocannabinoid or phytocannabinoid analogue.

8. The method of claim 1 wherein the yeast cell comprises a phosphopantetheinyl transferase polynucleotide coding for a phosphopantetheinyl transferase enzyme that increases the activity of the DiPKS polyketide synthase enzyme.

9. The method of claim 8 wherein the phosphopantetheinyl transferase comprises NpgA phosphopantetheinyl transferase enzyme from *A. nidulans*.

10. The method of claim 9 wherein the phosphopantetheinyl transferase polynucleotide comprises a coding sequence for the NpgA phosphopantetheinyl transferase enzyme from *A. nidulans* with a primary structure having between 80% and 100% amino acid residue sequence identity with a protein coded for by a reading frame defined by bases 1170 to 2201 of SEQ ID NO: 10.

11. The method of claim 1 wherein the polyketide synthase enzyme comprises an active site for synthesizing the at least one precursor chemical from malonyl-CoA without a longer chain ketyl-CoA.

12. The method of claim 11 wherein the at least one precursor chemical comprises a pentyl group at R1 and the at least one species of phytocannabinoid or phytocannabinoid analogue comprises a pentyl-phytocannabinoid or methylated pentyl-phytocannabinoid analogue.

13. The method of claim 12 wherein the at least one precursor chemical comprises at least one of olivetol olivetolic acid, methyl-olivetol, or methyl-olivetolic acid, and the at least one species of phytocannabinoid or phytocannabinoid analogue comprises at least one of CBG, CBGa, meCBG, or meCBGa.

14. The method of claim 1 wherein the cytosolic prenyltransferase enzyme comprises an NphB prenyltransferase enzyme from *Streptomyces* sp CL190.

15. The method of claim 14 wherein the second polynucleotide comprises a coding sequence for NphB prenyltransferase enzyme from *Streptomyces* sp CL190 with a primary structure having between 80% and 100% amino acid residue sequence identity with a protein coded for by a reading frame defined by bases 987 to 1913 of SEQ ID NO: 44.

16. The method of claim 1 wherein the at least one precursor chemical comprises a precursor chemical wherein R1 is an alkyl group with a chain length of 5 carbons, R2 is H, and R3 is H.

17. The method of claim 1 wherein the at least one precursor chemical comprises a precursor chemical wherein R1 is an alkyl group with a chain length of 5 carbons, R2 is carboxyl, and R3 is H.

18. The method of claim 1 wherein the at least one precursor chemical comprises a precursor chemical wherein R1 is an alkyl group with a chain length of 5 carbons, R2 is methyl, and R3 is H.

19. The method of claim 1 wherein the at least one precursor chemical comprises a precursor chemical wherein R1 is an alkyl group with a chain length of 5 carbons, R2 is carboxyl, and R3 is methyl.

20. The method of claim 1 wherein the yeast cell comprises a genetic modification to increase available geranylpyrophosphate.

21. The method of claim 20 wherein the genetic modification comprises an inactivation of the Erg20 enzyme.

22. The method of claim 21 wherein the yeast cell comprises an Erg20 polynucleotide including a coding sequence for Erg20$^{K197E}$ with a primary structure having between 80% and 100% amino acid residue sequence identity with a protein coded for by a reading frame defined by SEQ ID NO: 3.

23. The method of claim 1 wherein the yeast cell comprises a genetic modification to increase available malonyl-CoA.

24. The method of claim 23 wherein the genetic modification comprises increased expression of Maf1.

25. The method of claim 24 wherein the yeast cell comprises a Maf1 polynucleotide including a coding sequence for Maf1 with a primary structure having between 80% and 100% amino acid residue sequence identity with a protein coded for by a reading frame defined by bases 936 to 2123 of SEQ ID NO: 8.

26. The method of claim 23 wherein the genetic modification comprises a modification for increasing cytosolic expression of an aldehyde dehydrogenase and an acetyl-CoA synthase.

27. The method of claim 26 wherein the yeast cell comprises an Acs polynucleotide including a coding sequence for Acs$^{L641P}$ from *S. enterica* with a primary structure having between 80% and 100% amino acid residue sequence identity with a protein coded for by a reading frame defined by bases 3938 to 5893 of SEQ ID NO: 4, and a coding sequence for Ald6 from *S. cerevisiae* with a primary structure having between 80% and 100% amino acid residue sequence identity with a protein coded for by a reading frame defined by bases 1494 to 2999 of SEQ ID NO 4.

28. The method of claim 23 wherein the genetic modification comprises a modification for increasing malonyl-CoA synthase activity.

29. The method of claim 28 wherein the yeast cell comprises an Acc1 polynucleotide including a coding sequence for Acc1$^{S659A;\ S1157A}$ from *S. cerevisiae*.

30. The method of claim 29 wherein the Acc1 polynucleotide includes a coding sequence for the Acc1$^{S659A;\ S1157A}$ enzyme, with a portion thereof having a primary structure with between 80% and 100% amino acid residue sequence identity with a protein portion coded for by a reading frame defined by bases 9 to 1716 of SEQ ID NO: 7, Acc1$^{S659A;\ S1157A}$.

31. The method of claim 28 wherein the yeast cell comprises an Acc1 polynucleotide including the coding sequence for Acc1 from *S. cerevisiae* under regulation of a constitutive promoter.

32. The method of claim 31 wherein the constitutive promoter comprises a PGK1 promoter from *S. cerevisiae*.

33. The method of claim 32 wherein the PGK1 promoter has between 80% and 100% nucleotide identity with bases 7 to 750 of SEQ ID NO: 6.

34. The method of claim 23 wherein the genetic modification comprises increased expression of an activator for sterol biosynthesis.

35. The method of claim 34 wherein the yeast cell comprises a Upc2 polynucleotide including a coding sequence for Upc2$^{E888D}$ from *S. cerevisiae* with a primary structure having between 80% and 100% amino acid residue sequence identity with a protein coded for by a reading frame defined by bases 975 to 3701 of SEQ ID NO: 9.

36. The method of claim 1 wherein the second polynucleotide comprises a coding sequence for a cytosolic prenyltransferase enzyme with a primary structure having between 80% and 100% amino acid residue sequence identity with any one of SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO:

28, SEQ ID NO: 29, SEQ ID NO: 30, SEQ ID NO: 31, SEQ ID NO: 32, SEQ ID NO: 33, SEQ ID NO: 34, SEQ ID NO: 35 or SEQ ID NO: 36.

37. The method of claim 1 further comprising extracting the at least one species of phytocannabinoid or phytocannabinoid analogue from the yeast cell culture.

38. The method of claim 1 wherein the yeast cell is modified to increase the availability of the precursor chemical.

39. The method of claim 1 wherein the precursor chemical is provided to the yeast cell.

* * * * *

SEQUENCE LISTING

```
<160> NUMBER OF SEQ ID NOS: 47

<210> SEQ ID NO 1
<211> LENGTH: 927
<212> TYPE: DNA
<213> ORGANISM: Streptomyces coelicolor species 190

<400> SEQUENCE: 1
atgtctgaag ccgctgatgt cgaaagagtt tacgccgcta tggaagaggc cgctggtttg      60
ttgggtgttg cctgtgctag agacaagatt tacccattgt tatccacctt ccaagatact     120
ttggttgaag gtggttctgt tgtcgttttc tctatggcct ccggtagaca ctccaccgaa     180
ttggacttct ctatttctgt tccaacttct catggtgatc catacgccac tgtcgttgaa     240
aagggtttat ttcctgctac tggtcaccca gttgacgatt tgttagctga cactcaaaag     300
cacttacctg tttctatgtt cgctattgac ggtgaagtta ccggtggttt caaaaagact     360
tacgccttct tcccaactga caatatgcca ggtgttgctg aattgtctgc tatcccatcc     420
atgccaccag ccgttgccga gaatgctgaa ttgttcgctc gttatggttt ggacaaggtc     480
caaatgacct ccatggacta caagaaaaga caagtcaact tgtatttctc cgaattgtct     540
gctcaaactt agaagccga atctgttttg gctttggtta gagaattagg tttgcacgtt     600
ccaaacgaat tgggtttgaa gttttgtaaa cgttcttttct ctgtttatcc aactttgaac     660
tgggaaaccg gtaaaatcga cagattgtgc ttcgctgtca tctctaacga cccaaccttg     720
gtcccatcct ccgatgaagg tgatatcgaa aagttccaca actacgccac taaggctcct     780
tacgcttacg tcggtgagaa acgtaccttg gtctatggtt tgactttatc cccaaaggag     840
gaatactaca agttgggtgc ttactaccac attaccgacg tccaaagagg tttgttaaag     900
gccttcgact ctttagaaga cggctga                                         927

<210> SEQ ID NO 2
<211> LENGTH: 9444
```

```
<212> TYPE: DNA
<213> ORGANISM: Dictyostelium discoideum
<220> FEATURE:
<221> NAME/KEY: Motif 1
<222> LOCATION: (4528)..(4554)
<220> FEATURE:
<221> NAME/KEY: C-methyltransferase domain
<222> LOCATION: (4528)..(4890)
<220> FEATURE:
<221> NAME/KEY: Motif 2
<222> LOCATION: (4787)..(4809)
<220> FEATURE:
<221> NAME/KEY: Motif 3
<222> LOCATION: (4867)..(4899)

<400> SEQUENCE: 2
atgaacaaga actccaaaat ccagtcccca aactcttctg atgttgctgt tattggtgtt      60
ggttttagat tcccaggtaa ctctaatgac ccagaatctt tgtggaacaa cttgttggat     120
ggtttcgatg ctattaccca gtcccaaaa gaaagatggg ctacttcttt tagagagatg      180
ggtttgatca agaacaagtt cggtggtttc ttgaaggatt ctgaatggaa gaatttcgac     240
cctttgttct ttggtatcgg tccaaaagaa gctccattca ttgatccaca acaaggttg      300
ttgttgtcca tcgtttggga atctttggaa gatgcttaca tcagaccaga tgaattgaga     360
ggttctaaca ctggtgtttt catcggtgtt ctaacaacg attacaccaa gttgggtttc      420
caagacaact actctatttc tccatacact atgaccggct ctaactcttc attgaactcc     480
aacagaattt cctactgctt cgattttaga ggtccatcca ttactgttga taccgcttgt     540
tcttcttcct tggtttctgt taatttgggt gtccaatcca tccaaatggg tgaatgtaag     600
attgctattt gcggtggtgt taacgctttg tttgatccat ctacatctgt tgccttttcc     660
aagttgggtg ttttgtctga aaatggcaga tgcaactctt ttagtgatca agcctctggt     720
tacgttagat ctgaaggtgc tggtgttgtt gttttgaagt ctttggaaca agctaagttg     780
gatggtgata gaatctacgg tgttatcaag ggtgttttcct ctaatgaaga tggtgcttct    840
aatggtgaca agaactcttt gactactcca tcttgtgaag cccaatccat taacatttct     900
aaggctatgg aaaaggcctc cttgtctcca tctgatatct attacattga agcccatggt     960
actggtactc cagttggtga tccaattgaa gttaaggcct tgtccaagat cttctccaac    1020
tctaacaaca accagttgaa caacttctct accgatggta atgataacga tgatgatgat    1080
gacgataaca cctctccaga accattattg attggctcat tcaagtccaa catcggtcat    1140
ttggaatctg ctgctggtat tgcttctttg attaagtgtt gcttgatgtt gaagaacagg    1200
atgttggttc catccattaa ctgctctaat ttgaacccat ccattccatt cgatcagtac    1260
aacatctccg ttatcagaga aatcagacaa ttcccaaccg ataagttggt taacatcggt    1320
atcaattctt tcggtttcgg tggttctaac tgccatttga ttattcaaga gtacaacaac    1380
aacttcaaga caactctac catctgcaat aacaacaaca caacaataa caacatcgac     1440
tacttgatcc aatctcctc taagactaag aagtccttgg ataagtactt gattttgatc    1500
aagaccaact ccaactacca caaggatatt tctttcgatg acttcgtcaa gttccaaatc    1560
aagtctaagc agtacaactt gtccaacaga atgactacca ttgctaacga ttggaactcc    1620
ttcattaagg gttctaacga attccacaac ttgatcgaat ctaaggatgg tgaaggtggt    1680
tcttcatctt ctaacagagg tattgattcc gccaatcaaa tcaacactac tactacctct    1740
accatcaacg atatcgaacc tttgttggtt ttcgttttct gtggtcaagg tccacaatgg    1800
aatggtatga ttaagacctt gtacaactcc gagaacgttt tcaagaacac cgttgatcat    1860
```

```
gttgacagca tcttgtacaa gtacttcggt tactccattt tgaacgtctt gtctaagatc    1920
gatgataacg acgattccat caaccatcca atagttgctc aaccatcttt gttcttgttg    1980
caaattggtt tggtcgagtt gtttaagtac tggggtatct acccatctat ctctgttggt    2040
cattctttcg gtgaagtctc ttcttattac ttgtccggta tcatctcttt ggaaaccgct    2100
tgtaaaatcg tctacgtcag atcctctaat cagaacaaaa ctatgggttc cggtaagatg    2160
ttggttgttt ctatgggttt taagcaatgg aacgatcaat tctctgctga atggtccgat    2220
attgaaattg cttgttacaa cgctccagat tccatagttg ttactggtaa cgaagaaaga    2280
ttgaaagaat tgtccatcaa gttgtccgac gaatccaatc aaattttcaa caccttcttg    2340
aggtccccat gttcttttca ttcttcccat caagaagtca tcaagggttc tatgttcgaa    2400
gagttgtcta acttgcaatc tactggtgaa accgaaatcc ctttgttctc tactgttact    2460
ggtagacaag ttttgtctgg tcatgttact gctcaacaca tctacgataa tgttagagaa    2520
ccagtcttgt tccaaaagac gattgaatcc attacctcct acatcaagtc tcactaccca    2580
tccaatcaaa aggttatcta cgttgaaatt gctccacacc caaccttgtt ttcattgatc    2640
aaaaagtcca tcccatcctc caacaagaat tcctcttctg ttttgtgtcc attgaacaga    2700
aaagaaaact ccaacaactc ctacaagaag ttcgtttctc agttgtactt caacggtgtt    2760
aacgttgact tcaacttcca gttgaactcc atttgcgata acgttaacaa cgatcaccat    2820
ttgaacaacg tcaagcaaaa ctccttcaaa gagactacca attccttgcc aagataccaa    2880
tgggaacaag atgaatattg gtccgaacca ttgatctcca gaaagaatag attggaaggt    2940
ccaactactt ccttgttggg tcatagaatt atctacagct tcccagtttt ccaatccgtt    3000
ttggacttgc aatctgacaa ctacaaatac ttgttggacc acttggttaa cggtaagcca    3060
gttttttccag gtgctggtta tttggatatc atcatcgaat tcttcgacta ccaaaagcag    3120
cagttgaatt cctctgattc ctctaactcc tacatcatca cgttgacaa gatccaattc     3180
ttgaacccaa ttcacttgac cgaaaacaag ttgcaaacct tgcaatcttc tttcgaacct    3240
atcgttacta agaagtctgc cttctctgtt aacttcttca tcaaggatac cgtcgaggat    3300
caatctaagg ttaagtctat gtctgacgaa acttggacta acacttgtaa ggctaccatt    3360
tccttggaac aacaacagcc atctccatct tctactttga ctttgtctaa gaagcaagac    3420
ttgcagatct tgagaaacag atgcgatatt agcaagctag acaagtttga gttgtacgac    3480
aagatctcta agaatttggg cttgcagtac aactccttgt ttcaagttgt tgataccatc    3540
gaaactggta aggattgctc ttttgctact ttgtctttgc cagaagatac tttgttcacc    3600
accatttttga acccatgctt gttggataac tgtttccatg gtttgttgac cttgatcaac    3660
gaaaagggtt ctttcgttgt cgagtccatt tcttctgttt ctatctactt ggagaacatc    3720
ggttccttca atcaaacttc tgttggtaac gtccagttct acttgtacac cactatttct    3780
aaagccacct cctttagttc tgaaggtact tgtaagttgt tcaccaagga tggttccttg    3840
attttgtcta tcggtaagtt catcatcaag tccaccaatc aaagtctac taagaccaac     3900
gaaactatcg aatctccatt ggacgaaacc ttctctattg aatggcaatc taaggattct    3960
ccaattccaa ccccacaaca aatccaacaa caatctccat tgaactctaa cccatccttc    4020
attagatcta ccatcttgaa ggacatccag ttcgaacaat actgctcctc cattatccac    4080
aaagaattga tcaaccacga aaagtacaag aaccagcaat ccttcgatat caactccttg    4140
gaaaaccact tgaacgatga ccaattgatg gaatccttgt ccatctccaa agaatacttg    4200
agattcttca ccaggatcat ctccatcatt aagcaatacc caaagatctt gaacgaaaaa    4260
```

```
gagctaaaag aattgaaaga aatcatcgaa ttgaagtacc catccgaagt tcagttgttg    4320
gaattcgaag ttatcgagaa ggtgtccatg attatcccaa agttgttgtt cgaaaacgac    4380
aagcaatctt ccatgacctt gttccaagat aacttgttga ccaggttcta ctccaattct    4440
aactctacca gattctactt ggaaagggtt tccgaaatgg tcttggaatc tattagacca    4500
atcgtcagag aaagagggt gttcagaatt ttggaaattg gtgctggtac aggctctttg     4560
tctaatgttg ttttgactaa gttgaacacc tacttgtcca ccttgaattc taatggtggt    4620
tctggttaca acatcatcat tgagtacacc ttcaccgata tttccgccaa cttcattatt    4680
ggtgaaatcc aagaaccat gtgcaacttg tacccaaacg ttactttcaa gttctccgtc     4740
ttggacttgg agaaagagat tattaactcc tccgatttct tgatgggtga ttacgatata    4800
gttttgatgg cctacgttat ccatgccgtt tctaacatta agttctccat cgaacagttg    4860
tacaagttgt tgtctccaag aggttggttg ttgtgtattg aacctaagtc caacgttgtg    4920
ttctccgatt tggttttcgg ttgttttaat cagtggtgga actactacga tgatattaga   4980
actacccact gctccttgtc tgaatctcaa tggaatcagt tgttgttgaa ccagtccttg    5040
aacaacgaat cctcttcttc ttctaactgt tacggtggtt tctccaacgt ttcttttatt   5100
ggtggtgaaa aggatgtcga ctcccattct ttcatattgc actgccaaaa agaatccatc   5160
tcccaaatga agttagccac cactattaac aacggtttgt catctggttc catcgttatc   5220
gttttgaact ctcaacaatt gaccaacatg aagtcctacc caaaggttat tgagtatatt   5280
caagaggcta cctctttgtg caagaccatt gaaattatcg attccaagga cgtcttgaac   5340
tctaccaatt cagttttgga aaagatccaa aagtccttgt tggtgttctg tttgttgggt   5400
tatgacttgt tggagaacaa ctaccaagaa cagtctttcg aatacgttaa gttgttgaac   5460
ttgatctcta ctaccgcctc ttcatctaat gataagaaac caccaaaggt cttgttgatc   5520
accaagcaat ctgaaagaat ctccaggtct ttctactcca gatccttgat tggtatttcc   5580
agaacctcta tgaacgagta cccaaatttg tccattacct ctatcgattt ggataccaac   5640
gactactcat tgcagtcttt gttgaagcca atcttcagca actctaagtt ttccgacaac   5700
gagttcatct tcaaaaaggg cttgatgttc gtgtccagga tctttaagaa caagcagttg   5760
ctagaatcct ccaacgcttt tgaaactgac tcttctaact tgtactgtaa ggcctcttct   5820
gacttgtctt acaagtacgc tattaagcag tctatgttga ccgaaaatca gatcgaaatc   5880
aaggttgaat gcgtcggtat taacttcaag gacaacctat tctacaaggg cttgttgcca   5940
caagaaattt tcagaatggg tgacatctac aatccaccat atggtttgga atgctctggt   6000
gttattacca gaattggttc taacgtcacc gaatactcag ttggtcaaaa tgttttggt    6060 ttcgccagac attctttggg ttctcatgtt gttaccaaca aggatttggt tatcttgaag   6120
ccagatacca tctcatttc tgaagctgct tctatcccag ttgtttactg tactgcttgg   6180
tactccttgt tcaacattgg tcagttgtct aacgaagaat ccatcctaat tcattctgct   6240
actggtggtg taggtttggc ttcttttgaat ttgttgaaaa tgaagaatca gcaacagcaa   6300
ccattgacca atgtttatgc tactgttggc tctaacgaga agaagaagtt cttgatcgat   6360
aacttcaaca acttgttcaa agaggacggc gaaaacattt tctctaccag agacaaagaa   6420
tactccaacc agttggaatc caagatcgat gttatttgga acaccttgtc cggtgaattc   6480
gtcgaatcta atttcaagtc cttgagatcc ttccggtagat tgattgattt gtctgctact   6540
cacgtttacg ccaatcaaca aattggtcta ggtaacttca agttcgacca cttgtattct   6600
```

-continued

```
gctgttgact tggaaagatt gatcgacgaa aaacctaagt tgttgcagtc catcttgcaa    6660
agaattacca actctatcgt caacggttcc ttggaaaaaa ttccaattac catcttccca    6720
tccaccgaaa ctaaggatgc tatcgaatta ttgtccaaga gatcccatat cggtaaagtt    6780
gttgtagatt gcaccgatat ctctaagtgt aatcctgttg gtgatgtgat caccaacttc    6840
tctatgagat tgccaaagcc aaactaccag ttgaatttga actccacctt gttgattact    6900
ggtcagtctg gtttgtctat ccctttgttg aattggttgt tgtctaagtc tggtggtaac    6960
gttaagaacg ttgtcatcat ttctaagtcc accatgaagt ggaagttgca gactatgatt    7020
tcccatttcg tttccggttt cggtatccat tttaactacg ttcaagtcga catctccaac    7080
tacgatgctt tgtctgaagc tattaagcaa ttgccatctg atttgccacc aatcacctct    7140
gtttttcatt tggctgctat ctacaacgat gttccaatgg atcaagttac catgtctacc    7200
gttgaatctg ttcataaccc taaagttttg ggtgccgtta acttgcatag aatctctgtt    7260
tcttttggtt ggaagttgaa ccacttcgtc ttgttctctt ctattactgc tattaccggt    7320
tacccagacc aatctatcta caattctgcc aactctattt tggacgcttt gtccaacttt    7380
agaaggttta tgggttttgcc atccttctcc attaacttgg gtccaatgaa ggatgaaggt    7440
aaggtttcta ccaacaagag catcaagaag ctattcaagt ctagaggttt gccaagccta    7500
tccttgaaca agttatttgg tttgttggag gtcgtcatca acaacccatc taatcatgtt    7560
atcccatccc aattgatttg ctccccaatc gatttcaaga cctacatcga atctttctca    7620
actatgaggc caaagttgtt acacttgcaa cctaccattt ccaagcagca atcttctatc    7680
attaacgatt ctaccaaggc ttcctccaac atttcattgc aagataagat cacctccaag    7740
gtgtctgatt tgttgtccat tccaatctcc aagatcaact cgatcatcc attgaaacac    7800
tacggcttgg attctttgtt gaccgttcaa ttcaaatcct ggatcgacaa agaattcgaa    7860
aagaacttgt tcacccatat ccaattggcc accatctcta ttaactcatt cttggaaaag    7920
gtgaacggct tgtctacaaa caataacaac aacaacaatt ccaacgtcaa gtcctctcca    7980
tccattgtca agaagaaat cgttaccttg acaaggatc aacaaccatt gctattgaaa     8040
gaacaccagc acattatcat ctccccagat attagaatca acaagccaaa gagggaatcc    8100
ttgattagaa ccccaatctt gaacaaattc aaccagatca ccgaatccat tatcactcca    8160
tctacaccat ctttgtccca atccgatgtt tgaaaactc caccaatcaa gtctttgaac    8220
aacactaaga actccagctt gattaacacc ccaccaattc aatctgtcca caacatcaa     8280
aagcaacaac aaaaggtcca agtcatccaa caacagcaac aaccattatc cagattgtcc    8340
tacaagagca caacaactc tttcgttttg ggtatcggta tttctgttcc aggtgaacct    8400
atttcccaac aatccttgaa agactccatc tccaatgact tttctgataa ggctgaaact    8460
aacgagaagg tcaagagaat ctttgagcaa tctcaaatca gaccagaca cttggttaga    8520
gattacacta agccagagaa ctccatcaag ttcagacatt tggaaaccat taccgatgtg    8580
aacaaccagt tcaagaaagt tgttccagat ttggctcaac aagcctgttt gagagctttg    8640
aaagattggg gtggtgataa gggtgatatt acccatatag tttctgttac ctccaccggt    8700
attatcatcc cagatgttaa tttcaagttg atcgacttgt tgggcttgaa caaggatgtt    8760
gaaagagtgt ctttgaacct aatggggttgt ttggctggtt tgagttcttt gagaactgct    8820
gcttcttttgg ctaaggcttc tccaagaaat agaattttgg ttgtctgtac cgaagtctgc    8880
tccttgcatt tttctaatac tgatggtggt gatcaaatgg tcgcctcttc tattttttgct    8940
gatggttctg ctgcttacat tattggttgt aacccaagaa ttgaagaaac cccattatac    9000
```

```
gaagtcatgt gctccattaa cagatctttc ccaaataccg aaaacgccat ggtttgggat    9060
ttggaaaaag aaggttggaa cttgggtttg gatgcttcta ttccaattgt cattggttct    9120
ggtattgaag ccttcgttga tactttgttg ataaggcta  agttgcaaac ttccactgct    9180
atttctgcta aggattgcga attcttgatt catactggtg gcaagtccat cttgatgaac    9240
atcgaaaatt ccttgggtat cgacccaaag caaactaaga atacttggga tgtttaccat    9300
gcctacggca atatgtcatc tgcctctgtt attttcgtta tggatcatgc cagaaagtcc    9360
aagtctttgc caacttactc aatttctttg gcttttggtc caggtttggc ttttgaaggt    9420
tgtttcttga agaacgtcgt ctaa                                            9444
```

<210> SEQ ID NO 3
<211> LENGTH: 1059
<212> TYPE: DNA
<213> ORGANISM: Saccharomyces cerevisiae

<400> SEQUENCE: 3

```
atggcttcag aaaagaaat  taggagagag agattcttga acgttttccc taaattagta     60
gaggaattga acgcatcgct tttggcttac ggtatgccta aggaagcatg tgactggtat    120
gcccactcat tgaactacaa cactccaggc ggtaagctaa atagaggttt gtccgttgtg    180
gacacgtatg ctattctctc caacaagacc gttgaacaat ggggcaaga  agaatacgaa    240 aaggttgcca ttctaggttg gtgcattgag ttgttgcagg cttacttctt ggtcgccgat    300
gatatgatgg acaagtccat taccagaaga ggccaaccat gttggtacaa ggttcctgaa    360
gttggggaaa ttgccatcaa tgacgcattc atgttagagg ctgctatcta caagcttttg    420
aaatctcact tcagaaacga aaatactac  atagatatca ccgaattgtt ccatgaggtc    480
accttccaaa ccgaattggg ccaattgatg gacttaatca ctgcacctga agacaaagtc    540
gacttgagta agttctccct aaagaagcac tccttcatag ttactttcga gactgcttac    600
tattctttct acttgcctgt cgcattggcc atgtacgttg ccggtatcac ggatgaaaag    660
gatttgaaac aagccagaga tgtcttgatt ccattgggtg aatacttcca aattcaagat    720
gactacttag actgcttcgg tacccagaa  cagatcggta agatcggtac agatatccaa    780
gataacaaat gttcttgggt aatcaacaag gcattggaac ttgcttccgc agaacaaaga    840
aagactttag acgaaaatta cggtaagaag gactcagtcg cagaagccaa atgcaaaag     900 attttcaatg acttgaaaat tgaacagcta taccacgaat atgaagagtc tattgccaag    960
gatttgaagg ccaaaatttc tcaggtcgat gagtctcgtg gcttcaaagc tgatgtctta   1020
actgcgttct tgaacaaagt ttacaagaga agcaaataa                           1059
```

<210> SEQ ID NO 4
<211> LENGTH: 14025
<212> TYPE: DNA
<213> ORGANISM: Artificial Sequence
<220> FEATURE:
<223> OTHER INFORMATION: Plasmid
<220> FEATURE:
<221> NAME/KEY: C1:p506 primer homology
<222> LOCATION: (1)..(50)
<220> FEATURE:
<221> NAME/KEY: 19 UP
<222> LOCATION: (51)..(761)
<220> FEATURE:
<221> NAME/KEY: L0
<222> LOCATION: (762)..(800)
<220> FEATURE:
<221> NAME/KEY: THD3p

```
<222> LOCATION: (801)..(1453)
<220> FEATURE:
<221> NAME/KEY: L1
<222> LOCATION: (1454)..(1493)
<220> FEATURE:
<221> NAME/KEY: ALD6
<222> LOCATION: (1494)..(2999)
<220> FEATURE:
<221> NAME/KEY: L2
<222> LOCATION: (3000)..(3039)
<220> FEATURE:
<221> NAME/KEY: LTP1
<222> LOCATION: (3364)..(3403)
<220> FEATURE:
<221> NAME/KEY: Tef1p
<222> LOCATION: (3404)..(3897)
<220> FEATURE:
<221> NAME/KEY: L3
<222> LOCATION: (3898)..(3937)
<220> FEATURE:
<221> NAME/KEY: Acs L641P
<222> LOCATION: (3938)..(5893)
<220> FEATURE:
<221> NAME/KEY: L4
<222> LOCATION: (5894)..(5933)
<220> FEATURE:
<221> NAME/KEY: PRM9t
<222> LOCATION: (5934)..(6471)
<220> FEATURE:
<221> NAME/KEY: LTP2
<222> LOCATION: (6472)..(6511)

<400> SEQUENCE: 4
taaccctcac taagggaac aaaagctgga gctcgtttaa acggcgcgcc caccggagct      60
tggatatgat aaacgaaata ttcttgaatc gtgagatcgc ctgttttcaa aaccgttgga    120
ggcagaaaca attttgtcac aagatgggca ttctacccca tccttgctgt attattgtag    180
tctcgctttc ttttatgctg acaaatgag actactgcac attttatac gttcttggtt      240 tttttttaaag gtgtggtttc ggcattatcc tgccgcacgt ttcttggata attcatcctg   300
attctctatt ttaaacgctt cagcctatca ggatttggtt ttgatacata ctgcaagagt   360
gtatctcggg aacagtcatt tattccgcaa caaacttaat tgcggaacgc gttaggcgat   420
ttctagcata tatcaaatac cgttcgcgat ttcttctggg ttcgtctctt ttcttttaaa   480
tacttattaa cgtactcaaa caactacact tcgttgtatc tcagaatgag atccctcagt   540
atgacaatac atcattctaa acgttcgtaa aacacatatg aaacaacttt ataacaaagc   600
gaacaaaatg ggcaacatga gatgaaactc cgcgtccctt agctgaacta cccaaacgta   660
cgaatgcctg aacaattagt ttagatccga gattccgcgc ttccatcatt tagtataatc   720
catattttat ataatatata ggataagtaa cagcccgcga aaacaacaa ataatcataa    780 aaattttaga actagacata tcgagtttat cattatcaat actgccattt caaagaatac   840
gtaaataatt aatagtagtg attttcctaa ctttatttag tcaaaaaatt agccttttaa   900
ttctgctgta acccgtacat gcccaaaata ggggcgggt tacacagaat atataacatc    960
gtaggtgtct gggtgaacag tttattcctg gcatccacta aatataatgg agcccgcttt  1020
ttaagctggc atccagaaaa aaaagaatc ccagcaccaa aatattgttt tcttcaccaa   1080
ccatcagttc ataggtccat tctccttagcg caactacaga gaacagggg acaaacaggc  1140 aaaaaacggg cacaacctca atggagtgat gcaacctgcc tggagtaaat gatgacacaa  1200
ggcaattgac ccacgcatgt atctatctca ttttcttaca ccttctatta ccttctgctc   1260
tctctgattt ggaaaagct gaaaaaaag gttgaaacca gttccctgaa attattcccc   1320
tacttgacta ataagtatat aaagacggta ggtattgatt gtaattctgt aaatctatt   1380
```

```
cttaaacttc ttaaattcta cttttatagt tagtcttttt tttagtttta aaacaccaag    1440
aacttagttt cgactagaaa atttattata aaaggaagag aaataattaa acaatgacta    1500
agctacactt tgacactgct gaaccagtca agatcacact tccaaatggt ttgacatacg    1560
agcaaccaac cggtctattc attaacaaca agtttatgaa agctcaagac ggtaagacct    1620
atcccgtcga agatccttcc actgaaaaca ccgtttgtga ggtctcttct gccaccactg    1680
aagatgttga atatgctatc gaatgtgccg accgtgcttt ccacgacact gaatgggcta    1740
cccaagaccc aagagaaaga ggccgtctac taagtaagtt ggctgacgaa ttggaaagcc    1800
aaattgactt ggtttcttcc attgaagctt tggacaatgg taaaactttg ccttagccc     1860 gtgggdatgt taccattgca atcaactgtc taagagatgc tgctgcctat gccgacaaag    1920
tcaacggtag aacaatcaac accggtgacg gctacatgaa cttcaccacc ttagagccaa    1980
tcggtgtctg tggtcaaatt attccatgga actttccaat aatgatgttg gcttggaaga    2040
tcgccccagc attggccatg ggtaacgtct gtatcttgaa acccgctgct gtcacacctt    2100
taaatgccct atactttgct tctttatgta agaaggttgg tattccagct ggtgtcgtca    2160
acatcgttcc aggtcctggt agaactgttg gtgctgcttt gaccaacgac ccaagaatca    2220
gaaagctggc ttttaccggt tctacagaag tcggtaagag tgttgctgtc gactcttctg    2280
aatctaactt gaagaaaatc actttggaac taggtggtaa gtccgcccat ttggtctttg    2340
acgatgctaa cattaagaag actttaccaa atctagtaaa cggtatttc aagaacgctg     2400 gtcaaatttg ttcctctggt tctagaattt acgttcaaga aggtatttac gacgaactat    2460
tggctgcttt caaggcttac ttggaaaccg aaatcaaagt tggtaatcca tttgacaagg    2520
ctaacttcca aggtgctatc actaaccgtc aacaattcga cacaattatg aactacatcg    2580
atatcggtaa gaaagaaggc gccaagatct taactggtgg cgaaaaagtt ggtgacaagg    2640
gttacttcat cagaccaacc gttttctacg atgttaatga agacatgaga attgttaagg    2700
aagaaatttt tggaccagtt gtcactgtcg caaagttcaa gactttagaa gaaggtgtcg    2760
aaatggctaa cagctctgaa ttcggtctag gttctatggg tatcgaaaca gaatctttga    2820
gcacaggttt gaaggtggcc aagatgttga aggccggtac cgtctggatc aacacataca    2880
acgattttga ctccagagtt ccattcggtg gtgttaagca atctggttac ggtagagaaa    2940
tgggtgaaga agtctaccat gcatacactg aagtaaaagc tgtcagaatt aagttgtaaa    3000
gacataaaac tgaaacaaca ccaattaata atagacttt ggacttcttc gccagaggtt     3060
tggtcaagtc tccaatcaag gttgtcggct tgtctacctt gccagaaatt tacgaaaaga    3120
tggaaagggg tcaaatcgtt ggtagatacg ttgttgacac ttctaaataa gcgaatttct    3180 tatgattat gatttttatt attaaataag ttataaaaaa aataagtgta tacaaatttt      3240
aaagtgactc ttaggtttta aaacgaaaat tcttattctt gagtaactct ttcctgtagg    3300
tcaggttgct ttctcaggta tagcatgagg tcgctcttat tgaccacacc tctaccggca    3360
tggcttaaat aacatactca tcactaaaca ttcttaacaa tcaaagcaac aggcgcgttg    3420 gactttaat tttcgaggac cgcgaatcct tacatcacac ccaatccccc acaagtgatc      3480
ccccacacac catagcttca aaatgttct actcctttt tactcttcca gatttctcg       3540 gactccgcgc atcgccgtac cacttcaaaa cacccaagca cagcatacta aatttcccct    3600 cttcttcct ctagggtgtc gttaattacc cgtactaaag gtttggaaaa gaaaaaagag     3660
accgcctcgt ttctttttct tcgtcgaaaa aggcaataaa aattttatc acgtttctttt     3720
```

```
ttcttgaaaa tttttttttt tgatttttt ctctttcgat gacctcccat tgatatttaa    3780
gttaataaac ggtcttcaat ttctcaagtt tcagtttcat ttttcttgtt ctattacaac    3840
ttttttact  tcttgctcat tagaaagaaa gcatagcaat ctaatctaag ttttaataca    3900
tctaccagtc aacagccaac aattaactaa ttaaacaatg tcccaaactc ataagcacgc    3960
tattccagct aatattgctg atagatgctt gatcaaccca gaacagtacg aaactaagta    4020
caagcaatcc atcaacgatc cagatacttt tggggtgaa  caaggtaaga ttttggattg    4080
gattacccca taccaaaagg tcaagaatac ttcttttgct ccaggcaacg tttccattaa    4140
gtggtatgaa gatggtactt tgaacttggc tgctaactgt ttggatagac acttgcaaga    4200
aaacggtgat agaaccgcta ttatttggga aggtgatgat acctcccaat ccaaacatat    4260
ctcttacaga gaattgcaca gagatgtctg tagattcgct aacactttgt tggatttggg    4320
catcaaaaag ggtgatgttg ttgctatcta tatgccaatg gttcctgaag ctgctgttgc    4380
tatgttggct tgtgctagaa ttggtgctgt tcattctgtt attttcggtg gttttttcacc   4440
agaagctgtt gccggtagaa ttatcgattc ttcatccaga ttggttatca ccgctgatga    4500
aggtgttaga gctggtagat ctattccatt gaaaaagaac gttgatgacg ccttgaagaa    4560
cccaaatgtt acttctgttg aacacgtcat cgttttgaag agaactggtt ctgatatcga    4620
ttggcaagag ggtagagatt tgtggtggag agatttgatt gaaaaggctt ctccagaaca    4680
tcaaccagaa gctatgaacg ctgaagatcc tttgtttatc ttgtacactt ctggttctac    4740
tggtaagcca aaaggtgttt tacacactac tggtggttat ttggtttacg ctgctactac    4800
tttcaagtac gttttcgatt atcacccagg tgatatctat tggtgtactg ctgatgttgg    4860
ttgggttact ggtcattctt atttgttgta tggtccattg gcttgtggtg ctactacatt    4920
gatgtttgaa ggtgttccaa attggccaac tccagctaga atgtgtcaag ttgttgacaa    4980
acaccaagtc aacatcttgt atactgctcc aactgctatt agagctttga tggctgaagg    5040
tgataaggct attgaaggta ctgatagatc ctccttgaga atcttgggtt ctgttggtga    5100
acctattaac cctgaagcct gggaatggta ttggaagaaa attggtaaag aaaagtgccc    5160
agttgttgat acttggtggc aaactgaaac tggtggtttt atgattactc cattgccagg    5220
tgctattgaa ttgaaagctg gttctgctac tagaccattt ttttggtgttc aaccagcttt    5280
ggttgataac gaaggtcatc cacaagaagg tgctactgaa ggtaatttgg ttattactga    5340
ttcttggcca ggtcaagcta gaactttgtt tggtgatcac gaaagattcg aacagactta    5400
cttctctacc ttcaagaaca tgtacttctc tggtgatggt gctagaagag atgaagatgg    5460
ttactattgg attaccggta gagttgatga tgtcttgaat gtttctggtc acagattagg    5520
tactgccgaa attgaatctg ctttggttgc tcatccaaag attgctgaag ctgcagttgt    5580
tggtattcca catgctatta gggtcaagc tatctacgct tacgttactt tgaatcatgg    5640
tgaagaacca tctccagaat tatacgctga agttagaaac tgggtcagaa aagaaattgg    5700
tccattagct accccagatg ttttacattg gactgattct ttgccaaaga ccagatcagg    5760
taagatcatg agaagaatct tgagaaagat tgctgctggt gatacttcta acttgggtga    5820
tacttcaaca ttagctgatc caggtgttgt tgaaaagcct tggaagaaa  acaagctat    5880
tgccatgcca tcctaataat taaatactat tttcaaaatt ctacttaaaa ataacagaag    5940
acgggagaca ctagcacaca actttaccag gcaaggtatt tgacgctagc atgtgtccaa    6000
ttcagtgtca tttatgattt tttgtagtag gatataaata tatacagcgc tccaaatagt    6060
gcggttgccc caaaaacacc acggaacctc atctgttctc gtactttgtt gtgacaaagt    6120
```

```
agctcactgc cttattatca cattttcatt atgcaacgct tcggaaaata cgatgttgaa   6180
aatgcctcta gagatgaaaa acaatcgtaa aagggtcctg cgtaattgaa acatttgatc   6240
agtatgcagt ggcacagaaa caaccaggaa tactatagtc ataggcaata caaggtatat   6300
attggctatg cagacccctc cagaaagtac cgacgtcaag ttagatacac ttaacgaacc   6360
tagtgcacat ttaattgaga aaatgtggc tcttcctaag gacatattcc gttcgtactt    6420
gagttattgg atctatgaaa tcgctcgcta tacaccagtc atgattttgt cattgcgaag   6480
actatactga tatatgaatt taaactagag cggaccaact atcatccgct aattactgac   6540
attaccaaat gagatctgtg aatgggcaag ataaaaaaca aaaattgaaa tgtttgacgt   6600
tatgtaaaac tattaattcc ttcgctttcg gcggtcacag aatttgcgtg tagctgactc   6660
ttgttcaatc aatatcattt gttactttat ttgaaagtct gtattactgc gcctattgtc   6720
atccgtacca agaacgtca aaagaaaca agataatttt tgtgcttaca ccatttatag     6780
atcactgagc ccagaatatc gctggagctc agtgtaagtg gcatgaacac aactctgact   6840
gatcgcacat attgccgtta tcataaatac tagttgtact tgtcaatgcg acgaatggca   6900
tcatgcctat tattacgttc ctcttttcc gtttcatgtt tccagaatgc tattgaatct    6960
aacacttcaa ttataaaaa gaataaatcc gcaataattt taggctaatt gttgtactgt    7020
caagcgaacc taatggttaa aattcagagg aaccttcgac gtagtctgat cgctacttct   7080
atatcttatg ttcccagtca atcaaaagtt gatactataa tagctgccat ttatacctgt   7140
tagttatggc gatcgtttat cacggcggcc gcggtaccta ataacttcgt atagcataca   7200
ttatacgaag ttatattaag ggttctcgac gttttcgaca ctggatggcg gcgttagtat   7260
cgaatcgaca gcagtatagc gaccagcatt cacatacgat tgacgcatga tattactttc   7320
tgcgcactta acttcgcatc tgggcagatg atgtcgaggc gaaaaaaat ataaatcacg     7380
ctaacatttg attaaaatag aacaactaca atataaaaaa actatacaaa tgacaagttc   7440
ttgaaaacaa gaatcttttt attgtcagta ctgattagaa aaactcatcg agcatcaaat   7500
gaaactgcaa tttattcata tcaggattat caataccata tttttgaaaa agccgtttct   7560
gtaatgaagg agaaaactca ccgaggcagt tccataggat ggcaagatcc tggtatcggt   7620
ctgcgattcc gactcgtcca acatcaatac aacctattaa tttcccctcg tcaaaaataa   7680
ggttatcaag tgagaaatca ccatgagtga cgactgaatc cggtgagaat ggcaaaagct   7740
tatgcatttc tttccagact tgttcaacag gccagccatt acgctcgtca tcaaaatcac   7800
tcgcatcaac caaccgtta ttcattcgtg attgcgcctg agcgagacga aatacgcgat    7860
cgctgttaaa aggacaatta caaacaggaa tcgaatgcaa ccggcgcagg aacactgcca   7920
gcgcatcaac aatattttca cctgaatcag gatattcttc taatacctgg aatgctgttt   7980
tgccggggat cgcagtggtg agtaaccatg catcatcagg agtacggata aaatgcttga   8040
tggtcggaag aggcataaat tccgtcagcc agtttagtct gaccatctca tctgtaacat   8100
cattggcaac gctacctttg ccatgtttca gaaacaactc tggcgcatcg gcttcccat    8160
acaatcgata gattgtcgca cctgattgcc cgacattatc gcgagcccat ttatacccat   8220
ataaatcagc atccatgttg gaatttaatc gcggcctcga acgtgagtc ttttccttac    8280
ccatggttgt ttatgttcgg atgtgatgtg agaactgtat cctagcaaga ttttaaaagg   8340
aagtatatga aagaagaacc tcagtggcaa atcctaacct tttatatttc tctacagggg   8400
cgcggcgtgg ggacaattca acgcgtctgt gaggggagcg tttccctgct cgcaggtctg   8460
```

-continued

```
cagcgaggag ccgtaatttt tgcttcgcgc cgtgcggcca tcaaaatgta tggatgcaaa    8520
tgattataca tggggatgta tgggctaaat gtacgggcga cagtcacatc atgcccctga    8580
gctgcgcacg tcaagactgt caaggagggt attctgggcc tccatgtcgc tggccgggtg    8640
acccggcggg gacgaggcaa gctaaacaga tctctagacc taataacttc gtatagcata    8700
cattatacga agttatatta agggttgtct taattaaggg tgcccaattc gccctatagt    8760
gagtcgtatt acgcgcgctc actggccgtc gttttacaac gtcgtgactg ggaaaaccct    8820
ggcgttaccc aacttaatcg ccttgcagca catcccccTT tcgccagctg gcgtaatagc    8880
gaagaggccc gcaccgatcg cccttcccaa cagttgcgca gcctgaatgg cgaatggcgc    8940
gacgcgccct gtagcggcgc attaagcgcg gcgggtgtgg tggttacgcg cagcgtgacc    9000
gctacacttg ccagcgccct agcgcccgct cctttcgctt tcttcccttc ctttctcgcc    9060
acgttcgccg gctttccccg tcaagctcta atcgggggc tccctttagg gttccgattt    9120
agtgctttac ggcacctcga ccccaaaaaa cttgattagg gtgatggttc acgtagtggg    9180
ccatcgccct gatagacggt ttttcgccct ttgacgttgg agtccacgtt ctttaatagt    9240
ggactcttgt tccaaactgg aacaacactc aaccctatct cggtctattc ttttgattta    9300
taagggattt tgccgatttc ggcctattgg ttaaaaaatg agctgattta acaaaaattt    9360
aacgcgaatt ttaacaaaat attaacgttt acaatttcct gatgcggtat tttctcctta    9420
cgcatctgtg cggtatttca caccgcatag atccgtcgag ttcaagagaa aaaaaagaa    9480
aaagcaaaaa gaaaaaagga aagcgcgcct cgttcagaat gacacgtata gaatgatgca    9540
ttaccttgtc atcttcagta tcatactgtt cgtatacata cttactgaca ttcataggta    9600
tacatatata cacatgtata tatatcgtat gctgcagctt taaataatcg gtgtcaatgt    9660
ctgcccctat gtctgcccct aagaagatcg tcgttttgcc aggtgaccac gttggtcaag    9720
aaatcacagc cgaagccatt aaggttctta agctatttc tgatgttcgt tccaatgtca    9780
agttcgattt cgaaaatcat ttaattgtg gtgctgctat cgatgctaca ggtgtcccac    9840
ttccagatga ggcgctggaa gcctccaaga aggttgatgc cgttttgtta ggtgctgtgg    9900
gtggtcctaa atgggtgcc ggtagtgtta gacctgaaca aggtttacta aaaatccgta    9960
aagaacttca attgtacgcc aacttaagac catgtaactt tgcatccgac tctcttttag   10020
acttatctcc aatcaagcca caatttgcta aggtactga cttcgttgtt gtcagagaat   10080
tagtgggagg tatttacttt ggtaagagaa aggaagacga tggtgatggt gtcgcttggg   10140
atagtgaaca atacaccgtt ccagaagtgc aaagaatcac aagaatggcc gctttcatgg   10200
ccctacaaca tgagccacca ttgcctatTT ggtccttgga taaagctaat gttttggcct   10260
cttcaagatt atggagaaaa actgtggagg aaaccatcaa gaacgaattc cctacattga   10320
aggttcaaca tcaattgatt gattctgccg ccatgatcct agttaagaac ccaacccacc   10380
taaatggtat tataatcacc agcaacatgt ttggtgatat catctccgat gaagcctccg   10440
ttatcccagg ttccttgggt tgttgccat ctgcgtcctt ggcctctttg ccagacaaga   10500
acaccgcatt tggttTTgtac gaaccatgcc acggttctgc tccagatttg ccaagaata   10560
aggttgaccc tatcgccact atcttgtctg ctgcaatgat gttgaaattg tcattgaact   10620
tgcctgaaga aggtaaggcc attgaagatg cagttaaaaa ggttttggat gcaggtatca   10680
gaactggtga tttaggtggt tccaacagta ccaccgaagt cggtgatgct gtcgccgaag   10740
aagtTAAgaa aatccttgct taactttgcc ttcgttatc ttgcctgctc atttttTAGT   10800
atattcttcg aagaaatcac attacttTAT ataatgtata attcattatg tgataatgcc   10860
```

```
aatcgctaag aaaaaaaaag agtcatccgc tagggggaaaa aaaaaaatga aaatcattac   10920
cgaggcataa aaaaatatag agtgtactag aggaggccaa gagtaataga aaaagaaaat   10980
tgcgggaaag gactgtgtta tgacttccct gactaatgcc gtgttcaaac gatacctggc   11040
agtgactcct agcgctcacc aagctcttaa aacgggaatt tatggtgcac tctcagtaca   11100
atctgctctg atgccgcata gttaagccag ccccgacacc cgccaacacg cgctgacgcg   11160
ccctgacggg cttgtctgct cccggcatcc gcttacagac aagctgtgac cgtctccggg   11220
agctgcatgt gtcagaggtt ttcaccgtca tcaccgaaac gcgcgagacg aaagggcctc   11280
gtgatacgcc tattttttata ggttaatgtc atgataataa tggtttctta ggacggatcg   11340
cttgcctgta acttacacgc gcctcgtatc ttttaatgat ggaataattt gggaatttac   11400
tctgtgttta tttattttta tgttttgtat ttggattttta aaagtaaat aaagaaggta    11460 gaagagttac ggaatgaaga aaaaaaaata aacaaaggtt taaaaaattt caacaaaaag   11520
cgtactttac atatatattt attagacaag aaaagcagat taaatagata tacattcgat   11580
taacgataag taaaatgtaa aatcacagga ttttcgtgtg tggtcttcta cacagacaag   11640
atgaaacaat tcggcattaa tacctgagag caggaagagc aagataaaag gtagtatttg   11700
ttggcgatcc ccctagagtc ttttacatct tcggaaaaca aaaactattt tttcttttaat   11760 ttcttttttt actttctatt tttaatttat atatttatat taaaaaattt aaattataat   11820
tatttttata gcacgtgatg aaaaggaccc aggtggcact tttcggggaa atgtgcgcgg   11880 aaccccctatt tgtttatttt tctaaataca ttcaaatatg tatccgctca tgagacaata   11940
accctgataa atgcttcaat aatattgaaa aaggaagagt atgagtattc aacatttccg   12000
tgtcgccctt attccttttt tgcggcatt ttgccttcct gttttttgctc acccagaaac     12060 gctggtgaaa gtaaaagatg ctgaagatca gttgggtgca cgagtgggtt acatcgaact   12120
ggatctcaac agcggtaaga tccttgagag ttttcgcccc gaagaacgtt ttccaatgat   12180
gagcactttt aaagttctgc tatgtggcgc ggtattatcc cgtattgacg ccgggcaaga   12240
gcaactcggt cgccgcatac actattctca gaatgacttg gttgagtact caccagtcac   12300
agaaaagcat cttacggatg gcatgacagt aagagaatta tgcagtgctg ccataaccat   12360
gagtgataac actgcggcca acttacttct gacaacgatc ggaggaccga aggagctaac   12420
cgcttttttg cacaacatgg gggatcatgt aactcgcctt gatcgttggg aaccggagct   12480
gaatgaagcc ataccaaacg acgagcgtga ccacacgatg cctgtagcaa tggcaacaac   12540
gttgcgcaaa ctattaactg gcgaactact tactctagct tcccggcaac aattaataga   12600
ctggatggag gcggataaag ttgcaggacc acttctgcgc tcggcccttc cggctggctg   12660
gtttattgct gataaatctg gagccggtga gcgtgggtct cgcggtatca ttgcagcact   12720
ggggccagat ggtaagccct cccgtatcgt agttatctac acgacgggga gtcaggcaac   12780 tatgatgaa cgaaatagac agatcgctga gataggtgcc tcactgatta gcattggta    12840 actgtcagac caagtttact catatatact ttagattgat ttaaaacttc attttttaatt   12900 taaaaggatc taggtgaaga tccttttttga taatctcatg accaaaatcc cttaacgtga   12960
gttttcgttc cactgagcgt cagaccccgt agaaaagatc aaaggatctt cttgagatcc   13020 ttttttttctg cgcgtaatct gctgcttgca aacaaaaaaa ccaccgctac cagcggtggt   13080
ttgtttgccg gatcaagagc taccaactct ttttccgaag gtaactggct tcagcagagc   13140
gcagatacca aatactgtcc ttctagtgta gccgtagtta ggccaccact tcaagaactc   13200
```

| | | | |
|---|---|---|---|
| tgtagcaccg | cctacatacc | tcgctctgct | aatcctgtta ccagtggctg ctgccagtgg | 13260 |
| cgataagtcg | tgtcttaccg | ggttggactc | aagacgatag ttaccggata aggcgcagcg | 13320 |
| gtcgggctga | acgggggggtt | cgtgcacaca | gcccagcttg gagcgaacga cctacaccga | 13380 |
| actgagatac | ctacagcgtg | agctatgaga | aagcgccacg cttcccgaag ggagaaaggc | 13440 |
| ggacaggtat | ccggtaagcg | gcagggtcgg | aacaggagag cgcacgaggg agcttccagg | 13500 |
| gggaaacgcc | tggtatcttt | atagtcctgt | cgggtttcgc cacctctgac ttgagcgtcg | 13560 |
| atttttgtga | tgctcgtcag | ggggcggag | cctatggaaa aacgccagca acgcggcctt | 13620 |
| tttacggttc | ctggccttt | gctggccttt | tgctcacatg ttctttcctg cgttatcccc | 13680 |
| tgattctgtg | gataaccgta | ttaccgcctt | tgagtgagct gataccgctc gccgcagccg | 13740 |
| aacgaccgag | cgcagcgagt | cagtgagcga | ggaagcggaa gagcgcccaa tacgcaaacc | 13800 |
| gcctctcccc | gcgcgttggc | cgattcatta | atgcagctgg cacgacaggt ttcccgactg | 13860 |
| gaaagcgggc | agtgagcgca | acgcaattaa | tgtgagttac ctcactcatt aggcaccccca | 13920 |
| ggctttacac | tttatgcttc | cggctcctat | gttgtgtgga attgtgagcg gataacaatt | 13980 |
| tcacacagga | aacagctatg | accatgatta | cgccaagcgc gcaat | 14025 |

```
<210> SEQ ID NO 5
<211> LENGTH: 684
<212> TYPE: DNA
<213> ORGANISM: Saccharomyces cerevisiae
<220> FEATURE:
<221> NAME/KEY: Acc1 promoter
<222> LOCATION: (1)..(463)
<220> FEATURE:
<221> NAME/KEY: gRNA_3
<222> LOCATION: (53)..(72)
<220> FEATURE:
<221> NAME/KEY: gRNA_2
<222> LOCATION: (265)..(284)
<220> FEATURE:
<221> NAME/KEY: gRNA_1
<222> LOCATION: (339)..(358)
```

<400> SEQUENCE: 5

| | | | |
|---|---|---|---|
| ggtagaaact | tgatttttc | taattttctg | cgctgtttcg ggaacggaaa aaaattaagc | 60 |
| tagaagacga | atcggttatt | atactattat | atttgtatag tatagtagcg tgtcgtatcg | 120 |
| tatcgtgtcg | tatcgtatcg | tatcgttaaa | agaaaataca cgaataaata ataatatgtg | 180 |
| gagaagaaaa | agggaagttt | cttgtctctt | gctctgaatc tgaattccaa ttcaagttca | 240 |
| aattgttctc | tagtttattg | tccaaaaata | aggatgaagc gggagggaag ggcagaggga | 300 |
| aaagttcgta | tagtagaatg | aataaacttt | tataaacaca tgcaccgatc actcacagag | 360 |
| gataaaaaaa | tggcacaaca | aatatatata | tatagatgca aatggcgatt gcaaattagg | 420 |
| gaattggctt | tgttgttttt | tatcttcagg | taaactgtac gaaagggata aaagagtag | 480 |
| aataaggaaa | ggaaaattga | agagagcaga | acaattgtag aaccgataac aattgtgaca | 540 |
| gtgattgtgc | taggctatac | tgtgccagaa | tacgactggg agtgctgttc ttcttatata | 600 |
| tcttggcgct | gattgagcgt | atagcctagt | tcaccaagca gtagagagag tggcaatgag | 660 |
| cggttgaatt | tcgactgcga | cttg | | 684 |

```
<210> SEQ ID NO 6
<211> LENGTH: 971
<212> TYPE: DNA
<213> ORGANISM: Artificial Sequence
```

<220> FEATURE:
<223> OTHER INFORMATION: PGK1 promoter and integration sequences for
    Saccharomyces cerevisiae Acc1 promoter
<220> FEATURE:
<221> NAME/KEY: PGK1p
<222> LOCATION: (7)..(750)

<400> SEQUENCE: 6

```
tgttttatat ttgttgtaaa aagtagataa ttacttcctt gatgatctgt aaaaaagaga    60
aaaagaaagc atctaagaac ttgaaaaact acgaattaga aaagaccaaa tatgtatttc   120
ttgcattgac caatttatgc aagtttatat atatgtaaat gtaagtttca cgaggttcta   180
ctaaactaaa ccaccccctt ggttagaaga aaagagtgtg tgagaacagg ctgttgttgt   240
cacacgattc ggacaattct gtttgaaaga gagagagtaa cagtacgatc gaacgaactt   300
tgctctggag atcacagtgg gcatcatagc atgtggtact aaacccttc ccgccattcc   360
agaaccttcg attgcttgtt acaaaacctg tgagccgtcg ctaggacctt gttgtgtgac   420
gaaattggaa gctgcaatca ataggaagac aggaagtcga gcgtgtctgg gtttttcag    480
ttttgttctt tttgcaaaca aatcacgagc gacggtaatt tctttctcga taagaggcca   540
cgtgctttat gagggtaaca tcaattcaag aaggagggaa acacttcctt tttctggccc   600
tgataatagt atgagggtga agccaaaata aaggattcgc gcccaaatcg gcatctttaa   660
atgcaggtat gcgatagttc ctcactcttt ccttactcac gagtaattct tgcaaatgcc   720
tattatgcag atgttataat atctgtgcgt agggataaaa agagtagaat aaggaaagga   780
aaattgaaga gagcagaaca attgtagaac cgataacaat tgtgacagtg attgtgctag   840
gctatactgt gccagaatac gactgggagt gctgttcttc ttatatatct tggcgctgat   900
tgagcgtata gcctagttca ccaagcagta gagagagtgg caatgagcgg ttgaatttcg   960
actgcgactt g                                                        971
```

<210> SEQ ID NO 7
<211> LENGTH: 1724
<212> TYPE: DNA
<213> ORGANISM: Artificial Sequence
<220> FEATURE:
<223> OTHER INFORMATION: Cassette with Saccharomyces cerevisiae Acc1
    (S659A; S1157A) coding sequence, regulatory sequences and
    integration sequences
<220> FEATURE:
<221> NAME/KEY: T-G Ser659Ala
<222> LOCATION: (108)..(108)
<220> FEATURE:
<221> NAME/KEY: T-G Ser1157Ala
<222> LOCATION: (1602)..(1602)

<400> SEQUENCE: 7

```
ggcgcgccga gggtaaaaga tacaagttca cggtcgctaa atccggtaat gaccgctaca    60
cattatttat caatggttct aaatgtgata tcatactgcg tcaactagct gatggtgggc   120
tgctgatcgc tatcggcgct aaatcgcata ccatctattg gaaagaagaa gttgctgcta   180
caagattatc cgttgactct atgactactt tgttggaagt tgaaaacgat ccaacccagt   240
tgcgtactcc atcccctggt aaattggtta aattcttggt ggaaaatggt gaacacatta   300
tcaagggcca accatatgca gaaattgaag ttatgaaaat gcaatgcct ttggtttctc   360
aagaaaatgg tatcgtccag ttattaaagc aacctggttc taccattgtt gcaggtgata   420
tcatggctat tatgactctt gacgatccat ccaaggtcaa gcacgctcta ccatttgaag   480
gtatgctgcc agattttggt tctccagtta tcgaaggaac caaacctgcc tataaattca   540
```

-continued

```
agtcattagt gtctactttg gaaaacattt tgaagggtta tgacaaccaa gttattatga      600
acgcttcctt gcaacaattg atagaagttt tgagaaatcc aaaactgcct tactcagaat      660
ggaaactaca catctctgct ttacattcaa gattgcctgc taagctagat gaacaaatgg      720
aagagttagt tgcacgttct ttgagacgtg gtgctgtttt cccagctaga caattaagta      780
aattgattga tatggccgtg aagaatcctg aatacaaccc cgacaaattg ctgggcgcag      840
tcgtggaacc attggcggat attgctcata agtactctaa cggggttagaa gcccatgaac      900 attctatatt tgtccatttc ttggaagaat attacgaagt tgaaaagtta ttcaatggtc      960
caaatgttcg tgaggaaaat atcattctga aattgcgtga tgaaaaccct aaagatctag     1020
ataaagttgc gctaactgtt ttgtctcatt cgaaagtttc agcgaagaat aacctgatcc     1080
tagctatctt gaaacattat caaccattgt gcaagttatc ttctaaagtt tctgccattt     1140
tctctactcc tctacaacat attgttgaac tagaatctaa ggctaccgct aaggtcgctc     1200
tacaagcaag agaaattttg attcaaggcg ctttaccttc ggtcaaggaa agaactgaac     1260
aaattgaaca tatcttaaaa tcctctgttg tgaaggttgc ctatggctca tccaatccaa     1320
agcgctctga accagatttg aatatcttga aggacttgat cgattctaat tacgttgtgt     1380
tcgatgtttt acttcaattc ctaacccatc aagacccagt tgtgactgct gcagctgctc     1440
aagtctatat tcgtcgtgct tatcgtgctt acaccatagg agatattaga gttcacgaag     1500
gtgtcacagt tccaattgtt gaatggaaat tccaactacc ttcagctgcg ttctccacct     1560
ttccgactgt gaagtctaag atgggtatga acagggctgt tgctgtttca gatttgtcat     1620
atgttgcaaa cagtcagtca tctccgttaa gagaaggtat tttgatggct gtggatcatt     1680
tagatgatgt tgatgaaatt ttgtcacaaa gtttggggcg cgcc                      1724
```

<210> SEQ ID NO 8
<211> LENGTH: 3256
<212> TYPE: DNA
<213> ORGANISM: Artificial Sequence
<220> FEATURE:
<223> OTHER INFORMATION: Cassette with Saccharomyces cerevisiae Maf1
      coding sequence, regulatory sequences and integration sequences
<220> FEATURE:
<221> NAME/KEY: L0
<222> LOCATION: (362)..(401)
<220> FEATURE:
<221> NAME/KEY: Tef1
<222> LOCATION: (402)..(895)
<220> FEATURE:
<221> NAME/KEY: L1
<222> LOCATION: (896)..(935)
<220> FEATURE:
<221> NAME/KEY: MAF1
<222> LOCATION: (936)..(2123)
<220> FEATURE:
<221> NAME/KEY: L2
<222> LOCATION: (2124)..(2163)
<220> FEATURE:
<221> NAME/KEY: PRM9t
<222> LOCATION: (2164)..(2701)
<220> FEATURE:
<221> NAME/KEY: LTP2
<222> LOCATION: (2702)..(2741)

<400> SEQUENCE: 8

```
aatgatttaa gcgtgcgtga agataacact acaatccatt ttaaagcaac atccacattg       60
agtgtataca ccacaaaggt ttttttcaggg cgttttttctc gccactttat gttgaccaaa    120
attattaatg gaacttacaa cgtttccaaa agttagttaa atacatacgt ctatttacta     180
agcaagaaat atatcatgac aagcccaaat attatattgt tatgtttaca aaaaaaaaat     240
```

| | |
|---|---|
| ggctatatac atcaagtctg gaggcttttt ataacaagca agtggggtaa cttagacata | 300 |
| agattgactt ctttgaattc aacaaaaata catactttg atgatttcaa tggtagaagc | 360 |
| ataaacaaca aataatcata aaaattttag aactagacat aaagcaacag gcgcgttgga | 420 |
| cttttaattt tcgaggaccg cgaatcctta catcacaccc aatcccccac aagtgatccc | 480 |
| ccacacacca tagcttcaaa atgtttctac tccttttta ctcttccaga ttttctcgga | 540 |
| ctccgcgcat cgccgtacca cttcaaaaca cccaagcaca gcatactaaa tttcccctct | 600 |
| ttcttcctct agggtgtcgt taattacccg tactaaaggt ttggaaaaga aaaagagac | 660 |
| cgcctcgttt cttttcttc gtcgaaaaag gcaataaaaa tttttatcac gtttcttttt | 720 |
| cttgaaaatt ttttttttg attttttct ctttcgatga cctcccattg atatttaagt | 780 |
| taataaacgg tcttcaattt ctcaagtttc agtttcattt ttcttgttct attacaactt | 840 |
| tttttacttc ttgctcatta gaaagaaagc atagcaatct aatctaagtt ttaatctaga | 900 |
| aaatttatta taaaggaag agaaataatt aaacaatgaa atttattgat gagctagata | 960 |
| tagagagagt gaatcaaact ctcaattccg agacaaatga ctgtaaaatc gtgggcagtt | 1020 |
| gcgatatttt cacaacaaag gcggttgcat cagatagaaa attatataaa actattgatc | 1080 |
| agcatttgga tactatttta caggaaaatg agaattacaa tgctacccctt cagcaacagc | 1140 |
| tagctgctcc cgaaacaaac caatcaccct gctcgtcgcc attttattct aataggaggg | 1200 |
| atagcaactc ttttttggag caaaagagaa gaatatcttt tagtgaatac aatagcaata | 1260 |
| ataacactaa caacagtaat ggcaatagca gtaataacaa taactattct ggacctaatg | 1320 |
| gttcttctcc agcaactttt cccaaaagtg ccaagctaaa tgaccaaaat ttaaaagaat | 1380 |
| tagtctcgaa ttacgattct ggctctatga gctcatcgtc tcttgattct tcttctaaga | 1440 |
| atgatgagag gataagaaga aggagcagta gcagtattag cagtttcaaa agtggtaaat | 1500 |
| catcgaacaa taattacagt tctggtacag caaccaacaa tgttaacaaa agaagaaaat | 1560 |
| cttcgataaa cgaaaggcca agcaatttaa gtttgggtcc gtttggtccc ataaacgaac | 1620 |
| cgtcaagccg caaaatattt gcttatctga ttgctatcct caacgcttct tatcctgacc | 1680 |
| atgattttc atcggttgag ccaacggatt ttgtcaaaac atcattgaaa acttttattt | 1740 |
| ccaaatttga aaacaccta tattctcttg gtagacaacc agaggaatgg gtctgggagg | 1800 |
| taattaattc tcacatgact cttcgatt gcgtccttt tcaatattca ccttcaaact | 1860 |
| ctttttgga agatgagcct ggctatcttt ggaatcttat aggttttctt tacaacagga | 1920 |
| aaaggaaaag agtggcttac ctttacttga tttgctcgcg tctaaattcg agtacaggcg | 1980 |
| aagtggaaga tgccttggca aaaaaacctc agggaaagct tataatagat gatggctcaa | 2040 |
| atgaatacga aggagaatac gatttcactt atgatgagaa tgtaatagat gataaatcag | 2100 |
| atcaagaaga atccctacag tagagacata aaactgaaac aacaccaatt aataatagac | 2160 |
| tttacagaag acgggagaca ctagcacaca actttaccag gcaaggtatt tgacgctagc | 2220 |
| atgtgtccaa ttcagtgtca tttatgattt tttgtagtag gatataaata tatacagcgc | 2280 |
| tccaaatagt gcggttgccc caaaacacc acggaacctc atctgttctc gtactttgtt | 2340 |
| gtgacaaagt agctcactgc cttattatca cattttcatt atgcaacgct tcggaaaata | 2400 |
| cgatgttgaa aatgcctcta gagatgaaaa acaatcgtaa aagggtcctg cgtaattgaa | 2460 |
| acatttgatc agtatgcagt ggcacagaaa caaccaggaa tactatagtc ataggcaata | 2520 |
| caaggtatat attggctatg cagacccctc cagaaagtac cgacgtcaag ttagatacac | 2580 |

-continued

```
ttaacgaacc tagtgcacat ttaattgaga aaaatgtggc tcttcctaag gacatattcc    2640
gttcgtactt gagttattgg atctatgaaa tcgctcgcta tacaccagtc atgattttgt    2700
ccttaaataa catactcatc actaaacatt cttaacaatc agaaaacaac gcgtcatgaa    2760
aaagagttac tgaaccttca gatcctactt attgtaatgc ttcgcgacat ccaatccatt    2820
taataatcaa tttaaaacta gagttggtag agttccttgt tgaacgtgat aacccaaaag    2880
cataatacga gtaatgtttc agtattgcta ttatatgttt acacaaggaa acatataat     2940 aacaaacctc taatccggta gtacttaaga aactatagtt tctatgtaca aaaaggtaac    3000
tatgtaattc ttcatttac ataacgtata gaagggtcca ataaacttac taaacttact    3060
accttgttgt atataggcta gatcgtaatc cactacgtca acataaaaaa aacttaagaa    3120
gtttgaattt tatgtacaaa cagattgtta aaatataata taagattatg gaaacgaact    3180
tgctctaaaa aaaatttaaa gttttataaa atcctcgaac tatcgctgtt atacatgatg    3240
tccccaaagc gtgtac                                                    3256
```

<210> SEQ ID NO 9
<211> LENGTH: 4662
<212> TYPE: DNA
<213> ORGANISM: Artificial Sequence
<220> FEATURE:
<223> OTHER INFORMATION: Cassette with Saccharomyces cerevisiae
      UPC2E888D coding sequence, regulatory sequences and integration
      sequences
<220> FEATURE:
<221> NAME/KEY: L0
<222> LOCATION: (401)..(440)
<220> FEATURE:
<221> NAME/KEY: Tef1
<222> LOCATION: (441)..(934)
<220> FEATURE:
<221> NAME/KEY: L1
<222> LOCATION: (935)..(974)
<220> FEATURE:
<221> NAME/KEY: UPC2-1
<222> LOCATION: (975)..(3701)
<220> FEATURE:
<221> NAME/KEY: g-a G888D
<222> LOCATION: (3637)..(3637)
<220> FEATURE:
<221> NAME/KEY: L2
<222> LOCATION: (3702)..(3741)
<220> FEATURE:
<221> NAME/KEY: PRM9t
<222> LOCATION: (3742)..(4279)
<220> FEATURE:
<221> NAME/KEY: LTP2
<222> LOCATION: (4280)..(4319)

<400> SEQUENCE: 9

```
cccagttgtt tgtagctggt tcatatttag cggcaattct ctgttgcgta aatgaaaata      60
ttaatgtaaa caaaaaaga ccaaaacatt ttagcagtgt aagaaggtgt actgatacaa     120
aatgtgttta gagtctactg atatgttact gaccgttcgt tgggaaaaaa atactgtatc     180
atttattaat caaaagcgac ttttggtgga atattatgat atgtgttgtt aaaatatgac     240
gtaattttag aattgtctga ttcgtattca aatttggtga aggaataacg cagagttgac     300
aatttaatag aatggattaa tcgtaatttt cagaaacgta gaaaaagaaa acaattaaa     360 acattatatt aagattattg atttgccttt taagggtcca taaacaacaa ataatcataa     420
aaattttaga actagacata aagcaacagg cgcgttggac ttttaatttt cgaggaccgc     480
gaatccttac atcacaccca atcccccaca agtgatcccc cacacaccat agcttcaaaa     540
tgtttctact ccttttttac tcttccagat tttctcggac tccgcgcatc gccgtaccac     600
```

```
ttcaaaacac ccaagcacag catactaaat ttcccctctt tcttcctcta gggtgtcgtt      660
aattacccgt actaaaggtt tggaaaagaa aaaagagacc gcctcgtttc tttttcttcg      720
tcgaaaaagg caataaaaat ttttatcacg tttcttttc ttgaaaattt ttttttttga       780
tttttttctc tttcgatgac ctcccattga tatttaagtt aataaacggt cttcaatttc      840
tcaagtttca gtttcatttt tcttgttcta ttacaacttt ttttacttct tgctcattag      900
aaagaaagca tagcaatcta atctaagttt taatctagaa aatttattat aaaaggaaga     960
gaaataatta aacaatgagc gaagtcggta tacagaatca caagaaagcg gtgacaaaac    1020
ccagaagaag agaaaaagtc atcgagctaa ttgaagtgga cggcaaaaag gtgagtacga    1080
cttcaaccgg taaacgtaaa ttccataaca aatcaaagaa tgggtgcgat aactgtaaaa    1140
gaagaagagt taagtgtgat gaagggaagc cagcctgtag gaagtgcaca aatatgaagt    1200
tggaatgtca gtatacacca atccatttaa ggaaaggtag aggagcaaca gtagtgaagt    1260
atgtcacgag aaaggcagac ggtagcgtgg agtctgattc atcggtagat ttacctccta    1320
cgatcaagaa ggagcagaca ccgttcaatg atatccaatc agcggtaaaa gcttcaggct    1380
catccaatga ttcctttcca tcaagcgcct ctacaactaa gagtgagagc gaggaaaagt    1440
catcggcccc tatagaggac aaaaacaata tgactcctct aagtatgggc ctccagggta    1500
ccatcaataa gaaagatatg atgaataact ttttctctca aaatggcact attggttttg    1560
gttctcctga aagattgaat tcaggtatcg atggcttact attaccgcca ttgccttctg    1620
gaaatatggg tgcgttccaa cttcagcaac agcagcaagt gcagcagcaa tctcaaccac    1680
agacccaagc gcagcaagca agtggaactc caaacgagag atatggttca ttcgatcttg    1740
cgggtagtcc tgcattgcaa tccacgggaa tgagcttatc aaatagtcta agcgggatgt    1800
tactatgtaa caggattcct tccggccaaa actacactca acaacaatta caatatcaat    1860
tacaccagca gctgcaattg caacagcatc agcaagttca gctgcagcag tatcaacaat    1920
tacgtcagga acaacaccaa caagttcagc aacaacaaca ggaacaactc cagcaatacc    1980
aacaacattt tttgcaacag cagcaacaag tactgcttca gcaagagcaa caacctaacg    2040
atgaggaagg tggcgttcag gaagaaaaca gcaaaaaggt aaaggaaggg cctttacaat    2100
cacaaacaag cgaaactact ttaaacagcg atgctgctac attacaagct gatgcattat    2160
ctcagttaag taagatgggg ctaagcctaa agtcgttaag tacctttcca acagctggta    2220
ttggtggtgt ttcctatgac tttcaggaac tgttaggtat taagtttcca ataaataacg    2280
gcaattcaag agctactaag gccagcaacg cagaggaagc tttggccaat atgcaagagc    2340
atcatgaacg tgcagctgct tctgtaaagg agaatgatgg tcagctctct gatacgaaga    2400
gtccagcgcc atcgaataac gcccaagggg gaagtgctag tattatggaa cctcaggcgg    2460
ctgatgcggt ttcgacaatg gcgcctatat caatgattga agaaacatg aacagaaaca    2520 gcaacatttc tccatcaacg ccctctgcag tgttgaatga taggcaagag atgcaagatt    2580
ctataagttc tctaggaaat ctgacaaaag cagccttgga gaacaacgaa ccaacgataa    2640
gtttacaaac atcacagaca gagaatgaag acgatgcatc gcggcaagac atgacctcaa    2700
aaattaataa cgaagctgac cgaagttctg tttctgctgg taccagtaac atcgctaagc    2760
ttttagatct ttctaccaaa ggcaatctga acctgataga catgaaactg tttcatcatt    2820
attgcacaaa ggtctggcct acgattacag cggccaaagt ttctgggcct gaaatatgga    2880
gggactacat accggagtta gcatttgact atccattttt aatgcacgct tgttggcat    2940
```

```
tcagtgccac ccatctttcg aggactgaaa ctggactgga gcaatacgtt tcatctcacc   3000
gcctagacgc tctgagatta ttaagagaag ctgttttaga aatatctgag aataacaccg   3060
atgcgctagt tgccagcgcc ctgatactaa tcatggactc gttagcaaat gctagtggta   3120
acggcactgt aggaaaccaa agtttgaata gcatgtcacc aagcgcttgg atctttcatg   3180
tcaaaggtgc tgcaacaatt ttaaccgctg tgtggccttt gagtgaaaga tctaaatttc   3240
ataacattat atctgttgat cttagcgatt taggcgatgt cattaaccct gatgttggaa   3300
caattactga attggtatgt tttgatgaaa gtattgccga tttgtatcct gtcggcttag   3360
attcgccata tttgataaca ctagcttatt tagataaatt gcaccgtgaa aaaaaccagg   3420
gtgattttat tctgcgggta tttacatttc cagcattgct agacaagaca ttcctggcat   3480
tactgatgac aggtgattta ggtgcaatga gaattatgag atcatattat aaactacttc   3540
gaggatttgc cacagaggtc aaggataaag tctggtttct cgaaggagtc acgcaggtgc   3600
tgcctcaaga cgttgatgag tacaggggag gtggtgatat gcatatgatg ctaggattac   3660
catcgatgac aacaacaaat ttctctgatt tttcgttatg aagacataaa actgaaacaa   3720
caccaattaa taatagactt tacagaagac gggagacact agcacacaac tttaccaggc   3780
aaggtatttg acgctagcat gtgtccaatt cagtgtcatt tatgattttt tgtagtagga   3840
tataaatata tacagcgctc caaatagtgc ggttgcccca aaaacaccac ggaacctcat   3900
ctgttctcgt actttgttgt gacaaagtag ctcactgcct tattatcaca ttttcattat   3960
gcaacgcttc ggaaaatacg atgttgaaaa tgcctctaga gatgaaaaac aatcgtaaaa   4020
gggtcctgcg taattgaaac atttgatcag tatgcagtgg cacagaaaca accaggaata   4080
ctatagtcat aggcaataca aggtatatat tggctatgca gacccctcca gaaagtaccg   4140
acgtcaagtt agatacactt aacgaaccta gtgcacattt aattgagaaa atgtggctc   4200 ttcctaagga catattccgt tcgtacttga gttattggat ctatgaaatc gctcgctata   4260
caccagtcat gattttgtcc ttaaataaca tactcatcac taaacattct taacaatcac   4320
gatggatgat gattggttct tatcataatt tgatttcggc agaagcaata ttagaggtat   4380
tgttgtaacg aaattccaat gtcatctgct tagtattatt aatgttacct gcatattatc   4440
acatgccgct taaaaatgtg ttataagtat taaaatctag tgaaagttga atgtaatct   4500 aataggataa tgaaacatat gaaacggaat gaggaataat cgttgtatta ctatgtagag   4560
atatcgattt cattttgagg attcctatat tcttggggag aacttctact atattctgta   4620
tacatgatat aatagccttt accaacaatg gaatgccaac aa   4662
```

<210> SEQ ID NO 10
<211> LENGTH: 3564
<212> TYPE: DNA
<213> ORGANISM: Artificial Sequence
<220> FEATURE:
<223> OTHER INFORMATION: Cassette with Aspergillus nidulans NpgA coding
      sequence, regulatory sequences and integration sequences
<220> FEATURE:
<221> NAME/KEY: LTP1 (L0)
<222> LOCATION: (596)..(635)
<220> FEATURE:
<221> NAME/KEY: Tef1p
<222> LOCATION: (636)..(1129)
<220> FEATURE:
<221> NAME/KEY: L1
<222> LOCATION: (1130)..(1169)
<220> FEATURE:
<221> NAME/KEY: NpgA
<222> LOCATION: (1170)..(2201)
<220> FEATURE:

<220> FEATURE:
<221> NAME/KEY: L2
<222> LOCATION: (2205)..(2244)
<220> FEATURE:
<221> NAME/KEY: PRM9t
<222> LOCATION: (2245)..(2782)
<220> FEATURE:
<221> NAME/KEY: LTP2
<222> LOCATION: (2783)..(2822)

<400> SEQUENCE: 10

```
tcaatcaaag caacccacaa atcctaggct gaatcatgat atcgatggaa gcaatcaaca      60
attttatcaa gaccgcacca aagcacgact atctgacagg cggagttcat cattctggta     120
atgtagacgt gttacaatta agcggcaata agaagatgg tagtttagta tggaaccata      180
cttttgttga tgtagacaac aatgtggtag ctaagtttga agacgctctc gaaaaacttg     240
aaagtttgca ccggcgctca tcctcatcca caggcaatga agaacacgct aacgtttaac     300
cgagggagt cacttcataa tgatgtgaga ataagtgaa tattgtaata attgttggga       360
ctccattgtc aacaaaagct ataatgtagg tatacagtat atactagaag ttctcctcga     420
ggatcttgga atccacaaaa gggagtcgat aaatctatat aataaaaatt actttatctt     480
ctttcgtttt atacgttgtc gtttattatc ctattacgtt atcaatcttc gcatttcagc     540
tttcattaga tttgatgact gtttctcaaa ctttatgtca ttttcttaca ccgcataaac     600
aacaaataat cataaaaatt ttagaactag acataaagca acaggcgcgt tggacttta      660
attttcgagg accgcgaatc cttacatcac acccaatccc ccacaagtga tccccacac      720
accatagctt caaaatgttt ctactccttt tttactcttc cagattttct cggactccgc     780
gcatcgccgt accacttcaa acacccaag cacagcatac taaatttccc ctctttcttc      840
ctctagggtg tcgttaatta cccgtactaa aggtttggaa aagaaaaag agaccgcctc      900
gtttcttttt cttcgtcgaa aaaggcaata aaaattttta tcacgtttct ttttcttgaa     960
aattttttt tttgattttt ttctctttcg atgacctccc attgatattt aagttaataa    1020
acggtcttca atttctcaag tttcagtttc atttttcttg ttctattaca actttttta    1080
cttcttgctc attagaaaga aagcatagca atctaatcta agttttaatc tagaaaattt    1140
attataaaag gaagagaaat aattaaacaa tggttcaaga tacctcttct gcttctacct    1200
ctccaatttt gactagatgg tacattgata ccagaccatt gactgcttct actgctgctt    1260
tgccattatt ggaaaccttta caaccagccg atcaaatctc cgttcaaaag tactatcact    1320
tgaaggacaa gcacatgtct ttggcttcta acttgttgaa gtacttgttc gttcacagaa    1380
actgcagaat ccatggtcc tctatcgtta tttctagaac tccagatcca catagaaggc     1440
catgttatat tccaccatct ggttctcaag aggattcttt taagatggt tacaccggta      1500
tcaacgtcga gttaatgtt tctcatcaag cctccatggt tgctattgct ggtactgctt      1560
ttactccaaa ttctggtggt gattctaagt tgaaaccaga agttggtatc gatattacct    1620
gcgtcaacga aagacaaggt agaaatggtg aagaaaggtc cttggaatct ttgagacagt    1680
acatcgatat cttctccgaa gttttctcta ctgctgaaat ggccaacatt agaagattgg    1740
atggtgtctc ttcttcctca ttgtctgctg atagattggt tgattatggc tacaggttgt    1800
tctatactta ctgggctttg aaagaagcct acattaagat gactggtgaa gccttgttgg    1860
ctccatggtt gagagaattg gaattctcta atgttgttgc tccagctgct gttgctgaat    1920
ctggtgattc tgctggtgat tttggtgaac catatactgg tgttagaacc accttgtaca    1980
agaacttggt tgaagatgtt agaattgaag ttgctgcttct gggtggtgat tacttgtttg    2040
```

-continued

```
ctactgctgc tagaggtggt ggtattggtg cttcttctag accaggtggt ggtccagatg      2100
gttctggtat tagatctcaa gatccttgga ggccattcaa gaagttggat attgaaaggg      2160
atattcaacc atgtgctact ggtgtatgta actgcttgtc ttaaagacat aaaactgaaa      2220
caacaccaat taataataga ctttacagaa gacgggagac actagcacac aactttacca      2280
ggcaaggtat ttgacgctag catgtgtcca attcagtgtc atttatgatt ttttgtagta      2340
ggatataaat atatacagcg ctccaaatag tgcggttgcc ccaaaaacac cacgcaacct      2400
catctgttct cgtactttgt tgtgacaaag tagctcactg ccttattatc acattttcat      2460
tatgcaacgc ttcggaaaat acgatgttga aaatgcctct agagatgaaa acaatcgta       2520 aaagggtcct gcgtaattga acatttgat cagtatgcag tggcacagaa acaaccagga       2580
atactatagt cataggcaat acaaggtata tattggctat gcagacccct ccagaaagta     2640
ccgacgtcaa gttagataca cttaacgaac ctagtgcaca tttaattgag aaaaatgtgg     2700
ctcttcctaa ggacatattc cgttcgtact tgagttattg gatctatgaa atcgctcgct     2760
atacaccagt catgattttg tccttaaata acatactcat cactaaacat tcttaacaat     2820
cagaaaatgc aaccgataaa acattataaa tcttcgcggt tatctggcat tgttattaac     2880
caaaaaaatg ccggcctatt acaagctact gttcaataaa tattgttgta atgaagacgg     2940
tccaactgta caaatacagc aaactgtcat atataaggtg tcttatgtga cagcacttgc     3000
gttattgtca gccggagtat gtctttgtcg cattctgggc ttttttacttt ctgctcagaa    3060 ggaagtacga acaagaaaaa aaaatcacca atgcttccct tttcagtatt agtttcatat     3120
ttgtttacgt tcaaactcgt cgtttgcgcg ataacctcta aaaagtcag ttacgtaact      3180 atatcaatca gagaatgcaa aaagcactat cataaaaatg tctctagggg atgtgagaca    3240
tgtcaattat aagaagtgat ggtgtcatag tatatatatc ataaatgatt atcaaagttt    3300
caatcctttg tattttctag tttagcgcca acttttgaca aaacctaaac tttagataat    3360
catcattctt acaattttta tctggatggc aataatctcc tatataaagc ccagataaac    3420
tgtaaaaaga atccatcact atttgaaaaa aagtcatctg gcacgtttaa ttatcagagc    3480
agaaatgatg aagggtgtta gcgccgtcca ttgatgcgcc tggtagtcat gatttacgta    3540
taactaacac atcatgagga cggc                                           3564
```

<210> SEQ ID NO 11
<211> LENGTH: 336
<212> TYPE: PRT
<213> ORGANISM: Aspergillus terreus

<400> SEQUENCE: 11

```
Met Ile Gln Gln Val Gln Ala Val Phe Asp Pro Glu Arg Phe Leu
1               5                   10                  15

Val Asp Ile Glu Glu Thr Cys Arg Ala Ile Gly Ala Pro Tyr Ser Gln
                20                  25                  30

Glu Lys Thr Leu Lys Val Leu Glu Gly Phe Gln Ala Ser Phe Ala Arg
            35                  40                  45

Gly Ala Val Leu Trp Arg Ile Thr Asn Arg Pro Gly Asp Ala Leu Asn
        50                  55                  60

Tyr Arg Phe Tyr Glu Arg Val Ser Ile Asp Ala Val Ser Cys Ala Val
65                  70                  75                  80

Glu Ala Lys Leu Phe Gln Pro Asn His Pro Leu Ser Glu Leu Ile Val
                85                  90                  95
```

```
Ser Trp Thr Ala Leu Tyr Pro Gly Ala Ala Gln Gln Ser Cys Asp Phe
            100                 105                 110

Asp Ala Glu Gln Gly Phe Ser Lys Ile Trp Val Tyr Leu Gly Asp Met
            115                 120                 125

Arg Pro Leu Ser Asp Ile Leu Ser Ala Pro His Val Pro Leu Ser Ile
        130                 135                 140

Arg Lys His Ala Thr Thr Phe Tyr Asn Leu Gly Leu Glu Leu Val Arg
145                 150                 155                 160

His Val Ala Ala Asp Phe Thr Ser Asn Thr Ile Asn Ile Tyr Phe Arg
                165                 170                 175

Val Gln Gly Leu Leu Thr Leu Glu Arg Ala Arg Ser Leu Val Arg Leu
            180                 185                 190

Ser Asp Pro Ala Tyr Leu Leu Glu Cys Gly Glu Val Glu Glu Met Arg
        195                 200                 205

Arg Leu Leu Asn Pro Val Gly Phe Thr Phe Ala Val Thr Met Asp Tyr
        210                 215                 220

Ser Thr Gly Asp Ile Lys Arg Val Gly Ile Tyr Ala Leu Lys Leu Ala
225                 230                 235                 240

Pro Gly Thr Tyr Pro Ala Met Asp Glu Arg Leu Lys Ala Thr Arg Ala
                245                 250                 255

Ile Pro Leu Glu Lys Gln Ala Tyr Ile Leu Leu Ser Gln Gly Val Leu
            260                 265                 270

Met Ala Lys Glu Val Ala Ala Ala Phe Pro Val Pro Ser Glu Thr Ala
        275                 280                 285

Ala Val Asn Arg Pro Arg Glu Val Asp Val Glu Val Gly Val Gly Val
        290                 295                 300

Ala Ser Phe Met Phe Gln Pro Thr Thr Pro Ile Ala Pro Thr Val Asp
305                 310                 315                 320

Val Arg Asp Asn Val Val Val Ala Val Phe His Ala Val Glu Ser Pro
                325                 330                 335

<210> SEQ ID NO 12
<211> LENGTH: 305
<212> TYPE: PRT
<213> ORGANISM: Streptomyces sp CL190

<400> SEQUENCE: 12

Val Ser Gly Glu Thr Asp Ala Glu Glu Leu Cys Ser Ala Ile Glu Glu
1               5                   10                  15

Thr Ala Arg Leu Val Gly Ala Pro Cys Ser Arg Glu Lys Ile Trp Pro
            20                  25                  30

Ile Leu Thr Glu Tyr Arg Ser Gly Phe Ala Glu Gly Val Val Phe
            35                  40                  45

Ser Ala Gln Ala Gly Glu Asn His Ala Gly Glu Leu Asp Tyr Gly Leu
        50                  55                  60

Ala Val Pro Pro Arg Ile Asp Asp Pro Tyr Ala His Ala Leu Ala His
65                  70                  75                  80

Gly Phe Val Thr Glu Thr Asp His Pro Val Ala Leu Leu Ser Asp
                85                  90                  95

Ile Arg Glu Arg Cys Ala Val Thr Glu His Phe Ala Asp Cys Gly Val
            100                 105                 110

Val Gly Gly Phe Arg Lys Leu Tyr Ala His Phe Pro Arg Asp Leu Gln
        115                 120                 125
```

```
Lys Val Ser Glu Ile Ala Asp Ile Pro Ser Met Pro Arg Ala Val Ala
        130                 135                 140

Glu Asn Val Gly Leu Phe Thr Arg Tyr Gly Leu Glu Asn Val Val Met
145                 150                 155                 160

Val Gly Val Asn Tyr Lys Asn Lys Thr Val Ser Leu Tyr Phe Gln Phe
                165                 170                 175

Thr Ala Glu Gly Arg Pro Arg Pro Ser Ala Ile Arg Ser Met Leu Gly
            180                 185                 190

Asp Ile Gly Met Thr Glu Pro Asn Glu Arg Met Leu Asp Phe Ala Ser
        195                 200                 205

Asn Ser Phe Arg Ala Asn Ile Thr Leu Ser Trp Asp Ser Pro Lys Ile
210                 215                 220

Leu Arg Val Ala Phe Ala Pro Pro Gly Ala Gly Leu Asn Leu Ser
225                 230                 235                 240

Thr Val Pro Ile Pro Thr Gly Pro His Leu Glu Asp Phe Val Thr Arg
                245                 250                 255

Ala Pro Arg Ala Tyr Asp Gly Glu Arg Met Asn Leu Phe Ala Val Lys
            260                 265                 270

Trp Thr Gln Asp Lys Glu Phe Leu Glu Val Cys Ser Tyr Tyr Gln Leu
        275                 280                 285

Pro Ala Gly Tyr Glu Pro Ile Arg Gln Met Glu Ile His Lys Glu Gln
    290                 295                 300

Gly
305

<210> SEQ ID NO 13
<211> LENGTH: 299
<212> TYPE: PRT
<213> ORGANISM: Streptomyces sp CL190

<400> SEQUENCE: 13

Met Pro Glu Ala Thr Lys Leu Glu Thr Val Phe Ser Ala Val Glu Glu
1               5                   10                  15

Thr Ala Arg Leu Val Asp Ala Pro Cys Ser Arg Glu Lys Val Trp Pro
            20                  25                  30

Ala Leu Glu Thr Phe Gly Arg Trp Phe Asp Asp Ala His Ile Ile Phe
        35                  40                  45

Ser Met Gly Thr Gly His Lys Tyr Arg Gly Glu Leu Ala Phe Asp Phe
    50                  55                  60

Thr Val Pro Pro Glu Ala Gly Asp Pro Tyr Ala Ala Ala Val Ala Gly
65                  70                  75                  80

Gly Leu Leu Glu Lys Val Asp His Pro Val Thr Gly Leu Phe Ser Glu
                85                  90                  95

Ile Gly Asp Arg Phe Pro Val Asp Ala Tyr Ala Val Asp Tyr Gly Val
            100                 105                 110

Arg Gly Gly Phe Lys Lys Ala Cys Val Phe Phe Pro Leu Ala Arg Pro
        115                 120                 125

Gln Ser Met Lys Ala Leu Ala Glu Leu Pro Ser Ile Pro Pro Ala Leu
    130                 135                 140

Ala Ala His Ala Glu Tyr Phe Ala Ala Gly Leu Asp Gly Lys Val
145                 150                 155                 160

Ser Cys Ile Gly Ile Asp Tyr Gly Ser Arg Thr Trp Asn Leu Tyr Ile
                165                 170                 175
```

```
Ser Gly Leu Thr Pro Asp Tyr Thr Arg Pro Asp Ala Ile Val Ala Thr
            180                 185                 190

Leu Gly Glu Met Gly Leu Ser Lys Pro Ser Glu His Met Leu Glu Phe
        195                 200                 205

Ile Ser Thr Ser Phe Ala Met Tyr Pro Thr Phe Gly Trp Asp Thr Thr
    210                 215                 220

Arg Ile Glu Arg Met Cys Phe Ser Thr Arg Thr Ser Asp Pro Asn Leu
225                 230                 235                 240

Leu Pro Ala Arg Ile Glu Pro Asp Val Ala Lys Phe Ala Arg Asp Met
                245                 250                 255

Pro Thr Val His Gly Gly Glu Pro Ser Tyr Val Tyr Ala Gly Thr Val
            260                 265                 270

Ala Arg Gly Glu Glu Phe Phe Lys Leu Ala Ser Tyr Tyr Gln Met Ser
        275                 280                 285

Ser Lys Val Ser Glu Arg Val Arg Pro Ala Asp
    290                 295

<210> SEQ ID NO 14
<211> LENGTH: 304
<212> TYPE: PRT
<213> ORGANISM: Streptomyces sp CL190

<400> SEQUENCE: 14

Met Ser Gly Ala Lys Asp Val Glu Arg Val Tyr Ser Ala Met Glu Glu
1               5                   10                  15

Ala Ala Gly Leu Leu Asn Val Pro Val Ala Arg Asp Lys Ile Trp Pro
            20                  25                  30

Val Leu Thr Ala Tyr Gln Asp Ala Leu Ala Asp Ala Val Ile Val Phe
        35                  40                  45

Ser Met Ala Gly Gly Arg Arg Ser Thr Glu Leu Asp Phe Ser Ile Ser
    50                  55                  60

Val Pro Thr Asp His Gly Asp Pro Phe Thr Thr Ala Leu Glu Arg Gly
65                  70                  75                  80

Leu Thr Glu Lys Glu Asn His Pro Val Asp Asn Leu Leu Ala Glu Leu
                85                  90                  95

Arg Asp Gly Phe Pro Leu Gly Met Tyr Ala Ile Asp Gly Met Val Thr
            100                 105                 110

Thr Gly Phe Lys Lys Ala Tyr Ala Ser Phe Pro Thr Asn Glu Pro Gln
        115                 120                 125

Pro Leu Thr Ala Leu Leu Asp Leu Pro Ser Met Pro Glu Ser Ala Arg
    130                 135                 140

Ala Asn Ala Glu Leu Phe Ala Arg Tyr Gly Leu Asp Lys Val Gln Met
145                 150                 155                 160

Val Ser Val Asp Tyr Pro Lys Arg Gln Val Asn Leu Tyr Phe Ser Asp
                165                 170                 175

Leu Asn Ala Asp His Leu Thr Pro Glu Glu Val Lys Ser Thr Ala Ser
            180                 185                 190

Glu Met Gly Leu Val Glu Pro Asp Met Ala Leu Asp Phe Ala Thr
        195                 200                 205

Gly Ser Phe Ala Val Tyr Pro Thr Leu Gly Tyr Asp Ser Asp Val Val
    210                 215                 220

Asp Arg Ile Thr Tyr Ala Val Ile Ser Val Asp Pro Thr Leu Ala Pro
225                 230                 235                 240
```

```
Thr Thr Ser Glu Pro Glu Lys Thr Gln Ile Thr Thr Tyr Ala Asn Ser
            245                 250                 255

Ala Pro Tyr Ala Tyr Ala Gly Glu Asn Arg Thr Leu Val Tyr Gly Phe
        260                 265                 270

Thr Leu Thr Ser Lys Glu Glu Tyr Tyr Lys Leu Gly Ser Tyr Tyr Gln
        275                 280                 285

Ile Thr Asp Leu Gln Arg Thr Leu Val Lys Ala Phe Glu Ala Leu Asp
        290                 295                 300

<210> SEQ ID NO 15
<211> LENGTH: 299
<212> TYPE: PRT
<213> ORGANISM: Streptomyces sp CL190

<400> SEQUENCE: 15

Met Ser Ala Glu Pro Ala Ile Glu Arg Leu Cys Val Ala Ala Glu Asp
1               5                   10                  15

Ala Ala Gly Ile Val Gly Leu Glu Cys Pro Arg Glu Lys Met Thr Ala
            20                  25                  30

Val Leu Thr Ala Phe Pro Asn Val Thr Asp Ser Thr Val Val Phe
        35                  40                  45

Asn Val Val Asn Lys Gly Gly Arg Val Gly Asp Met Ser Phe Asp Phe
50                  55                  60

Thr Val Pro Leu Ala Ala Gly Asp Pro Tyr Glu Arg Ala Leu Ala His
65                  70                  75                  80

Gly Leu Ala Glu Lys Thr Asn His Pro Val Arg Gly Met Phe Ala Asp
                85                  90                  95

Met Leu Thr Thr Leu Pro Val Asp Cys Tyr Gly Val Asp Tyr Gly Val
            100                 105                 110

Asn Gly Gly Phe Asn Lys Ala Tyr Ala Val Phe Pro Met Gly Arg Leu
        115                 120                 125

Gln Glu Leu Asp Lys Leu Ala Ala Val Pro Ala Met Ala Asp Thr Leu
    130                 135                 140

Ser Lys Trp Met Gly Gln Leu Val Asp Tyr Gly Leu Asp Gly Arg Val
145                 150                 155                 160

Ser Thr Val Ala Val Asp His Ala Asn Arg Thr Trp Asn Val Tyr Phe
                165                 170                 175

Asn Gly Leu Ser Ala Glu His Phe Glu Arg Pro Thr Leu Gln Ala Met
            180                 185                 190

Ile Arg Asp Phe Gly Leu Pro Glu Pro Ser Ala Gln Leu Leu Asp Phe
        195                 200                 205

Ala Glu Thr Ser Ser Ala Leu Tyr Pro Thr Phe Ser Trp Asp Ser Pro
    210                 215                 220

Glu Ile Glu Arg Val Ser Phe Ser Thr Arg Thr Thr Asp Pro Asn Ala
225                 230                 235                 240

Leu Pro Ala His Val Glu Pro Lys Leu Gly Ala Leu Ala Ala Asn Ala
                245                 250                 255

Pro Tyr Thr Tyr Asp Gly Asp Arg Arg Leu Val Phe Ala Gly Ala Leu
            260                 265                 270

Thr Thr Gly Gly Glu Tyr Tyr Lys Leu Ala Thr Tyr Tyr Gln Met Ala
        275                 280                 285

Thr Ala Ala His Asp Arg Val Arg Arg Gly Ser
        290                 295
```

-continued

```
<210> SEQ ID NO 16
<211> LENGTH: 296
<212> TYPE: PRT
<213> ORGANISM: Streptomyces sp CL190

<400> SEQUENCE: 16
```

Met Ser Ala Thr Ala Glu Met Asp Glu Leu Tyr Ala Val Ile Glu Gln
1               5                   10                  15

Ser Ala Arg Thr Leu Gly Val Pro Cys Ala Pro Glu Lys Val Arg Pro
            20                  25                  30

Val Leu Ala Ala Tyr Glu Asp Ala Phe Gly His Ala Ala Thr Val Val
        35                  40                  45

Ala Phe Arg Val Ala Thr Ser Ile Arg His Ala Gly Glu Leu Asp Cys
    50                  55                  60

Arg Phe Thr Thr His Pro Asp Glu Arg Asp Pro Tyr Ala Thr Ala Leu
65                  70                  75                  80

Ala Ala Gly Leu Ala Gly Arg Thr Asp His Pro Val Gly Ala Val Leu
                85                  90                  95

Ala Gln Leu Gln Gly Arg Cys His Val Asp Ser His Gly Ile Asp Phe
            100                 105                 110

Gly Val Val Gly Gly Phe Lys Lys Val Tyr Ala Phe Phe Thr Pro Asp
        115                 120                 125

Asp Leu Gln Glu Val Ala Lys Phe Ala Asp Leu Pro Ala Met Pro Arg
    130                 135                 140

Ala Leu Ala Glu His Thr Gly Phe Phe Ala Arg His Gly Leu Ala Asp
145                 150                 155                 160

Arg Val Gly Val Val Gly Val Asp Tyr Gly His Arg Thr Leu Asn Val
                165                 170                 175

Tyr Phe Asn Asp Val Pro Ala Gln Leu Phe Glu Pro Gly Thr Ile Thr
            180                 185                 190

Ala Thr Leu Arg Glu Leu Gly Met Ala Arg Pro Ser Glu Gln Met Leu
        195                 200                 205

Lys Leu Gly Arg Glu Ala Phe Gly Leu Tyr Val Thr Leu Gly Trp Asp
    210                 215                 220

Ser Pro Arg Ile Glu Arg Ile Cys Tyr Ala Val Thr Thr Ala Asp Leu
225                 230                 235                 240

Ala Ala Leu Pro Val Pro Val Glu Pro Glu Ile Glu Arg Phe Val Arg
                245                 250                 255

Gly Val Pro Ala Asp Asp Gly Asp Arg Lys Phe Val Tyr Gly Val Ala
            260                 265                 270

Val Ala Pro Glu Gly Glu Tyr Tyr Lys Leu Glu Ser His Tyr Arg Trp
        275                 280                 285

Lys Pro Gly Thr Met Asp Phe Ile
    290                 295

```
<210> SEQ ID NO 17
<211> LENGTH: 305
<212> TYPE: PRT
<213> ORGANISM: Streptomyces sp CL190

<400> SEQUENCE: 17
```

Met Ser Gly Thr Ala Glu Leu Glu Lys Val Tyr Ser Ala Ile Glu Glu
1               5                   10                  15

Ser Ala Arg Leu Val Gly Val Ala Cys Ser Arg Asp Asn Val Trp Pro
            20                  25                  30

```
Ile Leu Thr Ala Phe Gly Glu Ser Ile Glu Asp Ala Leu Met Val Phe
        35                  40                  45

Ser Leu Gln Thr Gly Gly Arg His Ala Gly Glu Leu Asp Tyr Ser Phe
 50                  55                  60

Thr Ala Pro Pro Gly Ile Gly Asp Pro Tyr Pro Arg Ala Leu Ser Tyr
 65                  70                  75                  80

Gly Phe Val Thr Glu Thr Asp His Pro Val Gly Ser Val Leu Ser Asp
                 85                  90                  95

Leu Gln Gly Arg Trp Ala Ile Arg Glu His Phe Val Asp Cys Gly Val
            100                 105                 110

Thr Gly Gly Phe Lys Lys Leu Tyr Ala His Phe Pro Gln Asp Leu Gln
        115                 120                 125

Pro Ala Ala Arg Leu Ala Glu Ile Pro Ser Val Pro Arg Ala Val Ala
130                 135                 140

Asp Asn Ala Gly Leu Phe Ala Arg Tyr Gly Leu Asp Arg Val Ala Met
145                 150                 155                 160

Val Gly Val Asp Tyr Gln Arg Arg Thr Met Asn Leu Tyr Phe Gln Phe
                165                 170                 175

Thr Pro Asp Gly Arg Pro Glu Pro Gly Ala Leu Arg Ser Met Leu Arg
            180                 185                 190

Glu Ile Gly Leu His Glu Ala Asp Glu Gly Met Leu Glu Phe Ala Ser
        195                 200                 205

Arg Ser Met Arg Ala Asn Ile Thr Phe Ser Trp Asp Thr Ser Arg Ile
210                 215                 220

Val Arg Val Ala Phe Ala Pro Pro Gly Lys Gly Leu Asp Pro Ala
225                 230                 235                 240

Ala Val Pro Ala Pro Ile Glu Pro His Ile Ala Arg Phe Ala Thr Ser
                245                 250                 255

Ala Pro Tyr Ala Tyr Ala Gly Glu Arg Met Asn Leu Phe Gly Val Lys
            260                 265                 270

Trp Phe Pro Asp Gly Glu Phe Ile Asp Val Cys Ala Tyr Tyr Gln Leu
        275                 280                 285

Ser Ala Gly Tyr Glu Pro Val Arg Leu Met Glu Thr His Lys Asn Pro
290                 295                 300

Thr
305

<210> SEQ ID NO 18
<211> LENGTH: 296
<212> TYPE: PRT
<213> ORGANISM: Streptomyces atratus

<400> SEQUENCE: 18

Met Ser Gly Thr Pro Glu Val Ala Glu Leu Tyr Ser Ala Ile Glu Glu
 1               5                  10                  15

Ser Ala Arg Leu Leu Asp Val Ala Cys Ser Arg Asp Lys Val Trp Pro
             20                  25                  30

Ile Leu Thr Thr Tyr Gly Asp Ala Phe Ser His Ala Ala Thr Val Val
         35                  40                  45

Ala Phe Arg Val Ala Thr Gly Arg His Val Gly Glu Leu Asp Cys
 50                  55                  60

Arg Phe Thr Thr His Pro Asn Asp Arg Asp Pro Tyr Ala Phe Ala Leu
 65                  70                  75                  80
```

```
Ser Asn Gly Leu Thr Arg Gln Thr Asp His Pro Val Gly Ala Leu Leu
                85                  90                  95

Leu Asp Leu Gln Gly Arg Cys Pro Ile Asp Ser Tyr Gly Ile Asp Phe
            100                 105                 110

Gly Val Val Gly Gly Phe Lys Lys Ile Tyr Ala Phe Phe Thr Pro Asp
        115                 120                 125

Asn Leu Gln Lys Leu Ser Arg Ile Ala Asp Leu Pro Ser Met Pro Gly
    130                 135                 140

Ser Leu Ala Glu Asn Gly Asp Phe Phe Ala Arg His Gly Leu Asp Asp
145                 150                 155                 160

Arg Val Gly Val Ile Gly Ile Asp Tyr Pro His Arg Thr Val Asn Val
                165                 170                 175

Tyr Phe Asn Glu Val Pro Ala Glu Cys Phe Glu Ser Lys Thr Ile Leu
            180                 185                 190

Ser Met Leu Arg Glu Ile Gly Leu Pro Glu Pro Ser Glu Gln Met Leu
        195                 200                 205

Arg Leu Gly Gln Glu Ala Phe Gly Leu Tyr Val Thr Leu Asn Trp Asp
    210                 215                 220

Ser Ser Lys Ile Glu Arg Ile Cys Tyr Ala Val Thr Thr Ala Asp Leu
225                 230                 235                 240

Ala Thr Leu Pro Val Arg Met Glu Pro Glu Ile Glu Gln Phe Val Lys
                245                 250                 255

Asp Val Pro Asn Gly Gly Ala Asp Arg Lys Phe Val Tyr Gly Val Ala
            260                 265                 270

Ser Ser Pro Glu Gly Glu Tyr Tyr Lys Leu Glu Ser His Tyr Lys Trp
        275                 280                 285

Lys Pro Gly Met Met Asp Phe Ile
    290                 295

<210> SEQ ID NO 19
<211> LENGTH: 304
<212> TYPE: PRT
<213> ORGANISM: Streptomyces cinnamonensis

<400> SEQUENCE: 19

Met Ser Pro Val Thr Gly Thr Glu Glu Val Tyr Ala Ala Val Ala Ala
1               5                   10                  15

Ala Ala Arg Leu Ala Gly Val Pro Cys Thr Arg Glu Lys Val His Pro
            20                  25                  30

Val Leu Ser Ala Tyr Gly Glu Gly Leu Glu Arg Ala Gly Val Val Tyr
        35                  40                  45

Ser Val Ser Thr Ser His Ser Thr Pro Thr Glu Leu Asp Tyr Thr Val
    50                  55                  60

Thr Val Pro Ala Ala Gly Glu Asp Pro Tyr Ala Thr Ala Val Arg His
65                  70                  75                  80

Gly Phe Val Thr Pro Asp Gly His Pro Val His Thr Leu Leu Ser His
                85                  90                  95

Leu Gln Ser Arg Cys Glu Ile Ser Glu Tyr Leu Val Asp Gly Gly Val
            100                 105                 110

Val Gly Gly Phe Asn Lys Ile Tyr Ala His Phe Pro Gln Asp Val Gln
        115                 120                 125

Lys Ile Ser Arg Leu Ala Glu Leu Pro Gly Met Pro Pro Ala Leu Ala
    130                 135                 140

Arg Cys Ala Ala Leu Leu Glu Arg His Gly Leu Ser Asp Val Ala Met
145                 150                 155                 160
```

Ile Gly Ile Asp Tyr Pro Arg Arg Thr Leu Asn Leu Tyr Phe Thr Gln
            165                 170                 175

Leu Ser Glu Glu Cys Arg Ala Pro Gln Thr Ile Leu Ser Leu His Arg
        180                 185                 190

Glu Ile Gly Leu Pro Ala Pro Gly Gln Pro Met Leu Asp Phe Ala Arg
        195                 200                 205

Arg Ser Phe Arg Ile Tyr Thr Thr Leu Ser Trp Asp Ser Ala Gly Ile
210                 215                 220

Glu Arg Ile Cys Tyr Ala Pro Pro Pro Ala Arg Gly Trp Asp Pro Ala
225                 230                 235                 240

Ala Leu Pro Ala Glu Ile Thr Glu Gln Val Arg Gly Phe Val Asp Gly
            245                 250                 255

Ala Pro Arg Ala Tyr Glu Gly Glu Pro Ile Val Ile Ala Ala Val Lys
        260                 265                 270

Trp Ala Pro Glu Gly Pro Tyr Leu Asn Leu Gly Pro Tyr Tyr Gln Leu
        275                 280                 285

Ser Pro Leu Met Arg Lys Val Ile Ser Ala Val His Asn Lys Glu Ile
        290                 295                 300

<210> SEQ ID NO 20
<211> LENGTH: 303
<212> TYPE: PRT
<213> ORGANISM: Streptomyces iakyrus

<400> SEQUENCE: 20

Met Glu Gly Glu Met Ser Glu Ala Ser Glu Leu Ala Val Ile Tyr Ser
1               5                   10                  15

Ala Ile Glu Glu Thr Ala Gln Leu Leu Asp Val Pro Cys Ser Arg Asp
            20                  25                  30

Lys Val Gln Pro Ala Leu Ala Ala Phe Gly Asp Gly Leu Thr Asp Ala
        35                  40                  45

His Ile Val Phe Ser Met Ala Thr Gly Glu Arg Tyr Lys Gly Glu Leu
    50                  55                  60

Ala Phe Asp Phe Thr Val Pro Thr Ala Ala Gly Asp Pro Tyr Ala Ile
65                  70                  75                  80

Ala Leu Ala Asn Gly Leu Val Asp Glu Thr Asp His Pro Ile Arg Ser
            85                  90                  95

Leu Phe Ser Asp Val Gln Glu Arg Cys Pro Val Asp Ser Tyr Gly Val
        100                 105                 110

Asp Tyr Gly Leu Val Gly Gly Phe Lys Lys Thr Tyr Val Ser Phe Pro
        115                 120                 125

Leu Gly Asp Leu Gln Gly Leu Ser Thr Leu Val Asp Val Pro Ser Met
    130                 135                 140

Pro Arg Ala Leu Ala Glu His Ala Asp Phe Phe Ala Ser His Gly Leu
145                 150                 155                 160

Asp Asp Lys Val Ser Ala Ile Ala Asp Tyr Ala His Arg Thr Trp
            165                 170                 175

Asn Val Tyr Phe Ser Gly Ile Pro Ala Glu Val Lys Glu Pro Gln Thr
        180                 185                 190

Leu Arg Ser Val Leu Gln Arg Phe Gly Leu Pro Glu Pro Ser Glu Arg
        195                 200                 205

Leu Met Glu Phe Ile Arg Thr Ser Phe Ala Met Tyr Thr Thr Phe Gly
    210                 215                 220

Trp Asp Ser Thr Lys Ala Glu Arg Ile Cys Phe Ser Ala Arg Ser Ser
225                 230                 235                 240

Asp Pro Met Ala Leu Pro Ala Gln Phe Glu Pro Gln Ile Ala Lys Phe
            245                 250                 255

Ala Lys Ser Ala Pro Tyr Thr Tyr Thr Gly Glu Arg Val Leu Thr Tyr
        260                 265                 270

Ala Gly Ala Leu Ser Pro Ser Glu Glu Phe Tyr Lys Leu Ala Ser Phe
    275                 280                 285

Tyr Gln Lys Thr Ser Lys Leu Ser Asp Arg Val Arg Pro Ala Thr
290                 295                 300

<210> SEQ ID NO 21
<211> LENGTH: 305
<212> TYPE: PRT
<213> ORGANISM: Streptomyces tendae

<400> SEQUENCE: 21

Met Ser Gly Ala Ala Asp Val Glu Arg Val Tyr Ala Ala Met Glu Glu
1               5                   10                  15

Ala Ala Gly Leu Leu Asp Val Ser Cys Ala Arg Glu Lys Ile Tyr Pro
            20                  25                  30

Leu Leu Thr Val Phe Gln Asp Thr Leu Thr Asp Gly Val Val Val Phe
        35                  40                  45

Ser Met Ala Ser Gly Arg Arg Ser Thr Glu Leu Asp Phe Ser Ile Ser
    50                  55                  60

Val Pro Val Ser Gln Gly Asp Pro Tyr Ala Thr Val Val Lys Glu Gly
65                  70                  75                  80

Leu Phe Arg Ala Thr Gly Ser Pro Val Asp Glu Leu Leu Ala Asp Thr
                85                  90                  95

Val Lys His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Thr Glu Ile Pro Ser Met Pro Ala Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Asp
                165                 170                 175

Leu Lys Gln Glu Tyr Leu Gln Pro Glu Ala Val Val Ala Leu Ala Arg
            180                 185                 190

Glu Leu Gly Leu Gln Val Pro Gly Glu Leu Gly Leu Glu Phe Cys Lys
        195                 200                 205

Arg Ser Phe Ala Val Tyr Pro Thr Leu Asn Trp Asp Thr Gly Lys Ile
    210                 215                 220

Asp Arg Leu Cys Phe Ala Ala Ile Ser Thr Asp Pro Thr Leu Val Pro
225                 230                 235                 240

Ser Thr Asp Glu Arg Asp Ile Glu Met Phe Arg Glu Tyr Ala Thr Lys
                245                 250                 255

Ala Pro Tyr Ala Tyr Val Gly Glu Lys Arg Thr Leu Val Tyr Gly Leu
            260                 265                 270

Thr Leu Ser Ser Thr Glu Glu Tyr Tyr Lys Leu Gly Ala Tyr Tyr His
        275                 280                 285

Ile Thr Asp Ile Gln Arg Gln Leu Leu Lys Ala Phe Asp Ala Leu Glu
    290                 295                 300

Asp
305

<210> SEQ ID NO 22
<211> LENGTH: 296
<212> TYPE: PRT
<213> ORGANISM: Micromonospora sagamiensis

<400> SEQUENCE: 22

Met Pro Gly Thr Ser Glu Ala Ala Glu Leu Cys Ser Thr Ile Glu Glu
1               5                   10                  15

Ser Ala Arg Leu Leu Asn Val Ala Tyr Ser Arg Asp Arg Val Trp Ser
            20                  25                  30

Leu Leu Ser Ala Tyr Gly Asp Ala Phe Ala His Pro Gly Ala Val Val
        35                  40                  45

Ala Phe Arg Val Ala Thr Ala Met Arg His Val Gly Glu Leu Asp Cys
    50                  55                  60

Arg Phe Thr Thr His Pro Asp Asp Arg Asp Pro Tyr Ala Arg Ala Leu
65                  70                  75                  80

Ser His Gly Leu Thr Pro Glu Thr Asp His Pro Val Gly Ser Leu Leu
                85                  90                  95

Ala Glu Val Gln Gly Arg Cys Pro Val Glu Ser His Gly Ile Asp Phe
            100                 105                 110

Gly Val Val Gly Gly Phe Lys Lys Ile Tyr Ala Phe Phe Thr Pro Asp
        115                 120                 125

Asp Leu Gln Lys Thr Ser Lys Leu Ala Glu Ile Pro Ala Met Pro Arg
    130                 135                 140

Ser Leu Ala Gly Asn Val Glu Phe Phe Ala Arg His Gly Leu Asp Asp
145                 150                 155                 160

Arg Val Gly Val Phe Gly Ile Asp Tyr Pro Ser Arg Thr Val Asn Val
                165                 170                 175

Tyr Phe Asn Asp Val Pro Ala Gly Ser Phe Asp Pro Glu Thr Ile Arg
            180                 185                 190

Ser Thr Leu Arg Glu Ile Gly Met Ala Ala Pro Ser Glu Arg Met Leu
        195                 200                 205

Lys Leu Gly Glu Lys Ala Phe Gly Leu Tyr Val Thr Leu Gly Trp Glu
    210                 215                 220

Ser Ser Arg Ile Glu Arg Ile Cys Tyr Ala Ala Ala Thr Thr Asp Leu
225                 230                 235                 240

Thr Thr Leu Pro Val Pro Val Glu Pro Glu Ile Glu Lys Phe Val Arg
                245                 250                 255

Ser Val Pro Tyr Gly Gly Asp Asp Arg Lys Phe Val Tyr Gly Val Ala
            260                 265                 270

Leu Thr Pro Gln Gly Glu Tyr Tyr Lys Leu Glu Ser His Tyr Arg Trp
        275                 280                 285

Lys Pro Gly Ala Met Asp Phe Ile
    290                 295

<210> SEQ ID NO 23
<211> LENGTH: 293
<212> TYPE: PRT
<213> ORGANISM: Streptomyces sp.

<400> SEQUENCE: 23

Met Ser Ala Gln Ala Asp Val Glu Thr Val His Ser Ala Ile Glu Lys
1               5                   10                  15

Ala Ala Gly Leu Leu Asn Leu Thr Cys Ser Pro Gly Thr Val Arg Pro
            20                  25                  30

Ile Leu Glu Ala Phe Gly Pro Phe Glu Gly Val Ile Phe Ser Ala
        35                  40                  45

Ser Ala Gly Glu Gly His Ala Gly Asp Leu Asp Leu Thr Ile Gln Val
 50                  55                  60

Pro Arg Ala Ile Asp Asp Pro Tyr Thr His Ala Leu Thr His Gly Phe
 65                  70                  75                  80

Val Pro His Thr Asp His Pro Val Ser Thr Leu Leu Ser Asp Leu Lys
                85                  90                  95

Glu His Val Ser Val Asp Glu Phe Leu Ile Asp Phe Gly Val Ile Ala
            100                 105                 110

Gly Phe Asn Lys Ile Tyr Val His Phe Pro Arg Asp Leu Gln Gly Val
        115                 120                 125

Ala Gln Leu Ala Ala Leu Pro Ser Met Pro Arg Ala Leu Ala Asp Asn
130                 135                 140

Ala Gln Leu Phe Ala Arg His Gly Leu Asp Lys Val Ala Met Leu Ser
145                 150                 155                 160

Ile Asp Tyr His Lys Arg Thr Ile Asn Pro Phe Phe Thr Phe Pro Asn
                165                 170                 175

Gly Leu Glu Ala Lys Thr Ile Ser Ser Leu Leu His Glu Phe Gly Val
            180                 185                 190

Glu Glu Pro Asp Glu Leu Val Glu Ser Ser Lys Ile Phe Arg
        195                 200                 205

Ala Tyr Pro Thr Leu Gly Trp Glu Ser Ser Lys Ile Asp Arg Ile Ser
210                 215                 220

Phe Ala Arg Ser Leu Asp Leu Pro Thr Ile Arg Pro Arg Val Ala Pro
225                 230                 235                 240

Glu Ile Val Arg Phe Val Thr Gly Thr Pro Tyr Thr Tyr Asp Gly Asp
                245                 250                 255

Arg Phe Ser Ile Ser Ile Val Lys Trp Ser Pro Asp Asp Thr Trp Phe
            260                 265                 270

Asn Val Gly Ser Tyr Phe Gln Phe Gly Pro Leu Gln Arg Glu Val Leu
        275                 280                 285

Gly Lys Val Leu Arg
    290

<210> SEQ ID NO 24
<211> LENGTH: 309
<212> TYPE: PRT
<213> ORGANISM: Saccharomonospora saliphila

<400> SEQUENCE: 24

Val Pro Lys Asp Ala Asp Pro Arg Ser Ser Val Tyr Ser Ala Ile Glu
1               5                   10                  15

Glu Ala Ala Gly Leu Met Gly Ala Pro Cys Ser Arg Glu Arg Val Trp
            20                  25                  30

Pro Ile Leu Thr Ala Tyr Gly Asp Gly Ile Ser Glu Ala Gly Ile Val
        35                  40                  45

Phe Ser Val Gln Thr Gly Glu Arg His Ala Gly Glu Leu Asp Tyr Thr
 50                  55                  60

Ile Thr Val Pro Ala Asp Gly Pro Asp Pro Tyr Thr Ser Ala Leu Ser
65                  70                  75                  80

```
Asn Gly Phe Leu Glu Ala Thr Gln His Pro Val Thr Leu Leu Ser
                85                  90                  95

Asp Ile Arg Ala Arg Cys His Ile Ser Glu Tyr Phe Ile Asp Cys Gly
            100                 105                 110

Val Val Gly Gly Phe Asn Lys Val Tyr Ala His Phe Pro His Asp Pro
        115                 120                 125

Leu Ser Val Glu Arg Leu Ala Glu Val Pro Ser Leu Pro Arg Ser Leu
    130                 135                 140

Ala Asp Asn Leu Gly Phe Phe Leu Arg His Ala Leu Arg Asp Val Ala
145                 150                 155                 160

Met Ile Ala Ile Asp Tyr Arg Lys Lys Thr Val Asn Leu Tyr Phe Ala
                165                 170                 175

Gln Leu Ser Ala Glu Cys Leu Arg Ser Ala Asn Ile Arg Ala Met Leu
            180                 185                 190

Arg Glu Ser Gly Leu Ser Glu Leu Asp Gly Pro Met Leu Asp Phe Ala
        195                 200                 205

Leu Gly Ser Phe Arg Ile Tyr Val Thr Leu Ala Trp Asp Ser Ala Gly
    210                 215                 220

Val Glu Arg Ile Ser Phe Ala Ser Leu Met Ser Ser Gly Trp Val Asn
225                 230                 235                 240

Ala Ala Leu Ser Glu Phe Pro Val Arg Ile Glu Pro Glu Ile Glu Arg
                245                 250                 255

Phe Val Lys Asn Ala Pro Gln Ala Tyr Ser Gly Asp Arg Val Arg Ile
            260                 265                 270

Leu Ala Ile Lys Ser Ser Pro Gly Asp Glu Cys Leu Asn Phe Gly Ser
        275                 280                 285

Tyr Tyr Gln Ile Ser Pro Val Val Arg Asn Leu Leu Ala Ala Arg Ala
    290                 295                 300

Gly Asp Ala Glu Gln
305

<210> SEQ ID NO 25
<211> LENGTH: 298
<212> TYPE: PRT
<213> ORGANISM: Streptomyces sp.

<400> SEQUENCE: 25

Met Ser Gly Thr Ala Asp Ile Glu Arg Leu Tyr Pro Val Val Glu Glu
1               5                   10                  15

Ala Ala Gly Leu Leu Asp Ile Ala Cys Pro Pro Glu Arg Met Arg Pro
            20                  25                  30

Val Leu Thr Ala Phe Arg Asp Ala Leu Ala Asp Pro Val Val Phe Asn
        35                  40                  45

Ala Val Thr Lys Gly Gly Arg Ile Ala Asp Leu Ser Phe Asp Phe Thr
    50                  55                  60

Leu Pro Ala Ser Ala Gly Asp Pro Tyr Ala Ile Ala Val Ala His Gly
65                  70                  75                  80

Leu Ala Glu Glu Thr Asp His Pro Ile Arg Thr Leu Phe Ser Asp Leu
                85                  90                  95

Arg Ala Arg Leu Pro Val Gln Gly Tyr Gly Val Asp Tyr Gly Val Asn
            100                 105                 110

Gly Gly Phe Asn Lys Thr Tyr Ala Phe Phe Pro Leu Gly Asp Leu Gln
        115                 120                 125

Ala Leu Ala Glu Leu Ala Ala Leu Pro Ser Met Pro Pro Ala Leu Ser
    130                 135                 140
```

```
Glu His Leu Ala Leu Phe Thr Glu His Gly Leu Gly His Lys Val Ser
145                 150                 155                 160

Ala Leu Ala Ile Asp Tyr Ala Arg Arg Thr Trp Asn Val Tyr Phe Asn
            165                 170                 175

Gly Leu Pro Ala Asp Phe Val Arg Arg Thr Ala Val Leu Pro Met Leu
        180                 185                 190

Arg Ala Phe Gly Leu Pro Glu Pro Ser Glu Gln Leu Leu Asp Phe Ile
    195                 200                 205

Glu Thr Ser Ser Ala Leu Tyr Pro Thr Phe Gly Trp Asp Ser Ser Lys
210                 215                 220

Ile Glu Arg Ile Ser Phe Ser Thr Arg Thr Thr Asn Pro Val Ala Leu
225                 230                 235                 240

Pro Ala Arg Ile Glu Pro Lys Leu Glu Lys Phe Ala Arg Ser Ala Pro
            245                 250                 255

Tyr Ala Tyr Glu Gly Glu Arg Val Leu Val Tyr Ala Gly Ala Leu Ser
        260                 265                 270

Pro Ser Glu Glu Tyr Tyr Lys Leu Ala Thr Tyr Tyr Arg Met Ser Ala
    275                 280                 285

Ala Ala His Asp Arg Val Arg Ala Ala Asn
290                 295

<210> SEQ ID NO 26
<211> LENGTH: 306
<212> TYPE: PRT
<213> ORGANISM: Streptomyces sp.

<400> SEQUENCE: 26

Met Ser Lys Ala Thr Glu Val Asp Arg Val Tyr Ala Ala Val Glu Lys
1               5                   10                  15

Ala Ala Ala Leu Ala Gly Thr Thr Cys Ala Gly Asp Lys Val Arg Pro
            20                  25                  30

Val Leu Thr Gly His Gln Asp Leu Leu Asp Glu Ala Val Ile Val Phe
        35                  40                  45

Ser Met Thr Ala Ser Gly Ser His Ser Gly Gly Leu Asp Leu Ser Met
50                  55                  60

Thr Val Pro Ala Glu His Val Asp Pro Tyr Ser Phe Ala Leu Ser Glu
65                  70                  75                  80

Gly Leu Ile Glu Pro Thr Asp His Pro Val Gly Ser Val Ile Ser Asp
            85                  90                  95

Phe Gln Glu Arg Phe Pro Ile Gly Met Tyr Gly Ile Asp Val Asp Val
        100                 105                 110

Ala Gly Gly Phe Lys Lys Ala Tyr Ala Ala Phe Pro Ser Asn Asp Leu
    115                 120                 125

Arg Glu Leu Lys Gln Leu Phe Asp Leu Pro Ser Met Pro Ser Ala Ala
130                 135                 140

Ala Glu Asn Ala Glu Leu Phe Ala Arg Tyr Gly Leu Asp Arg Val Thr
145                 150                 155                 160

Gly Val Ser Val Asp Tyr Lys Arg His Glu Leu Asn Leu Tyr Cys Asp
            165                 170                 175

Arg Ala Thr Thr Glu Pro Leu Asp Pro Asp Tyr Val Gln Ser Met Leu
        180                 185                 190

Arg Asp Met Gly Leu Lys Glu Ala Ser Glu Gln Gly Leu Glu Phe Ala
    195                 200                 205

Lys Lys Thr Phe Ala Ile Tyr Pro Thr Leu Asn Trp Asp Ser Ser Glu
210                 215                 220
```

```
Ile Val Arg Ile Cys Phe Ala Val Ile Thr Thr Asp Pro Ala Thr Thr
225                 230                 235                 240

Pro Thr Arg Ser Glu Pro Glu Leu Gly Gln Met Trp Glu Tyr Ala Asn
            245                 250                 255

Thr Ala Pro Tyr Ala Tyr Val Gly Glu Gln Arg Ala Leu Val Tyr Gly
        260                 265                 270

Leu Ala Leu Ser Pro Glu Lys Glu Tyr Tyr Lys Leu Gly Ala Tyr Tyr
            275                 280                 285

Gln Ile Ser Asp Tyr Gln Arg Lys Leu Val Lys Ala Phe Asp Ala Leu
        290                 295                 300

Pro Glu
305

<210> SEQ ID NO 27
<211> LENGTH: 311
<212> TYPE: PRT
<213> ORGANISM: Streptomyces sp.

<400> SEQUENCE: 27

Met Tyr Gly Gly Thr Glu Val Glu Val Tyr Ser Ala Leu Glu Lys
1               5                   10                  15

Ser Ala Gly Leu Val Gly Val Pro Cys Asn Arg Asp Lys Val Trp Pro
            20                  25                  30

Ala Leu Ser Thr Tyr Gln Asp Ala Leu Gly Glu Ala Val Ile Val Phe
        35                  40                  45

Ser Val Ala Thr Asp Glu Arg His Ala Gly Glu Leu Asp Tyr Thr Ile
    50                  55                  60

Thr Val Pro Thr Gly Gly Ala Asp Pro Tyr Ala Leu Ala Leu Ala Lys
65                  70                  75                  80

Gly Leu Thr Pro Glu Thr Asp His Pro Val Gly Thr Leu Leu Ala Gly
            85                  90                  95

Val Gln Glu Arg Cys Pro Val Ala Gly Tyr Ala Val Asp Cys Gly Val
        100                 105                 110

Val Gly Gly Phe Lys Lys Ile Tyr Ser Phe Pro Gln Asp Asp Leu
        115                 120                 125

Gln Gly Leu Ala Lys Leu Ala Glu Ile Pro Ser Met Pro Arg Ala Leu
    130                 135                 140

Ala Glu Asn Ala Ala Leu Phe Ala Arg His Gly Leu Asp His Lys Val
145                 150                 155                 160

Thr Met Leu Gly Ile Asp Tyr Gln Arg Glu Ser Val Asn Leu Tyr Phe
            165                 170                 175

Gly Lys Leu Pro Glu Glu Cys Leu Gln Pro Asp Ser Ile Arg Ala Ile
        180                 185                 190

Leu Arg Asp Ile Gly Leu Pro Glu Pro Thr Glu Pro Met Leu Glu Phe
    195                 200                 205

Ala Arg Lys Ser Phe Ala Ile Tyr Val Thr Leu Ser Trp Asp Ala Ala
210                 215                 220

Lys Val Glu Arg Ile Cys Phe Ala Val Pro Pro Gly Arg Asp Leu Ile
225                 230                 235                 240

Thr Leu Asp Pro Ser Ala Leu Pro Ala Arg Ile Ala Pro Glu Ile Glu
            245                 250                 255

His Phe Ala Arg Asn Ser Pro Tyr Ala Tyr Pro Gly Asp Arg Met Leu
        260                 265                 270
```

```
Val Tyr Gly Val Thr Trp Ser Pro Glu Glu Tyr Tyr Lys Leu Gly
        275                 280                 285

Ser Tyr Tyr Gln Leu Pro Val Gln Thr Arg Lys Leu Leu Val Ala Phe
290                 295                 300

Asp Ser Val Lys Asp Gln Glu
305                 310

<210> SEQ ID NO 28
<211> LENGTH: 310
<212> TYPE: PRT
<213> ORGANISM: Streptomyces sp.

<400> SEQUENCE: 28

Met Pro Glu Ser Lys Asn Ala Glu Ala Val Tyr Ser Ala Ile Glu Glu
1               5                   10                  15

Ser Ala Gly Leu Leu Asp Ile Pro Cys Ser Arg Gln Lys Val Met Ser
            20                  25                  30

Val Leu Ser Ala Phe Gly Asp Gly Val Ser Glu Ser Val Ile Val
        35                  40                  45

Met Ala Met Ala Gly Gly Glu Arg His Gly Gly Asp Ile Asp Tyr Asn
50                  55                  60

Phe Thr Val Pro Thr Glu Val Gly Asp Pro Tyr Glu Ile Ala Val Ala
65                  70                  75                  80

Asn Gly Trp Ile Glu Ala Leu Asp His Pro Ile Ala Asn Leu Leu Pro
                85                  90                  95

Glu Ile Val Glu Ser Ser Pro Val Thr Phe Tyr Gly Val Glu Ala Gly
            100                 105                 110

Val Val Glu Gly Phe Lys Lys Thr Tyr Ile Phe Phe Pro Leu Asp Asn
        115                 120                 125

Leu Gly Lys Leu Ser Thr Leu Ala Ser Leu Pro Ser Met Pro Arg Ser
130                 135                 140

Val Ala Glu His Ala Arg Thr Phe Asp Gly Leu Asn Gly Met Gly Asp
145                 150                 155                 160

Arg Ile Ser Ile Ile Gly Ile Asp Tyr Ile Lys Arg Thr Val Asn Val
                165                 170                 175

Tyr Phe Met Ala Gly Thr Leu Gly Glu Lys Ser Val Leu Ser Leu Leu
            180                 185                 190

Glu Asp Thr Asn Leu Pro Ala Pro Thr Pro Asp Phe Leu Glu Phe Val
        195                 200                 205

Gln Asn Ser Phe Ser Ile Tyr Pro Thr Phe Thr Tyr Glu Ser Ser Asp
210                 215                 220

Ile His Arg Ile Cys Phe Ser Ser Val Ser Pro Asp Asp Thr Ala Tyr
225                 230                 235                 240

Pro Thr Thr Leu His Glu Glu Ile Ala Arg Phe Thr Lys Asn Ala Pro
                245                 250                 255

Tyr Glu Tyr Asp Gly Ala Arg Val Leu Val Tyr Gly Ala Thr Ile Ser
            260                 265                 270

Arg Arg Glu Glu Tyr His Lys Leu Gly Val Tyr Phe Arg Arg Pro Pro
        275                 280                 285

Ala Phe Trp Asp Asn Leu Pro Leu Ala Ala Thr Phe Glu Lys Leu Ala
290                 295                 300

Ala Ala His Arg Gly Ala
305                 310
```

<210> SEQ ID NO 29
<211> LENGTH: 302
<212> TYPE: PRT
<213> ORGANISM: Streptomyces sp.

<400> SEQUENCE: 29

```
Met Ser Glu Thr Ala Glu Leu Thr Lys Leu Tyr Ser Ile Ile Glu Lys
1               5                   10                  15

Thr Ala Gln Val Val Asp Val Thr Ala Ser Arg Asp Lys Val Gln Pro
            20                  25                  30

Ile Leu Gln Ala Phe Gln Asp Val Phe Gly Gln Ser Val Ile Ser Phe
        35                  40                  45

Arg Ala Ser Thr Gly Arg Thr Ser Glu Glu Leu Asp Cys Arg Phe
    50                  55                  60

Thr Met Leu Pro Lys Gly Phe Asp Pro Tyr Ala Arg Ala Leu Glu His
65                  70                  75                  80

Gly Leu Thr Pro Lys Gln Asp His Pro Val Gly Thr Leu Leu Lys Glu
                85                  90                  95

Val His Gln Glu Leu Pro Ile Asp Ser Cys Gly Val Asp Phe Gly Val
            100                 105                 110

Val Gly Gly Phe Ala Lys Thr Trp Ser Phe Pro Ser Ala Ala Asn Leu
        115                 120                 125

Leu Ser Ile Ser Gln Leu Thr Glu Leu Pro Ser Ile Pro Gly Gly Val
    130                 135                 140

Ala Glu Asn Leu Asp Phe Phe Lys Lys Tyr Gly Leu Asp Asp Ile Val
145                 150                 155                 160

Ser Thr Val Gly Ile Asp Tyr Thr Asn Arg Thr Met Asn Leu Tyr Phe
                165                 170                 175

Gly Ala Gly Glu His Arg Cys Arg Pro Asn Val Ser Arg Ala Lys Gly
            180                 185                 190

Val Lys Ala Ile Leu Lys Glu Cys Gly Leu Pro Glu Pro Ser Glu Glu
        195                 200                 205

Leu Leu Lys Leu Ala Glu Arg Ala Phe Ser Ile Tyr Ile Thr Met Asn
    210                 215                 220

Trp Asp Ser Pro Lys Ile Leu Arg Val Ser Tyr Ala Ala Met Thr Pro
225                 230                 235                 240

Lys Pro Arg Ser Leu Ala Val Lys Met Ala Pro Ala Phe Asp Gln Leu
                245                 250                 255

Leu Asn Asn Ala Pro Tyr Ser Thr Glu Gly His Asn Phe Val Tyr Gly
            260                 265                 270

Ile Ala Ala Thr Pro Lys Gly Glu Tyr His Lys Ile Ala Ser Tyr Tyr
        275                 280                 285

Gln Trp Gln Thr Arg Val Glu Gly Leu Leu His Ser Glu Ser
    290                 295                 300
```

<210> SEQ ID NO 30
<211> LENGTH: 300
<212> TYPE: PRT
<213> ORGANISM: Streptomyces cinnamonensis

<400> SEQUENCE: 30

```
Met Met Ser Gly Thr Ala Asp Leu Ala Gly Val Tyr Ala Ala Val Glu
1               5                   10                  15

Glu Ser Ala Gly Leu Leu Asp Val Ser Cys Ala Arg Glu Lys Val Trp
            20                  25                  30
```

-continued

```
Pro Ile Leu Ala Ala Phe Glu Asp Val Leu Pro Thr Ala Val Ile Ala
        35                  40                  45

Phe Arg Val Ala Thr Asn Ala Arg His Glu Gly Glu Phe Asp Cys Arg
 50                  55                  60

Phe Thr Val Pro Gly Ser Ile Asp Pro Tyr Ala Val Ala Leu Asp Lys
 65                  70                  75                  80

Gly Leu Thr His Arg Ser Gly His Pro Ile Glu Thr Leu Val Ala Asp
                 85                  90                  95

Val Gln Lys His Cys Ala Val Asp Ser Tyr Gly Val Asp Phe Gly Val
            100                 105                 110

Val Gly Gly Phe Lys Lys Ile Trp Val Tyr Phe Pro Gly Gly Arg His
        115                 120                 125

Glu Ser Leu Ala His Leu Gly Glu Ile Pro Ser Met Pro Pro Gly Leu
130                 135                 140

Ala Ala Thr Glu Gly Phe Phe Ala Arg Tyr Gly Leu Ala Asp Lys Val
145                 150                 155                 160

Asp Leu Ile Gly Val Asp Tyr Ala Ser Lys Thr Met Asn Val Tyr Phe
                165                 170                 175

Ala Ala Ser Pro Glu Val Val Ser Ala Pro Thr Val Leu Ala Met His
            180                 185                 190

Arg Glu Ile Gly Leu Pro Asp Pro Ser Glu Gln Met Leu Asp Phe Cys
        195                 200                 205

Ser Arg Ala Phe Gly Val Tyr Thr Thr Leu Asn Trp Asp Ser Ser Lys
210                 215                 220

Val Glu Arg Ile Ala Tyr Ser Val Lys Thr Glu Asp Pro Leu Glu Leu
225                 230                 235                 240

Ser Ala Arg Leu Gly Ser Lys Val Glu Gln Phe Leu Lys Ser Val Pro
                245                 250                 255

Tyr Gly Ile Asp Thr Pro Lys Met Val Tyr Ala Ala Val Thr Ala Gly
            260                 265                 270

Gly Glu Glu Tyr Tyr Lys Leu Gln Ser Tyr Gln Trp Arg Thr Asp
        275                 280                 285

Ser Arg Leu Asn Leu Ser Tyr Ile Gly Gly Arg Ser
290                 295                 300
```

<210> SEQ ID NO 31
<211> LENGTH: 298
<212> TYPE: PRT
<213> ORGANISM: Nocardia concava

<400> SEQUENCE: 31

```
Met Gly Thr Ser Glu Leu Val Thr Leu Glu Arg Ile Arg Arg Asp Leu
1               5                  10                  15

Gln Glu Phe Ala Arg Leu Ala Glu Ala Pro Tyr Glu Ala Ala Ala Val
            20                  25                  30

Asp Pro Val Leu Asp Ala Leu Glu Leu Trp Thr Thr Ser Ile Leu
        35                  40                  45

Gly Val Arg Thr Thr Thr His Pro Val Pro Arg Arg Leu Asn Val
 50                  55                  60

Arg Leu Met Asn Ser Gly Ser Gly Ala Asp Pro Val Thr Thr Leu Arg
 65                  70                  75                  80

Glu Ala Gly Leu Leu Glu Phe Thr Gly His Pro Met Glu Gln Leu Leu
                 85                  90                  95

Thr Glu Ile Pro Ala Ala Val Pro Val Leu Phe Gly Val Asp Val Gly
            100                 105                 110
```

```
Val Ala Gln Gly Val Glu Lys Val Trp Met Met Phe Pro Glu Pro Ile
            115                 120                 125

Ser Val Gln Arg Val Leu Ala Phe Pro Gly Ile Pro Asp Ala Ala Arg
    130                 135                 140

Thr His Ala Pro His Leu Asn Arg Tyr Gly Glu Ile Ala Ile Met
145                 150                 155                 160

Ala Leu Asp Phe Ala Ser Arg Thr Met Asn Leu Tyr Ser Gln Val Phe
                165                 170                 175

Ala Pro Gly Leu Leu Thr Ala Thr Asp Ile Thr Thr Ile Leu Ala Asp
            180                 185                 190

Leu Glu Phe Ala Pro Pro Thr Asp Glu Glu Leu Ser Leu Leu Arg Gln
    195                 200                 205

Thr Phe Asn Leu Tyr Arg Thr Phe Ser Trp Thr Ser Pro Arg Met Gln
210                 215                 220

Arg Ile Cys Phe Pro Val Arg His Gln Pro Ala Thr Phe Pro Thr His
225                 230                 235                 240

Leu Asp Pro Val Leu Ala Arg Phe Val Ser Ala Ala Pro Tyr Ala Gly
                245                 250                 255

Thr Gly Ser Gln Thr Phe Thr Phe Tyr Thr Ala Tyr Gly Pro Thr Asp
            260                 265                 270

Arg Tyr Tyr Lys Ile Gln Ala Glu Tyr Thr Ser Pro Arg His Ile Pro
    275                 280                 285

Phe Pro Gly Gly Thr Glu Pro Pro Val Asn
            290                 295

<210> SEQ ID NO 32
<211> LENGTH: 293
<212> TYPE: PRT
<213> ORGANISM: Myxococcus stipitatus

<400> SEQUENCE: 32

Met Pro Ala Leu Ser Leu Gly Leu Glu Arg Leu Cys Ala Asp Val Glu
1               5                   10                  15

Ala Ala Ala Ala Leu Ala Gly Ala Ser Phe Ser Arg Glu Val Thr Arg
                20                  25                  30

Asn Val Leu Lys Ser Tyr Pro Arg Phe Phe Thr Ser Ser Ala Val Ser
            35                  40                  45

Phe Arg Thr Ser Thr Arg Lys Pro Glu Lys Arg Glu Leu Asn Val Arg
    50                  55                  60

Phe Val Glu Leu Glu Thr Pro Glu Asp Pro His Ala Val Ala Leu Ala
65                  70                  75                  80

Glu Gly Leu Ile His Arg Ser Gly His Pro Ile Asp Asp Leu Phe Glu
                85                  90                  95

Gln Val Gln Arg Asn Val Pro Ile Leu Gly Tyr Gly Leu Asp Phe Gly
            100                 105                 110

Val Ala Tyr Gly Val Glu Lys Ile Trp Pro Phe Phe Pro His Arg Pro
    115                 120                 125

Gln Pro Leu Glu Val Leu Arg Thr Leu Pro Ser Leu Pro Gln Ser Val
130                 135                 140

Gln Ala His Ser Gly Phe Leu Val Glu His Asp Leu Thr Asp Leu Ser
145                 150                 155                 160

Leu Phe Ala Leu Asp Tyr Arg Ser Arg Ser Val Asn Leu Tyr Phe Met
                165                 170                 175

Cys Arg Pro Gly His Phe Ser Thr Ala Gln Leu Ala Asp Leu Leu Gly
            180                 185                 190
```

```
Gly Leu Gly Phe Glu Ser Pro Gly Glu Leu Leu Glu His Cys Thr
            195                 200                 205

Arg Ala Val Pro Ile Tyr Phe Thr Phe Arg Trp Asp Arg Pro Arg Ile
210                 215                 220

Glu Arg Val Cys Phe Gly Val Ile Ala Pro Gly Pro Gly Leu Leu Pro
225                 230                 235                 240

Thr His Leu His Pro Ile Ile Gly Gln Phe Ala Ala Gly Val Pro Phe
                245                 250                 255

Ala Thr Glu Arg Arg Asn Phe Ile Tyr Ser Val Thr Val Ser Arg Glu
                260                 265                 270

Glu Thr Phe Ile Lys Ile Glu Asn Asp Tyr Ser Gly Thr Met Thr Ala
            275                 280                 285

Leu Met Gln Val Phe
            290

<210> SEQ ID NO 33
<211> LENGTH: 300
<212> TYPE: PRT
<213> ORGANISM: Unknown
<220> FEATURE:
<223> OTHER INFORMATION: Baceterial or Fungal Prenyltransferase

<400> SEQUENCE: 33

Met Met Ser Gly Thr Ala Asp Leu Ala Gly Val Tyr Ala Ala Val Glu
1               5                   10                  15

Glu Ser Ala Gly Leu Leu Asp Val Ser Cys Ala Arg Glu Lys Val Trp
                20                  25                  30

Pro Ile Leu Ala Ala Phe Glu Asp Val Leu Pro Thr Ala Val Ile Ala
            35                  40                  45

Phe Arg Val Ala Thr Asn Ala Arg His Glu Gly Glu Phe Asp Cys Arg
50                  55                  60

Phe Thr Val Pro Gly Ser Ile Asp Pro Tyr Ala Val Ala Leu Asp Lys
65                  70                  75                  80

Gly Leu Thr His Arg Ser Gly His Pro Ile Glu Thr Leu Val Ala Asp
                85                  90                  95

Val Gln Lys His Cys Ala Val Asp Ser Tyr Gly Val Asp Phe Gly Val
            100                 105                 110

Val Gly Gly Phe Lys Lys Ile Trp Val Tyr Phe Pro Gly Gly Arg His
            115                 120                 125

Glu Ser Leu Ala His Leu Gly Glu Ile Pro Ser Met Pro Pro Gly Leu
130                 135                 140

Ala Ala Thr Glu Gly Phe Phe Ala Arg Tyr Gly Leu Ala Asp Lys Val
145                 150                 155                 160

Asp Leu Ile Gly Val Asp Tyr Ala Ser Lys Thr Met Asn Val Tyr Phe
                165                 170                 175

Ala Ala Ser Pro Glu Val Val Ser Ala Pro Thr Val Leu Ala Met His
            180                 185                 190

Arg Glu Ile Gly Leu Pro Asp Pro Ser Glu Gln Met Leu Asp Phe Cys
        195                 200                 205

Ser Arg Ala Phe Gly Val Tyr Thr Thr Leu Asn Trp Asp Ser Ser Lys
210                 215                 220

Val Glu Arg Ile Ala Tyr Ser Val Lys Thr Glu Asp Pro Leu Glu Leu
225                 230                 235                 240

Ser Ala Arg Leu Gly Ser Lys Val Glu Gln Phe Leu Lys Ser Val Pro
                245                 250                 255
```

```
Tyr Gly Ile Asp Thr Pro Lys Met Val Tyr Ala Ala Val Thr Ala Gly
            260                 265                 270

Gly Glu Glu Tyr Tyr Lys Leu Gln Ser Tyr Tyr Gln Trp Arg Thr Asp
            275                 280                 285

Ser Arg Leu Asn Leu Ser Tyr Ile Gly Gly Arg Ser
            290                 295                 300

<210> SEQ ID NO 34
<211> LENGTH: 304
<212> TYPE: PRT
<213> ORGANISM: Unknown
<220> FEATURE:
<223> OTHER INFORMATION: S. cinnamonensis

<400> SEQUENCE: 34

Met Ser Pro Val Thr Gly Thr Glu Glu Val Tyr Ala Ala Val Ala Ala
1               5                   10                  15

Ala Ala Arg Leu Ala Gly Val Pro Cys Thr Arg Glu Lys Val His Pro
            20                  25                  30

Val Leu Ser Ala Tyr Gly Glu Gly Leu Glu Arg Ala Gly Val Val Tyr
        35                  40                  45

Ser Val Ser Thr Ser His Ser Thr Pro Thr Glu Leu Asp Tyr Thr Val
    50                  55                  60

Thr Val Pro Ala Ala Gly Glu Asp Pro Tyr Ala Thr Ala Val Arg His
65                  70                  75                  80

Gly Phe Val Thr Pro Asp Gly His Pro Val His Thr Leu Leu Ser His
                85                  90                  95

Leu Gln Ser Arg Cys Glu Ile Ser Glu Tyr Leu Val Asp Gly Gly Val
            100                 105                 110

Val Gly Gly Phe Asn Lys Ile Tyr Ala His Phe Pro Gln Asp Val Gln
        115                 120                 125

Lys Ile Ser Arg Leu Ala Glu Leu Pro Gly Met Pro Pro Ala Leu Ala
    130                 135                 140

Arg Cys Ala Ala Leu Leu Glu Arg His Gly Leu Ser Asp Val Ala Met
145                 150                 155                 160

Ile Gly Ile Asp Tyr Pro Arg Arg Thr Leu Asn Leu Tyr Phe Thr Gln
                165                 170                 175

Leu Ser Glu Glu Cys Arg Ala Pro Gln Thr Ile Leu Ser Leu His Arg
            180                 185                 190

Glu Ile Gly Leu Pro Ala Pro Gly Gln Pro Met Leu Asp Phe Ala Arg
        195                 200                 205

Arg Ser Phe Arg Ile Tyr Thr Thr Leu Ser Trp Asp Ser Ala Gly Ile
    210                 215                 220

Glu Arg Ile Cys Tyr Ala Pro Pro Ala Arg Gly Trp Asp Pro Ala
225                 230                 235                 240

Ala Leu Pro Ala Glu Ile Thr Glu Gln Val Arg Gly Phe Val Asp Gly
                245                 250                 255

Ala Pro Arg Ala Tyr Glu Gly Pro Ile Val Ile Ala Ala Val Lys
            260                 265                 270

Trp Ala Pro Glu Gly Pro Tyr Leu Asn Leu Gly Pro Tyr Tyr Gln Leu
        275                 280                 285

Ser Pro Leu Met Arg Lys Val Ile Ser Ala Val His Asn Lys Glu Ile
    290                 295                 300
```

```
<210> SEQ ID NO 35
<211> LENGTH: 307
<212> TYPE: PRT
<213> ORGANISM: Unknown
<220> FEATURE:
<223> OTHER INFORMATION: Streptomyces sp. (strain KO-3988)

<400> SEQUENCE: 35
```

Met Pro Gly Thr Asp Asp Val Ala Val Asp Ala Ser Val Tyr Ser
1               5                   10                  15

Ala Ile Glu Lys Ser Ala Gly Leu Leu Asp Val Thr Ala Ala Arg Glu
            20                  25                  30

Val Val Trp Pro Val Leu Thr Ala Phe Glu Asp Val Leu Glu Gln Ala
            35                  40                  45

Val Ile Ala Phe Arg Val Ala Thr Asn Ala Arg His Glu Gly Asp Phe
50                  55                  60

Asp Val Arg Phe Thr Val Pro Glu Glu Val Asp Pro Tyr Ala Val Ala
65                  70                  75                  80

Leu Ser Arg Ser Leu Ile Ala Lys Thr Asp His Pro Val Gly Ser Leu
                85                  90                  95

Leu Ser Asp Ile Gln Gln Leu Cys Ser Val Asp Thr Tyr Gly Val Asp
            100                 105                 110

Leu Gly Val Lys Ser Gly Phe Lys Lys Val Trp Val Tyr Phe Pro Ala
            115                 120                 125

Gly Glu His Glu Thr Leu Ala Arg Leu Thr Gly Leu Thr Ser Met Pro
            130                 135                 140

Gly Ser Leu Ala Gly Asn Val Asp Phe Phe Thr Arg Tyr Gly Leu Ala
145                 150                 155                 160

Asp Lys Val Asp Val Ile Gly Ile Asp Tyr Arg Ser Arg Thr Met Asn
                165                 170                 175

Val Tyr Phe Ala Ala Pro Ser Glu Cys Phe Glu Arg Glu Thr Val Leu
            180                 185                 190

Ala Met His Arg Asp Ile Gly Leu Pro Ser Pro Ser Glu Gln Met Phe
            195                 200                 205

Lys Phe Cys Glu Asn Ser Phe Gly Leu Tyr Thr Thr Leu Asn Trp Asp
            210                 215                 220

Thr Met Glu Ile Glu Arg Ile Ser Tyr Gly Val Lys Thr Glu Asn Pro
225                 230                 235                 240

Met Thr Phe Phe Ala Arg Leu Gly Thr Lys Val Glu His Phe Val Lys
                245                 250                 255

Asn Val Pro Tyr Gly Val Asp Thr Gln Lys Met Val Tyr Ala Ala Val
            260                 265                 270

Thr Ser Ser Gly Glu Glu Tyr Tyr Lys Leu Gln Ser Tyr Tyr Arg Trp
            275                 280                 285

Arg Ser Val Ser Arg Leu Asn Ala Ala Tyr Ile Ala Ala Arg Asp Lys
290                 295                 300

Glu Ser Thr
305

```
<210> SEQ ID NO 36
<211> LENGTH: 327
<212> TYPE: PRT
<213> ORGANISM: Unknown
<220> FEATURE:
<223> OTHER INFORMATION: Streptomyces aculeolatus
```

<400> SEQUENCE: 36

```
Met Val Gly Ser His Thr Arg Ile Ser Gln Asn Leu Ile Gly Ile Asp
1               5                   10                  15

Cys Leu Glu Cys Leu Val Ser Gly Ala Thr Gly Ala Glu Lys Leu Tyr
            20                  25                  30

Ser Ala Ile Glu Glu Ser Ala Arg Met Val Asp Ala Pro Phe Ser Arg
        35                  40                  45

Asp Lys Val Trp Pro Thr Leu Ser Ala Phe Glu Gly Gly Phe Ser Asp
    50                  55                  60

Ala Gly Gly Val Ile Leu Ser Leu Gln Ala Gly Thr His Val Pro Glu
65                  70                  75                  80

Met Glu Tyr Ser Ala Gln Val Ser Pro Gly Ile Ser Asp Pro Tyr Ala
                85                  90                  95

Arg Ala Leu Ala Ser Gly Ile Leu Thr Glu Thr Asp His Pro Val Ser
            100                 105                 110

Thr Val Leu Ala Glu Ile Val Ser Leu Ala Pro Thr Ser Glu His Tyr
        115                 120                 125

Ile Asp Cys Gly Ile Val Gly Gly Phe Lys Lys Ile Tyr Ala Asn Phe
    130                 135                 140

Pro His Asp Gln Gln Thr Val Ala Ala Leu Ala Gly Leu Pro Ser Met
145                 150                 155                 160

Pro Arg Ala Val Gly Gly Asn Ala Glu Phe Phe Ala Arg His Gly Leu
                165                 170                 175

Asp Arg Val Ala Leu Ile Gly Val Asp Tyr Val Asn Lys Thr Ile Asn
            180                 185                 190

Leu Tyr Phe Gln Val Ser Ala Ala Thr Ala Gly Asn Leu Asp Gln Lys
        195                 200                 205

Thr Val Ser Ala Met Leu His Glu Thr Gly Met Ser Glu Pro Ser Asp
    210                 215                 220

Ala Met Val Ala Tyr Ala Cys Gln Ala Tyr Arg Ile Tyr Thr Thr Leu
225                 230                 235                 240

Ser Trp Asp Ala Glu Glu Ile Leu Arg Ile Ala Phe Ala Pro Lys Pro
                245                 250                 255

Arg Arg Gly Ile Asp Pro Ala Asp Leu Pro Ala Arg Leu Glu Pro Arg
            260                 265                 270

Ile Glu Lys Phe Leu Arg Ala Thr Pro His Lys Tyr Pro Gly Ala Leu
        275                 280                 285

Ile Asn Ala Thr Ala Ala Lys Trp Ser Pro Glu Arg Glu Val Leu Asp
    290                 295                 300

Leu Ala Ala His Tyr Gln Val Ser Ala Val Gln Met Lys Ala Ile Glu
305                 310                 315                 320

Ala Glu Glu Gly Gln Ala Ser
                325
```

<210> SEQ ID NO 37
<211> LENGTH: 10584
<212> TYPE: DNA
<213> ORGANISM: Artificial Sequence
<220> FEATURE:
<223> OTHER INFORMATION: Cassette with Dictyostelium discoideum DiPKS
      (G1516D; G1518A) coding sequence, regulatory sequences and
      integration sequences
<220> FEATURE:
<221> NAME/KEY: LV3
<222> LOCATION: (1)..(40)
<220> FEATURE:
<221> NAME/KEY: S. cerevisiae GAL1 promoter

```
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: C-methyltransferase domain
<222> LOCATION: (5050)..(5412)
<220> FEATURE:
<221> NAME/KEY: Motif 1
<222> LOCATION: (5050)..(5076)
<220> FEATURE:
<221> NAME/KEY: G1516D
<222> LOCATION: (5068)..(5070)
<220> FEATURE:
<221> NAME/KEY: G1518A
<222> LOCATION: (5074)..(5076)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: L2
<222> LOCATION: (9967)..(10006)
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)

<400> SEQUENCE: 37
```

| | | | | |
|---|---|---|---|---|
| aggaatactc | tgaataaaac | aacttatata | ataaaaatgc | cggattagaa gccgccgagc | 60 |
| gggtgacagc | cctccgaagg | aagactctcc | tccgtgcgtc | ctcgtcttca ccggtcgcgt | 120 |
| tcctgaaacg | cagatgtgcc | tcgcgccgca | ctgctccgaa | caataaagat tctacaatac | 180 |
| tagcttttat | ggttatgaag | aggaaaaatt | ggcagtaacc | tggccccaca aaccttcaaa | 240 |
| tgaacgaatc | aaattaacaa | ccataggatg | ataatgcgat | tagttttta gccttatttc | 300 |
| tggggtaatt | aatcagcgaa | gcgatgattt | tgatctatt | aacagatata taatgcaaa | 360 |
| aactgcataa | ccactttaac | taatactttc | aacattttcg | gtttgtatta cttcttattc | 420 |
| aaatgtaata | aaagtatcaa | caaaaaattg | ttaatatacc | tctatacttt aacgtcaagg | 480 |
| agctagaaaa | tttattataa | aaggaagaga | ataattaaa | caatgaacaa gaactccaaa | 540 |
| atccagtccc | caaactcttc | tgatgttgct | gttattggtg | ttggttttag attcccaggt | 600 |
| aactctaatg | acccagaatc | tttgtggaac | aacttgttgg | atggtttcga tgctattacc | 660 |
| caagtcccaa | agaaagatg | ggctacttct | tttagagaga | tgggtttgat caagaacaag | 720 |
| ttcggtggtt | tcttgaagga | ttctgaatgg | aagaatttcg | acccttttgtt ctttggtatc | 780 |
| ggtccaaaag | aagctccatt | cattgatcca | caacaaggt | tgttgttgtc catcgtttgg | 840 |
| gaatctttgg | aagatgctta | catcagacca | gatgaattga | gaggtctaa cactggtgtt | 900 |
| ttcatcggtg | tttctaacaa | cgattacacc | aagttgggtt | tccaagacaa ctactctatt | 960 |
| tctccataca | ctatgaccgg | ctctaactct | tcattgaact | ccaacagaat ttcctactgc | 1020 |
| ttcgatttta | gaggtccatc | cattactgtt | gataccgctt | gttcttcttc cttggtttct | 1080 |
| gttaatttgg | gtgtccaatc | catccaaatg | ggtgaatgta | agattgctat tgcggtggt | 1140 |
| gttaacgctt | tgtttgatcc | atctacatct | gttgcctttt | ccaagttggg tgttttgtct | 1200 |
| gaaaatggca | gatgcaactc | ttttagtgat | caagcctctg | gttacgttag atctgaaggt | 1260 |

```
gctggtgttg ttgttttgaa gtctttggaa caagctaagt tggatggtga tagaatctac    1320
ggtgttatca agggtgtttc ctctaatgaa gatggtgctt ctaatggtga caagaactct    1380
ttgactactc catcttgtga agcccaatcc attaacattt ctaaggctat ggaaaaggcc    1440
tccttgtctc catctgatat ctattacatt gaagcccatg gtactggtac tccagttggt    1500
gatccaattg aagttaaggc cttgtccaag atcttctcca actctaacaa caaccagttg    1560
aacaacttct ctaccgatgg taatgataac gatgatgatg atgacgataa cacctctcca    1620
gaaccattat tgattggctc attcaagtcc aacatcggtc atttggaatc tgctgctggt    1680
attgcttctt tgattaagtg ttgcttgatg ttgaagaaca ggatgttggt tccatccatt    1740
aactgctcta atttgaaccc atccattcca ttcgatcagt acaacatctc cgttatcaga    1800
gaaatcagac aattcccaac cgataagttg gttaacatcg gtatcaattc tttcggtttc    1860
ggtggttcta actgccattt gattattcaa gagtacaaca caacttcaa gaacaactct    1920 accatctgca ataacaacaa caacaacaat aacaacatcg actacttgat cccaatctcc    1980
tctaagacta agaagtcctt ggataagtac ttgattttga tcaagaccaa ctccaactac    2040
cacaaggata tttctttcga tgacttcgtc aagttccaaa tcaagtctaa gcagtacaac    2100
ttgtccaaca gaatgactac cattgctaac gattggaact ccttcattaa gggttctaac    2160
gaattccaca acttgatcga atctaaggat ggtgaaggtg gttcttcatc ttctaacaga    2220
ggtattgatt ccgccaatca aatcaacact actactacct ctaccatcaa cgatatcgaa    2280
cctttgttgg ttttcgtttt ctgtggtcaa ggtccacaat ggaatggtat gattaagacc    2340
ttgtacaact ccgagaacgt tttcaagaac accgttgatc atgttgacag catcttgtac    2400
aagtacttcg gttactccat tttgaacgtc ttgtctaaga tcgatgataa cgacgattcc    2460
atcaaccatc caatagttgc tcaaccatct ttgttcttgt tgcaaattgg tttggtcgag    2520
ttgtttaagt actgggqtat ctacccatct atctctgttg gtcattcttt cggtgaagtc    2580
tcttcttatt acttgtccgg tatcatctct ttggaaaccg cttgtaaaat cgtctacgtc    2640
agatcctcta atcagaacaa aactatgggt tccggtaaga tgttggttgt ttctatgggt    2700
tttaagcaat ggaacgatca attctctgct gaatggtccg atattgaaat tgcttgttac    2760
aacgctccag attccatagt tgttactggt aacgaagaaa gattgaaaga attgtccatc    2820
aagttgtccg acgaatccaa tcaaatttc aacaccttct tgaggtcccc atgttctttt    2880
cattcttccc atcaagaagt catcaagggt tctatgttcg aagagttgtc taacttgcaa    2940
tctactggtg aaaccgaaat cccttttgttc tctactgtta ctggtagaca gttttgtct    3000 ggtcatgtta ctgctcaaca catctacgat aatgttagag aaccagtctt gttccaaaag    3060
acgattgaat ccattacctc ctacatcaag tctcactacc catccaatca aaaggttatc    3120
tacgttgaaa ttgctccaca cccaaccttg ttttcattga tcaaaaagtc catcccatcc    3180
tccaacaaga attcctcttc tgttttgtgt ccattgaaca gaaagaaaa ctccaacaac    3240 tcctacaaga agttcgtttc tcagttgtac ttcaacggtg ttaacgttga cttcaacttc    3300
cagttgaact ccatttgcga taacgttaac aacgatcacc atttgaacaa cgtcaagcaa    3360
aactccttca aagagactac caattccttg ccaagatacc aatgggaaca agatgaatat    3420
tggtccgaac cattgatctc cagaaagaat agattggaag gtccaactac ttccttgttg    3480
ggtcatagaa ttatctacag cttcccagtt ttccaatccg ttttggactt gcaatctgac    3540
aactacaaat acttgttgga ccacttggtt aacggtaagc cagttttttcc aggtgctggt    3600 tatttggata tcatcatcga attcttcgac taccaaaagc agcagttgaa ttcctctgat    3660
```

```
tcctctaact cctacatcat caacgttgac aagatccaat tcttgaaccc aattcacttg    3720
accgaaaaca agttgcaaac cttgcaatct tctttcgaac ctatcgttac taagaagtct    3780
gccttctctg ttaacttctt catcaaggat accgtcgagg atcaatctaa ggttaagtct    3840
atgtctgaca aaacttggac taacacttgt aaggctacca tttccttgga caacaacag    3900 ccatctccat cttctacttt gactttgtct aagaagcaag acttgcagat cttgagaaac    3960
agatgcgata ttagcaagct agacaagttt gagttgtacg acaagatctc taagaatttg    4020
ggcttgcagt acaactcctt gtttcaagtt gttgatacca tcgaaactgg taaggattgc    4080
tcttttgcta ctttgtcttt gccagaagat actttgttca ccaccatttt gaacccatgc    4140
ttgttggata actgtttcca tggtttgttg accttgatca acgaaaaggg ttctttcgtt    4200
gtcgagtcca tttcttctgt ttctatctac ttggagaaca tcggttcctt caatcaaact    4260
tctgttggta acgtccagtt ctacttgtac accactattt ctaaagccac ctcctttagt    4320
tctgaaggta cttgtaagtt gttcaccaag atggttcct tgattttgtc tatcggtaag    4380
ttcatcatca agtccaccaa tccaaagtct actaagacca acgaaactat cgaatctcca    4440
ttggacgaaa ccttctctat tgaatggcaa tctaaggatt ctccaattcc aaccccacaa    4500
caaatccaac aacaatctcc attgaactct aacccatcct tcattagatc taccatcttg    4560
aaggacatcc agttcgaaca atactgctcc tccattatcc acaaagaatt gatcaaccac    4620
gaaaagtaca agaaccagca atccttcgat atcaactcct tggaaaacca cttgaacgat    4680
gaccaattga tggaatcctt gtccatctcc aaagaatact tgagattctt caccaggatc    4740
atctccatca ttaagcaata cccaaagatc ttgaacgaaa aagagctaaa agaattgaaa    4800
gaaatcatcg aattgaagta cccatccgaa gttcagttgt tggaattcga agttatcgag    4860
aaggtgtcca tgattatccc aaagttgttg ttcgaaaacg acaagcaatc ttccatgacc    4920
ttgttccaag ataacttgtt gaccaggttc tactccaatt ctaactctac cagattctac    4980
ttggaaaggg tttccgaaat ggtcttggaa tctattagac aatcgtcag agaaaagagg    5040 gtgttcagaa ttttggaaat tggtgctgat acagcctctt tgtctaatgt tgttttgact    5100
aagttgaaca cctacttgtc caccttgaat tctaatggtg gttctggtta caacatcatc    5160
attgagtaca ccttcaccga tatttccgcc aacttcatta ttggtgaaat ccaagaaacc    5220
atgtgcaact tgtacccaaa cgttactttc aagttctccg tcttggactt ggagaaagag    5280
attattaact cctccgattt cttgatgggt gattacgata tagttttgat ggcctacgtt    5340
atccatgccg tttctaacat taagttctcc atcgaacagt tgtacaagtt gttgtctcca    5400
agaggttggt tgttgtgtat tgaacctaag tccaacgttg tgttctccga tttggttttc    5460
ggttgtttta atcagtggtg gaactactac gatgatatta gaactaccca ctgctccttg    5520
tctgaatctc aatggaatca gttgttgttg aaccagtcct tgaacaacga atcctcttct    5580
tcttctaact gttacggtgg tttctccaac gtttctttta ttggtggtga aaaggatgtc    5640
gactcccatt cttttcatatt gcactgccaa aaagaatcca tctcccaaat gaagttagcc    5700
accactatta caacggttt gtcatctggt tccatcgtta tcgttttgaa ctctcaacaa    5760
ttgaccaaca tgaagtccta cccaaaggtt attgagtata ttcaagaggc tacctctttg    5820
tgcaagacca ttgaaattat cgattccaag gacgtcttga actctaccaa ttcagttttg    5880
gaaaagatcc aaaagtcctt gttggtgttc tgttgttgg gttatgactt gttggagaac    5940
aactaccaag aacagtcttt cgaatacgtt aagttgttga acttgatctc tactaccgcc    6000
```

```
tcttcatcta atgataagaa accaccaaag gtcttgttga tcaccaagca atctgaaaga    6060
atctccaggt ctttctactc cagatccttg attggtattt ccagaacctc tatgaacgag    6120
tacccaaatt tgtccattac ctctatcgat ttggatacca acgactactc attgcagtct    6180
ttgttgaagc caatcttcag caactctaag ttttccgaca acgagttcat cttcaaaaag    6240
ggcttgatgt tcgtgtccag gatctttaag aacaagcagt tgctagaatc ctccaacgct    6300
tttgaaactg actcttctaa cttgtactgt aaggcctctt ctgacttgtc ttacaagtac    6360
gctattaagc agtctatgtt gaccgaaaat cagatcgaaa tcaaggttga atgcgtcggt    6420
attaacttca aggacaacct attctacaag ggcttgttgc cacaagaaat tttcagaatg    6480
ggtgacatct acaatccacc atatggtttg gaatgctctg gtgttattac cagaattggt    6540
tctaacgtca ccgaatactc agttggtcaa aatgttttg gtttcgccag acattctttg    6600
ggttctcatg ttgttaccaa caaggatttg gttatcttga agccagatac catctcattt    6660
tctgaagctg cttctatccc agttgtttac tgtactgctt ggtactcctt gttcaacatt    6720
ggtcagttgt ctaacgaaga atccatccta attcattctg ctactggtgg tgtaggtttg    6780
gcttctttga atttgttgaa aatgaagaat cagcaacagc aaccattgac caatgtttat    6840
gctactgttg gctctaacga agaagaagaa ttcttgatcg ataacttcaa caacttgttc    6900
aaagaggacg gcgaaaacat tttctctacc agagacaaag aatactccaa ccagttggaa    6960
tccaagatcg atgttatttt gaacaccttg tccggtgaat tcgtcgaatc taatttcaag    7020
tccttgagat ccttcggtag attgattgat ttgtctgcta ctcacgttta cgccaatcaa    7080
caaattggtc taggtaactt caagttcgac cacttgtatt ctgctgttga cttggaagaa    7140
ttgatcgacg aaaaacctaa gttgttgcag tccatcttgc aaagaattac caactctatc    7200
gtcaacggtt ccttggaaaa aattccaatt accatcttcc catccaccga aactaaggat    7260
gctatcgaat tattgtccaa gagatccat atcggtaaag ttgttgtaga ttgcaccgat    7320
atctctaagt gtaatcctgt tggtgatgtg atcaccaact tctctatgag attgccaaag    7380
ccaaactacc agttgaattt gaactccacc ttgttgatta ctggtcagtc tggtttgtct    7440
atcccttttgt tgaattggtt gttgtctaag tctggtggta acgttaagaa cgttgtcatc    7500
atttctaagt ccaccatgaa gtggaagttg cagactatga tttcccattt cgtttccggt    7560
ttcggtatcc attttaacta cgttcaagtc gacatctcca actacgatgc tttgtctgaa    7620
gctattaagc aattgccatc tgatttgcca ccaatcacct ctgtttttca tttggctgct    7680
atctacaacg atgttccaat ggatcaagtt accatgtcta ccgttgaatc tgttcataac    7740
cctaaagttt tgggtgccgt taacttgcat agaatctctg tttcttttgg ttggaagttg    7800
aaccacttcg tcttgttctc ttctattact gctattaccg gttacccaga ccaatctatc    7860
tacaattctg ccaactctat tttggacgct ttgtccaact ttagaaggtt tatgggtttg    7920
ccatccttct ccattaactt gggtccaatg aaggatgaag gtaaggtttc taccaacaag    7980
agcatcaaga agctattcaa gtctagaggt ttgccaagcc tatccttgaa caagttattt    8040
ggtttgttgg aggtcgtcat caacaaccca tctaatcatg ttatcccatc ccaattgatt    8100
tgctccccaa tcgatttcaa gacctacatc gaatctttct caactatgag gccaaagttg    8160
ttacacttgc aacctaccat ttccaagcag caatcttcta tcattaacga ttctaccaag    8220
gcttcctcca catttcatt gcaagataag atcacctcca aggtgtctga tttgttgtcc    8280
attccaatct ccaagatcaa cttcgatcat ccattgaaac actacggctt ggattctttg    8340
ttgaccgttc aattcaaatc ctggatcgac aaagaattcg aaaagaactt gttcacccat    8400
```

```
atccaattgg ccaccatctc tattaactca ttcttggaaa aggtgaacgg cttgtctaca   8460
aacaataaca acaacaacaa ttccaacgtc aagtcctctc catccattgt caaagaagaa   8520
atcgttacct tggacaagga tcaacaacca ttgctattga agaacacca gcacattatc    8580 atctccccag atattagaat caacaagcca aagagggaat ccttgattag aaccccaatc   8640
ttgaacaaat tcaaccagat caccgaatcc attatcactc catctacacc atctttgtcc   8700
caatccgatg ttttgaaaac tccaccaatc aagtctttga acaacactaa gaactccagc   8760
ttgattaaca ccccaccaat tcaatctgtc caacaacatc aaaagcaaca acaaaaggtc   8820
caagtcatcc aacaacagca acaaccatta tccagattgt cctacaagag caacaacaac   8880
tctttcgttt tgggtatcgg tatttctgtt ccaggtgaac ctatttccca acaatccttg   8940
aaagactcca tctccaatga cttttctgat aaggctgaaa ctaacgagaa ggtcaagaga   9000
atctttgagc aatctcaaat caagaccaga cacttggtta gagattacac taagccagag   9060
aactccatca agttcagaca tttggaaacc attaccgatg tgaacaacca gttcaagaaa   9120
gttgttccag atttggctca acaagcctgt ttgagagctt gaaagattg gggtggtgat    9180 aagggtgata ttacccatat agtttctgtt acctccaccg gtattatcat cccagatgtt   9240
aatttcaagt tgatcgactt gttgggcttg aacaaggatg ttgaaagagt gtctttgaac   9300
ctaatgggtt gtttggctgg tttgagttct ttgagaactg ctgcttcttt ggctaaggct   9360
tctccaagaa atagaatttt ggttgtctgt accgaagtct gctccttgca tttttctaat   9420
actgatggtg gtgatcaaat ggtcgcctct tctattttg ctgatggttc tgctgcttac    9480
attattggtt gtaacccaag aattgaagaa accccattat acgaagtcat gtgctccatt   9540
aacagatctt tcccaaatac cgaaaacgcc atggtttggg atttggaaaa agaaggttgg   9600
aacttgggtt tggatgcttc tattccaatt gtcattggtt ctggtattga agccttcgtt   9660
gatactttgt tggataaggc taagttgcaa acttccactg ctatttctgc taaggattgc   9720
gaattcttga ttcatactgg tggcaagtcc atcttgatga acatcgaaaa ttccttgggt   9780
atcgacccaa agcaaactaa gaatacttgg gatgtttacc atgcctacgg caatatgtca   9840
tctgcctctg ttattttcgt tatggatcat gccagaaagt ccaagtcttt gccaacttac   9900
tcaatttctt tggcttttgg tccaggtttg gcttttgaag ttgtttctt gaagaacgtc    9960 gtctaaagac ataaaactga acaacacca ttaataata gactttacag aagacgggag    10020
acactagcac acaactttac caggcaaggt atttgacgct agcatgtgtc caattcagtg   10080
tcatttatga ttttttgtag taggatataa atatatacag cgctccaaat agtgcggttg   10140
ccccaaaaac accacggaac ctcatctgtt ctcgtacttt gttgtgacaa agtagctcac   10200
tgccttatta tcacattttc attatgcaac gcttcggaaa atacgatgtt gaaaatgcct   10260
ctagagatga aaacaatcg taaaagggtc ctgcgtaatt gaaacatttg atcagtatgc    10320
agtggcacag aaacaaccag gaatactata gtcataggca atacaaggta tatattggct   10380
atgcagaccc ctccagaaag taccgacgtc aagttagata cacttaacga acctagtgca   10440
catttaattg agaaaaatgt ggctcttcct aaggacatat tccgttcgta cttgagttat   10500
tggatctatg aaatcgctcg ctatacacca gtcatgattt tgtccctctt tatattacat   10560
caaaataaga aaataattat aaca                                         10584
```

<210> SEQ ID NO 38
<211> LENGTH: 10584
<212> TYPE: DNA

```
<213> ORGANISM: Artificial Sequence
<220> FEATURE:
<223> OTHER INFORMATION: Cassette with Dictyostelium discoideum DiPKS
      (G1516R) coding sequence, regulatory sequences and integration
      sequences
<220> FEATURE:
<221> NAME/KEY: LV3
<222> LOCATION: (1)..(40)
<220> FEATURE:
<221> NAME/KEY: S. cerevisiae GAL1 promoter
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: C-methyltransferase domain
<222> LOCATION: (5050)..(5412)
<220> FEATURE:
<221> NAME/KEY: G1516R
<222> LOCATION: (5069)..(5070)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: Type III PKS domain
<222> LOCATION: (8881)..(9966)
<220> FEATURE:
<221> NAME/KEY: L2
<222> LOCATION: (9967)..(10006)
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)

<400> SEQUENCE: 38
aggaatactc tgaataaaac aacttatata ataaaaatgc cggattagaa gccgccgagc    60
gggtgacagc cctccgaagg aagactctcc tccgtgcgtc ctcgtcttca ccggtcgcgt   120
tcctgaaacg cagatgtgcc tcgcgccgca ctgctccgaa caataaagat tctacaatac   180
tagcttttat ggttatgaag aggaaaaatt ggcagtaacc tggccccaca aaccttcaaa   240
tgaacgaatc aaattaacaa ccataggatg ataatgcgat tagttttta gccttatttc    300 tggggtaatt aatcagcgaa gcgatgattt tgatctatt aacagatata taaatgcaaa    360
aactgcataa ccactttaac taatactttc aacattttcg gtttgtatta cttcttattc   420
aaatgtaata aaagtatcaa caaaaaattg ttaatatacc tctatacttt aacgtcaagg   480
agctagaaaa tttattataa aaggaagaga ataattaaa caatgaacaa gaactccaaa    540
atccagtccc caaactcttc tgatgttgct gttattggtg ttggttttag attcccaggt   600
aactctaatg acccagaatc tttgtggaac aacttgttgg atggtttcga tgctattacc   660
caagtcccaa agaaagatg ggctacttct tttagagaga tgggtttgat caagaacaag    720
ttcggtggtt tcttgaagga ttctgaatgg aagaatttcg acccttgtt ctttggtatc    780 ggtccaaaag aagctccatt cattgatcca caacaaggt tgttgttgtc catcgtttgg    840
gaatctttgg aagatgctta catcagacca gatgaattga gaggttctaa cactggtgtt    900
ttcatcggtg tttctaacaa cgattacacc aagttgggtt ccaagacaa ctactctatt    960 tctccataca ctatgaccgg ctctaactct tcattgaact ccaacagaat ttcctactgc   1020
ttcgatttta gaggtccatc cattactgtt gataccgctt gttcttcttc cttggttct   1080
```

```
gttaatttgg gtgtccaatc catccaaatg ggtgaatgta agattgctat ttgcggtggt    1140
gttaacgctt tgtttgatcc atctacatct gttgcctttt ccaagttggg tgttttgtct    1200
gaaaatggca gatgcaactc ttttagtgat caagcctctg gttacgttag atctgaaggt    1260
gctggtgttg ttgttttgaa gtctttggaa caagctaagt tggatggtga tagaatctac    1320
ggtgttatca agggtgtttc ctctaatgaa gatggtgctt ctaatggtga caagaactct    1380
ttgactactc catcttgtga agcccaatcc attaacattt ctaaggctat ggaaaaggcc    1440
tccttgtctc catctgatat ctattacatt gaagcccatg gtactggtac tccagttggt    1500
gatccaattg aagttaaggc cttgtccaag atcttctcca actctaacaa caaccagttg    1560
aacaacttct ctaccgatgg taatgataac gatgatgatg atgacgataa cacctctcca    1620
gaaccattat tgattggctc attcaagtcc aacatcggtc atttggaatc tgctgctggt    1680
attgcttctt tgattaagtg ttgcttgatg ttgaagaaca ggatgttggt tccatccatt    1740
aactgctcta atttgaaccc atccattcca ttcgatcagt acaacatctc cgttatcaga    1800
gaaatcagac aattcccaac cgataagttg gttaacatcg gtatcaattc tttcggtttc    1860
ggtggttcta actgccattt gattattcaa gagtacaaca caacttcaa gaacaactct    1920 accatctgca ataacaacaa caacaacaat aacaacatcg actacttgat cccaatctcc    1980
tctaagacta gaagtccctt ggataagtac ttgattttga tcaagaccaa ctccaactac    2040
cacaaggata tttctttcga tgacttcgtc aagttccaaa tcaagtctaa gcagtacaac    2100
ttgtccaaca gaatgactac cattgctaac gattggaact ccttcattaa gggttctaac    2160
gaattccaca acttgatcga atctaaggat ggtgaaggtg ttcttcatc ttctaacaga    2220 ggtattgatt ccgccaatca aatcaacact actactacct ctaccatcaa cgatatcgaa    2280
cctttgttgg ttttcgtttt ctgtggtcaa ggtccacaat ggaatggtat gattaagacc    2340
ttgtacaact ccgagaacgt tttcaagaac accgttgatc atgttgacag catcttgtac    2400
aagtacttcg gttactccat tttgaacgtc ttgtctaaga tcgatgataa cgacgattcc    2460
atcaaccatc caatagttgc tcaaccatct ttgttcttgt tgcaaattgg tttggtcgag    2520
ttgtttaagt actggggtat ctacccatct atctctgttg gtcattcttt cggtgaagtc    2580
tcttcttatt acttgtccgg tatcatctct ttggaaaccg cttgtaaaat cgtctacgtc    2640
agatcctcta atcagaacaa aactatgggt tccggtaaga tgttggttgt ttctatgggt    2700
tttaagcaat ggaacgatca attctctgct gaatggtccg atattgaaat tgcttgttac    2760
aacgctccag attccatagt tgttactggt aacgaagaaa gattgaaaga attgtccatc    2820
aagttgtccg acgaatccaa tcaaattttc aacaccttct tgaggtcccc atgttctttt    2880
cattcttccc atcaagaagt catcaagggt tctatgttcg aagagttgtc taacttgcaa    2940
tctactggtg aaaccgaaat ccctttgttc tctactgtta ctggtagaca agttttgtct    3000
ggtcatgtta ctgctcaaca catctacgat aatgttagag aaccagtctt gttccaaaag    3060
acgattgaat ccattaccct ctacatcaag tctcactacc catccaatca aaaggttatc    3120
tacgttgaaa ttgctccaca cccaaccttg ttttcattga tcaaaaagtc catcccatcc    3180
tccaacaaga attcctcttc tgttttgtgt ccattgaaca gaaagaaaa ctccaacaac    3240 tcctacaaga agttcgtttc tcagttgtac ttcaacggtg ttaacgttga cttcaacttc    3300
cagttgaact ccatttgcga taacgttaac aacgatcacc atttgaacaa cgtcaagcaa    3360
aactccttca aagagactac caattccttg ccaagatacc aatgggaaca agatgaatat    3420
```

```
tggtccgaac cattgatctc cagaaagaat agattggaag gtccaactac ttccttgttg    3480
ggtcatagaa ttatctacag cttcccagtt ttccaatccg ttttggactt gcaatctgac    3540
aactacaaat acttgttgga ccacttggtt aacggtaagc cagttttttcc aggtgctggt   3600
tatttggata tcatcatcga attcttcgac taccaaaagc agcagttgaa ttcctctgat    3660
tcctctaact cctacatcat caacgttgac aagatccaat tcttgaaccc aattcacttg    3720
accgaaaaca agttgcaaac cttgcaatct tctttcgaac ctatcgttac taagaagtct    3780
gccttctctg ttaacttctt catcaaggat accgtcgagg atcaatctaa ggttaagtct    3840
atgtctgacg aaacttggac taacacttgt aaggctacca tttccttgga caacaacag    3900
ccatctccat cttctacttt gactttgtct aagaagcaag acttgcagat cttgagaaac    3960
agatgcgata ttagcaagct agacaagttt gagttgtacg acaagatctc taagaatttg    4020
ggcttgcagt acaactcctt gtttcaagtt gttgatacca tcgaaactgg taaggattgc    4080
tcttttgcta ctttgtcttt gccagaagat actttgttca ccaccatttt gaacccatgc    4140
ttgttggata actgtttcca tggtttgttg accttgatca acgaaaaggg ttctttcgtt    4200
gtcgagtcca tttcttctgt ttctatctac ttggagaaca tcggttcctt caatcaaact    4260
tctgttggta acgtccagtt ctacttgtac accactattt ctaaagccac ctcctttagt    4320
tctgaaggta cttgtaagtt gttcaccaag gatggttcct tgattttgtc tatcggtaag    4380
ttcatcatca agtccaccaa tccaaagtct actaagacca acgaaactat cgaatctcca    4440
ttggacgaaa ccttctctat tgaatggcaa tctaaggatt ctccaattcc aaccccacaa    4500
caaatccaac aacaatctcc attgaactct aacccatcct tcattagatc taccatcttg    4560
aaggacatcc agttcgaaca atactgctcc tccattatcc acaaagaatt gatcaaccac    4620
gaaaagtaca agaaccagca atccttcgat atcaactcct tggaaaacca cttgaacgat    4680
gaccaattga tggaatcctt gtccatctcc aaagaatact tgagattctt caccaggatc    4740
atctccatca ttaagcaata cccaaagatc ttgaacgaaa aagagctaaa agaattgaaa    4800
gaaatcatcg aattgaagta cccatccgaa gttcagttgt tggaattcga agttatcgag    4860
aaggtgtcca tgattatccc aaagttgttg ttcgaaaacg acaagcaatc ttccatgacc    4920
ttgttccaag ataacttgtt gaccaggttc tactccaatt ctaactctac cagattctac    4980
ttggaaaggg tttccgaaat ggtcttggaa tctattagac aatcgtcag agaaaagagg    5040
gtgttcagaa ttttagagat cggtgctcgt acaggctctt tgtctaatgt tgttttgact    5100
aagttgaaca cctacttgtc caccttgaat tctaatggtg gttctggtta caacatcatc    5160
attgagtaca ccttcaccga tatttccgcc aacttcatta ttggtgaaat ccaagaaacc    5220
atgtgcaact tgtacccaaa cgttactttc aagttctccg tcttggactt ggagaaagag    5280
attattaact cctccgattt cttgatgggt gattacgata tagttttgat ggcctacgtt    5340
atccatgccg tttctaacat taagttctcc atcgaacagt tgtacaagtt gttgtctcca    5400
agaggttggt tgttgtgtat tgaacctaag tccaacgttg tgttctccga tttggtttcc    5460
ggttgtttta atcagtggtg gaactactac gatgatatta aactaccca ctgctccttg    5520
tctgaatctc aatggaatca gttgttgttg aaccagtcct tgaacaacga atcctcttct    5580
tcttctaact gttacggtgg tttctccaac gtttcttta ttggtggtga aaaggatgtc    5640
gactcccatt ctttcatatt gcactgccaa aaagaatcca tctcccaaat gaagttagcc    5700
accactatta caacggttt gtcatctggt tccatccgtta tcgttttgaa ctctcaacaa    5760
ttgaccaaca tgaagtccta cccaaaggtt attgagtata ttcaagaggc tacctctttg    5820
```

```
tgcaagacca ttgaaattat cgattccaag gacgtcttga actctaccaa ttcagttttg    5880
gaaaagatcc aaaagtcctt gttggtgttc tgtttgttgg gttatgactt gttggagaac    5940
aactaccaag aacagtcttt cgaatacgtt aagttgttga acttgatctc tactaccgcc    6000
tcttcatcta atgataagaa accaccaaag gtcttgttga tcaccaagca atctgaaaga    6060
atctccaggt ctttctactc cagatccttg attggtattt ccagaacctc tatgaacgag    6120
tacccaaatt tgtccattac ctctatcgat ttggatacca acgactactc attgcagtct    6180
ttgttgaagc caatcttcag caactctaag ttttccgaca acgagttcat cttcaaaaag    6240
ggcttgatgt tcgtgtccag gatctttaag aacaagcagt tgctagaatc ctccaacgct    6300
tttgaaactg actcttctaa cttgtactgt aaggcctctt ctgacttgtc ttacaagtac    6360
gctattaagc agtctatgtt gaccgaaaat cagatcgaaa tcaaggttga atgcgtcggt    6420
attaacttca aggacaacct attctacaag ggcttgttgc cacaagaaat tttcagaatg    6480
ggtgacatct acaatccacc atatggtttg gaatgctctg gtgttattac cagaattggt    6540
tctaacgtca ccgaatactc agttggtcaa atgttttttg gtttcgccag acattctttg    6600
ggttctcatg ttgttaccaa caaggatttg gttatcttga agccagatac catctcattt    6660
tctgaagctg cttctatccc agttgtttac tgtactgctt ggtactcctt gttcaacatt    6720
ggtcagttgt ctaacgaaga atccatccta attcattctg ctactggtgg tgtaggtttg    6780
gcttctttga atttgttgaa aatgaagaat cagcaacagc aaccattgac caatgtttat    6840
gctactgttg gctctaacga gaagaagaag ttcttgatcg ataacttcaa caacttgttc    6900
aaagaggacg gcgaaaacat tttctctacc agagacaaag aatactccaa ccagttggaa    6960
tccaagatcg atgttatttt gaacaccttg tccggtgaat tcgtcgaatc taatttcaag    7020
tccttgagat ccttcggtag attgattgat ttgtctgcta ctcacgttta cgccaatcaa    7080
caaattggtc taggtaactt caagttcgac cacttgtatt ctgctgttga cttggaaaga    7140
ttgatcgacg aaaaacctaa gttgttgcag tccatcttgc aaagaattac caactctatc    7200
gtcaacggtt ccttggaaaa aattccaatt accatcttcc catccaccga aactaaggat    7260
gctatcgaat tattgtccaa gagatcccat atcggtaaag ttgttgtaga ttgcaccgat    7320
atctctaagt gtaatcctgt tggtgatgtg atcaccaact tctctatgag attgccaaag    7380
ccaaactacc agttgaattt gaactccacc ttgttgatta ctggtcagtc tggtttgtct    7440 atcccttttgt tgaattggtt gttgtctaag tctggtggta acgttaagaa cgttgtcatc    7500
atttctaagt ccaccatgaa gtggaagttg cagactatga tttcccattt cgtttccggt    7560
ttcggtatcc attttaacta cgttcaagtc gacatctcca actacgatgc tttgtctgaa    7620
gctattaagc aattgccatc tgatttgcca ccaatcacct ctgttttca tttggctgct    7680 atctacaacg atgttccaat ggatcaagtt accatgtcta ccgttgaatc tgttcataac    7740
cctaaagttt gggtgccgt taacttgcat agaatctctg tttctttttgg ttggaagttg    7800 aaccacttcg tcttgttctc ttctattact gctattaccg gttacccaga ccaatctatc    7860
tacaattctg ccaactctat tttggacgct tgtccaact ttagaaggtt tatgggtttg    7920
ccatccttct ccattaactt gggtccaatg aaggatgaag gtaaggtttc taccaacaag    7980
agcatcaaga agctattcaa gtctagaggt ttgccaagcc tatccttgaa caagttattt    8040
ggtttgttgg aggtcgtcat caacaaccca tctaatcatg ttatcccatc ccaattgatt    8100
tgctccccaa tcgatttcaa gacctacatc gaatctttct caactatgag gccaaagttg    8160
```

```
ttacacttgc aacctaccat ttccaagcag caatcttcta tcattaacga ttctaccaag    8220
gcttcctcca acatttcatt gcaagataag atcacctcca aggtgtctga tttgttgtcc    8280
attccaatct ccaagatcaa cttcgatcat ccattgaaac actacggctt ggattctttg    8340
ttgaccgttc aattcaaatc ctggatcgac aaagaattcg aaaagaactt gttcacccat    8400
atccaattgg ccaccatctc tattaactca ttcttggaaa aggtgaacgg cttgtctaca    8460
aacaataaca acaacaacaa ttccaacgtc aagtcctctc catccattgt caaagaagaa    8520
atcgttacct tggacaagga tcaacaacca ttgctattga aagaacacca gcacattatc    8580
atctccccag atattagaat caacaagcca aagagggaat ccttgattag aaccccaatc    8640
ttgaacaaat tcaaccagat caccgaatcc attatcactc catctacacc atctttgtcc    8700
caatccgatg ttttgaaaac tccaccaatc aagtctttga caacactaa gaactccagc     8760
ttgattaaca ccccaccaat tcaatctgtc caacaacatc aaaagcaaca acaaaaggtc    8820
caagtcatcc aacaacagca acaaccatta tccagattgt cctacaagag caacaacaac    8880
tctttcgttt tgggtatcgg tatttctgtt ccaggtgaac ctatttccca acaatccttg    8940
aaagactcca tctccaatga ctttttctgat aaggctgaaa ctaacgagaa ggtcaagaga    9000
atctttgagc aatctcaaat caagaccaga cacttggtta gagattacac taagccagag    9060
aactccatca gttcagaca tttggaaacc attaccgatg tgaacaacca gttcaagaaa    9120
gttgttccag atttggctca acaagcctgt ttgagagctt tgaaagattg gggtggtgat    9180
aagggtgata ttacccatat agtttctgtt acctccaccg gtattatcat cccagatgtt    9240
aatttcaagt tgatcgactt gttgggcttg aacaaggatg ttgaaagagt gtctttgaac    9300
ctaatgggtt gtttggctgg tttgagttct ttgagaactg ctgcttcttt ggctaaggct    9360
tctccaagaa atagaatttt ggttgtctgt accgaagtct gctccttgca ttttcctaat    9420
actgatggtg gtgatcaaat ggtcgcctct tctattttg ctgatggttc tgctgcttac    9480
attattggtt gtaacccaag aattgaagaa accccattat acgaagtcat gtgctccatt    9540
aacagatctt tcccaaatac cgaaaacgcc atggtttggg atttggaaaa agaaggttgg    9600
aacttgggtt tggatgcttc tattccaatt gtcattggtt ctggtattga agccttcgtt    9660
gatactttgt tggataaggc taagttgcaa acttccactg ctatttctgc taaggattgc    9720
gaattcttga ttcatactgg tggcaagtcc atcttgatga acatcgaaaa ttccttgggt    9780
atcgacccaa agcaaactaa gaatacttgg gatgtttacc atgcctacgg caatatgtca    9840
tctgcctctg ttattttcgt tatggatcat gccagaaagt ccaagtcttt gccaacttac    9900
tcaatttctt tggcttttgg tccaggtttg gcttttgaag gttgtttctt gaagaacgtc    9960
gtctaaagac ataaaactga acaacacca attaataata gactttacag aagacgggag    10020
acactagcac acaactttac caggcaaggt atttgacgct agcatgtgtc caattcagtg    10080
tcatttatga ttttttgtag taggatataa atatatacag cgctccaaat agtgcggttg    10140
ccccaaaaac accacggaac ctcatctgtt ctcgtacttt gttgtgacaa agtagctcac    10200
tgccttatta tcacattttc attatgcaac gcttcggaaa atacgatgtt gaaaatgcct    10260
ctagagatga aaaacaatcg taaaagggtc ctgcgtaatt gaaacatttg atcagtatgc    10320
agtggcacag aaacaaccag gaatactata gtcataggca atacaaggta tatattggct    10380
atgcagaccc ctccagaaag taccgacgtc aagttagata cacttaacga acctagtgca    10440
catttaattg agaaaaatgt ggctcttcct aaggacatat tccgttcgta cttgagttat    10500
```

```
tggatctatg aaatcgctcg ctatacacca gtcatgattt tgtccctctt tatattacat    10560
caaaataaga aaataattat aaca                                           10584

<210> SEQ ID NO 39
<211> LENGTH: 6034
<212> TYPE: DNA
<213> ORGANISM: Artificial Sequence
<220> FEATURE:
<223> OTHER INFORMATION: Plasmid
<220> FEATURE:
<221> NAME/KEY: LV5
<222> LOCATION: (1)..(40)
<220> FEATURE:
<221> NAME/KEY: pYES2-LEU2
<222> LOCATION: (1915)..(4123)
<220> FEATURE:
<221> NAME/KEY: LEU2 ORF
<222> LOCATION: (1996)..(3090)
<220> FEATURE:
<221> NAME/KEY: LEU2 promoter
<222> LOCATION: (3091)..(3999)
<220> FEATURE:
<221> NAME/KEY: misc_feature
<222> LOCATION: (3759)..(3760)
<223> OTHER INFORMATION: n is a, c, g, or t
<220> FEATURE:
<221> NAME/KEY: LV3
<222> LOCATION: (5995)..(6034)

<400> SEQUENCE: 39
cctctttata ttacatcaaa ataagaaaat aattataaca cctgcattaa tgaatcggcc      60
aacgcgcggg gagaggcggt ttgcgtattg ggcgctcttc cgcttcctcg ctcactgact     120
cgctgcgctc ggtcgttcgg ctgcggcgag cggtatcagc tcactcaaag gcggtaatac     180
ggttatccac agaatcaggg gataacgcag gaaagaacat gtgagcaaaa ggccagcaaa     240
agcccaggaa ccgtaaaaag gccgcgttgc tggcgttttt ccataggctc cgcccccctg     300
acgagcatca caaaaatcga cgctcaagtc agaggtggcg aaacccgaca ggactataaa     360
gataccaggc gtttccccct ggaagctccc tcgtgcgctc tcctgttccg accctgccgc     420
ttaccggata cctgtccgcc tttctccctt cgggaagcgt ggcgctttct catagctcac     480
gctgtaggta tctcagttcg gtgtaggtcg ttcgctccaa gctgggctgt gtgcacgaac     540
cccccgttca gcccgaccgc tgcgccttat ccggtaacta tcgtcttgag tccaacccgg     600
taagacacga cttatcgcca ctggcagcag ccactggtaa caggattagc agagcgaggt     660
atgtaggcgg tgctacagag ttcttgaagt ggtggcctaa ctacggctac actagaagga     720
cagtatttgg tatctgcgct ctgctgaagc cagttacctt cggaaaaaga gttggtagct     780
cttgatccgg caaacaaacc accgctggta gcggtggttt ttttgtttgc aagcagcaga     840
ttacgcgcag aaaaaaagga tctcaagaag atcctttgat cttttctacg ggtctgacg     900 ctcagtggaa cgaaaactca cgttaaggga ttttggtcat gagattatca aaaaggatct     960
tcacctagat ccttttaaat taaaaatgaa gttttaaatc aatctaaagt atatatgagt    1020
aaacttggtc tgacagttac caatgcttaa tcagtgaggc acctatctca gcgatctgtc    1080
tatttcgttc atccatagtt gcctgactcc ccgtcgtgta gataactacg atacgggagc    1140
gcttaccatc tggccccagt gctgcaatga taccgcgaga cccacgctca ccggctccag    1200
atttatcagc aataaaccag ccagccggaa gggccgagcg cagaagtggt cctgcaactt    1260
tatccgcctc cattcagtct attaattgtt gccgggaagc tagagtaagt agttcgccag    1320
ttaatagttt gcgcaacgtt gttggcattg ctacaggcat cgtggtgtca ctctcgtcgt    1380
```

```
ttggtatggc ttcattcagc tccggttccc aacgatcaag gcgagttaca tgatcccca       1440 tgttgtgcaa aaaagcggtt agctccttcg gtcctccgat cgttgtcaga agtaagttgg       1500
ccgcagtgtt atcactcatg gttatggcag cactgcataa ttctcttact gtcatgccat       1560
ccgtaagatg ctttttctgtg actggtgagt actcaaccaa gtcattctga aatagtgta       1620 tgcggcgacc gagttgctct tgcccggcgt caatacggga taatagtgta tcacatagca       1680
gaactttaaa agtgctcatc attggaaaac gttcttcggg gcgaaaactc tcaaggatct       1740
taccgctgtt gagatccagt tcgatgtaac ccactcgtgc acccaactga tcttcagcat       1800
cttttacttt caccagcgtt tctgggtgag caaaaacagg aaggcaaaat gccgcaaaaa       1860
agggaataag ggcgacacgg aaatgttgaa tactcatact cttccttttt caatgggtaa       1920
taactgatat aattaaattg aagctctaat ttgtgagttt agtatacatg catttactta       1980
taatacagtt ttttattaag caaggatttt cttaacttct tcggcgacag catcaccgac       2040
ttcggtggta ctgttggaac cacctaaatc accagttctg atacctgcat ccaaaacctt       2100
tttaactgca tcttcaatgg ccttaccttc ttcaggcaag ttcaatgaca atttcaacat       2160
cattgcagca gacaagatag tggcgatagg gttgaccctta ttctttggca aatctggagc       2220
agaaccgtgg catggttcgt acaaaccaaa tgcggtgttc ttgtctggca agaggccaa       2280 ggacgcagat ggcaacaaac ccaaggaacc tgggataacg gaggcttcat cggagatgat       2340
atcaccaaac atgttgctgg tgattataat accatttagg tgggttgggt tcttaactag       2400
gatcatggcg gcagaatcaa tcaattgatg ttgaaccttc aatgtaggga attcgttctt       2460
gatggtttcc tccacagttt ttctccataa tcttgaagag gccaaaacat tagctttatc       2520
caaggaccaa ataggcaatg gtggctcatg ttgtagggcc atgaaagcgg ccattcttgt       2580
gattctttgc acttctggaa cggtgtattg ttcactatcc caagcgacac catcaccatc       2640
gtcttccttt ctcttaccaa agtaaatacc tcccactaat tctctgacaa caacgaagtc       2700 agtacccttta gcaaattgtg gcttgattgg agataagtct aaaagagagt cggatgcaaa       2760
gttacatggt cttaagttgg cgtacaattg aagttcttta cggatttta gtaaaccttg       2820 ttcaggtcta acactaccgg taccccattt aggaccaccc acagcaccta acaaaacggc       2880
atcagccttc ttggaggctt ccagcgcctc atctggaagt ggaacacctg tagcatcgat       2940
agcagcacca ccaattaaat gattttcgaa atcgaacttg acattggaac gaacatcaga       3000
aatagcttta agaaccttaa tggcttcggc tgtgatttct tgaccaacgt ggtcacctgg       3060
caaaacgacg atcttcttag gggcagacat tagaatggta tatccttgaa atatatatat       3120
atattgctga atgtaaaag gtaagaaaag ttagaaagta agacgattgc taaccaccta       3180
ttggaaaaaa caataggtcc ttaaataata ttgtcaactt caagtattgt gatgcaagca       3240
tttagtcatg aacgcttctc tattctatat gaaaagccgg ttccggcgct ctcacctttc       3300 cttttctcc caattttca gttgaaaaag gtatatgcgt caggcgacct ctgaaattaa       3360
caaaaatttt ccagtcatcg aatttgattc tgtgcgatag cgccctgtg tgttctcgtt       3420 atgttgagga aaaaaataat ggttgctaag agattcgaac tcttgcatct tacgatacct       3480
gagtattccc acagttaact gcggtcaaga tatttcttga atcaggcgcc ttagaccgct       3540
cggccaaaca accaattact tgttgagaaa tagagtataa ttatcctata aatataacgt       3600
ttttgaacac acatgaacaa ggaagtacag gacaattgat tttgaagaga atgtggattt       3660
tgatgtaatt gttgggattc cattttaat aaggcaataa tattaggtat gtagatatac       3720
```

```
tagaagttct cctcgaggat ttaggaatcc ataaaaggnn atctgcaatt ctacacaatt    3780
ctagaaatat tattatcatc attttatatg ttaatattca ttgatcctat tacattatca    3840
atccttgcgt ttcagcttcc actaatttag atgactattt ctcatcattt gcgtcatctt    3900
ctaacaccgt atatgataat atactagtaa cgtaaatact agttagtaga tgatagttga    3960
tttttattcc aacataccac ccataatgta atagatctag cttatcgatg ataagctgtc    4020
aaagatgaga attaattcca cggactatag actataccta gtatactccg tctactgtac    4080
gatacacttc cgctcaggtc cttgtccttt aacgaggcct taccactctt ttgttactct    4140
attgatccag ctcagcaaag gcagtgtgat ctaagattct atcttcgcga tgtagtaaaa    4200
ctagctagac cgagaaagag actagaaatg caaaaggcac ttctacaatg gctgccatca    4260
ttattatccg atgtgacgct gcagcttctc aatgatattc gaatacgctt tgaggagata    4320
cagcctaata tccgacaaac tgttttacag atttacgatc gtacttgtta cccatcattg    4380
aattttgaac atccgaacct gggagttttc cctgaaacag atagtatatt tgaacctgta    4440
taataatata tagtctagcg ctttacgaaa gacaatgtat gtatttcggt tcctggagaa    4500
actattgcat ctattgcata ggtaatcttg cacgtcgcat ccccggttca tttctgcgt    4560
ttccatcttg cacttcaata gcatatcttt gttaacgaag catctgtgct tcattttgta    4620
gaacaaaaat gcaacgcgag agcgctaatt tttcaaacaa agaatctgag ctgcattttt    4680
acagaacaga aatgcaacgc gaaagcgcta ttttaccaac gaagaatctg tgcttcattt    4740
ttgtaaaaca aaatgcaac gcgacgagag cgctaatttt tcaaacaaag aatctgagct    4800
gcattttac agaacagaaa tgcaacgcga gagcgctatt ttaccaacaa gaatctata    4860
cttcttttt gttctacaaa aatgcatccc gagagcgcta ttttctaac aaagcatctt    4920
agattacttt tttctccttt gtgcgctct ataatgcagt ctcttgataa cttttgcac    4980
tgtaggtccg ttaaggttag aagaaggcta ctttggtgtc tattttctct tccataaaaa    5040
aagcctgact ccactcccg cgtttactga ttactagcga agctgcgggt gcatttttc    5100
aagataaagg catccccgat tatattctat accgatgtgg attgcgcata ctttgtgaac    5160
agaaagtgat agcgttgatg attcttcatt ggtcagaaaa ttatgaacgg ttcttctat    5220
tttgtctcta tatactacgt ataggaaatg tttacatttt cgtattgttt tcgattcact    5280
ctatgaatag ttcttactac aatttttttg tctaaagagt aatactagag ataaacataa    5340
aaaatgtaga ggtcgagttt agatgcaagt tcaaggagcg aaaggtggat gggtaggtta    5400
tatagggata tagcacagag atatatagca aagagatact tttgagcaat gtttgtggaa    5460
gcggtattcg caatgggaag ctccaccccg gttgataatc agaaaagccc caaaacagg    5520
aagattgtat aagcaaatat ttaaattgta aacgttaata ttttgttaaa attcgcgtta    5580
aattttgtt aaatcagctc attttttaac gaatagcccg aaatcggcaa aatcccttat    5640
aaatcaaaag aatagaccga gatagggttg agtgttgttc cagtttccaa caagagtcca    5700
ctattaaaga acgtggactc caacgtcaaa gggcgaaaaa gggtctatca gggcgatggc    5760
ccactacgtg aaccatcacc ctaatcaagt ttttttgggt cgaggtgccg taaagcagta    5820
aatcggaagg gtaaacggat gcccccattt agagcttgac ggggaaagcc ggcgaacgtg    5880
gcgagaaagg aagggaagaa agcgaaagga gcggggggcta gggcggtggg aagtgtaggg    5940
gtcacgctgg gcgtaaccac cacacccgcc gcgcttaatg gggcgctaca gggcaggaat    6000
actctgaata aaacaactta tataataaaa atgc                                6034
```

```
<210> SEQ ID NO 40
<211> LENGTH: 5056
<212> TYPE: DNA
<213> ORGANISM: Artificial Sequence
<220> FEATURE:
<223> OTHER INFORMATION: Plasmid
<220> FEATURE:
<221> NAME/KEY: LV5
<222> LOCATION: (1)..(40)
<220> FEATURE:
<221> NAME/KEY: pYES backbone
<222> LOCATION: (41)..(5016)
<220> FEATURE:
<221> NAME/KEY: AmpR
<222> LOCATION: (1040)..(1699)
<220> FEATURE:
<221> NAME/KEY: URA3
<222> LOCATION: (1915)..(3022)
<220> FEATURE:
<221> NAME/KEY: LV3
<222> LOCATION: (5017)..(5056)

<400> SEQUENCE: 40
```

| | | | | | |
|---|---|---|---|---|---|
| cctctttata | ttacatcaaa | ataagaaaat | aattataaca | cctgcattaa | tgaatcggcc | 60 |
| aacgcgcggg | gagaggcggt | ttgcgtattg | ggcgctcttc | cgcttcctcg | ctcactgact | 120 |
| cgctgcgctc | ggtcgttcgg | ctgcggcgag | cggtatcagc | tcactcaaag | gcggtaatac | 180 |
| ggttatccac | agaatcaggg | gataacgcag | gaaagaacat | gtgagcaaaa | ggccagcaaa | 240 |
| agcccaggaa | ccgtaaaaag | gccgcgttgc | tggcgttttt | ccataggctc | cgcccccctg | 300 |
| acgagcatca | caaaaatcga | cgctcaagtc | agaggtggcg | aaacccgaca | ggactataaa | 360 |
| gataccaggc | gtttccccct | ggaagctccc | tcgtgcgctc | tcctgttccg | accctgccgc | 420 |
| ttaccggata | cctgtccgcc | tttctccctt | cgggaagcgt | ggcgctttct | catagctcac | 480 |
| gctgtaggta | tctcagttcg | gtgtaggtcg | ttcgctccaa | gctgggctgt | gtgcacgaac | 540 |
| cccccgttca | gcccgaccgc | tgcgccttat | ccggtaacta | tcgtcttgag | tccaacccgg | 600 |
| taagacacga | cttatcgcca | ctggcagcag | ccactggtaa | caggattagc | agagcgaggt | 660 |
| atgtaggcgg | tgctacagag | ttcttgaagt | ggtggcctaa | ctacggctac | actagaagga | 720 |
| cagtatttgg | tatctgcgct | ctgctgaagc | cagttacctt | cggaaaaaga | gttggtagct | 780 |
| cttgatccgg | caaacaaacc | accgctggta | gcggtggttt | ttttgtttgc | aagcagcaga | 840 |
| ttacgcgcag | aaaaaaagga | tctcaagaag | atcctttgat | cttttctacg | ggtctgacg | 900 |
| ctcagtggaa | cgaaaactca | cgttaaggga | ttttggtcat | gagattatca | aaaaggatct | 960 |
| tcacctagat | ccttttaaat | taaaaatgaa | gttttaaatc | aatctaaagt | atatatgagt | 1020 |
| aaacttggtc | tgacagttac | caatgcttaa | tcagtgaggc | acctatctca | gcgatctgtc | 1080 |
| tatttcgttc | atccatagtt | gcctgactcc | ccgtcgtgta | gataactacg | atacgggagc | 1140 |
| gcttaccatc | tggccccagt | gctgcaatga | taccgcgaga | cccacgctca | ccggctccag | 1200 |
| atttatcagc | aataaaccag | ccagccggaa | gggccgagcg | cagaagtggt | cctgcaactt | 1260 |
| tatccgcctc | cattcagtct | attaattgtt | gccgggaagc | tagagtaagt | agttcgccag | 1320 |
| ttaatagttt | gcgcaacgtt | gttggcattg | ctacaggcat | cgtggtgtca | ctctcgtcgt | 1380 |
| ttggtatggc | ttcattcagc | tccggttccc | aacgatcaag | gcgagttaca | tgatccccca | 1440 |
| tgttgtgcaa | aaaagcggtt | agctccttcg | gtcctccgat | cgttgtcaga | agtaagttgg | 1500 |
| ccgcagtgtt | atcactcatg | gttatggcag | cactgcataa | ttctcttact | gtcatgccat | 1560 |
| ccgtaagatg | cttttctgtg | actggtgagt | actcaaccaa | gtcattctga | gaatagtgta | 1620 |
| tgcggcgacc | gagttgctct | tgcccggcgt | caatacggga | taatagtgta | tcacatagca | 1680 |

```
gaactttaaa agtgctcatc attggaaaac gttcttcggg gcgaaaactc tcaaggatct    1740
taccgctgtt gagatccagt tcgatgtaac ccactcgtgc acccaactga tcttcagcat    1800
cttttacttt caccagcgtt tctgggtgag caaaaacagg aaggcaaaat gccgcaaaaa    1860
agggaataag ggcgacacgg aaatgttgaa tactcatact cttccttttt caatgggtaa    1920
taactgatat aattaaattg aagctctaat ttgtgagttt agtatacatg catttactta    1980
taatacagtt ttttagtttt gctggccgca tcttctcaaa tatgcttccc agcctgcttt    2040
tctgtaacgt tcaccctcta ccttagcatc ccttcccttt gcaaatagtc ctcttccaac    2100
aataataatg tcagatcctg tagagaccac atcatccacg gttctatact gttgacccaa    2160
tgcgtctccc ttgtcatcta aacccacacc gggtgtcata atcaaccaat cgtaaccttc    2220
atctcttcca cccatgtctc tttgagcaat aaagccgata acaaaatctt tgtcgctctt    2280
cgcaatgtca acagtaccct tagtatattc tccagtagat agggagccct tgcatgacaa    2340
ttctgctaac atcaaaaggc ctctaggttc ctttgttact tcttctgccg cctgcttcaa    2400
accgctaaca atacctgggc ccaccacacc gtgtgcattc gtaatgtctg cccattctgc    2460
tattctgtat acacccgcag agtactgcaa tttgactgta ttaccaatgt cagcaaattt    2520
tctgtcttcg aagagtaaaa aattgtactt ggcggataat gcctttagcg cttaactgt     2580 gccctccatg gaaaaatcag tcaagatatc cacatgtgtt tttagtaaac aaattttggg    2640
acctaatgct tcaactaact ccagtaattc cttggtggta cgaacatcca atgaagcaca    2700
caagtttgtt tgcttttcgt gcatgatatt aaatagcttg gcagcaacag gactaggatg    2760
agtagcagca cgttccttat atgtagcttt cgacatgatt tatcttcgtt tcctgcaggt    2820
ttttgttctg tgcagttggg ttaagaatac tgggcaattt catgtttctt caacactaca    2880
tatgcgtata tataccaatc taagtctgtg ctccttcctt cgttcttcct tctgttcgga    2940
gattaccgaa tcaaaaaaat ttcaaagaaa ccgaaatcaa aaaaagaat aaaaaaaaa      3000 tgatgaattg aattgaaaag ctagcttatc gatgataagc tgtcaaagat gagaattaat    3060
tccacggact atagactata ctagatactc cgtctactgt acgatacact tccgctcagg    3120
tccttgtcct ttaacgaggc cttaccactc ttttgttact ctattgatcc agctcagcaa    3180
aggcagtgtg atctaagatt ctatcttcgc gatgtagtaa aactagctag accgagaaag    3240
agactagaaa tgcaaaaggc acttctacaa tggctgccat cattattatc cgatgtgacg    3300
ctgcagcttc tcaatgatat tcgaatacgc tttgaggaga tacagcctaa tatccgacaa    3360
actgttttac agatttacga tcgtacttgt tacccatcat tgaattttga acatccgaac    3420
ctgggagttt tccctgaaac agatagtata tttgaacctg tataataata tatagtctag    3480
cgctttacgg aagacaatgt atgtatttcg gttcctggag aaactattgc atctattgca    3540
taggtaatct tgcacgtcgc atccccggtt catttctgc gtttccatct tgcacttcaa     3600
tagcatatct ttgttaacga agcatctgtg cttcattttg tagaacaaaa atgcaacgcg    3660
agagcgctaa tttttcaaac aaagaatctg agctgcattt ttacagaaca gaaatgcaac    3720
gcgaaagcgc tattttacca acgaagaatc tgtgcttcat ttttgtaaaa caaaaatgca    3780
acgcgacgag agcgctaatt tttcaaacaa agaatctgag ctgcattttt acagaacaga    3840
aatgcaacgc gagagcgcta tttaccaac aaagaatcta tacttctttt tgttctaca    3900 aaaatgcatc ccgagagcgc tatttttcta acaaagcatc ttagattact ttttttctcc    3960
tttgtgcgct ctataatgca gtctcttgat aactttttgc actgtaggtc cgttaaggtt    4020
```

```
agaagaaggc tactttggtg tctattttct cttccataaa aaaagcctga ctccacttcc    4080
cgcgtttact gattactagc gaagctgcgg gtgcattttt tcaagataaa ggcatccccg    4140
attatattct ataccgatgt ggattgcgca tactttgtga acagaaagtg atagcgttga    4200
tgattcttca ttggtcagaa aattatgaac ggtttcttct attttgtctc tatatactac    4260
gtataggaaa tgtttacatt ttcgtattgt tttcgattca ctctatgaat agttcttact    4320 acaattttt tgtctaaaga gtaatactag agataaacat aaaaaatgta gaggtcgagt    4380
ttagatgcaa gttcaaggag cgaaaggtgg atgggtaggt tatatatggga tatagcacag    4440 agatatatag caaagagata cttttgagca atgtttgtgg aagcggtatt cgcaatggga    4500
agctccaccc cggttgataa tcagaaaagc cccaaaaaca ggaagattgt ataagcaaat    4560
atttaaattg taaacgttaa tattttgtta aaattcgcgt taaattttg ttaaatcagc    4620 tcattttta acgaatagcc cgaaatcggc aaaatccctt ataaatcaaa agaatagacc    4680
gagatagggt tgagtgttgt tccagttttcc aacaagagtc cactattaaa gaacgtggac    4740
tccaacgtca aagggcgaaa aagggtctat cagggcgatg gcccactacg tgaaccatca    4800
ccctaatcaa gttttttggg gtcgaggtgc cgtaaagcag taaatcggaa gggtaaacgg    4860 atgccccat ttagagcttg acggggaaag ccggcgaacg tggcgagaaa ggaagggaag    4920
aaagcgaaag gagcggggc tagggcggtg ggaagtgtag gggtcacgct gggcgtaacc    4980
accacacccg ccgcgcttaa tgggggcgcta cagggcagga atactctgaa taaaacaact    5040
tatataataa aaatgc                                                   5056
```

<210> SEQ ID NO 41
<211> LENGTH: 1703
<212> TYPE: DNA
<213> ORGANISM: Artificial Sequence
<220> FEATURE:
<223> OTHER INFORMATION: Cassette with green fluorescent protein coding
      sequence, regulatory sequences and integration sequences
<220> FEATURE:
<221> NAME/KEY: LV3
<222> LOCATION: (1)..(40)
<220> FEATURE:
<221> NAME/KEY: Tdh3p
<222> LOCATION: (41)..(693)
<220> FEATURE:
<221> NAME/KEY: S65T-GFP
<222> LOCATION: (700)..(1413)
<220> FEATURE:
<221> NAME/KEY: CYC1 Terminator
<222> LOCATION: (1414)..(1663)
<220> FEATURE:
<221> NAME/KEY: LV5
<222> LOCATION: (1664)..(1703)

<400> SEQUENCE: 41

```
aggaatactc tgaataaaac aacttatata ataaaaatgc tcgagtttat cattatcaat      60
actgccattt caaagaatac gtaaataatt aatagtagtg attttcctaa ctttatttag     120
tcaaaaaatt agccttttaa ttctgctgta acccgtacat gcccaaaata gggggcgggt     180
tacacagaat atataacatc gtaggtgtct gggtgaacag tttattcctg gcatccacta     240
aatataatgg agcccgcttt ttaagctggc atccagaaaa aaaagaatc ccagcaccaa     300 aatattgttt tcttcaccaa ccatcagttc ataggtccat tctcttagcg caactacaga     360
gaacaggggc acaaacaggc aaaaacggg cacaacctca atggagtgat gcaacctgcc     420
tggagtaaat gatgacacaa ggcaattgac ccacgcatgt atctatctca ttttcttaca     480
ccttctatta ccttctgctc tctctgattt ggaaaaagct gaaaaaaaag gttgaaacca     540
```

```
gttccctgaa attattcccc tacttgacta ataagtatat aaagacggta ggtattgatt      600
gtaattctgt aaatctattt cttaaacttc ttaaattcta cttttatagt tagtcttttt      660
tttagtttta aaacaccaag aacttagttt cgaaaaacaa tgagtaaagg agaagaactt      720
ttcactggag ttgtcccaat tcttgttgaa ttagatggtg atgttaatgg gcacaaattt      780
tctgtcagtg gagagggtga aggtgatgca acatacggaa aacttaccct taaatttatt      840
tgcactactg gaaaactacc tgttccatgg ccaacacttg tcactacttt cacttatggt      900
gttcaatgca tttcaagata cccagatcat atgaaagagc atgactttt caagagtgcc      960 atgcccgaag ttatgtaca ggaaagaact atatttttca agatgacgg aactacaag     1020 acacgtgctg aagtcaagtt tgaaggtgat acccttgtta atagaatcga gttaaaaggt     1080
attgatttta agaagatgg aaacattctt ggacacaaat tggaatacaa ctataactca     1140
cacaatgtat acatcatggc agacaaacaa aagaatggaa tcaaagttaa cttcaaaatt     1200
agacacaaca ttgaagatgg aagcgttcaa ctagcagacc attatcaaca aaatactcca     1260
attggcgatg gccctgtcct tttaccagac aaccattacc tgtccacaca atctgccctt     1320
tcgaaagatc ccaacgaaaa gagagaccac atggtccttc ttgagtttgt aacagctgct     1380
gggattacac atggcatgga tgaactatac aaatcatgta attagttatg tcacgcttac     1440
attcacgccc tcctcccaca tccgctctaa ccgaaaagga aggagttaga caacctgaag     1500
tctaggtccc tatttatttt ttttaatagt tatgttagta ttaagaacgt tatttatatt     1560
tcaaattttt ctttttttc tgtacaaacg cgtgtacgca tgtaacatta tactgaaaac     1620
cttgcttgag aaggttttgg gacgctcgaa ggctttaatt tgccctcttt atattacatc     1680
aaaataagaa aataattata aca                                             1703
```

<210> SEQ ID NO 42
<211> LENGTH: 2942
<212> TYPE: DNA
<213> ORGANISM: Artificial Sequence
<220> FEATURE:
<223> OTHER INFORMATION: Cassette with Cannabis sativa
      prenyltransferase-green fluorescent protein fusion protein coding
      sequence, regulatory sequences and integration sequences
<220> FEATURE:
<221> NAME/KEY: LV3
<222> LOCATION: (1)..(40)
<220> FEATURE:
<221> NAME/KEY: TDH3
<222> LOCATION: (41)..(692)
<220> FEATURE:
<221> NAME/KEY: CBGA Synthase
<222> LOCATION: (702)..(1892)
<220> FEATURE:
<221> NAME/KEY: GFP_linker
<222> LOCATION: (1893)..(1928)
<220> FEATURE:
<221> NAME/KEY: GFP
<222> LOCATION: (1929)..(2645)
<220> FEATURE:
<221> NAME/KEY: LV5
<222> LOCATION: (2903)..(2942)

<400> SEQUENCE: 42

```
aggaatactc tgaataaaac aacttatata ataaaaatgc tcgagtttat cattatcaat       60
actgccattt caagaatac gtaaataatt aatagtagtg attttcctaa ctttatttag      120
tcaaaaaatt agccttttaa ttctgctgta acccgtacat gcccaaaata gggggcgggt      180
tacacagaat atataacatc gtaggtgtct gggtgaacag tttattcctg gcatccacta      240
```

```
aatataatgg agcccgcttt ttaagctggc atccagaaaa aaaaagaatc ccagcaccaa    300
aatattgttt tcttcaccaa ccatcagttc ataggtccat tctcttagcg caactacaga    360
gaacagggc acaaacaggc aaaaaacggg cacaacctca atggagtgat gcaacctgcc    420
tggagtaaat gatgacacaa ggcaattgac ccacgcatgt atctatctca ttttcttaca    480
ccttctatta ccttctgctc tctctgattt ggaaaaagct gaaaaaaaag gttgaaacca    540
gttccctgaa attattcccc tacttgacta ataagtatat aaagacggta ggtattgatt    600
gtaattctgt aaatctattt cttaaacttc ttaaattcta cttttatagt tagtcttttt    660
tttagtttta aaacaccaag aacttagttt cgaaaacaat gatgggttta tcttctgttt    720
gtactttctc tttccaaacc aactatcaca ctttgttgaa tccacataac aacacccaa    780
agacttcttt gttatgttac agacatccaa agaccccaat caagtactct tacaacaact    840
tcccatctaa gcactgttct accaagtctt tccacttgca aaataagtgt tctgaatctt    900
tgtctattgc taagaattcc attagagctg ctaccactaa ccaaaccgaa ccaccagaat    960
ctgacaacca ctccgtcgcc accaagatct tgaacttcgg taaggcttgt tggaagttgc   1020
aaagaccata caccatcatt gccttcacct cctgtgcctg tggtttgttt ggtaaggaat   1080
tgttgcataa caccaacttg atctcttggt ctttaatgtt caaggctttt ttttttcttgg   1140
tcgccatctt gtgtattgcc tcctttacca ctactattaa tcaaatctac gacttacata   1200
ttgaccgtat caataagcca gatttgccat tggcctctgg tgaaatttcc gtcaacaccg   1260
cctggattat gtctattatc gttgccttgt tcggtttaat tattactatt aagatgaagg   1320
gtggtccatt atacatcttc ggttactgtt tcggtatctt cggtggtatc gtctactccg   1380
ttccaccttt cagatggaag caaaaaccat ccaccgcttt cttgttgaac ttcttagccc   1440
acatcattac taactttacc ttctactatg cctctagagc cgctttaggt ttaccatttg   1500
aattgcgtcc atctttcact ttcttgttgg ctttcatgaa gtctatgggt tccgccttgg   1560
ctttaattaa ggatgcctct gatgttgagg gtgatactaa gttcggtatt ctaccttag    1620
cttccaaata cggttccaga aacttgactt tgttctgttc cggtattgtt ttattgtctt   1680
acgtcgctgc tatcttggct ggtatcattt ggcctcaagc tttcaactct aacgttatgt   1740
tgttatccca tgctatcttg gctttctggt tgatcttgca aaccagagac ttcgctttga   1800
ctaactacga tccagaagct ggtagaagat tctacgaatt tatgtggaaa ttatattacg   1860
ccgaatactt ggtttacgtt ttcatcggct gaggcgccgc tggctccgct gctggttctg   1920
gcgaattcat gagtaaagga gaagaacttt tcactggagt tgtcccaatt cttgttgaat   1980
tagatggtga tgttaatggg cacaaatttt ctgtcagtgg agagggtgaa ggtgatgcaa   2040
catacggaaa acttaccctt aaatttattt gcactactgg aaaactacct gttccatggc   2100
caacacttgt cactactttc acttatggtg ttcaatgcat ttcaagatac ccagatcata   2160
tgaaacggca tgacttttc aagagtgcca tgcccgaagg ttatgtacag aaagaactta   2220
tatttttcaa agatgacggg aactacaaga cacgtgctga agtcaagttt gaaggtgata   2280
cccttgttaa tagaatcgag ttaaaaggta ttgatttaa agaagatgga acattcttg    2340
gacacaaatt ggaatacaac tataactcac acaatgtata catcatggca gacaaacaaa   2400
agaatggaat caaagttaac ttcaaaatta gacacaacat tgaagatgga agcgttcaac   2460
tagcagacca ttatcaacaa atactccaa ttggcgatgg ccctgtcctt ttaccagaca    2520
accattacct gtccacacaa tctgcccttt cgaaagatcc caacgaaaag agagaccaca   2580
tggtccttct tgagtttgta acagctgctg ggattacaca tggcatggat gaactataca   2640
```

-continued

```
aataaggcgc ctaatcatgt aattagttat gtcacgctta cattcacgcc ctccccccac    2700
atccgctcta accgaaaagg aaggagttag acaacctgaa gtctaggtcc ctatttattt    2760
ttttatagtt atgttagtat taagaacgtt atttatattt caaattttc ttttttttct    2820 gtacaaacgc gtgtacgcat gtaacattat actgaaaacc ttgcttgaga aggttttggg    2880
acgctcgaag gctttaattt gccctctta tattacatca aaataagaaa ataattataa    2940
ca                                                                  2942

<210> SEQ ID NO 43
<211> LENGTH: 2678
<212> TYPE: DNA
<213> ORGANISM: Artificial Sequence
<220> FEATURE:
<223> OTHER INFORMATION: Cassette with AltPT-green fluorescent protein
      fusion protein coding sequence, regulatory sequences and
      integration sequences
<220> FEATURE:
<221> NAME/KEY: LV3
<222> LOCATION: (1)..(40)
<220> FEATURE:
<221> NAME/KEY: TDH3
<222> LOCATION: (41)..(692)
<220> FEATURE:
<221> NAME/KEY: Alt PT
<222> LOCATION: (702)..(1628)
<220> FEATURE:
<221> NAME/KEY: GFP_linker
<222> LOCATION: (1629)..(1664)
<220> FEATURE:
<221> NAME/KEY: GFP
<222> LOCATION: (1665)..(2381)
<220> FEATURE:
<221> NAME/KEY: LV5
<222> LOCATION: (2639)..(2678)

<400> SEQUENCE: 43
aggaatactc tgaataaaac aacttatata ataaaaatgc tcgagtttat cattatcaat      60
actgccattt caaagaatac gtaaataatt aatagtagtg attttcctaa ctttatttag     120
tcaaaaaatt agccttttaa ttctgctgta acccgtacat gcccaaaata ggggggcgggt    180 tacacagaat atataacatc gtaggtgtct gggtgaacag tttattcctg gcatccacta     240
aatataatgg agcccgcttt ttaagctggc atccagaaaa aaaagaatc ccagcaccaa      300 aatattgttt tcttcaccaa ccatcagttc ataggtccat tctcttagcg caactacaga    360
gaacaggggc acaaacaggc aaaaaacggg cacaacctca atggagtgat gcaacctgcc    420
tggagtaaat gatgacacaa ggcaattgac ccacgcatgt atctatctca ttttcttaca    480
ccttctatta ccttctgctc tctctgattt ggaaaaagct gaaaaaaaag gttgaaacca    540
gttccctgaa attattcccc tacttgacta ataagtatat aaagacggta ggtattgatt    600
gtaattctgt aaatctattt cttaaacttc ttaaattcta cttttatagt tagtcttttt    660
tttagtttta aaacaccaag aacttagttt cgaaacaat gatgtctgaa gccgctgatg    720
tcgaaagagt ttacgccgct atggaagagg ccgctggttt gttgggtgtt gcctgtgcta    780
gagacaagat ttacccattg ttatccacct tccaagatac tttggttgaa ggtggttctg    840
ttgtcgtttt ctctatggcc tccggtagac actccaccga attggacttc tctatttctg    900
ttccaacttc tcatggtgat ccatacgcca ctgtcgttga aaagggttta ttcctgcta    960 ctggtcaccc agttgacgat tgttagctg acactcaaaa gcacttacct gtttctatgt   1020
tcgctattga cggtgaagtt accggtggtt caaaaagac ttacgccttc ttcccaactg    1080
```

-continued

```
acaatatgcc aggtgttgct gaattgtctg ctatcccatc catgccacca gccgttgccg   1140
agaatgctga attgttcgct cgttatggtt tggacaaggt ccaaatgacc tccatggact   1200
acaagaaaag acaagtcaac ttgtatttct ccgaattgtc tgctcaaact ttagaagccg   1260
aatctgtttt ggctttggtt agagaattag gtttgcacgt tccaaacgaa ttgggtttga   1320
agttttgtaa acgttctttc tctgtttatc caactttgaa ctgggaaacc ggtaaaatcg   1380
acagattgtg cttcgctgtc atctctaacg acccaacctt ggtcccatcc tccgatgaag   1440
gtgatatcga aaagttccac aactacgcca ctaaggctcc ttacgcttac gtcggtgaga   1500
aacgtacctt ggtctatggt ttgactttat ccccaaagga ggaatactac aagttgggtg   1560
cttactacca cattaccgac gtccaaagag gtttgttaaa ggccttcgac tctttagaag   1620
acggctgagg cgccgctggc tccgctgctg gttctggcga attcatgagt aaaggagaag   1680
aacttttcac tggagttgtc ccaattcttg ttgaattaga tggtgatgtt aatgggcaca   1740
aattttctgt cagtggagag ggtgaaggtg atgcaacata cggaaaactt acccttaaat   1800
ttatttgcac tactggaaaa ctacctgttc catggccaac acttgtcact actttcactt   1860
atggtgttca atgcatttca agatacccag atcatatgaa acggcatgac ttttcaaga   1920
gtgccatgcc cgaaggttat gtacaggaaa gaactatatt tttcaaagat gacgggaact   1980
acaagacacg tgctgaagtc aagtttgaag gtgatccct tgttaataga atcgagttaa   2040
aaggtattga ttttaaagaa gatggaaaca ttccttggac caaattggaa tacaactata   2100
actcacacaa tgtatacatc atggcagaca acaaaagaa tggaatcaaa gttaacttca   2160
aaattagaca caacattgaa gatggaagcg ttcaactagc agaccattat caacaaaata   2220
ctccaattgg cgatggccct gtccttttac cagacaacca ttacctgtcc acacaatctg   2280
ccctttcgaa agatcccaac gaaaagagag accacatggt ccttcttgag tttgtaacag   2340
ctgctgggat tacacatggc atggatgaac tatacaaata aggcgcctaa tcatgtaatt   2400
agttatgtca cgcttacatt cacgccctcc ccccacatcc gctctaaccg aaaaggaagg   2460
agttagacaa cctgaagtct aggtccctat ttattttttt atagttatgt tagtattaag   2520
aacgttattt atatttcaaa tttttctttt ttttctgtac aaacgcgtgt acgcatgtaa   2580
cattatactg aaaaccttgc ttgagaaggt tttgggacgc tcgaaggctt taatttgccc   2640
tctttatatt acatcaaaat aagaaaataa ttataaca                          2678
```

```
<210> SEQ ID NO 44
<211> LENGTH: 2399
<212> TYPE: DNA
<213> ORGANISM: Artificial Sequence
<220> FEATURE:
<223> OTHER INFORMATION: Cassette with AltPT from Streptomyces sp CL190
      with coding sequence, regulatory sequences and integration
      sequences
<220> FEATURE:
<221> NAME/KEY: LV3
<222> LOCATION: (1)..(40)
<220> FEATURE:
<221> NAME/KEY: PMA1p
<222> LOCATION: (47)..(946)
<220> FEATURE:
<221> NAME/KEY: L1
<222> LOCATION: (947)..(986)
<220> FEATURE:
<221> NAME/KEY: AltPT
<222> LOCATION: (987)..(1913)
<220> FEATURE:
<221> NAME/KEY: Eno2t
<222> LOCATION: (1954)..(2353)
<220> FEATURE:
```

```
<221> NAME/KEY: LV5
<222> LOCATION: (2360)..(2399)

<400> SEQUENCE: 44
aggaatactc tgaataaaac aacttatata ataaaaatgc gtatccacag gcattgctgg      60
gatcacccat acatcactct gttttgcctg accttttccg gtaatttgaa aacaaacccg     120
gtctcgaagc ggagatccgg cgataattac cgcagaaata aacccataca cgagacgtag     180
aaccagccgc acatggccgg agaaactcct gcgagaattt cgtaaactcg cgcgcattgc     240
atctgtattt cctaatgcgg cacttccagg cctcgagacc tctgacatgc ttttgacagg     300
aatagacatt ttcagaatgt tatccatatg cctttcgggt ttttttcctt ccttttccat     360
catgaaaaat ctctcgagac cgtttatcca ttgcttttt gttgtctttt tccctcgttc     420
acagaaagtc tgaagaagct atagtagaac tatgagcttt ttttgtttct gttttccttt     480
tttttttttt tacctctgtg gaaattgtta ctctcacact ctttagttcg tttgtttgtt     540
ttgtttattc caattatgac cggtgacgaa acgtggtcga tggtgggtac cgcttatgct     600
cccctccatt agtttcgatt atataaaaag gccaaatatt gtattatttt caaatgtcct     660
atcattatcg tctaacatct aatttctctt aaattttttc tctttctttc ctataacacc     720
aatagtgaaa atcttttttt cttctatatc tacaaaaact ttttttttct atcaacctcg     780
ttgataaatt ttttctttaa caatcgttaa taattaatta attggaaaat aaccattttt     840
tctctcttt atacacacat tcaaaagaaa gaaaaaaaat atccccagc tagttaaaga     900
aaatcattga aaagaataag aagataagaa agatttaatt atcaaactag aaaatttatt     960
ataaaaggaa gagaaataat taaacaatgt ctgaagccgc tgatgtcgaa agagtttacg    1020
ccgctatgga agaggccgct ggtttgttgg gtgttgcctg tgctagagac aagatttacc    1080
cattgttatc caccttccaa gatactttgg ttgaaggtgg ttctgttgtc gttttctcta    1140
tggcctccgg tagacactcc accgaattgg acttctctat ttctgttcca acttctcatg    1200
gtgatccata cgccactgtc gttgaaaagg gtttatttcc tgctactggt cacccagttg    1260
acgatttgtt agctgacact caaaagcact tacctgtttc tatgttcgct attgacggtg    1320
aagttaccgg tggtttcaaa aagacttacg ccttcttccc aactgacaat atgccaggtg    1380
ttgctgaatt gtctgctatc ccatccatgc caccagccgt tgccgagaat gctgaattgt    1440
tcgctcgtta tggtttggac aaggtccaaa tgacctccat ggactacaag aaaagacaag    1500
tcaacttgta tttctccgaa ttgtctgctc aaactttaga agccgaatct gttttggctt    1560
tggttagaga attaggtttg cacgttccaa acgaattggg tttgaagttt tgtaaacgtt    1620
ctttctctgt ttatccaact ttgaactggg aaaccggtaa aatcgacaga ttgtgcttcg    1680
ctgtcatctc taacgaccca accttggtcc catcctccga tgaaggtgat atcgaaaagt    1740
tccacaacta cgccactaag gctccttacg cttacgtcgg tgagaaacgt accttggtct    1800
atggtttgac tttatcccca aaggaggaat actacaagtt gggtgcttac taccacatta    1860
ccgacgtcca aagaggtttg ttaaaggcct tcgactcttt agaagacggc tgaagacata    1920
aaactgaaac aacaccaatt aataatagac tttagtgctt ttaactaaga attattagtc    1980
ttttctgctt atttttcat catagtttag aacactttat attaacgaat agtttatgaa    2040
tctatttagg tttaaaaatt gatacagttt tataagttac ttttcaaag actcgtgctg    2100
tctattgcat aatgcactgg aaggggaaaa aaaaggtgca cacgcgtggc ttttccttga    2160
atttgcagtt tgaaaaataa ctacatggat gataagaaaa catggagtac agtcactttg    2220
```

```
agaaccttca atcagctggt aacgtcttcg ttaattggat actcaaaaaa gatggatagc   2280
atgaatcaca agatggaagg aaatgcgggc cacgaccaca gtgatatgca tatgggagat   2340
ggagatgata cctggatacc ctcttttatat tacatcaaaa taagaaaata attataaca   2399
```

<210> SEQ ID NO 45
<211> LENGTH: 5616
<212> TYPE: DNA
<213> ORGANISM: Artificial Sequence
<220> FEATURE:
<223> OTHER INFORMATION: Cassette with Cannabis sativa OAS coding
      sequence, regulatory sequences and integration sequences
<220> FEATURE:
<221> NAME/KEY: LV3
<222> LOCATION: (1)..(40)
<220> FEATURE:
<221> NAME/KEY: THD3p
<222> LOCATION: (41)..(693)
<220> FEATURE:
<221> NAME/KEY: L1
<222> LOCATION: (694)..(733)
<220> FEATURE:
<221> NAME/KEY: Hex1
<222> LOCATION: (734)..(2899)
<220> FEATURE:
<221> NAME/KEY: T3
<222> LOCATION: (2900)..(3303)
<220> FEATURE:
<221> NAME/KEY: ADH1 terminator
<222> LOCATION: (3071)..(3263)
<220> FEATURE:
<221> NAME/KEY: P5
<222> LOCATION: (3264)..(3837)
<220> FEATURE:
<221> NAME/KEY: LTP2
<222> LOCATION: (3264)..(3303)
<220> FEATURE:
<221> NAME/KEY: Tef1p
<222> LOCATION: (3304)..(3797)
<220> FEATURE:
<221> NAME/KEY: L3
<222> LOCATION: (3798)..(3837)
<220> FEATURE:
<221> NAME/KEY: OAS
<222> LOCATION: (3841)..(4995)
<220> FEATURE:
<221> NAME/KEY: PRM9t
<222> LOCATION: (5039)..(5576)
<220> FEATURE:
<221> NAME/KEY: LV5
<222> LOCATION: (5577)..(5616)

<400> SEQUENCE: 45

```
aggaatactc tgaataaaac aacttatata ataaaaatgc tcgagtttat cattatcaat     60
actgccattt caaagaatac gtaaataatt aatagtagtg attttcctaa ctttatttag    120
tcaaaaaatt agccttttaa ttctgctgta acccgtacat gcccaaaata gggggcgggt    180
tacacagaat atataacatc gtaggtgtct gggtgaacag tttattcctg gcatccacta    240
aatataatgg agcccgcttt ttaagctggc atccagaaaa aaaagaatc ccagcaccaa     300 aatattgttt tcttcaccaa ccatcagttc ataggtccat tctcttagcg caactacaga    360 gaacagggc acaaacaggc aaaaacggg cacaacctca atggagtgat gcaacctgcc     420
tggagtaaat gatgacacaa ggcaattgac ccacgcatgt atctatctca tttcttaca    480 ccttctatta ccttctgctc tctctgattt ggaaaaagct gaaaaaaaag gttgaaacca    540
gttccctgaa attattcccc tacttgacta ataagtatat aaagacggta ggtattgatt    600
gtaattctgt aaatctattt cttaaacttc ttaaattcta cttttatagt tagtcttttt    660
tttagtttta aaacaccaag aacttagttt cgactagaaa atttattata aaggaagag     720
```

```
aaataattaa acaatgggta aaaactataa gtctttagac tccgttgtcg cctccgactt      780
tattgctttg ggtatcacct ccgaagttgc tgaaacttta cacggtagat tagctgagat      840
tgtttgtaac tacggtgccg ccactccaca aacttggatt aatatcgcta accatatttt      900
gtctccagac ttaccattct ccttgcatca aatgttgttt tacggttgtt ataaagattt      960
tggtccagct cctccagctt ggatcccaga tcctgaaaaa gttaagtcta ctaacttagg     1020
tgctttgtta gaaaaagag gtaaagaatt cttgggtgtt aagtataaag atccaatctc     1080
ttccttctct cattttcaag aattctccgt tagaaaccca gaagtttatt ggagaaccgt     1140
tttgatggac gaaatgaaga tctccttctc taaggatcct gaatgtattt tgagacgtga     1200
cgatatcaac aatccaggtg gttctgaatg gttaccaggt ggttatttga actctgctaa     1260
aaattgtttg aacgtcaatt ccaacaaaaa attgaacgac accatgattg tttggagaga     1320
cgaaggtaac gatgacttac cattaaacaa gttgaccttg gaccaattga gaaagcgtgt     1380
ctggttggtc ggttacgcct tggaggaaat gggtttggaa aaaggttgtg ccatcgctat     1440
cgatatgcca atgcacgtcg acgccgtcgt tatctatttg gccatcgttt tagctggtta     1500
cgtcgtcgtc tccatcgctg actctttctc cgctccagaa atttccacta gattgagatt     1560
atccaaggcc aaggctattt tcactcaaga tcacattatt agaggtaaga agcgtattcc     1620
attgtactcc agagtcgtcg aagccaagtc tcctatggcc attgttatcc catgttctgg     1680
ttctaacatt ggtgctgaat gagagatgg tgacatttcc tgggactatt tcttggaaag     1740
agctaaggaa tttaagaact gcgaatttac cgccagagaa caacctgttg atgcctacac     1800
taacattttg ttctcttctg gtacaactgg tgagccaaag gctatcctt ggactcaagc     1860 taccccatta aaggccgccg ctgatggttg gtcccacttg acattcgta agggtgacgt     1920 catcgtctgg ccaactaact gggttggat gatgggtcca tggttagttt acgcctcttt     1980
gttaaacggt gcttccattg ccttgtacaa cggttctcca ttggtttctg gtttcgctaa     2040
gtttgtccaa gacgccaagg ttaccatgtt aggtgttgtt ccatctatcg tcagatcttg     2100
gaagtctact aactgtgtct ctggttacga ttggtctact atcagatgct tctcttcctc     2160
tggtgaagcc tctaacgttg atgaatattt gtggttgatg ggtcgtgcca actacaagcc     2220
agttatcgaa atgtgtggtg gtacagagat cggtggtgct ttttccgctg gttccttttt     2280
gcaagctcaa tctttgtctt ctttctcttc tcaatgtatg ggttgtactt tgtatatttt     2340
ggataagaac ggttacccaa tgcctaagaa caaaccaggt atcggtgaat tagctttggg     2400
tccagttatg ttcggtgctt ccaagacctt gttgaacggt aatcaccatg atgtctattt     2460
caaaggtatg ccaactttaa acggtgaagt cttgagacgt cacggtgaca tctttgaatt     2520
gacttctaac ggttactacc atgctcacgg tagagctgat gatactatga acattggtgg     2580
tattaagatt tcttctatcg aaatcgaaag agtttgtaat gaagttgacg acagagtctt     2640
tgaaaccact gctattggtg tcccaccatt gggtggtggt ccagaacaat tagtcatttt     2700
cttcgttttg aaggattcta acgacactac catcgactta aaccaattga gattgtcttt     2760
caacttgggt ttgcaaaaga gttgaaccc attatttaaa gtcactagag ttgttccatt     2820
gtcttctttg ccaagaaccg ccaccaacaa gattatgaga agagttttga gacaacaatt     2880
ttctcatttc gaaggctgaa gacataaaac tgaaacaaca ccaattaata atagactttt     2940
ggacttcttc gccagaggtt tggtcaagtc tccaatcaag gttgtcggct tgtctacctt     3000
gccagaaatt tacgaaaaga tggaaaaggg tcaaatcgtt ggtagatacg ttgttgacac     3060
```

```
ttctaaataa gcgaatttct tatgatttat gatttttatt attaaataag ttataaaaaa    3120
aataagtgta tacaaatttt aaagtgactc ttaggtttta aaacgaaaat tcttattctt    3180
gagtaactct ttcctgtagg tcaggttgct ttctcaggta tagcatgagg tcgctcttat    3240
tgaccacacc tctaccggca tgccttaaat aacatactca tcactaaaca ttcttaacaa    3300
tcaaagcaac aggcgcgttg gactttaat tttcgaggac cgcgaatcct tacatcacac    3360
ccaatccccc acaagtgatc ccccacacac catagcttca aaatgtttct actccttttt    3420
tactcttcca gattttctcg gactccgcgc atcgccgtac cacttcaaaa cacccaagca    3480
cagcatacta aatttcccct ctttcttcct ctagggtgtc gttaattacc cgtactaaag    3540
gtttggaaaa gaaaaagag accgcctcgt ttcttttct tcgtcgaaaa aggcaataaa    3600
aatttttatc acgtttcttt ttcttgaaaa tttttttttt tgatttttt ctctttcgat    3660 gacctcccat tgatatttaa gttaataaac ggtcttcaat ttctcaagtt tcagtttcat    3720
ttttcttgtt ctattacaac ttttttttact tcttgctcat tagaaagaaa gcatagcaat    3780
ctaatctaag ttttaataca tctaccagtc aacagccaac aattaactaa ttaaacaatg    3840
aaccacttga gagctgaagg tccagcttcc gttttggcta tcggtacagc taaccctgaa    3900
aacatcttgt tgcaagatga attcccagac tattacttca gagttaccaa gtctgaacat    3960
atgactcaat tgaaggaaaa gtttagaaag atttgtgata agtctatgat cagaaagcgt    4020
aattgttttt tgaacgaaga acatttaaaa caaaatccaa gattggttga gcacgaaatg    4080
caaactttgg atgctagaca agatatgtta gtcgtcgaag tcccaaagtt gggtaaggat    4140
gcttgtgcta aggctattaa ggagtggggt caaccaaagt ccaaaatcac ccacttgatt    4200
ttcacttccg cttctactac cgacatgcca ggtgctgatt accactgtgc taagttgttg    4260
ggtttatccc cttctgttaa aagagttatg atgtaccaat tgggttgcta cggtggtggt    4320
actgttttga gaattgccaa ggacatcgct gagaataaca agggtgctag agttttggcc    4380
gtctgttgtg acatcatggc ttgtttattc agaggtccat ctgaatccga cttggaattg    4440
ttagtcggtc aagccatctt tggtgatggt gctgccgccg ttattgttgg tgctgaacca    4500
gatgaatccg tcggtgaaag accaatcttt gagttggtct ctactggtca aaccattttg    4560
ccaaactccg aaggtactat tggtggtcac atccgtgaag ctggtttgat ttttgattta    4620
cacaaggatg tcccaatgtt gatctctaac aacatcgaga agtgtttaat tgaagccttc    4680
accccaattg gtatttccga ctggaactct attttctgga ttactcatcc aggtggtaag    4740
gctattttag ataaggttga agaaaagttg cacttgaagt ctgataaatt cgttgactct    4800
agacacgttt tgtctgaaca tggtaatatg tcttcttcca ctgttttgtt cgttatggat    4860
gaattgagaa agagatcttt ggaagaaggt aagtccacta ctggtgacgg tttcgaatgg    4920
ggtgttttgt tcggtttcgg tccaggtttg actgttgaaa gagtcgttgt ccgttctgtt    4980
ccaatcaagt acgctaata ataattaaat actattttca aaattctact taaaataac    5040 agaagacggg agacactagc acacaacttt accaggcaag gtatttgacg ctagcatgtg    5100
tccaattcag tgtcatttat gattttttgt agtaggatat aaatatatac agcgctccaa    5160
atagtgcggt tgccccaaaa acaccacgga acctcatctg ttctcgtact tgttgtgac    5220 aaagtagctc actgccttat tatcacattt tcattatgca acgcttcgga aaatacgatg    5280
ttgaaaatgc ctctagagat gaaaacaat cgtaaaggg tcctgcgtaa ttgaaacatt    5340
tgatcagtat gcagtggcac agaaacaacc aggaatacta tagtcatagg caatacaagg    5400
tatatattgg ctatgcagac ccctccagaa agtaccgacg tcaagttaga tacacttaac    5460
```

```
gaacctagtg cacatttaat tgagaaaaat gtggctcttc ctaaggacat attccgttcg    5520
tacttgagtt attggatcta tgaaatcgct cgctatacac cagtcatgat tttgtccctc    5580
tttatattac atcaaaataa gaaaataatt ataaca                              5616
```

```
<210> SEQ ID NO 46
<211> LENGTH: 10584
<212> TYPE: DNA
<213> ORGANISM: Artificial Sequence
<220> FEATURE:
<223> OTHER INFORMATION: Cassette with Dictyostelium discoideum DiPKS
      coding sequence, regulatory sequences and integration sequences
<220> FEATURE:
<221> NAME/KEY: LV3
<222> LOCATION: (1)..(40)
<220> FEATURE:
<221> NAME/KEY: S. cerevisiae GAL1 promoter
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: Motif 1
<222> LOCATION: (5050)..(5076)
<220> FEATURE:
<221> NAME/KEY: C-methyltransferase domain
<222> LOCATION: (5050)..(5412)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: L2
<222> LOCATION: (9967)..(10006)
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)

<400> SEQUENCE: 46
aggaatactc tgaataaaac aacttatata ataaaaatgc cggattagaa gccgccgagc      60
gggtgacagc cctccgaagg aagactctcc tccgtgcgtc ctcgtcttca ccggtcgcgt     120
tcctgaaacg cagatgtgcc tcgcgccgca ctgctccgaa caataaagat tctacaatac     180
tagcttttat ggttatgaag aggaaaaatt ggcagtaacc tggccccaca aaccttcaaa     240
tgaacgaatc aaattaacaa ccataggatg ataatgcgat tagtttttta gccttatttc     300
tggggtaatt aatcagcgaa gcgatgattt ttgatctatt aacagatata taaatgcaaa     360
aactgcataa ccactttaac taatactttc aacattttcg gtttgtatta cttcttattc     420
aaatgtaata aagtatcaa caaaaaattg ttaatatacc tctatacttt aacgtcaagg      480
agctagaaaa tttattataa aaggaagaga ataattaaa caatgaacaa gaactccaaa      540
atccagtccc caaactcttc tgatgttgct gttattggtg ttggttttag attcccaggt     600
aactctaatg acccagaatc tttgtggaac aacttgttgg atggtttcga tgctattacc     660
caagtcccaa agaaagatg gctacttct tttagagaga tgggtttgat caagaacaag      720
ttcggtggtt tcttgaagga ttctgaatgg aagaatttcg accctttgtt ctttggtatc     780
ggtccaaaag aagctccatt cattgatcca caacaaaggt tgttgttgtc catcgtttgg     840
```

```
gaatctttgg aagatgctta catcagacca gatgaattga gaggttctaa cactggtgtt    900
ttcatcggtg tttctaacaa cgattacacc aagttgggtt tccaagacaa ctactctatt    960
tctccataca ctatgaccgg ctctaactct tcattgaact ccaacagaat tcctactgc    1020
ttcgatttta gaggtccatc cattactgtt gataccgctt gttcttcttc cttggtttct   1080
gttaatttgg gtgtccaatc catccaaatg ggtgaatgta agattgctat tgcggtggt    1140
gttaacgctt tgtttgatcc atctacatct gttgcctttt ccaagttggg tgttttgtct   1200
gaaaatggca gatgcaactc ttttagtgat caagcctctg gttacgttag atctgaaggt   1260
gctggtgttg ttgttttgaa gtctttggaa caagctaagt tggatggtga tagaatctac   1320
ggtgttatca agggtgtttc ctctaatgaa gatggtgctt ctaatggtga caagaactct   1380
ttgactactc catcttgtga agcccaatcc attaacattt ctaaggctat ggaaaaggcc   1440
tccttgtctc catctgatat ctattacatt gaagcccatg gtactggtac tccagttggt   1500
gatccaattg aagttaaggc cttgtccaag atcttctcca actctaacaa caaccagttg   1560
aacaacttct ctaccgatgg taatgataac gatgatgatg atgacgataa cacctctcca   1620
gaaccattat tgattggctc attcaagtcc aacatcggtc attcgaatc tgctgctggt    1680
attgcttctt tgattaagtg ttgcttgatg ttgaagaaca ggatgttggt tccatccatt   1740
aactgctcta atttgaaccc atccattcca ttcgatcagt acaacatctc cgttatcaga   1800
gaaatcagac aattcccaac cgataagttg gttaacatcg gtatcaattc tttcggtttc   1860
ggtggttcta actgccattt gattattcaa gagtacaaca caacttcaa gaacaactct    1920
accatctgca ataacaacaa caacaacaat aacaacatcg actacttgat cccaatctcc   1980
tctaagacta agaagtcctt ggataagtac ttgattttga tcaagaccaa ctccaactac   2040
cacaaggata tttctttcga tgacttcgtc aagttccaaa tcaagtctaa gcagtacaac   2100
ttgtccaaca gaatgactac cattgctaac gattggaact ccttcattaa gggttctaac   2160
gaattccaca cttgatcga atctaaggat ggtgaaggtg gttcttcatc ttctaacaga    2220
ggtattgatt ccgccaatca aatcaacact actactacct ctaccatcaa cgatatcgaa   2280
cctttgttgg ttttcgtttt ctgtggtcaa ggtccacaat ggaatggtat gattaagacc   2340
ttgtacaact ccgagaacgt tttcaagaac accgttgatc atgttgacag catcttgtac   2400
aagtacttcg ttactccat tttgaacgtc ttgtctaaga tcgatgataa cgacgattcc    2460
atcaaccatc caatagttgc tcaaccatct ttgttcttgt tgcaaattgg tttggtcgag   2520
ttgtttaagt actggggtat ctacccatct atctctgttg gtcattcttt cggtgaagtc   2580
tcttcttatt acttgtccgg tatcatctct ttggaaaccg cttgtaaaat cgtctacgtc   2640
agatcctcta atcagaacaa aactatgggt tccggtaaga gttggttgt ttctatgggt    2700
tttaagcaat ggaacgatca attctctgct gaatggtccg atattgaaat tgcttgttac   2760
aacgctccag attccatagt tgttactggt aacgaagaaa gattgaaaga attgtccatc   2820
aagttgtccg acgaatccaa tcaaattttc aacaccttct gaggtcccc atgttctttt    2880
cattcttccc atcaagaagt catcaagggt tctatgttcg aagagttgtc taacttgcaa   2940
tctactggta aaaccgaaat ccctttgttc tctactgtta ctggtagaca agttttgtct   3000
ggtcatgtta ctgctcaaca catctacgat aatgttagag aaccagtctt gttccaaaag   3060
acgattgaat ccattacctc ctacatcaag tctcactacc catccaatca aaaggttatc   3120
tacgttgaaa ttgctccaca cccaacccttg ttttcattga tcaaaaagtc catcccatcc   3180
tccaacaaga attcctcttc tgttttgtgt ccattgaaca gaaaagaaaa ctccaacaac   3240
```

```
tcctacaaga agttcgtttc tcagttgtac ttcaacggtg ttaacgttga cttcaacttc    3300
cagttgaact ccatttgcga taacgttaac aacgatcacc atttgaacaa cgtcaagcaa    3360
aactccttca aagagactac caattccttg ccaagatacc aatgggaaca agatgaatat    3420
tggtccgaac cattgatctc cagaaagaat agattggaag gtccaactac ttccttgttg    3480
ggtcatagaa ttatctacag cttcccagtt ttccaatccg ttttggactt gcaatctgac    3540
aactacaaat acttgttgga ccacttggtt aacggtaagc cagttttcc aggtgctggt     3600 tatttggata tcatcatcga attcttcgac taccaaaagc agcagttgaa ttcctctgat    3660
tcctctaact cctacatcat caacgttgac aagatccaat tcttgaaccc aattcacttg    3720
accgaaaaca agttgcaaac cttgcaatct tctttcgaac ctatcgttac taagaagtct    3780
gccttctctg ttaacttctt catcaaggat accgtcgagg atcaatctaa ggttaagtct    3840
atgtctgacg aaacttggac taacacttgt aaggctacca tttccttgga caacaacag    3900 ccatctccat cttctacttt gactttgtct aagaagcaag acttgcagat cttgagaaac    3960
agatgcgata ttagcaagct agacaagttt gagttgtacg acaagatctc taagaatttg    4020
ggcttgcagt acaactcctt gtttcaagtt gttgatacca tcgaaactgg taaggattgc    4080
tcttttgcta ctttgtcttt gccagaagat actttgttca ccaccatttt gaacccatgc    4140
ttgttggata actgtttcca tggtttgttg accttgatca acgaaaaggg ttctttcgtt    4200
gtcgagtcca tttcttctgt ttctatctac ttggagaaca tcggttcctt caatcaaact    4260
tctgttggta acgtccagtt ctacttgtac accactattt ctaaagccac ctcctttagt    4320
tctgaaggta cttgtaagtt gttcaccaag gatggttcct tgattttgtc tatcggtaag    4380
ttcatcatca agtccaccaa tccaaagtct actaagacca cgaaactat cgaatctcca    4440 ttggacgaaa ccttctctat tgaatggcaa tctaaggatt ctccaattcc aaccccacaa    4500
caaatccaac aacaatctcc attgaactct aacccatcct tcattagatc taccatcttg    4560
aaggacatcc agttcgaaca atactgctcc tccattatcc acaaagaatt gatcaaccac    4620
gaaaagtaca agaaccagca atccttcgat atcaactcct tggaaaaacca cttgaacgat    4680 gaccaattga tggaatcctt gtccatctcc aaagaatact tgagattctt caccaggatc    4740
atctccatca ttaagcaata cccaaagatc ttgaacgaaa aagagctaaa agaattgaaa    4800
gaaatcatcg aattgaagta cccatccgaa gttcagttgt tggaattcga agttatcgag    4860
aaggtgtcca tgattatccc aaagttgttg ttcgaaaacg acaagcaatc ttccatgacc    4920
ttgttccaag ataacttgtt gaccaggttc tactccaatt ctaactctac cagattctac    4980
ttggaaaggg tttccgaaat ggtcttggaa tctattagac caatcgtcag agaaaagagg    5040
gtgttcagaa ttttggaaat tggtgctggt acaggctctt tgtctaatgt tgttttgact    5100
aagttgaaca cctacttgtc caccttgaat tctaatggtg ttctggtta caacatcatc     5160 attgagtaca ccttcaccga tatttccgcc aacttcatta ttggtgaaat ccaagaaacc    5220
atgtgcaact tgtacccaaa cgttactttc aagttctccg tcttggactt ggagaaagag    5280
attattaact cctccgattt cttgatgggt gattacgata tagttttgat ggcctacgtt    5340
atccatgccg tttctaacat taagttctcc atcgaacagt tgtacaagtt gttgtctcca    5400
agaggttggt tgttgtgtat tgaacctaag tccaacgttg tgttctccga tttggttttc    5460
ggttgtttta atcagtggtg gaactactac gatgatatta gaactaccca ctgctccttg    5520
tctgaatctc aatggaatca gttgttgttg aaccagtcct tgaacaacga atcctcttct    5580
```

```
tcttctaact gttacggtgg tttctccaac gtttcttttta ttggtggtga aaaggatgtc   5640
gactcccatt ctttcatatt gcactgccaa aaagaatcca tctcccaaat gaagttagcc   5700
accactatta acaacggttt gtcatctggt tccatcgtta tcgttttgaa ctctcaacaa   5760
ttgaccaaca tgaagtccta cccaaaggtt attgagtata ttcaagaggc tacctctttg   5820
tgcaagacca ttgaaattat cgattccaag gacgtcttga actctaccaa ttcagttttg   5880
gaaaagatcc aaaagtcctt gttggtgttc tgtttgttgg ttatgactt gttggagaac    5940
aactaccaag aacagtcttt cgaatacgtt aagttgttga acttgatctc tactaccgcc   6000
tcttcatcta atgataagaa accaccaaag gtcttgttga tcaccaagca atctgaaaga   6060
atctccaggt ctttctactc cagatccttg attggtattt ccagaacctc tatgaacgag   6120
tacccaaatt tgtccattac ctctatcgat ttggatacca acgactactc attgcagtct   6180
ttgttgaagc caatcttcag caactctaag ttttccgaca acgagttcat cttcaaaaag   6240
ggcttgatgt tcgtgtccag gatctttaag aacaagcagt tgctagaatc ctccaacgct   6300
tttgaaactg actcttctaa cttgtactgt aaggcctctt ctgacttgtc ttacaagtac   6360
gctattaagc agtctatgtt gaccgaaaat cagatcgaaa tcaaggttga atgcgtcggt   6420
attaacttca aggacaacct attctacaag ggcttgttgc cacaagaaat tttcagaatg   6480
ggtgacatct acaatccacc atatggtttg gaatgctctg gtgttattac cagaattggt   6540
tctaacgtca ccgaatactc agttggtcaa aatgttttg gtttcgccag acattctttg    6600
ggttctcatg ttgttaccaa caaggatttg gttatcttga agccagatac catctcattt   6660
tctgaagctg cttctatccc agttgtttac tgtactgctt ggtactcctt gttcaacatt   6720
ggtcagttgt ctaacgaaga atccatccta attcattctg ctactggtgg tgtaggtttg   6780
gcttctttga atttgttgaa aatgaagaat cagcaacagc aaccattgac caatgtttat   6840
gctactgttg gctctaacga aagaagaag ttcttgatcg ataacttcaa caacttgttc    6900
aaagaggacg cgcgaaaacat tttctctacc agagacaaag aatactccaa ccagttggaa   6960
tccaagatcg atgttatttt gaacaccttg tccggtgaat tcgtcgaatc taatttcaag   7020
tccttgagat cctccggtag attgattgat ttgtctgcta ctcacgttta cgccaatcaa   7080
caaattggtc taggtaactt caagttcgac cacttgtatt ctgctgttga cttggaaaga   7140
ttgatcgacg aaaaacctaa gttgttgcag tccatcttgc aaagaattac caactctatc   7200
gtcaacggtt ccttggaaaa aattccaatt accatcttcc catccaccga aactaaggat   7260
gctatcgaat tattgtccaa gagatccat atcggtaaag ttgttgtaga ttgcaccgat    7320
atctctaagt gtaatcctgt tggtgatgtg atcaccaact tctctatgag attgccaaag   7380
ccaaactacc agttgaattt gaactccacc ttgttgatta ctggtcagtc tggtttgtct   7440
atcccttttgt tgaattggtt gttgtctaag tctggtggta acgttaagaa cgttgtcatc   7500
atttctaagt ccaccatgaa gtggaagttg cagactatga tttcccatttt cgtttccggt   7560
ttcggtatcc atttttaacta cgttcaagtc gacatctcca actacgatgc tttgtctgaa   7620
gctattaagc aattgccatc tgatttgcca ccaatcacct ctgttttca tttggctgct    7680
atctacaacg atgttccaat ggatcaagtt accatgtcta ccgttgaatc tgttcataac   7740
cctaaagttt tgggtgccgt taacttgcat agaatctctg tttcttttgg ttggaagttg   7800
aaccacttcg tcttgttctc ttctattact gctattaccg gttacccaga ccaatctatc   7860
tacaattctg ccaactctat tttggacgct ttgtccaact ttagaaggtt tatgggtttg   7920
ccatccttct ccattaactt gggtccaatg aaggatgaag gtaaggtttc taccaacaag   7980
```

-continued

```
agcatcaaga agctattcaa gtctagaggt ttgccaagcc tatccttgaa caagttattt   8040
ggtttgttgg aggtcgtcat caacaaccca tctaatcatg ttatcccatc ccaattgatt   8100
tgctccccaa tcgatttcaa gacctacatc gaatctttct caactatgag gccaaagttg   8160
ttacacttgc aacctaccat ttccaagcag caatcttcta tcattaacga ttctaccaag   8220
gcttcctcca acatttcatt gcaagataag atcacctcca aggtgtctga tttgttgtcc   8280
attccaatct ccaagatcaa cttcgatcat ccattgaaac actacggctt ggattctttg   8340
ttgaccgttc aattcaaatc ctggatcgac aaagaattcg aaaagaactt gttcacccat   8400
atccaattgg ccaccatctc tattaactca ttccttggaaa aggtgaacgg cttgtctaca   8460
aacaataaca acaacaacaa ttccaacgtc aagtcctctc catccattgt caaagaagaa   8520
atcgttacct tggacaagga tcaacaacca ttgctattga agaacacca gcacattatc   8580 atctccccag atattagaat caacaagcca agagggaat ccttgattag aaccccaatc   8640
ttgaacaaat tcaaccagat caccgaatcc attatcactc catctacacc atctttgtcc   8700
caatccgatg ttttgaaaac tccaccaatc aagtctttga caacactaa gaactccagc   8760 ttgattaaca ccccaccaat tcaatctgtc caacaacatc aaaagcaaca acaaaaggtc   8820
caagtcatcc aacaacagca acaaccatta tccagattgt cctacaagag caacaacaac   8880
tctttcgttt tgggtatcgg tatttctgtt ccaggtgaac ctatttccca acaatccttg   8940
aaagactcca tctccaatga cttttctgat aaggctgaaa ctaacgagaa ggtcaagaga   9000
atctttgagc aatctcaaat caagaccaga cacttggtta gagattacac taagccagag   9060
aactccatca agttcagaca tttggaaacc attaccgatg tgaacaacca gttcaagaaa   9120
gttgttccag atttggctca acaagcctgt ttgagagctt tgaaagattg gggtggtgat   9180
aagggtgata ttacccatat agtttctgtt acctccaccg gtattatcat cccagatgtt   9240
aatttcaagt tgatcgactt gttgggcttg aacaaggatg ttgaaagagt gtctttgaac   9300
ctaatgggtt gtttggctgg tttgagttct ttgagaactg ctgcttcttt ggctaaggct   9360
tctccaagaa atagaatttt ggttgtctgt accgaagtct gctccttgca ttttttctaat   9420 actgatggtg gtgatcaaat ggtcgcctct tctattttg ctgatggttc tgctgcttac   9480
attattggtt gtaacccaag aattgaagaa accccattat acgaagtcat gtgctccatt   9540
aacagatctt tcccaaatac cgaaaacgcc atggtttggg atttggaaaa agaaggttgg   9600
aacttgggtt tggatgcttc tattccaatt gtcattggtt ctggtattga agccttcgtt   9660
gatactttgt tggataaggc taagttgcaa acttccactg ctatttctgc taaggattgc   9720
gaattcttga ttcatactgg tggcaagtcc atcttgatga acatcgaaaa ttccttgggt   9780
atcgacccaa agcaaactaa gaatacttgg gatgtttacc atgcctacgg caatatgtca   9840
tctgcctctg ttattttcgt tatggatcat gccagaaagt ccaagtcttt gccaacttac   9900
tcaatttctt tggcttttgg tccaggtttg gcttttgaag ttgtttcttt gaagaacgtc   9960
gtctaaagac ataaaactga aacaacacca attaataata gactttacag aagacgggag  10020
acactagcac acaactttac caggcaaggt atttgacgct agcatgtgtc caattcagtg  10080
tcatttatga tttttttgtag taggatataa atatatacag cgctccaaat agtgcggttg  10140
ccccaaaaac accacggaac ctcatctgtt ctcgtacttt gttgtgacaa agtagctcac  10200
tgccttatta tcacattttc attatgcaac gcttcggaaa atacgatgtt gaaaatgcct  10260
ctagagatga aaaacaatcg taaagggtc ctgcgtaatt gaaacatttg atcagtatgc  10320
```

```
                                              -continued agtggcacag aaacaaccag gaatactata gtcataggca atacaaggta tatattggct    10380
atgcagaccc ctccagaaag taccgacgtc aagttagata cacttaacga acctagtgca    10440
catttaattg agaaaaatgt ggctcttcct aaggacatat tccgttcgta cttgagttat    10500
tggatctatg aaatcgctcg ctatacacca gtcatgattt tgtccctctt tatattacat    10560
caaaataaga aataattat aaca                                            10584

<210> SEQ ID NO 47
<211> LENGTH: 4909
<212> TYPE: DNA
<213> ORGANISM: Artificial Sequence
<220> FEATURE:
<223> OTHER INFORMATION: Cassette with Cas9 coding sequence, regulatory
      sequences and integration sequences
<220> FEATURE:
<221> NAME/KEY: LV3
<222> LOCATION: (1)..(40)
<220> FEATURE:
<221> NAME/KEY: TEF1p
<222> LOCATION: (41)..(446)
<220> FEATURE:
<221> NAME/KEY: Cas9
<222> LOCATION: (470)..(4609)
<220> FEATURE:
<221> NAME/KEY: LV5
<222> LOCATION: (4870)..(4909)

<400> SEQUENCE: 47
aggaatactc tgaataaaac aacttatata ataaaaatgc atagcttcaa aatgtttcta      60 ctccttttt actcttccag attttctcgg actccgcgca tcgccgtacc acttcaaaac     120
acccaagcac agcatactaa atttcccctc tttcttcctc tagggtgtcg ttaattaccc     180
gtactaaagg tttggaaaag aaaaagagaa ccgcctcgtt tcttttcttt cgtcgaaaaa     240
ggcaataaaa attttatca cgtttctttt tcttgaaaat ttttttttg attttttct       300 ctttcgatga cctcccattg atatttaagt taataaacgg tcttcaattt ctcaagtttc     360
agtttcattt ttcttgttct attacaactt tttttacttc ttgctcatta gaaagaaagc     420
atagcaatct aatctaagtt ttctagaact agtggatccc ccgggaaaaa tggacaagaa     480
gtactccatt gggctcgata tcggcacaaa cagcgtcggc tgggccgtca ttacggacga     540
gtacaaggtg ccgagcaaaa aattcaaagt tctgggcaat accgatcgcc acagcataaa     600
gaagaacctc attggcgccc tcctgttcga ctccggggag acggccgaag ccacgcggct     660
caaaagaaca gcacggcgca gatatacccg cagaaagaat cggatctgct acctgcagga     720
gatctttagt aatgagatgg ctaaggtgga tgactctttc ttccataggc tggaggagtc     780
ctttttggtg gaggaggata aaaagcacga gcgccaccca atctttggca atatcgtgga     840
cgaggtggcg taccatgaaa agtacccaac catatatcat ctgaggaaga agcttgtaga     900
cagtactgat aaggctgact tgcggttgat ctatctcgcg ctggcgcata tgatcaaatt     960
tcggggacac ttcctcatcg agggggacct gaacccagac aacagcgatg tcgacaaact    1020
ctttatccaa ctggttcaga cttacaatca gcttttcgaa gagaacccga tcaacgcatc    1080
cggagttgac gccaaagcaa tcctgagcgc taggctgtcc aaatcccggc ggctcgaaaa    1140
cctcatcgca cagctccctg gggagaagaa gaacggcctg tttggtaatc ttatcgccct    1200
gtcactcggg ctgaccccca actttaaatc taacttcgac ctggccgaag atgccaagct    1260
tcaactgagc aaagacacct acgatgatga tctcgacaat ctgctggccc agatcggcga    1320
ccagtacgca gaccttttt tggcggcaaa gaacctgtca gacgccattc tgctgagtga    1380
```

-continued

```
tattctgcga gtgaacacgg agatcaccaa agctccgctg agcgctagta tgatcaagcg    1440
ctatgatgag caccaccaag acttgacttt gctgaaggcc cttgtcagac agcaactgcc    1500
tgagaagtac aaggaaattt tcttcgatca gtctaaaaat ggctacgccg gatacattga    1560
cggcggagca agccaggagg aattttacaa atttattaag cccatcttgg aaaaaatgga    1620
cggcaccgag gagctgctgg taaagcttaa cagagaagat ctgttgcgca acagcgcac     1680 tttcgacaat ggaagcatcc cccaccagat tcacctgggc gaactgcacg ctatcctcag    1740
gcggcaagag gatttctacc cctttttgaa agataacagg gaaaagattg agaaaatcct    1800
cacatttcgg ataccctact atgtaggccc cctcgcccgg ggaaattcca gattcgcgtg    1860
gatgactcgc aaatcagaag agaccatcac tccctggaac ttcgaggaag tcgtggataa    1920
gggggcctct gcccagtcct tcatcgaaag gatgactaac tttgataaaa atctgcctaa    1980
cgaaaaggtg cttcctaaac actctctgct gtacgagtac ttcacagttt ataacgagct    2040
caccaaggtc aaatacgtca cagaagggat gagaaagcca gcattcctgt ctggagagca    2100
gaagaaagct atcgtggacc tcctcttcaa gacgaaccgg aaagttaccg tgaaacagct    2160
caaagaagac tatttcaaaa agattgaatg tttcgactct gttgaaatca gcggagtgga    2220
ggatcgcttc aacgcatccc tgggaacgta tcacgatctc ctgaaaatca ttaaagacaa    2280
ggacttcctg gacaatgagg agaacgagga cattcttgag acattgtcc tcacccttac     2340 gttgtttgaa gataggggaga tgattgaaga acgcttgaaa acttacgctc atctcttcga    2400
cgacaaagtc atgaaacagc tcaagaggcg ccgatataca ggatgggggc ggctgtcaag    2460
aaaactgatc aatgggatcc gagacaagca gagtggaaag acaatcctgg attttcttaa    2520
gtccgatgga tttgccaacc ggaacttcat gcagttgatc catgatgact ctctcacctt    2580
taaggaggac atccagaaag cacaagtttc tggccagggg gacagtcttc acgagcacat    2640
cgctaatctt gcaggtagcc cagctatcaa aaagggaata ctgcagaccg ttaaggtcgt    2700
ggatgaactc gtcaaagtaa tgggaaggca taagcccgag aatatcgtta tcgagatggc    2760
ccgagagaac caaactaccc agaagggaca gaagaacagt agggaaagga tgaagaggat    2820
tgaagagggt ataaaagaac tggggtccca aatccttaag gaacacccag ttgaaaacac    2880
ccagcttcag aatgagaagc tctacctgta ctacctgcag aacggcaggg acatgtacgt    2940
ggatcaggaa ctggacatca atcggctctc cgactacgac gtggatcata tcgtgcccca    3000
gtcttttctc aaagatgatt ctattgataa taaagtgttg acaagatccg ataaaaatag    3060
agggaagagt gataacgtcc cctcagaaga agttgtcaag aaaatgaaaa attattggcg    3120
gcagctgctg aacgccaaac tgatcacaca acggaagttc gataatctga ctaaggctga    3180
acgaggtggc ctgtctgagt tggataaagc cggcttcatc aaaaggcagc ttgttgagac    3240
acgccagatc accaagcacg tggcccaaat tctcgattca cgcatgaaca ccaagtacga    3300
tgaaaatgac aaactgattc gagaggtgaa agttattact ctgaagtcta agctggtctc    3360
agatttcaga aaggactttc agttttataa ggtgagagag atcaacaatt accaccatgc    3420
gcatgatgcc tacctgaatg cagtggtagg cactgcactt atcaaaaaat atcccaagct    3480
tgaatctgaa tttgtttacg gagactataa agtgtacgat gttaggaaaa tgatcgcaaa    3540
gtctgagcag gaaataggca aggccaccgc taagtacttc ttttacagca atattatgaa    3600
ttttttcaag accgagatta cactggccaa tggagagatt cggaagcgac cacttatcga    3660
aacaaacgga gaaacaggag aaatcgtgtg ggacaagggg agggatttcg cgacagtccg    3720
gaaggtcctg tccatgccgc aggtgaacat cgttaaaaag accgaagtac agaccggagg    3780
```

```
cttctccaag gaaagtatcc tcccgaaaag gaacagcgac aagctgatcg cacgcaaaaa    3840
agattgggac cccaagaaat acggcggatt cgattctcct acagtcgctt acagtgtact    3900
ggttgtggcc aaagtggaga aagggaagtc taaaaaactc aaaagcgtca aggaactgct    3960
gggcatcaca atcatggagc gatcaagctt cgaaaaaaac cccatcgact ttctcgaggc    4020
gaaaggatat aaagaggtca aaaaagacct catcattaag cttcccaagt actctctctt    4080
tgagcttgaa aacggccgga aacgaatgct cgctagtgcg ggcgagctgc agaaaggtaa    4140
cgagctggca ctgccctcta aatacgttaa tttcttgtat ctggccagcc actatgaaaa    4200
gctcaaaggg tctcccgaag ataatgagca gaagcagctg ttcgtggaac aacacaaaca    4260
ctaccttgat gagatcatcg agcaaataag cgaattctcc aaaagagtga tcctcgccga    4320
cgctaacctc gataaggtgc tttctgctta caataagcac agggataagc ccatcaggga    4380
gcaggcagaa aacattatcc acttgtttac tctgaccaac ttgggcgcgc ctgcagcctt    4440
caagtacttc gacaccacca tagacagaaa gcggtacacc tctacaaagg aggtcctgga    4500
cgccacactg attcatcagt caattacggg gctctatgaa acaagaatcg acctctctca    4560
gctcggtgga gacagcaggg ctgacccaa gaagaagagg aaggtgtgat ctcttctcga    4620
gtcatgtaat tagttatgtc acgcttacat tcacgccctc cccccacatc cgctctaacc    4680
gaaaaggaag gagttagaca acctgaagtc taggtcccta tttatttttt tatagttatg    4740
ttagtattaa gaacgttatt tatatttcaa atttttcttt tttttctgta cagacgcgtg    4800
tacgcatgta acattatact gaaaaccttg cttgagaagg ttttgggacg ctcgaaggct    4860
ttaatttgcc ctctttatat tacatcaaaa taagaaaata attataaca                4909
```